US006015660A

United States Patent [19]
Lipkin et al.

[11] Patent Number: 6,015,660
[45] Date of Patent: Jan. 18, 2000

[54] BORNA DISEASE VIRAL SEQUENCES, DIAGNOSTICS AND THERAPEUTICS FOR NERVOUS SYSTEM DISEASES

[75] Inventors: W. Ian Lipkin; Thomas Briese, both of Laguna Beach; Stefanie Kliche; Patrick A. Schneider, both of Irvine, all of Calif.; Lothar Stitz, Wetzlar, Germany; Anette Schneemann, Santa Ana, Calif.

[73] Assignee: The Regents of the University of California, Oakland, Calif.

[21] Appl. No.: 08/369,822

[22] Filed: Jan. 6, 1995

[51] Int. Cl.⁷ .......................... C12Q 1/70; G01N 33/543; G01N 33/569

[52] U.S. Cl. .............................. 435/5; 435/7.1; 435/975; 436/501; 436/518

[58] Field of Search .............................. 435/5, 7.1, 975; 424/9.2; 436/501, 518

[56] References Cited

U.S. PATENT DOCUMENTS

| | | |
|---|---|---|
| 4,676,980 | 6/1987 | Segal et al. . |
| 4,683,195 | 7/1987 | Mullis et al. . |
| 4,683,202 | 7/1987 | Mullis . |
| 4,800,159 | 1/1989 | Mullis et al. . |
| 4,965,188 | 10/1990 | Mullis et al. . |
| 5,219,740 | 6/1993 | Miller et al. . |
| 5,256,553 | 10/1993 | Overell . |
| 5,654,401 | 8/1997 | Clements et al. .................. 530/350 |

FOREIGN PATENT DOCUMENTS

| | | |
|---|---|---|
| 36776 | 3/1981 | European Pat. Off. . |
| 73657 | 8/1982 | European Pat. Off. . |
| 320308 | 12/1988 | European Pat. Off. . |
| 336731 | 4/1989 | European Pat. Off. . |
| 439182 | 1/1991 | European Pat. Off. . |
| 89/09835 | 10/1989 | WIPO . |
| 89/12696 | 12/1989 | WIPO . |
| 90/01069 | 2/1990 | WIPO . |
| 91/12329 | 8/1991 | WIPO . |

OTHER PUBLICATIONS

Barik, S., et al., "Nucleotide Sequence Analysis of the L Gene of vescular Stomatitis Virus (New Jersey Sterotype): Identification of Conserved Domains in L Proteins of Non-segmented Negative–Strand RNA Viruses", *Virology*, 175:332 (1990).

Battegay, M., et al., "Impairment and Delay of Neutralizing Antiviral Antibody Responses by Virus–Specific Cytotoxic T Cells", *J. Immunol.*, 151:5408 (1993).

Bause–Niedrig, I.M., et al., "Borna disease virus–specific antigens. II. The soluble antigen is a protein complex", *Vet. Immunol. Immunopathol.*, 31:361 (1992).

Bode, L., et al., "Borna Disease Virus–specific Antibodies in Patients with HIV Infectiona dn with Mental Disorders", *Lancet* ii:689 (1988).

Briese, T., et al., "Borna disease virus, a negative–strand RNA virus, transcribes in the nucleus of infected cells", *Proc. Natl. Acad. Sci.*, USA, 89:11486 (1992).

Briese, T., et al., "Genomic organization of Borna disease virus", *Proc. Natl. Acad. Sci. USA*, 91:4362 (1994).

Briese, T., et al., "Enzyme–Linked Immunosorbent Assay for Detecting Antibodies to Borna Disease Virus–Specific Proteins", *J. Clin. Microbiol.*, 33:348 (1995).

Carbone, K.M., et al., "Borna Disease Virus Replicates in Astrocytes, Schwann Cells and Ependymal Cells in Persistently Infected Rats: Location of Viral Genomic and Messenger RNAs by In Situ Hybridization", *J. Neuropathol. Exp. Neurol.*, 50:205 (1991).

Carbone, K.M. et al., "Characterization of a Glial Cell Line Persistently Infected with Borna Disease Virus (BDV): Influence of Neurotrophic Factors on BDV Protein and RNA Expression", *J. Virol.*, 67:1452 (1993).

Cubitt, B., et al., "Sequence and Genome Organization of Borna Disease Virus", *J. Virol.*, 68:1382 (1994).

de la Torre, J.C., "Molecular Biology of Borna Disease Virus: Prototype of a New Group of Animal Viruses", *J. Virol.*, 68:7669 (1994).

de la Torre, J.C., et al., "Molecular Characterization of the Borna Disease Agent", *Virology* 179:853 (1990).

Dietzschold, B., et al., "Delineation of putative mechanisms involved in antibody–mediated clearance of rabies virus from the central nervous system", *Proc. Natl. Acad. Sci. USA*, 89:7252 (1992).

Dimmock, N.J., "Neutralization of Animal Viruses", A. Capron, et al. (ed.), "Current Topics in Microbiology and Immunology", Springer–Verlag, Berlin (1993).

Fu, Z.F., et al., "Detection of Borna Disease virus–reactive antibodies from patients with affective disorders by Western immunoblot technique", *J. Affect. Disorders*, 27:61 (1993).

Fujinami, R.S., et al., "Survival of Athymic (nu/nu Mice after Theiler's Murine Encephalomyelitis Virus Infection by Passive Administration of Neutralizing Monoclonal Antibody", *J. Virol.*, 63:2081 (1989).

Haas, b., et al., "Purification and Properties of an Intra-nuclear Virus–specific Antigen from Tissue Infected with Borna Disease Virus", *J. Gen. Virol.*, 67:235 (1986).

Hatalski, C.G., et al., "Neutralizing Antibodies in Borna Disease Virus–Infected Rats", *J. Virol.*, 69:741 (1995).

Herzog, S., et al., "Effect of Borna Disease Virus Infection on Athymic Rats", *J. Gen. Virol.*, 66:503 (1985).

Keene, J.D., et al., "Terminal Sequences of Vesicular Stomatitis Virus RNA Are both Complementary and Conserved", *J. Virol.* 32:167 (1979).

(List continued on next page.)

*Primary Examiner*—Mary E. Mosher
*Attorney, Agent, or Firm*—Margaret Churchill Fulbright & Jaworski

[57] ABSTRACT

The present invention presents: genomic nucleotide sequence of Borna disease virus, nucleotide and amino acid sequences of Borna disease virus proteins, recombinant viral proteins, vectors and cells containing the sequences or encoding the proteins, ligand binding to these proteins such as antibodies, and the diagnostic and therapeutic uses of the foregoing.

18 Claims, 27 Drawing Sheets

OTHER PUBLICATIONS

Kliche, S., et al., "Characterization of a Borna Disease Virus Glycoprotein, gp18", *J. Virol.*, 68:6918 (1994).

Kozak, M., "An analysis of 5'-noncoding sequences from 699 vertebrate messenger RNAs", *Nucleic Acids Res.*, 15:8125 (1987).

Lipkin, W.I., et al., "Isolation and characterization of Borna disease agent cDNA clones", *Proc. Natl. Acad. Sci USA*, 87:4184 (1990).

Lipkin, W.I., et al., "Borna disease virus: molecular analysis of a neurotropic infections agent", *Microbial Pathogenesis*, 13:167 (1992).

Ludwig, H., et al., "The Cerebrospinal Fluid of Rabbits Infected with Borna Disease Virus", *Arch. Virol.*, 55:209 (1977).

Ludwig, H., et al., "Biology and neurobiology of Borna disease viruses (BDV), defined by antibodies, neutralizability and their pathogenic potential", *Arch. Virol. [Suppl]*, 7:111 (1993).

Mandl, C.W., et al., "Sequencing the Terminal of Capped Viral RNA by 5'-3' Ligation and PCR", *BioTechniques*, 10:484 (1991).

McClure, M.A., et al., "Sequence Similarity between Borna Disease Virus p40 and a Duplicated domain within the Paramyxovirus and Rhabodovirus Polymerase Proteins", *J. Virol.*, 66:6572 (1992).

Narayan, O., et al., "Pathogenesis of Borna Disease in Rats: Immune-Mediated Viral Ophthalmoencephalopathy Causing Blindness and Behavioral Abnormalities", *J. Inf. Des.*, 148:305 (1983).

Narayan, O., et al., "Behavorial Disease in Rats Caused by Immunopathological Responses to Persistent Borna Virus in the Brain", *Science*, 220:1401 (1983).

Poch, O., et al., "Identifiction of four conserved motifs among the RNA-dependent polymerase encoding elements", *EMBO J.*, 8:3867 (1989).

Pringle, C.R., et al., "The order Mononegavirales", *Arch. Virol..* 117:137 (1991).

Pyper, J.M., et al., "Genomic Organization of the Structural Proteins of Borna Disease Virus Revealed by a cDNA Clone Encoding the 38–kDa Protein", *virology*, 195:229 (1993).

Richt, J.A., et al., "Analysis of Borna disease virus-specific RNAs in Infected cells and tissue", *J. Gen. Virol.*, 72:2251 (1991).

Richt, J.A., et al., "Infection with Borna Disease Virus: molecular and Immunobiological Characterization of the Agent", *Clin. Infections Diseases*, 14:1240 (1992).

Rott, R., et al., "Detection of Serum Antibodies to Borna Disease Virus in Patients with Psychiatric Disorders", *Science*, 228:755 (1985).

Schädler, R., et al., "Isolation and Characterization of a 14500 Molecular Weight Protein from Brains and tissue Cultures Persistently Infected with Borna Disease Virus", *J. gen. Virol.*, 66:2479 (1985).

Schneeman, A., et al., "identification of Signal Sequences That Control Transcription of Borna Disease Virus, a Nonsegmented, Negative-Strand RNA Virus", *J. Virol.*, 68:6514 (1994).

Schneider, P.A., et al., "Sequence Conservation in Field and Experimental Isolates of Borna Disease Virus", *J. Virol.*, 68:63 (1994).

Schneider, P.A., et al., "RNA Splicing in Borna Disease Virus, A Nonsegmented, Negative-Stranad RNA Virus", *J. Virol.*, 68:5007 (1994).

Schnell, M.J., "Infectious rabies viruses from cloned cDNA", *EMBO J.*, 13(18):4195 (1994).

Stitz, L., et al., "Borna Disease In Rhesus Monkeys as a Model for Uveo-Cerebral Symptoms", *J. Med. Virol.*, 6:333 (1980).

Stitz, L., et al., "Preventive Effects of Early Anti-CD4 or Anti-CD8 Treatment on Borna Disease in Rats", *J. Virol.*, 66:3316 (1992).

Thibault, K.J., M.S. thesis, "Identification and Preliminary Characterization of cDNAs Encoding Borna Disease Virus p24 and p40", University of California, Irvine (1992) Title Page and Table of Contenst and Figures.

Thiedemann, N., et al., "Antigenic relationship and further charaterization of two major Borna disease virus-specific proteins", *J. Gen. Virol.*, 73:1057 (1992).

Thierer, J., et al., "The 24K protein of Borna disease virus", *J. Gen. Virol.*, 73:413 (1992).

Tsang, S.S., et al., "Loss of Resolution in Gel Electrophoresis of RNA: A Problem Associated with the Presence of Forlmaldehyde Gradients", *BioTechniques*, 14:380 (1993).

Tyler, K.L., et al., "Antibody Inhibits defined Stages in the Pathogenesis of Reovirus Serotype 3 Infection of the Central Nervous System", *J. Exp. Med.*, 170:887 (1989).

VandeWoude, S., et al., "A Borna Virus cDNA Encoding a Protein Recognized by Antibodies in Humans with Behavioral Diseases", *Science*, 250:1278 (1990).

Bode, L., et al., "Borna disease virus genome transcribed and expressed in psychiatric patients", *Nature*, 1:232 (1995).

Clements, J.E., "cDNA Clone Specific for the Borna Disease Virus", Computer Internet printout (date unknown).

Crabb, B.S., et al., "Identification of Equine Herpesvirus 4 Glycoprotein G: A Type-Specific, Secreted Glycoprotein", *Virology*, 190:143 (1992).

Garreis-Wabritz, c., et al., "Intracellular appearance of glycoprotein in VSV-infected BHK cells lacking the membrane-anchoring oligopeptide of the viral G-protein", *EMBO J.*, 3(7):1469–1476 (1984).

Maniatis, et al., *Molecular Cloning—A Laboratory Manual*, Cold Spring Harbor (1984).

Schneeman, A., et al., "The Remarkable Coding Strategy of Borna Disease Virus: A New Member of the Nonsegmented Negative Strand RNA Viruses", *Virology* (Minireview), 210:1 (1995).

Waltrip, R.W., II, et al., "Borna disease virus and schizophrenia", *Psychiatry Res.*, 56:33 (1995).

Zimmerman, W., "Detection of Borna disease virus RNA in naturally infected animals by a nested polymerase chain reaction", *J. Virol. Meths.*, 46:144–143 (1994).

Boswell et al. "Sequence comparison and alignment: the measurement and interpretation of sequence similarity." In Computational Molecular Biology, ed. A. M. Lesk, Oxford University Press, 1988, pp. 161–178.

Bause–Niedrig, I. et al. Veterinary Immunology and Immunopathology, vol. 27, pp. 293–301, 1991.

Kao, M., et al., "detection of antibodies against Borna disease virus in sera and cerebrospinal fluid of horses in the USA", *Vet. Rec.*, 132:241 (1993).

Ludwig, H., et al., "Demonstration of Specific Antibodies in the Central Nervous System of Horses Naturally Infected with Borna Disease Virus", *Med. Microbiol. Immunol.*, 163:215 (1977).

Ludwig, H., et al., "Borna Disease: A Persistent Virus Infection of the Central Nervous System", *Prog. Med. Virol.*, 35:107 (1988).

Rubin, S.A., et al., "Borna Disease Virus in Mice: Host–Specific Differences in Disease Expression", *J. Virol.*, 67:548 (1993).

Sprankel, H., et al., "Behavior Alterations in Tree Shrews (*Tupaia glis*, Diard 1820) Induced by Borna Disease Virus", *Med. Microbiol. Immunol.*, 165:1 (1978).

Virgin, H.W., IV, et al., "Antibody Protects against Lethal Infection with the Neurally Spreading Reovirus Type 3 (Dearing)", *J. Virol.*, 62:4594 (1988).

Waelchli, R.O., et al., "Borna disease in a sheep", *Vet. Rec.*, 117:499 (1985).

FIG. 2(1)

```
   1 GTTGCGTTAACAACAAACCACTCATCATTCTTCTAACAAAATGAACACACGCAATGCCACCCAAGAGACGCCTGGTTGATGACGCCGATGCCATGGAGGA  100
                                                    M  P  P  K  R  R  L  V  D  D  A  D  A  M  E  D

101 TCAAGATCTATATGAACCCCCAGCGAGCCTCCCTAAGCTCCCTGGGAAATTCCTACAATACACCGTTGGGGGGTCTGACCCGCATCCGGGTATAGGGCAT  200
      Q  D  L  Y  E  P  P  A  S  L  P  K  L  P  G  K  F  L  Q  Y  T  V  G  G  S  D  P  H  P  G  I  G  H

201 GAGAAAGACATCAGGCAGAACGCAGTGGCATTGTTAGACCAGTCACGGCGCGATATGTTTCACACAGTAACGCCTAGCCTTGTGTTTCTATGTTTGCTAA  300
      E  K  D  I  R  Q  N  A  V  A  L  L  D  Q  S  R  R  D  M  F  H  T  V  T  P  S  L  V  F  L  C  L  L  I

301 TCCCAGGACTGCACGCTGCGTTTGTTCACGGAGGGGTGCCTCGTGAATCCTACCTGTCGACGCCTGTCACGCGTGGAGAACAGACTGTTGTTAAGACTGC  400
       P  G  L  H  A  A  F  V  H  G  G  V  P  R  E  S  Y  L  S  T  P  V  T  R  G  E  Q  T  V  V  K  T  A

401 GAAGTTTTACGGGGAAAAGACGACGCAGCGTGATCTCACCGAGCTGGAGATCTCCTCTATCTTCAGCCATTGTTGCTCATTACTAATAGGGGTTGTGATA  500
       K  F  Y  G  E  K  T  T  Q  R  D  L  T  E  L  E  I  S  S  I  F  S  H  C  C  S  L  L  I  G  V  V  I

501 GGATCGTCGTCTAAGATCAAAGCAGGAGCCGAGCAGATCAAGAAAAGGTTTAAAACTATGATGGCAGCCTTAAACCGGCCATCCCATGGTGAGACTGCTA  600
       G  S  S  S  K  I  K  A  G  A  E  Q  I  K  K  R  F  K  T  M  M  A  A  L  N  R  P  S  H  G  E  T  A  T

601 CACTACTCCAGATGTTTAATCCACATGAGGCTATAGATTGGATTAACGGCCAACCCTGGGTAGGCTCCTTTGTGTTGTCTCTACTAACTACAGACTTTGA  700
       L  L  Q  M  F  N  P  H  E  A  I  D  W  I  N  G  Q  P  W  V  G  S  F  V  L  S  L  L  T  T  D  F  E

701 GTCCCCAGGTAAAGAATTTATGGACCAGATTAAGCTTGTCGCAAGTTATGCACAGATGACTACGTACACTACTATAAAGGAGTACCTCGCAGAATGCATG  800
       S  P  G  K  E  F  M  D  Q  I  K  L  V  A  S  Y  A  Q  M  T  T  Y  T  T  I  K  E  Y  L  A  E  C  M

801 GATGCTACCCTTACAATCCCCGTAGTTGCATATGAGATCCGTGACTTTTTAGAAGTTTCAGCAAAGCTTAAGGAGGATCATGCTGACCTGTTCCCGTTTC  900
       D  A  T  L  T  I  P  V  V  A  Y  E  I  R  D  F  L  E  V  S  A  K  L  K  E  D  H  A  D  L  F  P  F  L

901 TGGGGGCCATTAGACACCCCGACGCTATCAAGCTGGCGCCACGAAGCTTTCCCAATCTGGCCTCCGCAGCGTTTTACTGGAGTAAGAAGGAAAACCCCAC 1000
       G  A  I  R  H  P  D  A  I  K  L  A  P  R  S  F  P  N  L  A  S  A  A  F  Y  W  S  K  K  E  N  P  T

1001 AATGGCAGGCTACCGGGCCTCCACCATCCAGCCGGGCGCAAGTGTCAAGGAAACCCAGCTTGCCCGGTATAGGCGCCGCGAGATATCTCGTGGAGAGGAC 1100
       M  A  G  Y  R  A  S  T  I  Q  P  G  A  S  V  K  E  T  Q  L  A  R  Y  R  R  R  E  I  S  R  G  E  D

1101 GGGGCAGAGCTCTCAGGTGAGATCTCTGCCATAATGAAGATGATAGGTGTGACTGGTCTAAACTAAAAAACAATGAACAAACCAATAAAAAACCAAATGC 1200
       G  A  E  L  S  G  E  I  S  A  I  M  K  M  I  G  V  T  G  L  N  *

1201 GGCAAACCCTCCGCGACCTGCGATGAGCTCCGACCTCCGGCTGACATTGCTTGAACTAGTCAGGAGGCTCAATGGCAACGCGACCATCGAGTCTGGTCGA 1300
                                                                      M  A  T  R  P  S  S  L  V  D

1301 CTCCCTGGAGGACGAAGAAGATCCCCAGACACTACGACGGGAACGACCGGGGTCACCAAGACCACGGAAGGTCCCAAGGAATGCATTGACCCAACCAGTA 1400
       S  L  E  D  E  E  D  P  Q  T  L  R  R  E  R  P  G  S  P  R  P  R  K  V  P  R  N  A  L  T  Q  P  V

1401 GACCAGCTCCTGAAGGACCTCAGGAAGAACCCCTCCATGATCTCAGACCCAGACCAGCGAACCGGAAGGGAGCAGCTGTCGAATGATGAGCTAATCAAGA 1500
       D  Q  L  L  K  D  L  R  K  N  P  S  M  I  S  D  P  D  Q  R  T  G  R  E  Q  L  S  N  D  E  L  I  K  K

1501 AGTTAGTGACGGAGCTGGCCGAGAATAGCATGATCGAGGCTGAGGAGGTGCGGGGCACTCTTGGAGACATCTCGGCTCGTATCGAGGCAGGGTTTGAGTC 1600
       L  V  T  E  L  A  E  N  S  M  I  E  A  E  E  V  R  G  T  L  G  D  I  S  A  R  I  E  A  G  F  E  S

1601 CCTGTCCGCCCTCCAAGTGGAAACCATCCAGACAGCTCAGCGGTGCGATCACTCCGACAGCATCAGGATCCTCGGCGAGAACATCAAGATACTAGATCGC 1700
       L  S  A  L  Q  V  E  T  I  Q  T  A  Q  R  C  D  H  S  D  S  I  R  I  L  G  E  N  I  K  I  L  D  R

1701 TCCATGAAGACAATGATGGAGACAATGAAGCTCATGATGGAGAAGGTGGATCTCCTCTACGCATCAACCGCCGTTGGGACCTCTGCACCCATGTTGCCCT 1800
       S  M  K  T  M  M  E  T  M  K  L  M  M  E  K  V  D  L  L  Y  A  S  T  A  V  G  T  S  A  P  M  L  P  S
```

FIG. 2(2)

```
1801 CCCATCCTGCACCTCCGCGCATTTATCCCCAGCTCCCAAGTGCCCCGACAACGGATGAATGGGACATCATACCATAAAAAAATCGAATCACCATGAATTC 1900
      H P A P P R I Y P Q L P S A P T T D E W D I I P *             M N S

1901 AAAACATTCCTATGTGGAGCTCAAGGACAAGGTAATCGTCCCTGGATGGCCCACACTCATGCTTGAGATAGACTTTGTAGGGGGGACTTCACGGAACCAG 2000
      K H S Y V E L K D K V I V P G W P T L M L E I D F V G G T S R N Q

2001 TTCCTTAACATCCCATTTCTTTCAGTGAAAGAGCCTCTGCAGCTTCCACGCGAGAAGAAGTTGACCGACTACTTTACTATTGACGTAGAACCAGCAGGTC 2100
      F L N I P F L S V K E P L Q L P R E K K L T D Y F T I D V E P A G H

2101 ATTCCCTGGTCAATATATACTTCCAGATTGACGACTTCTTGCTCCTAACACTCAACTCACTATCTGTGTACAAGGACCCGATTAGAAAATACATGTTCCT 2200
      S L V N I Y F Q I D D F L L L T L N S L S V Y K D P I R K Y M F L

2201 ACGCCTCAACAAGGACCAGAGCAAGCACGCAATCAATGCAGCCTTCAATGTCTTTTCTTATCGGCTTCGGAACATTGGTGTTGGTCCTCTCGGCCCGGAC 2300
      R L N K D Q S K H A I N A A F N V F S Y R L R N I G V G P L G P D
                                    M Q P S M S F L I G F G T L V L V L S A R T

2301 ATTCGATCTTCAGGGCCTTAGCTGCAATACTGACTCCACTCCTGGACTGATTGACCTGGAGATAAGGCGACTTTGCCACACCCCAACGGAAAATGTCATT 2400
      I R S S G P *
      F D L Q G L S C N T D S T P G L I D L E I R R L C H T P T E N V I

2401 TCATGCGAGGTTAGTTATCTCAACCACACGACTATTAGCCTCCCGGCAGTCCACACATCATGCCTCAAGTACCACTGCAAAACCTATTGGGGATTCTTTG 2500
      S C E V S Y L N H T T I S L P A V H T S C L K Y H C K T Y W G F F G

2501 GTAGCTACAGCGCTGACCGAATCATAAATCGGTACACTGGTACTGTTAAGGGTTGTCTAAACAACTCAGCACCAGAGGACCCCTTCGAGTGCAACTGGTT 2600
      S Y S A D R I I N R Y T G T V K G C L N N S A P E D P F E C N W F

2601 CTACTGCTGCTCGGCGATTACAACAGAGATCTGCCGATGCTCTATTACAAATGTCACGGTGGCTGTGCAAACATTCCCACCGTTCATGTACTGCAGTTTT 2700
      Y C C S A I T T E I C R C S I T N V T V A V Q T F P P P F M Y C S F

2701 GCAGACTGCAGTACCGTGAGCCAACAGGAGCTAGAGAGTGGAAAGGCAATGCTGAGCGATGGCAGTACATTAACTTATACCCCGTATATCCTACAGTCAG 2800
      A D C S T V S Q Q E L E S G K A M L S D G S T L T Y T P Y I L Q S E

2801 AAGTCGTGAACAAAACCCTCAATGGGACCATACTCTGCAACTCATCCTCTAAGATAGTTTCCTTCGATGAATTTAGGCGTTCATACTCCCTAACGAATGG 2900
      V V N K T L N G T I L C N S S S K I V S F D E F R R S Y S L T N G

2901 TAGTTACCAGAGCTCATCAATCAATGTGACGTGTGCAAACTACACGTCGTCCTGCCGGCCCAGGTTGAAAAGGCGGCGTAGGGACACCCAGCAGATTGAG 3000
      S Y Q S S S I N V T C A N Y T S S C R P R L K R R R R D T Q Q I E

3001 TATCTAGTTCACAAGCTTAGGCCCACACTGAAAGATGCATGGGAGGACTGTGAGATCCTCCAGTCTCTGCTCCTAGGGGTGTTTGGTACTGGGATCGCAA 3100
      Y L V H K L R P T L K D A W E D C E I L Q S L L L G V F G T G I A S

3101 GTGCTTCTCAATTTTTGAGGAGCTGGCTCAACCACCCTGACATCATCGGGTATATAGTTAATGGAGTTGGGGTTGTCTGGCAATGCCATCGTGTTAATGT 3200
      A S Q F L R S W L N H P D I I G Y I V N G V G V W Q C H R V N V

3201 CACGTTCATGGCGTGGAATGAGTCCACCTATTACCCTCCAGTAGATTACAATGGGCGGAAGTACTTCCTGAATGATGAGGGAAGGTTACAAACAAACACC 3300
      T F M A W N E S T Y Y P P V D Y N G R K Y F L N D E G R L Q T N T

3301 CCCGAGGCAAGGCCAGGGCTTAAGCGGGTCATGTGGTTCGGCAGGTACTTCCTAGGGACAGTAGGGTCTGGGGTGAAACCGAGGAGGATTCGGTACAATA 3400
      P E A R P G L K R V M W F G R Y F L G T V G S G V K P R R I R Y N K

3401 AGACCTCACATGACTACCACCTGGAGGAGTTTGAGGCAAGTCTCAACATGACCCCTCAGACCAGTATCGCCTCGGGTCATGAGACAGACCCCATAAATCA 3500
      T S H D Y H L E E F E A S L N M T P Q T S I A S G H E T D P I N H

3501 TGCCTACGGAACGCAGGCTGATCTCCTTCCATACACCAGGTCTAGTAATATAACATCTACGGATACAGGCTCAGGCTGGGTGCACATCGGCCTACCCTCA 3600
      A Y G T Q A D L L P Y T R S S N I T S T D T G S G W V H I G L P S
```

FIG. 2(3)

```
3601 TTTGCTTTCCTCAATCCCCTCGGGTGGCTCAGGGACCTACTTGCATGGGCAGCCTGGTTGGGTGGGGTTCTATACTTAATAAGTCTTTGTGTTTCCTTAC 3700
      F A F L N P L G W L R D L L A W A A W L G G V L Y L I S L  V S L P

3701 CAGCCTCCTTCGCGAGGAGGAGACGCCTCGGCCGGTGGCAGGAATAAACCGTACCGACCAGTCTCTTAAAAACCCTCTCCTCGGAACAGAGGT TCTTTC 3800
      A S F A R R R R L G R W Q E *

3801 TGCCTTAAGTCGAGCTCACTCCCCCATCATGTACGAGCACTAGGCCAGATTAAAGCAAGGAACCTGGCATCCTGTGACTATTACTTGCTATTCCGCCAAG 3900

3901 TTGTATTGCCCCCTGAAGTATATCCCATTGGTGTTCTAATAAGAGCTGCGGAGGCTATACTAACAGTTATAGTATCAGCTTGGAAGCTGGATCATATGAC 4000
                                                                                                    M T

4001 GAAGACCCTATACTCCTCTGTGAGATATGCACTCACCAATCCCCGGGTCCGAGCCCAACTTGAGCTTCACATTGCCTACCAGCGCATAGTGGGTCAGGTC 4100
      K T L Y S S V R Y A L T N P R V R A Q L E L H I A Y Q R I V G Q V

4101 TCGTACAGCCGGGAGGCAGACATAGGGCCAAAAAGGCTTGGGAATATGTCATTGCAATTCATCCAATCTCTCGTTATTGCCACCATAGACACGACAAGCT 4200
      S Y S R E A D I G P K R L G N M S L Q F I Q S L V I A T I D T T S C

4201 GCCTAATGACCTACAACCACTTTCTTGCTGCAGCAGACACAGCCAAGAGCAGATGCCATCTCCTAATCGCCTCAGTGGTCCAGGGGGCCCTTTGGGAACA 4300
      L M T Y N H F L A A A D T A K S R C H L L I A S V V Q G A L W E Q

4301 AGGGTCATTTCTTGATCATATAATCAACATGATCGACATAATTGACTCAATCAACCTCCCCCATGATGATTACTTCACAATTATTAAGTCTATCTTTCCC 4400
      G S F L D H I I N M I D I I D S I N L P H D D Y F T I I K S I F P

4401 TACTCCCAAGGGCTTGTTATGGGGAGGCATAATGTATCAGTCTCCTCTGATTTCGCGTCCGTATTTGCCATTCCTGAATTATGCCCGCAACTAGACAGCT 4500
      Y S Q G L V M G R H N V S V S S D F A S V F A I P E L C P Q L D S L

4501 TACTAAAAAAACTGCTCCAACTTGACCCCGTTCTCCTCCTCATGGTCTCTTCGGTGCAGAAGTCATGGTACTTCCCTGAGATCCGAATGGTCGACGGGTC 4600
      L K K L L Q L D P V L L L M V S S V Q K S W Y F P E I R M V D G S

4601 ACGGGAGCAGCTCCACAAGATGCGTGTCGAGCTGGAAACGCCCCAAGCCCTGCTGTCGTACGGCCATACCCTCCTGTCAATATTTCGGGCAGAGTTTATC 4700
      R E Q L H K M R V E L E T P Q A L L S Y G H T L L S I F R A E F I

4701 AAAGGCTATGTCTCAAAGAATGCGAAGTGGCCGCCCGTACACCTGCTCCCAGGCTGTGACAAATCCATAAAAAATGCGAGAGAGCTGGGCCGCTGGAGCC 4800
      K G Y V S K N A K W P P V H L L P G C D K S I K N A R E L G R W S P

4801 CGGCATTTGACCGACGATGGCAGCTCTTCGAGAAGGTTGTCATTCTAAGAATTGCTGACCTAGATATGGATCCCGACTTCAACGATATTGTTAGCGATAA 4900
      A F D R R W Q L F E K V V I L R I A D L D M D P D F N D I V S D K

4901 GGCGATAATCAGCTCAAGAAGGGACTGGGTATTCGAGTACAATGCAGCGGCCTTTTGGAAGAAATACGGTGAACGGTTGGAGAGGCCTCCTGCCAGGTCG 5000
      A I I S S R R D W V F E Y N A A A F W K K Y G E R L E R P P A R S

5001 GGACCGTCACGACTTGTGAATGCTCTAATCGATGGACGCTTAGACAATATCCCAGCCCTGCTAGAGCCATTTTACAGGGGAGCGGTTGAGTTCGAGGATC 5100
      G P S R L V N A L I D G R L D N I P A L L E P F Y R G A V E F E D R

5101 GGTTGACTGTGCTCGTGCCTAAGGAGAAAGAGTTAAAGGTAAAGGGAAGGTTCTTCTCGAAGCAAACATTGGCAATCAGGATATATCAGGTTGTTGCTGA 5200
      L T V L V P K E K E L K V K G R F F S K Q T L A I R I Y Q V V A E

5201 AGCTGCACTTAAGAATGAGGTTATGCCATACCTAAAGACACACTCAATGACCATGAGCTCAACGGCTCTAACTCACCTTCTTAACCGGCTATCACATACT 5300
      A A L K N E V M P Y L K T H S M T M S S T A L T H L L N R L S H T

5301 ATCACTAAGGGTGACTCCTTTGTTATTAACCTTGACTATAGTTCCTGGTGCAACGGTTTCCGACCAGAACTGCAGGCCCCAATCTGTCGTCAGTTGGATC 5400
      I T K G D S F V I N L D Y S S W C N G F R P E L Q A P I C R Q L D Q
```

FIG. 2(4)

```
5401 AGATGTTCAATTGCGGGTACTTCTTCAGGACTGGGTGCACACTGCCATGCTTTACCACGTTTATTATTCAAGAuAuGTTCAACCCGCCCTATTCCCTCAG 5500
       M  F  N  C  G  Y  F  F  R  T  G  C  T  L  P  C  F  T  T  F  I  I  Q  D  R  F  N  i  P  Y  S  L  S

5501 TGGTGAGCCCGTTGAAGACGGAGTTACATGCGCGGTTGGGACTAAAACAATGGGGGAGGGCATGAGGCAGAAACTATGGACAATCCTTACGAGCTGCTGG 5600
       G  E  P  V  E  D  G  V  T  C  A  V  G  T  K  T  M  G  E  G  M  R  Q  K  L  W  T  I  L  T  S  C  W

5601 GAGATAATTGCTCTTCGGGAAATTAACGTGACGTTTAACATACTAGGCCAAGGTGATAATCAGACAATCATCATACATAAATCTGCAAGCCAAAATAACC 5700
       E  I  I  A  L  R  E  I  N  V  T  F  N  I  L  G  Q  G  D  N  Q  T  I  I  I  H  K  S  A  S  Q  N  N  Q

5701 AGCTATTAGCGGAGCGAGCACTAGGGGCCCTGTACAAGCATGCTAGATTAGCTGGCCATAACCTCAAGGTAGAGGAATGCTGGGTGTCAGATTGTCTGTA 5800
       L  L  A  E  R  A  L  G  A  L  Y  K  H  A  R  L  A  G  H  N  L  K  V  E  E  C  W  V  S  D  C  L  Y

5801 TGAGTATGGAAAGAAGCTTTTCTTCCGTGGTGTACCTGTCCCGGGCTGTTTGAAGCAGCTCTCACGGGTGACGGATTCTACTGGAGAGCTATTCCCAAAC 5900
       E  Y  G  K  K  L  F  F  R  G  V  P  V  P  G  C  L  K  Q  L  S  R  V  T  D  S  T  G  E  L  F  P  N

5901 CTATACTCAAAGTTAGCCTGCTTAACATCATCGTGTTTAAGCGCAGCGATGGCAGACACATCTCCATGGGTGGCACTCGCGACAGGTGTCTGTCTGTATC 6000
       L  Y  S  K  L  A  C  L  T  S  S  C  L  S  A  A  M  A  D  T  S  P  W  V  A  L  A  T  G  V  C  L  Y  L

6001 TTATCGAGTTATATGTTGAGCTGCCTCCAGCAATCATGCAGGATGAGTCGCTATTGACGACCCTCTGCCTCGTAGGCCCATCCATTGGTGGGCTTCCGAC 6100
       I  E  L  Y  V  E  L  P  P  A  I  M  Q  D  E  S  L  L  T  T  L  C  L  V  G  P  S  I  G  G  L  P  T

6101 CCCTGCAACCCTACCCAGTGTCTTTTTCAGAGGAATGTCCGACCCACTGCCCTTTCAGCTAGCACTCTTGCAGACCCTCATTAAGACGACAGGGGTGACC 6200
       P  A  T  L  P  S  V  F  F  R  G  M  S  D  P  L  P  F  Q  L  A  L  L  Q  T  L  I  K  T  T  G  V  T

6201 TGTAGCTTGGTGAATCGTGTGGTCAAGTTACGGATAGCACCCTATCCAGACTGGCTCTCTCTAGTGACTGACCCGACCTCACTCAACATTGCCCAAGTGT 6300
       C  S  L  V  N  R  V  V  K  L  R  I  A  P  Y  P  D  W  L  S  L  V  T  D  P  T  S  L  N  I  A  Q  V  Y

6301 ACCGGCCAGAACGTCAGATCAGGAGGTGGATTGAGGAAGCGATAGCGACAAGCTCACACTCGTCACGCATAGCAACTTTCTTCCAGCAGCCCCTCACGGA 6400
       R  P  E  R  Q  I  R  R  W  I  E  E  A  I  A  T  S  S  H  S  S  R  I  A  T  F  F  Q  Q  P  L  T  E

6401 GATGGCTCAGTTGCTTGCGAGGGACCTTTCAACAATGATGCCTCTTCGACCCCGGGATATGTCGGCCTTATTCGCATTATCAAATGTCGCATACGGTTTA 6500
       M  A  Q  L  L  A  R  D  L  S  T  M  M  P  L  R  P  R  D  M  S  A  L  F  A  L  S  N  V  A  Y  G  L

6501 AGCATTATAGATCTATTTCAAAAATCCTCTACCGTTGTTTCTGCAAGTCAAGCTGTCCATATCGAGGATGTTGCCCTAGAGAGTGTAAGGTATAAGGAAT 6600
       S  I  I  D  L  F  Q  K  S  S  T  V  V  S  A  S  Q  A  V  H  I  E  D  V  A  L  E  S  V  R  Y  K  E  S

6601 CTATCATCCAGGGTCTGTTAGACACCACTGAGGGGTATAACATGCAACCTTATTTGGAAGGTTGCACTTACCTTGCAGCCAAACAGTTACGTAGGTTGAC 6700
       I  I  Q  G  L  L  D  T  T  E  G  Y  N  M  Q  P  Y  L  E  G  C  T  Y  L  A  A  K  Q  L  R  R  L  T

6701 ATGGGGTCGAGACCTAGTTGGAGTCACAATGCCGTTTGTTGCCGAGCAATTCCATCCTCACAGTTCTGTGGGTGCAAAGGCGGAACTCTACCTCGACGCT 6800
       W  G  R  D  L  V  G  V  T  M  P  F  V  A  E  Q  F  H  P  H  S  S  V  G  A  K  A  E  L  Y  L  D  A

6801 ATTATATACTGCCCACAGGAGACATTGCGGTCACACCATCTGACTACCAGGGGGGACCAGCCGCTTTACCTCGGATCCAATACGGCTGTCAAGGTCCAGC 6900
       I  I  Y  C  P  Q  E  T  L  R  S  H  H  L  T  T  R  G  D  Q  P  L  Y  L  G  S  N  T  A  V  K  V  Q  R

6901 GAGGTGAGATCACGGGCCTAACAAAGTCAAGGGCTGCAAATCTAGTCAGGGACACTCTCGTTCTCCATCAGTGGTATAAAGTCCGTAAAGTTACCGATCC 7000
       G  E  I  T  G  L  T  K  S  R  A  A  N  L  V  R  D  T  L  V  L  H  Q  W  Y  K  V  R  K  V  T  D  P

7001 ACACTTGAACACCCTCATGGCACGCTTCTTACTTGAGAAGGGGTACACATCTGACGCTCGACCTAGCATCCAGGGTGGGACCCTCACGCATCGTCTCCCA 7100
       H  L  N  T  L  M  A  R  F  L  L  E  K  G  Y  T  S  D  A  R  P  S  I  Q  G  G  T  L  T  H  R  L  P

7101 TCCCGCGGGAGACTCACGGCAGGGGCTTACTGGGTATGTAAATATACTAAGTACGTGGCTTCGATTCTCAAGTGATTATCTTCACTCTTTCTCGAAATCAT 7200
       S  R  G  D  S  R  Q  G  L  T  G  Y  V  N  I  L  S  T  W  L  R  F  S  S  D  Y  L  H  S  F  S  K  S  S
```

FIG. 2(5)

```
7201 CAGACGACTATACAATCCACTTTCAGCATGTATTCACATACGGTTGCCTCTATGCTGATTCGGTGATTAGATC GCGGTGT   TCCACTCCTTACCT 7300
        D  D  Y  T  I  H  F  Q  H  V  F  T  Y  G  C  L  Y  A  D  S  V  I  R  S  G  G  V  I  S  T  P  Y  L

7301 TTTGAGTGCAAGTTGTAAAACATGCTTTGAGAAGATAGACTCAGAGGAGTTCGTCCTGGCATGTGAACCCCAATACAGGGGTGCTGAGTGGCTGATATCA 7400
        L  S  A  S  C  K  T  C  F  E  K  I  D  S  E  E  F  V  L  A  C  E  P  Q  Y  R  G  A  E  W  L  I  S

7401 AAGCCAGTCACTGTCCCTGAGCAGATAACTGATGCTGAAGTCGAGTTTGACCCCTGTGTGAGTGCGGGTTATTGTCTCGGGATTCTCATTGGCAAGTCAT 7500
        K  P  V  T  V  P  E  Q  I  T  D  A  E  V  E  F  D  P  C  V  S  A  G  Y  C  L  G  I  L  I  G  K  S  F

7501 TCTTAGTTGACATAAGGGCAAGTGGGCATGATATCATGGAGCAGCGGACATGGGCTAACCTGGAGAGGTTTTCTGTATCGGACATGCAGAAACTTCCGTG 7600
        L  V  D  I  R  A  S  G  H  D  I  M  E  Q  R  T  W  A  N  L  E  R  F  S  V  S  D  M  Q  K  L  P  W

7601 GAGTATTGTAATTCGGTCTCTCTGGAGATTCCTTATTGGCGCACGGCTCCTTCAGTTTGAGAAGGCTGGCCTCATTAGAATGCTGTATGCTGCGACAGGT 7700
        S  I  V  I  R  S  L  W  R  F  L  I  G  A  R  L  L  Q  F  E  K  A  G  L  I  R  M  L  Y  A  A  T  G

7701 CCAACCCCTAGCTTCCTAATGAAAGTTTTTCAAGACTCAGCCCTCCTCATGGACTGCGCACCCCTCGATCGGCTGTCCCCTAGGATCAACTTTCATAGTC 7800
        P  T  P  S  F  L  M  K  V  F  Q  D  S  A  L  L  M  D  C  A  P  L  D  R  L  S  P  R  I  N  F  H  S  R

7801 GGGGAGACCTCGTTGCTAAGCTTGTTTTATTGCCCTTCATCAACCCGGGTATAGTGGAGATTGAAGTGTCTGGAATTAATAGCAAGTACCATGCAGTATC 7900
        G  D  L  V  A  K  L  V  L  L  P  F  I  N  P  G  I  V  E  I  E  V  S  G  I  N  S  K  Y  H  A  V  S

7901 GGAGGCCAATATGGATCTGTACATCGCTGCTGCCAAGTCTGTGGGCGTGAAgcccacacagTTTGTTGAGGAAACAAACGACTTTACGGCCCGCggccac 8000
        E  A  N  M  D  L  Y  I  A  A  A  K  S  V  G  V  K  P  T  Q  F  V  E  E  T  N  D  F  T  A  R  G  H 8001 cACCATGGTTGTTATTCCCTTTCTTGGTCTAAGTCACGCAATCAATCACAGGTCCTAAAGATGGTAGTACGGAAGCTGAAGCTCTGTGTCCTGTATATAT 8100
        H  H  G  C  Y  S  L  S  W  S  K  S  R  N  Q  S  Q  V  L  K  M  V  V  R  K  L  K  L  C  V  L  Y  I  Y 8101 ACCCCACAGTCGATCCCGCCGTTGCTCTCGACCTGTGCCATCTACCAGCATTAACTATAATCCTAGTGCTCGGCGGTGACCCAGCGTACTATGAGCGATT 8200
        P  T  V  D  P  A  V  A  L  D  L  C  H  L  P  A  L  T  I  I  L  V  L  G  G  D  P  A  Y  Y  E  R  L 8201 ACTTGAGATGGACCTGTGCGGGGCTGTGTCAAGTCGAGTCGATATCCCCCATTCTCTGGCTGGCAGAACGCACAGGGGGTTCGCAGTGGGCCCAGACGCT 8300
        L  E  M  D  L  C  G  A  V  S  S  R  V  D  I  P  H  S  L  A  G  R  T  H  R  G  F  A  V  G  P  D  A 8301 GGTCCAGGTGTAATTAGACTCGACAGGTTAGAGTCAGTTTGTTATGCTCACCCCTGTTTAGAGGAACTAGAGTTTAATGCATATCTAGACTCTGAGTTGG 8400
        G  P  G  V  I  R  L  D  R  L  E  S  V  C  Y  A  H  P  C  L  E  E  L  E  F  N  A  Y  L  D  S  E  L  V 8401 TTGACATTAGTGATATGTGCTGCCTCCCCTTagCGACACCCTGTAAggCCCTTTTCAGGCCAATATATCGGAGCTTACAGTCGTTCAGGTTAGCCTTAAT 8500
        D  I  S  D  M  C  C  L  P  L  A  T  P  C  K  A  L  F  R  P  I  Y  R  S  L  Q  S  F  R  L  A  L  M 8501 GGACAACTATAGTTTTGTCATGGACCTCATTATGATCCGAGGACTGGACATTAGGCCTCACCTTGAGGAATTTGAGGAGCTGCTTGTGGTAGGACAGCAC 8600
        D  N  Y  S  F  V  M  D  L  I  M  I  R  G  L  D  I  R  P  H  L  E  E  F  D  E  L  L  V  V  G  Q  H 8601 ATcCTCGGCCAGCCCGTCCTAGTAGAGGTTGTTTACTACGTTGGAGTTGTTAGGAAGCGCCCTGTGTTAGCGAGGCATCCGTGGTCAGCAGATCTTAAGC 8700
        I  L  G  Q  P  V  L  V  E  V  V  Y  Y  V  G  V  V  R  K  R  P  V  L  A  R  H  P  W  S  A  D  L  K  R 8701 GAATTACTGTGGGGGGGCGGGCTCCCTGCCcCTCTGCTGCCAGATTGCGTGATGAGGATTGTCAGGGGTCTCTGTTGGTTGGGCTTCCTGCTGGGTTGAC 8800
        I  T  V  G  G  R  A  P  C  P  S  A  A  R  L  R  D  E  D  C  Q  G  S  L  L  V  G  L  P  A  G  L  T 8801 GCAGTTATTGATAATTGATTAAGATCAAGCCACCTACTACCCTATTCTTAAAAAACCATATGTCAGTGGTGCAGTGCTTGGGCTTGGTTGTTGCTTTGTT 8900
        Q  L  L  I  I  D  *

8901 GTAGCGCGTT
```

FIG. 4(1)

```
              1                                                                                                         x                                                                       *       ***    *      x        *  **   x    x    * x x  150
443 RaV  twppkhivdl vgd.tWHkIp itqifeipes mDpseildDK shsftrtria swLse.......................nrgg .pvp....se kviitalskp pvnprefIrs idlgg.Lpde dIiigLkpKE rEIkIeGRFF aIMswnLRIy fVitEkLIan
430 VSV  twptaakiqd fgd.nWHkIp liqcfeipdl iDpsviysDK shsmnkkevi qhvrs.....................kpni .pip....sn kvlqtmLtnr atnwkaflkd ideng.Lddd dIiiglkgKE rEIkIaGRFF sIMswrLRey fVitEyLikt
465 SYN  nkkifqrssl ynhkdWdqvv ilqafqipks vnLatmikDK aismtrseli esvnt......................knsv fdst....kr RgilkWlneq sdkiynflmr iddkg.Lded dciigLypKE rEmktkaRFF sIMsykLRmy vtstEeLlgk
274 BDV>>rwql...........Fekvv ilriadldmd pDFndivsDK aiissrrdw feYnaaafwk kygerlerpp arsg....ps RIvnalidgr ldnipallep fyrga.vefe drltvLypKE kEIkvkGRFF skqtlaiRiy qVvaEaalkn<<
429 MeV  egit.heqtv dnwksFagvk fgcfmplsld sDLtmyIkDK alaalgrewd svYpkefIr.......ydp....pkgtgsr RIvdvFlnds sfdpydvimy vvsgayLhdp efnlsYslqE kEIketGRLF akMtykMRac qVIaEnlisn
437 SeV  tais.yecav dnytsFigfk frkfiepqld eDLtiymkDK alsprkeawd svYpdsnly........yka...peseetr RIievFinde nfnpeeiny vesgdWLkde efnisYsIKE kEIkqeGRLF akMtykMRav qVIaEtLIak
433 NDV  aeis.hdimi reykslsale fepcieydpv tnLsmfIkDK aiahpndnwl asFrrnlIs.......edqk khvkeatstn RIlieFLesn dfdpykemey lttleyLrdd dvavsYsIKE kEvKvn6RiF akltkkLRnc qIMaEgilad
450 MaV  sfps.qaeIy qhlweWyfve heplfsttki sDLsifikDr ltavnqecwd svFdrsvIg.......ynpp vrfq....sk RvpeqFLgqa dfsinqilef aekIeyLaps ynnfsFsIKE kEIni.6RtF gkLpyrvRnv qtLaEaLlad
501 RSV  typslielte rdlivLsglr fyrefrlpkk vDLeminDK aispphkn1iw tsFpnymps hiqnyiehek lkfsesdksr RvIeyYLrdn kfnecdlync vvnqsyLnnp nhvvsltgkE rEIsy.6RMF ampgmFRqv qlIaEKMiae
con       ----------------------W-------------DL------DK-----------------------------------------------------------------1----------L--KE--E-K-6RFF---m---1R---Y--E-1--

151                                                                                                                                                                *                              x      **     x                  300
RaV  yIIpLFdalt M...tdnLnk vfkkL.........................idrvt gggLLdysrv tyafhlDVeK HhnhqRIEst edvfsvldqv FGIkrvFsRt HeFfqkawiY ysdrsdligl
VSV  yyypLFkglt M...addLts vikkM.........................mdsss gggLLdyssv clanhiDVeK WnnhqRKEsn gpifrvmgqf LGypsLieRt HeFfeksliY yngrpdimti
SYN  yVIkYfpmit M...sdnLls mvirL.........................fdmtt ligdkgva.v tysmniDFsK HnqnmRertn agifdhldri LGfrsLisRt HsifKacyIY lcsgeyypvi
BDV>>eVmpYIkths Hmnsstalth llnrL.........shtit kgd.......sfvinlDVss WcngfvRpEIq apicrqldqm FncgyFF.Rt gctLpcftF iiqdrfnppy<<
MeV  gIgkYFkdng Makdeqdltk alhtlavsgv pkdlkeshrg gpvIktysrs pvhtstrnvr aakgfigfpq virqdqdtdh penmeayetv safittDLkK YclnwRyEti slfaqrlnei YGlpsFFqWI HkrLetsvlY vsdphcppdl
SeV  gIgeLfseng Hvkgeidllk rlttlsvsgv p......rt dsvynnskss ekrnegmqnk nsggywdekk rsrhefkatd sst.dgyetl scflttDLkK YclnwRFEst alfggrcnei FGfktFFnWm HpvLerctiY vgdqycpvad
NDV  qIapFFggng viqdsisLtk s..tlamsql sfnsnkkrit dckervssnr nhdpksknrr ........rv atfittBLqK YclnwRyqti klfahainql mGlphFFeWi vGvknLFdWm HIrLmdttmF vgdpfnppsd
MaV  gIakafpsnm Hvtereqke allhqa...........swhhnsasi genaivr.............gasfvtDLeK YnlafRyEft rhfidycnrc YGvknLFdWm HfIipLcymh vsdfyspphc
RSV  nllqFFpesl trygdleLqk ilelkagi..snksnry ndhynnyisk.........csiitDLsK FnqafRyEts clcsdvldel HLtiphvtii ctyrhappyi
Con  -l-[-----M-----------l----l-------------------------------------------------------------DL-k---------R-E-------Fg-----F-W-h---L------Y-------
```

FIG. 4(2)

```
               B
        *    * *                                  C                                                                                                                D
     301                                                                                                                                                                             450
RaV  redqiyclda sngptcwngq dGGiEGlrQK gWslvsllmi dresqirnntr tkiLaqGDNQ vlcptymlsp glsqegllye lerisrnals iyraveegas klGliikKeE TmcSydFLiY gKtpLFrGni lvpeskrwaR vscvsndqiv
VSV  rngtlc..ns tkhrvcwngq KGGiEGlrQK gWsivnllvi qreakirnta vkvLaqGDNQ vlctqyktk trselelrav lhqmagnnnk imeeikrgte klGliinddE TmqSadyLnV gKipifrGvi rgletkrwsR vtcvtndqip
SYN  snmql....t aqspwsrtgd esGkEtlrQK gWTittvcdi lslafkynar iqligGGDNQ vltvtmlpse smqsggrdsq llkvrennts fnnalakkmv krGlpLKlEF TwiShnLLmY nKimYYsqvp IrqrlKvisR Ifsnsnvgvt
BDV>>s...lsqepv edgytcavgt KtmgEmrQK lwtiltsewe iialreinvt fnilggGDNQ tliihksasq mnqllaera. ..........  .lgaLykthar laGhnlKveE cwvSdclYeY gKKlFFrGvp vpgclKqlsR vtdstgelfp<<
MeV  dahi.plykv pndqifikyp mGGiEGycQK lWTistipyl ylaayesgvr iaslvqGDNQ tlavtkrvps twpynlkre aarvtrd... yfviltqrlh diGhhlKanE TivSshHFvY sKgiYYdgII vsqslKsiaR cvfwsetivd
SeV  rmhi.plykv pndqifikyp mGGiEGycQK lWTistipyl ylaayesgvr iaslvqGDNQ tlavtkrvps twpynlkre aarvtrd... yghsLthbmg fbHhrlKlnR YIiDdkMFvY sKriYYdski lpqclKaltk cvfwsetivd
NDV  ptdc.disrv pnddiyivsa rGGiEGlcQK lWTciscaqi tlvelkttlk lkssvmGDNQ cittislfpi dapndyqene aelnaar... yghsLthbmg fbHhrlKlnR YIiDdkMFvY sKriYYdski lpqclKaltk cvfwsetivd
MaV  vted.nrnnp pdcanayhyh lGGiEGlqQK lWTciscaqi tlvelkttlk lkssvmGDNQ cittislfpi dapndyqene aelnaar... vaveLaittg ysGifKpeE IfvhsgFlyF gKKqYLnGvq lpqsLKtmaR cgplsdsifd
RSV  gdhivdlnnv deqsglyryh mGGiEGwcQK lWTieaisll dlislkgkfs italinGDNQ sldiskpirl meqqthaqad .yllaln... slKlLykeya giGhkLKgtE TyiSrdMqfm sKtiqhmGvy ypasiKvlR vgpwintild
Con  ---------- ---------- gg-EG-QK -NT------ ---------- -L-GDNQ -L- ---------- ---------- ---------- ---------- -G-- -LK-E t-S--F-Y -K-V--G--- -----k--R

*                                                                                                                              x           x590
     451
RaV  nlanimstVs tnaltvaqhs .....qslik pmrdfllmsv qavf...... ........ ..........  ........ il saegesflla Msrnityldps lGGisgms.l grfhiRqfsD PvseqLsfwr                926
VSV  tcanlmssVs tnaltvahfa .....enpin amiqynyfgt farl...... ........ ..........  ........ ..lylidps iGGvcqma.l srfLiRafpD PvtesLsfwk                                912
SYN  slggittslg tgfqsistkd ytptlawlis rvftdiyist qridkqylms rqnirlqrne lggetsvpii nkirnhaala tdhtldldsl licvlyyhki lGGpgigp.p taywmkgfpD PlsegLtfny                 979
BDV>>nlysklaclt ssclsaamad tspwvalatg vclyliel.. .......... ......Yvel ppaimQd... ........ ..........  .....esl Lttlclvgps iGGlptpatl psvfFRgmsD Plpfqlallq <<      725
MeV  etraacsnla ttmaksierg ..ydrylay sl......... ..........  nFlkv i...qQilis lgftinstmt rdvv..ipll tnndllirma L..... lpap iGGmnyln.m srlfvRnigD Pvtssiad..         961
SeV  enrsacsnls tsiakaieng ..yspilgy ci......... ..........  alykt c...qQlvcis lgmtinptis ptvr..dqyf kgknwlrcav L..... ipan vgGfnyms.t srcFvRnigD Pavaalad..        961
NDV  ntvmscanla stvarlceng ...lpkdfcy yl......... ..........  nVims c...vQtyfd sefsynnnsh pdln..qswi edisfvnsyv L..... tpaq lGGlsnlq.y srlYtRnigD PgttaFae..        939
MaV  dlgslaslg tsfergtset rhifpsrwia sf......... ..........  hsmla lnllnQnhlg fplgfnidis c.fk..kplt fsekli..al i..... tpqv lGGlsfln.p ekliyRnisD PltsgLfq..        934
RSV  dfkvsleslg sltqeleyrg esllcslifr nv........ ..........  wLynq ialqlkhhal cnnklyldil kvlkhiktff nldnidtalt L..ymnlpml fGGgdpnl.l yrsFyRrtpD flteaivhsv          1013
Con  ---------- ---------- ---------- ---------- ---------- -[------- ]---------- ---------- ---------- ---------- -[------ ---------- ------- -F-R---D P----L---
```

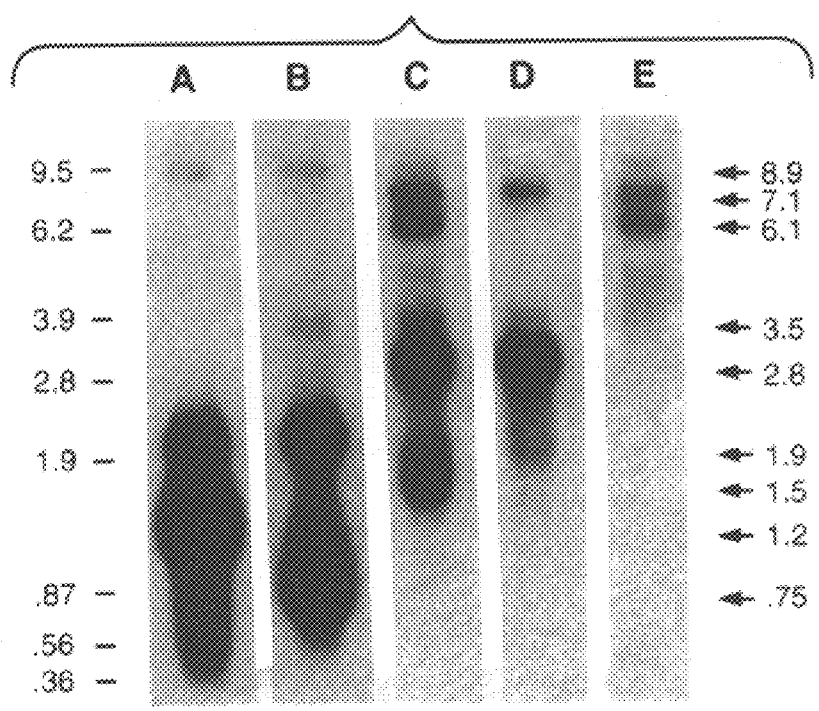

FIG. 6a

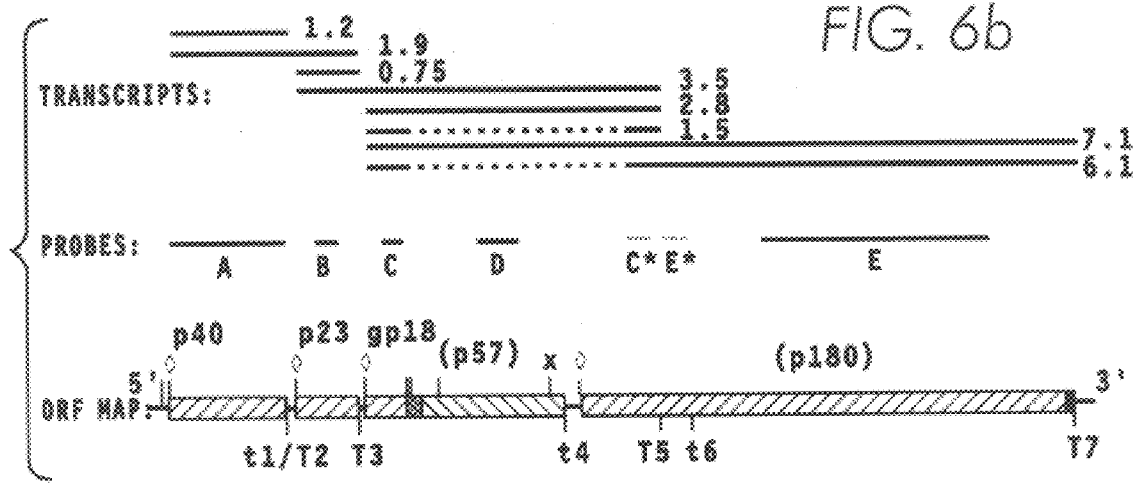

FIG. 6b

```
        (t1)
p40  5'-GUcU AAa cua aaa aaC AAU GAA caa acc aau aaaaaa CCA AAU GCG   (T2)
P23  5'-CGAC AAC GGA UGA AUG GGA CAU cau acc aua aaaaaa UCG AAU CAC   (T3)
gp18 5'-UUAG CUG CAA UAC UGA CUC CAC UCC UGG ACU          GAU UGA CCU
P57  5'-GGCA GGA AUA AAC CGU ACC GAC cag Ucu cuu aaaaa   CCC UCU CCU  (t4)
     5'-CUGA AUU AUG CCC GCA ACU AGA cag cuu acu aaaaaaACUG CUC CAA   (T5)
     5'-UACA CCU GCU CCC AGG CUG UGA caa auc cau aaaaaa UGC GAG AGA   (t6)
P180 5'-UUAA GAU CAA GCC ACC UAC UAC ccu auu cuu aaaaaa CCA UAU GUC   (T7)
```

```
                    ORF p40         ORF p23    ORF gp18
5' ----------- [              ][          ][          ] --------- 3'
```

```
RB     ATGAATTCAAAAACATTCCTATGTGGAGCTCAAGGACAAGGTATCGTCCCCGGATGGCCCACACTGATGCTTGAGATAGACTTTGTAGGAGGACTTCACGGAACCAGTTCCTTAACATC
SV     ................................................................................................................+ 120
        1   M  N  S  K  H  S  Y  V  E  L  K  D  K  V  I  V  P  G  W  P  T  L  M  L  E  I  D  F  V  G  G  T  S  R  N  Q  F  L  N  I
RB
SV          M  N  S  K  H  S  Y  V  E  L                                  P#2= L  E  I  D  F  V  G  G
       P#1= N  S  K  H  S  Y  V  E  L

RB     CCATTTCTTTCAGTGAAAGAGCCTCTGCAGCTTCCACGGGAGAAGAAGTTGACCGACTACTTCACCATTGACGTAGAGCCAGGTCATTCCCTGGTCAACATATACTTCCAGATTGAC
SV     ............T...............................................................A.....................................+ 240
121     P  F  L  S  V  K  E  P  L  Q  L  P  R  E  K  K  L  T  D  Y  F  T  I  D  V  E  P  A  G  H  S  L  V  N  I  Y  F  Q  I  D
RB
SV                                                                                                         N  I  Y  F  Q  I  D

RB     GACTTCTTGCTCCTAACACTCAACTCAACTGTCCGTATACAAGGAACCGATTAGGAAATACATGTTCCTACGCCCTCAACAAGGAACAGAGCAAGCACGCCAATCAATGCAGCTTTCAATGTC
SV     ..............................A..T..G............................A..................................T..........C........+ 360
241     D  F  L  L  L  T  L  N  S  L  S  V  Y  K  D  P  I  R  K  Y  M  F  L  R  L  N  K  E  Q  S  K  H  A  I  N  A  A  F  N  V
RB                                   D                                                                                 *
SV      D  F  L  L  T  L  N  S  L  S  V  Y  K  D  P  I  R  K  Y  M  F  L  R  L  N  K  E  Q  S  K  H  A  I  N  A  A  F  N  V

RB     TTCTCTTATCGGCTTCGGAACATTGGTGTTGGTCCTCTCGGGCCCAGACATTCGATCTTCAGGGCCTTAG
SV     ....T................................................G.................+ 429
361     F  S  Y  R  L  R  N  I  G  V  G  P  L  G  P  D  I  R  S  S  G  P  *
RB                                                                           *
SV      F  S  Y  R  L  R  N  I  G  V  G  P  L  G
```

POLYMERASE NUCLEOTIDE SEQUENCE    FIG. 18(1)

```
              I-2
       ATGTCATTTCATGCGAG\  /CCTCCTTCGCGAGGAGGAGACGCCTCGGCCGGTGGCAGGA
2393   ------+---------+ V  ------+---------+---------+---------+---  3743
       TACAGTAAAGTACGCTC     GGAGGAAGCGCTCCTCCTCTGCGGAGCCGGCCACCGTCCT

ATAAACCGTACCGACCAGTCTCTTAAAAACCCTCTCCTCGGAACAGAGGTCTCTTTCTGC
3744   ------+---------+---------+---------+---------+---------+---  3803
       TATTTGGCATGGCTGGTCAGAGAATTTTTGGGAGAGGAGCCTTGTCTCCAGAGAAAGACG

CTTAAGTCGAGCTCACTCCCCCATCATGTACGAGCACTAGGCCAGATTAAAGCAAGGAAC
3804   ------+---------+---------+---------+---------+---------+---  3863
       GAATTCAGCTCGAGTGAGGGGGTAGTACATGCTCGTGATCCGGTCTAATTTCGTTCCTTG

CTGGCATCCTGTGACTATTACTTGCTATTCCGCCAAGTTGTATTGCCCCCTGAAGTATAT
3864   ------+---------+---------+---------+---------+---------+---  3923
       GACCGTAGGACACTGATAATGAACGATAAGGCGGTTCAACATAACGGGGGACTTCATATA

CCCATTGGTGTTCTAATAAGAGCTGCGGAGGCTATACTAACAGTTATAGTATCAGCTTGG
3924   ------+---------+---------+---------+---------+---------+---  3983
       GGGTAACCACAAGATTATTCTCGACGCCTCCGATATGATTGTCAATATCATAGTCGAACC

AAGCTGGATCATATGACGAAGACCCTATACTCCTCTGTGAGATATGCACTCACCAATCCC
3984   ------+---------+---------+---------+---------+---------+---  4043
       TTCGACCTAGTATACTGCTTCTGGGATATGAGGAGACACTCTATACGTGAGTGGTTAGGG

CGGGTCCGAGCCCAACTTGAGCTTCACATTGCCTACCAGCGCATAGTGGGTCAGGTCTCG
4044   ------+---------+---------+---------+---------+---------+---  4103
       GCCCAGGCTCGGGTTGAACTCGAAGTGTAACGGATGGTCGCGTATCACCCAGTCCAGAGC

TACAGCCGGGAGGCAGACATAGGGCCAAAAAGGCTTGGGAATATGTCATTGCAATTCATC
4104   ------+---------+---------+---------+---------+---------+---  4163
       ATGTCGGCCCTCCGTCTGTATCCCGGTTTTTCCGAACCCTTATACAGTAACGTTAAGTAG

CAATCTCTCGTTATTGCCACCATAGACACGACAAGCTGCCTAATGACCTACAACCACTTT
4164   ------+---------+---------+---------+---------+---------+---  4223
       GTTAGAGAGCAATAACGGTGGTATCTGTGCTGTTCGACGGATTACTGGATGTTGGTGAAA

CTTGCTGCAGCAGACACAGCCAAGAGCAGATGCCATCTCCTAATCGCCTCAGTGGTCCAG
4224   ------+---------+---------+---------+---------+---------+---  4283
       GAACGACGTCGTCTGTGTCGGTTCTCGTCTACGGTAGAGGATTAGCGGAGTCACCAGGTC

GGGGCCCTTTGGGAACAAGGGTCATTTCTTGATCATATAATCAACATGATCGACATAATT
4284   ------+---------+---------+---------+---------+---------+---  4343
       CCCCGGGAAACCCTTGTTCCCAGTAAAGAACTAGTATATTAGTTGTACTAGCTGTATTAA

GACTCAATCAACCTCCCCCATGATGATTACTTCACAATTATTAAGTCTATCTTTCCCTAC
4344   ------+---------+---------+---------+---------+---------+---  4403
       CTGAGTTAGTTGGAGGGGGTACTACTAATGAAGTGTTAATAATTCAGATAGAAAGGGATG

TCCCAAGGGCTTGTTATGGGGAGGCATAATGTATCAGTCTCCTCTGATTTCGCGTCCGTA
4404   ------+---------+---------+---------+---------+---------+---  4463
       AGGGTTCCCGAACAATACCCCTCCGTATTACATAGTCAGAGGAGACTAAAGCGCAGGCAT

TTTGCCATTCCTGAATTATGCCCGCAACTAGACAGCTTACTAAAAAAACTGCTCCAACTT
4464   ------+---------+---------+---------+---------+---------+---  4523
       AAACGGTAAGGACTTAATACGGGCGTTGATCTGTCGAATGATTTTTTTGACGAGGTTGAA

GACCCCGTTCTCCTCCTCATGGTCTCTTCGGTGCAGAAGTCATGGTACTTCCCTGAGATC
4524   ------+---------+---------+---------+---------+---------+---  4583
       CTGGGGCAAGAGGAGGAGTACCAGAGAAGCCACGTCTTCAGTACCATGAAGGGACTCTAG
```

FIG. 18(2)

```
         CGAATGGTCGACGGGTCACGGGAGCAGCTCCACAAGATGCGTGTCGAGCTGGAAACGCCC
4584     ------+---------+---------+---------+---------+---------+---  4643
         GCTTACCAGCTGCCCAGTGCCCTCGTCGAGGTGTTCTACGCACAGCTCGACCTTTGCGGG

CAAGCCCTGCTGTCGTACGGCCATACCCTCCTGTCAATATTTCGGGCAGAGTTTATCAAA
4644     ------+---------+---------+---------+---------+---------+---  4703
         GTTCGGGACGACAGCATGCCGGTATGGGAGGACAGTTATAAAGCCCGTCTCAAATAGTTT

GGCTATGTCTCAAAGAATGCGAAGTGGCCGCCCGTACACCTGCTCCCAGGCTGTGACAAA
4704     ------+---------+---------+---------+---------+---------+---  4763
         CCGATACAGAGTTTCTTACGCTTCACCGGCGGGCATGTGGACGAGGGTCCGACACTGTTT

TCCATAAAAAATGCGAGAGAGCTGGGCCGCTGGAGCCCGGCATTTGACCGACGATGGCAG
4764     ------+---------+---------+---------+---------+---------+---  4823
         AGGTATTTTTTACGCTCTCTCGACCCGGCGACCTCGGGCCGTAAACTGGCTGCTACCGTC

CTCTTCGAGAAGGTTGTCATTCTAAGAATTGCTGACCTAGATATGGATCCCGACTTCAAC
4824     ------+---------+---------+---------+---------+---------+---  4883
         GAGAAGCTCTTCCAACAGTAAGATTCTTAACGACTGGATCTATACCTAGGGCTGAAGTTG

GATATTGTTAGCGATAAGGCGATAATCAGCTCAAGAAGGGACTGGGTATTCGAGTACAAT
4884     ------+---------+---------+---------+---------+---------+---  4943
         CTATAACAATCGCTATTCCGCTATTAGTCGAGTTCTTCCCTGACCCATAAGCTCATGTTA

GCAGCGGCCTTTTGGAAGAAATACGGTGAACGGTTGGAGAGGCCTCCTGCCAGGTCGGGA
4944     ------+---------+---------+---------+---------+---------+---  5003
         CGTCGCCGGAAAACCTTCTTTATGCCACTTGCCAACCTCTCCGGAGGACGGTCCAGCCCT

CCGTCACGACTTGTGAATGCTCTAATCGATGGACGCTTAGACAATATCCCAGCCCTGCTA
5004     ------+---------+---------+---------+---------+---------+---  5063
         GGCAGTGCTGAACACTTACGAGATTAGCTACCTGCGAATCTGTTATAGGGTCGGGACGAT

GAGCCATTTTACAGGGGAGCGGTTGAGTTCGAGGATCGGTTGACTGTGCTCGTGCCTAAG
5064     ------+---------+---------+---------+---------+---------+---  5123
         CTCGGTAAAATGTCCCCTCGCCAACTCAAGCTCCTAGCCAACTGACACGAGCACGGATTC

GAGAAAGAGTTAAAGGTAAAGGGAAGGTTCTTCTCGAAGCAAACATTGGCAATCAGGATA
5124     ------+---------+---------+---------+---------+---------+---  5183
         CTCTTTCTCAATTTCCATTTCCCTTCCAAGAAGAGCTTCGTTTGTAACCGTTAGTCCTAT

TATCAGGTTGTTGCTGAAGCTGCACTTAAGAATGAGGTTATGCCATACCTAAAGACACAC
5184     ------+---------+---------+---------+---------+---------+---  5243
         ATAGTCCAACAACGACTTCGACGTGAATTCTTACTCCAATACGGTATGGATTTCTGTGTG

TCAATGACCATGAGCTCAACGGCTCTAACTCACCTTCTTAACCGGCTATCACATACTATC
5244     ------+---------+---------+---------+---------+---------+---  5303
         AGTTACTGGTACTCGAGTTGCCGAGATTGAGTGGAAGAATTGGCCGATAGTGTATGATAG

ACTAAGGGTGACTCCTTTGTTATTAACCTTGACTATAGTTCCTGGTGCAACGGTTTCCGA
5304     ------+---------+---------+---------+---------+---------+---  5363
         TGATTCCCACTGAGGAAACAATAATTGGAACTGATATCAAGGACCACGTTGCCAAAGGCT

CCAGAACTGCAGGCCCCAATCTGTCGTCAGTTGGATCAGATGTTCAATTGCGGGTACTTC
5364     ------+---------+---------+---------+---------+---------+---  5423
         GGTCTTGACGTCCGGGGTTAGACAGCAGTCAACCTAGTCTACAAGTTAACGCCCATGAAG

TTCAGGACTGGGTGCACACTGCCATGCTTTACCACGTTTATTATTCAAGACAGGTTCAAC
5424     ------+---------+---------+---------+---------+---------+---  5483
         AAGTCCTGACCCACGTGTGACGGTACGAAATGGTGCAAATAATAAGTTCTGTCCAAGTTG

CCGCCCTATTCCCTCAGTGGTGAGCCCGTTGAAGACGGAGTTACATGCGCGGTTGGGACT
5484     ------+---------+---------+---------+---------+---------+---  5543
         GGCGGGATAAGGGAGTCACCACTCGGGCAACTTCTGCCTCAATGTACGCGCCAACCCTGA
```

FIG. 18(3)

```
     AAAACAATGGGGGAGGGCATGAGGCAGAAACTATGGACAATCCTTACGAGCTGCTGGGAG
5544 ------+---------+---------+---------+---------+---------+--- 5603
     TTTTGTTACCCCCTCCCGTACTCCGTCTTTGATACCTGTTAGGAATGCTCGACGACCCTC

ATAATTGCTCTTCGGGAAATTAACGTGACGTTTAACATACTAGGCCAAGGTGATAATCAG
5604 ------+---------+---------+---------+---------+---------+--- 5663
     TATTAACGAGAAGCCCTTTAATTGCACTGCAAATTGTATGATCCGGTTCCACTATTAGTC

ACAATCATCATACATAAATCTGCAAGCCAAAATAACCAGCTATTAGCGGAGCGAGCACTA
5664 ------+---------+---------+---------+---------+---------+--- 5723
     TGTTAGTAGTATGTATTTAGACGTTCGGTTTTATTGGTCGATAATCGCCTCGCTCGTGAT

GGGGCCCTGTACAAGCATGCTAGATTAGCTGGCCATAACCTCAAGGTAGAGGAATGCTGG
5724 ------+---------+---------+---------+---------+---------+--- 5783
     CCCCGGGACATGTTCGTACGATCTAATCGACCGGTATTGGAGTTCCATCTCCTTACGACC

GTGTCAGATTGTCTGTATGAGTATGGAAAGAAGCTTTTCTTCCGTGGTGTACCTGTCCCG
5784 ------+---------+---------+---------+---------+---------+--- 5843
     CACAGTCTAACAGACATACTCATACCTTTCTTCGAAAAGAAGGCACCACATGGACAGGGC

GGCTGTTTGAAGCAGCTCTCACGGGTGACGGATTCTACTGGAGAGCTATTCCCAAACCTA
5844 ------+---------+---------+---------+---------+---------+--- 5903
     CCGACAAACTTCGTCGAGAGTGCCCACTGCCTAAGATGACCTCTCGATAAGGGTTTGGAT

TACTCAAAGTTAGCCTGCTTAACATCATCGTGTTTAAGCGCAGCGATGGCAGACACATCT
5904 ------+---------+---------+---------+---------+---------+--- 5963
     ATGAGTTTCAATCGGACGAATTGTAGTAGCACAAATTCGCGTCGCTACCGTCTGTGTAGA

CCATGGGTGGCACTCGCGACAGGTGTCTGTCTGTATCTTATCGAGTTATATGTTGAGCTG
5964 ------+---------+---------+---------+---------+---------+--- 6023
     GGTACCCACCGTGAGCGCTGTCCACAGACAGACATAGAATAGCTCAATATACAACTCGAC

CCTCCAGCAATCATGCAGGATGAGTCGCTATTGACGACCCTCTGCCTCGTAGGCCCATCC
6024 ------+---------+---------+---------+---------+---------+--- 6083
     GGAGGTCGTTAGTACGTCCTACTCAGCGATAACTGCTGGGAGACGGAGCATCCGGGTAGG

ATTGGTGGGCTTCCGACCCCTGCAACCCTACCCAGTGTCTTTTTCAGAGGAATGTCCGAC
6084 ------+---------+---------+---------+---------+---------+--- 6143
     TAACCACCCGAAGGCTGGGGACGTTGGGATGGGTCACAGAAAAAGTCTCCTTACAGGCTG

CCACTGCCCTTTCAGCTAGCACTCTTGCAGACCCTCATTAAGACGACAGGGGTGACCTGT
6144 ------+---------+---------+---------+---------+---------+--- 6203
     GGTGACGGGAAAGTCGATCGTGAGAACGTCTGGGAGTAATTCTGCTGTCCCCACTGGACA

AGCTTGGTGAATCGTGTGGTCAAGTTACGGATAGCACCCTATCCAGACTGGCTCTCTCTA
6204 ------+---------+---------+---------+---------+---------+--- 6263
     TCGAACCACTTAGCACACCAGTTCAATGCCTATCGTGGGATAGGTCTGACCGAGAGAGAT

GTGACTGACCCGACCTCACTCAACATTGCCCAAGTGTACCGGCCAGAACGTCAGATCAGG
6264 ------+---------+---------+---------+---------+---------+--- 6323
     CACTGACTGGGCTGGAGTGAGTTGTAACGGGTTCACATGGCCGGTCTTGCAGTCTAGTCC

AGGTGGATTGAGGAAGCGATAGCGACAAGCTCACACTCGTCACGCATAGCAACTTTCTTC
6324 ------+---------+---------+---------+---------+---------+--- 6383
     TCCACCTAACTCCTTCGCTATCGCTGTTCGAGTGTGAGCAGTGCGTATCGTTGAAAGAAG

CAGCAGCCCCTCACGGAGATGGCTCAGTTGCTTGCGAGGGACCTTTCAACAATGATGCCT
6384 ------+---------+---------+---------+---------+---------+--- 6443
     GTCGTCGGGGAGTGCCTCTACCGAGTCAACGAACGCTCCCTGGAAAGTTGTTACTACGGA

CTTCGACCCCGGGATATGTCGGCCTTATTCGCATTATCAAATGTCGCATACGGTTTAAGC
6444 ------+---------+---------+---------+---------+---------+--- 6503
     GAAGCTGGGGCCCTATACAGCCGGAATAAGCGTAATAGTTTACAGCGTATGCCAAATTCG
```

FIG. 18(4)

```
      ATTATAGATCTATTTCAAAAATCCTCTACCGTTGTTTCTGCAAGTCAAGCTGTCCATATC
6504  ------+---------+---------+---------+---------+---------+--- 6563
      TAATATCTAGATAAAGTTTTTAGGAGATGGCAACAAAGACGTTCAGTTCGACAGGTATAG

GAGGATGTTGCCCTAGAGAGTGTAAGGTATAAGGAATCTATCATCCAGGGTCTGTTAGAC
6564  ------+---------+---------+---------+---------+---------+--- 6623
      CTCCTACAACGGGATCTCTCACATTCCATATTCCTTAGATAGTAGGTCCCAGACAATCTG

ACCACTGAGGGGTATAACATGCAACCTTATTTGGAAGGTTGCACTTACCTTGCAGCCAAA
6624  ------+---------+---------+---------+---------+---------+--- 6683
      TGGTGACTCCCCATATTGTACGTTGGAATAAACCTTCCAACGTGAATGGAACGTCGGTTT

CAGTTACGTAGGTTGACATGGGGTCGAGACCTAGTTGGAGTCACAATGCCGTTTGTTGCC
6684  ------+---------+---------+---------+---------+---------+--- 6743
      GTCAATGCATCCAACTGTACCCCAGCTCTGGATCAACCTCAGTGTTACGGCAAACAACGG

GAGCAATTCCATCCTCACAGTTCTGTGGGTGCAAAGGCGGAACTCTACCTCGACGCTATT
6744  ------+---------+---------+---------+---------+---------+--- 6803
      CTCGTTAAGGTAGGAGTGTCAAGACACCCACGTTTCCGCCTTGAGATGGAGCTGCGATAA

ATATACTGCCCACAGGAGACATTGCGGTCACACCATCTGACTACCAGGGGGGACCAGCCG
6804  ------+---------+---------+---------+---------+---------+--- 6863
      TATATGACGGGTGTCCTCTGTAACGCCAGTGTGGTAGACTGATGGTCCCCCCTGGTCGGC

CTTTACCTCGGATCCAATACGGCTGTCAAGGTCCAGCGAGGTGAGATCACGGGCCTAACA
6864  ------+---------+---------+---------+---------+---------+--- 6923
      GAAATGGAGCCTAGGTTATGCCGACAGTTCCAGGTCGCTCCACTCTAGTGCCCGGATTGT

AAGTCAAGGGCTGCAAATCTAGTCAGGGACACTCTCGTTCTCCATCAGTGGTATAAAGTC
6924  ------+---------+---------+---------+---------+---------+--- 6983
      TTCAGTTCCCGACGTTTAGATCAGTCCCTGTGAGAGCAAGAGGTAGTCACCATATTTCAG

CGTAAAGTTACCGATCCACACTTGAACACCCTCATGGCACGCTTCTTACTTGAGAAGGGG
6984  ------+---------+---------+---------+---------+---------+--- 7043
      GCATTTCAATGGCTAGGTGTGAACTTGTGGGAGTACCGTGCGAAGAATGAACTCTTCCCC

TACACATCTGACGCTCGACCTAGCATCCAGGGTGGGACCCTCACGCATCGTCTCCCATCC
7044  ------+---------+---------+---------+---------+---------+--- 7103
      ATGTGTAGACTGCGAGCTGGATCGTAGGTCCCACCCTGGGAGTGCGTAGCAGAGGGTAGG

CGCGGAGACTCACGGCAGGGGCTTACTGGGTATGTAAATATACTAAGTACGTGGCTTCGA
7104  ------+---------+---------+---------+---------+---------+--- 7163
      GCGCCTCTGAGTGCCGTCCCCGAATGACCCATACATTTATATGATTCATGCACCGAAGCT

TTCTCAAGTGATTATCTTCACTCTTTCTCGAAATCATCAGACGACTATACAATCCACTTT
7164  ------+---------+---------+---------+---------+---------+--- 7223
      AAGAGTTCACTAATAGAAGTGAGAAAGAGCTTTAGTAGTCTGCTGATATGTTAGGTGAAA

CAGCATGTATTCACATACGGTTGCCTCTATGCTGATTCGGTGATTAGATCGGGCGGTGTT
7224  ------+---------+---------+---------+---------+---------+--- 7283
      GTCGTACATAAGTGTATGCCAACGGAGATACGACTAAGCCACTAATCTAGCCCGCCACAA

ATTTCCACTCCTTACCTTTTGAGTGCAAGTTGTAAAACATGCTTTGAGAAGATAGACTCA
7284  ------+---------+---------+---------+---------+---------+--- 7343
      TAAAGGTGAGGAATGGAAAACTCACGTTCAACATTTTGTACGAAACTCTTCTATCTGAGT

GAGGAGTTCGTCCTGGCATGTGAACCCCAATACAGGGGTGCTGAGTGGCTGATATCAAAG
7344  ------+---------+---------+---------+---------+---------+--- 7403
      CTCCTCAAGCAGGACCGTACACTTGGGGTTATGTCCCCACGACTCACCGACTATAGTTTC

CCAGTCACTGTCCCTGAGCAGATAACTGATGCTGAAGTCGAGTTTGACCCCTGTGTGAGT
7404  ------+---------+---------+---------+---------+---------+--- 7463
      GGTCAGTGACAGGGACTCGTCTATTGACTACGACTTCAGCTCAAACTGGGGACACACTCA
```

FIG. 18(5)

```
      GCGGGTTATTGTCTCGGGATTCTCATTGGCAAGTCATTCTTAGTTGACATAAGGGCAAGT
7464  ------+---------+---------+---------+---------+---------+---  7523
      CGCCCAATAACAGAGCCCTAAGAGTAACCGTTCAGTAAGAATCAACTGTATTCCCGTTCA

GGGCATGATATCATGGAGCAGCGGACATGGGCTAACCTGGAGAGGTTTTCTGTATCGGAC
7524  ------+---------+---------+---------+---------+---------+---  7583
      CCCGTACTATAGTACCTCGTCGCCTGTACCCGATTGGACCTCTCCAAAAGACATAGCCTG

ATGCAGAAACTTCCGTGGAGTATTGTAATTCGGTCTCTCTGGAGATTCCTTATTGGCGCA
7584  ------+---------+---------+---------+---------+---------+---  7643
      TACGTCTTTGAAGGCACCTCATAACATTAAGCCAGAGAGACCTCTAAGGAATAACCGCGT

CGGCTCCTTCAGTTTGAGAAGGCTGGCCTCATTAGAATGCTGTATGCTGCGACAGGTCCA
7644  ------+---------+---------+---------+---------+---------+---  7703
      GCCGAGGAAGTCAAACTCTTCCGACCGGAGTAATCTTACGACATACGACGCTGTCCAGGT

ACCCCTAGCTTCCTAATGAAAGTTTTTCAAGACTCAGCCCTCCTCATGGACTGCGCACCC
7704  ------+---------+---------+---------+---------+---------+---  7763
      TGGGGATCGAAGGATTACTTTCAAAAAGTTCTGAGTCGGGAGGAGTACCTGACGCGTGGG

CTCGATCGGCTGTCCCCTAGGATCAACTTTCATAGTCGGGGAGACCTCGTTGCTAAGCTT
7764  ------+---------+---------+---------+---------+---------+---  7823
      GAGCTAGCCGACAGGGGATCCTAGTTGAAAGTATCAGCCCCTCTGGAGCAACGATTCGAA

GTTTTATTGCCCTTCATCAACCCGGGTATAGTGGAGATTGAAGTGTCTGGAATTAATAGC
7824  ------+---------+---------+---------+---------+---------+---  7883
      CAAAATAACGGGAAGTAGTTGGGCCCATATCACCTCTAACTTCACAGACCTTAATTATCG

AAGTACCATGCAGTATCGGAGGCCAATATGGATCTGTACATCGCTGCTGCCAAGTCTGTG
7884  ------+---------+---------+---------+---------+---------+---  7943
      TTCATGGTACGTCATAGCCTCCGGTTATACCTAGACATGTAGCGACGACGGTTCAGACAC

GGCGTGAAGCCCACACAGTTTGTTGAGGAAACAAACGACTTTACGGCCCGCGGCCACCAC
7944  ------+---------+---------+---------+---------+---------+---  8003
      CCGCACTTCGGGTGTGTCAAACAACTCCTTTGTTTGCTGAAATGCCGGGCGCCGGTGGTG

CATGGTTGTTATTCCCTTTCTTGGTCTAAGTCACGCAATCAATCACAGGTCCTAAAGATG
8004  ------+---------+---------+---------+---------+---------+---  8063
      GTACCAACAATAAGGGAAAGAACCAGATTCAGTGCGTTAGTTAGTGTCCAGGATTTCTAC

GTAGTACGGAAGCTGAAGCTCTGTGTCCTGTATATATACCCCACAGTCGATCCCGCCGTT
8064  ------+---------+---------+---------+---------+---------+---  8123
      CATCATGCCTTCGACTTCGAGACACAGGACATATATATGGGGTGTCAGCTAGGGCGGCAA

GCTCTCGACCTGTGCCATCTACCAGCATTAACTATAATCCTAGTGCTCGGCGGTGACCCA
8124  ------+---------+---------+---------+---------+---------+---  8183
      CGAGAGCTGGACACGGTAGATGGTCGTAATTGATATTAGGATCACGAGCCGCCACTGGGT

GCGTACTATGAGCGATTACTTGAGATGGACCTGTGCGGGGCTGTGTCAAGTCGAGTCGAT
8184  ------+---------+---------+---------+---------+---------+---  8243
      CGCATGATACTCGCTAATGAACTCTACCTGGACACGCCCCGACACAGTTCAGCTCAGCTA

ATCCCCATTCTCTGGCTGGCAGAACGCACAGGGGGTTCGCAGTGGGCCCAGACGCTGGT
8244  ------+---------+---------+---------+---------+---------+---  8303
      TAGGGGGTAAGAGACCGACCGTCTTGCGTGTCCCCCAAGCGTCACCCGGGTCTGCGACCA

CCAGGTGTAATTAGACTCGACAGGTTAGAGTCAGTTTGTTATGCTCACCCCTGTTTAGAG
8304  ------+---------+---------+---------+---------+---------+---  8363
      GGTCCACATTAATCTGAGCTGTCCAATCTCAGTCAAACAATACGAGTGGGGACAAATCTC

GAACTAGAGTTTAATGCATATCTAGACTCTGAGTTGGTTGACATTAGTGATATGTGCTGC
8364  ------+---------+---------+---------+---------+---------+---  8423
      CTTGATCTCAAATTACGTATAGATCTGAGACTCAACCAACTGTAATCACTATACACGACG
```

FIG. 18(6)

```
     CTCCCCTTAGCGACACCCTGTAAGGCCCTTTTCAGGCCAATATATCGGAGCTTACAGTCG
8424 ------+---------+---------+---------+---------+---------+--- 8483
     GAGGGGAATCGCTGTGGGACATTCCGGGAAAAGTCCGGTTATATAGCCTCGAATGTCAGC

TTCAGGTTAGCCTTAATGGACAACTATAGTTTTGTCATGGACCTCATTATGATCCGAGGA
8484 ------+---------+---------+---------+---------+---------+--- 8543
     AAGTCCAATCGGAATTACCTGTTGATATCAAAACAGTACCTGGAGTAATACTAGGCTCCT

CTGGACATTAGGCCTCACCTTGAGGAATTTGACGAGCTGCTTGTGGTAGGACAGCACATC
8544 ------+---------+---------+---------+---------+---------+--- 8603
     GACCTGTAATCCGGAGTGGAACTCCTTAAACTGCTCGACGAACACCATCCTGTCGTGTAG

CTCGGCCAGCCCGTCCTAGTAGAGGTTGTTTACTACGTTGGAGTTGTTAGGAAGCGCCCT
8604 ------+---------+---------+---------+---------+---------+--- 8663
     GAGCCGGTCGGGCAGGATCATCTCCAACAAATGATGCAACCTCAACAATCCTTCGCGGGA

GTGTTAGCGAGGCATCCGTGGTCAGCAGATCTTAAGCGAATTACTGTGGGGGGGCGGCCT
8664 ------+---------+---------+---------+---------+---------+--- 8723
     CACAATCGCTCCGTAGGCACCAGTCGTCTAGAATTCGCTTAATGACACCCCCCGCCCGA

CCCTGCCCCTCTGCTGCCAGATTGCGTGATGAGGATTGTCAGGGGTCTCTGTTGGTTGGG
8724 ------+---------+---------+---------+---------+---------+--- 8783
     GGGACGGGGAGACGACGGTCTAACGCACTACTCCTAACAGTCCCCAGAGACAACCAACCC

CTTCCTGCTGGGTTGACGCAGTTATTGATAATTGATTA
8784 ------+---------+---------+---------+- 8821
     GAAGGACGACCCAACTGCGTCAATAACTATTAACTAAT
```

FIG. 19(1)

```
   1  GGTAGACCAG CTCCTGAAGA ACCTCAGGAA GAACCCCTCC ATGATCTCAG
  51  ACCCAGACCA GCGAACCGGA AGGGAGCAGC TATCGAATGA TGAGCTTATC
 101  AAGAAGCTAG TGACGGAGCT GGCCGAGAAT AGCATGATCG AGGCTGAGGA
 151  GGTGCGGGGC ACTCTTGGGG ACATCTCGGC TCGCATCGAG GCAGGGTTTG
 201  AGTCCCTGTC CGCCCTCCAA GTGGAAACCA TCCAGACAGC TCAGCGGTGC
 251  GACCACTCCG ATAGCATCAG AATCCTTGGC GAGAACATCA AGATACTGGA
 301  TCGCTCCATG AAGACAATGA TGGAGACAAT GAAGCTCATG ATGGAGAAGG
 351  TGGACCTCCT CTACGCATCA ACCGCCGTTG GGACCTCTGC ACCCATGTTG
 401  CCCTCCCATC CTGCACCTCC GCGCATTTAT CCCCAGCTCC CAAGTGCCCC
 451  GACAGCGGAT GAGTGGGACA TCATACCATA AAAAAATCGA ATCACCATGA
 501  ATTCAAAGCA TTCCTATGTG GAGCTCAAGG ACAAGGTAAT CGTCCCTGGA
 551  TGGCCCACAC TGATGCTTGA GATAGACTTT GTAGGAGGGA CTTCACGGAA
 601  CCAGTTCCTT AACATCCCAT TTCTTTCAGT GAAAGAGCCT CTGCAGCTTC
 651  CACGCGAGAA GAAGTTGACC GACTACTTCA CCATTGACGT AGAGCCAGCA
 701  GGTCATTCCC TGGTCAACAT ATACTTCCAG ATTGACGACT TCTTGCTCCT
 751  AACACTCAAC TCACTGTCCG TATACAAGGA CCCGATTAGG AAATACATGT
 801  TCCTACGCCT CAACAAGGAA CAGAGCAAGC ACGCAATTAA TGCAGCTTTC
 851  AATGTCTTCT CTTATCGGCT TCGGAACATT GGTGTTGGCC CTCTCGGCCC
 901  AGACATTCGA TCTTCAGGGC CTTAGTTGCA ATACTGACTC CACTCCTGGA
 951  TTAATCGATC TGGAGATAAG GCGACTTTGA CACACCCCAA CGGAAAATGT
1001  CATTTCATGC GAGGTTAGTT ATCTTAACCA CACGACTATT AGCCTCCCGG
1051  CAGTCCACAC GTCATGCCTC AAGTACCACT GCAAAACCTA TTGGGGATTC
1101  TTTGGTAGCT ACAGCGCTGA CCGAATCATC AATCGGTACA CTGGTACTGT
1151  TAAGGGTTGT TTAAACAACT CAGCGCCAGA GGATCCCTTC GAGTGCAACT
1201  GGTTCTACTG CTGCTCGGCG ATTACAACAG AGATCTGCCG ATGCTCTATT
1251  ACAAATGTCA CGGTGGCTGT ACAGACATTC CCACCGTTCA TGTACTGCAG
1301  TTTCGCGGAC TGTAGTACTG TGAGTCAGCA GGAGCTAGAG AGTGGAAAGG
1351  CAATGCTGAG CGATGGCAGT ACCTTAACTT ATACCCCGTA TATCTTACAA
1401  TCAGAAGTCG TGAACAAAAC CCTTAATGGG ACTATACTCT GCAACTCATC
1451  CTCCAAGATA GTTTCCTTCG ATGAATTTAG GCGTTCATAC TCCCTAGCGA
```

FIG. 19(2)

```
1501  ATGGTAGTTA CCAGAGCTCA TCAATCAATG TGACGTGTGT AAACTACACG
1551  TCGTCCTGCC GGTCCAAGTT GAGAAGGCGG CGTAGGGATA CTCAACAGAT
1601  TGAGTACCTA GTTCACAAGC TTAGGCCTAC ACTGAAAGAT GCGTGGGAGG
1651  ACTGTGAGAT CCTCCAGTCT CTGCTCCTAG GGGTGTTTGG TACTGGGATT
1701  GCAAGTGCTT CGCAATTCTT GAGGGGCTGG CTCAACCACC CTGATATCAT
1751  CGGGTATATA GTTAATGGAG TTGGGGTAGT CTGGCAATGC CATCGTGTTG
1801  ATGTCACGTT CATGGCGTGG AATGAGTCCA CATATTACCC TCCAGTAGAT
1851  TACAATGGAC GGAAGTACTT TCTGAATGAT GAGGGGAGGC TACAAACAAA
1901  CACCCCCGAG GCAAGGCCAG GGCTTAAGCG GTCATGTGG TTCGGCAGGT
1951  ACTTCCTAGG GACAGTAGGG TCTGGGGTGA AACCGAGGAG GATTCGGTAC
2001  AATAAGACCT CACATGATTA CCATCTAGAG GAGTTTGAGG CAAGTCTCAA
2051  CATGACCCCC CAGACCAGTA TCGCCTCGGG TCATGAGACA GACCCCATAA
2101  ATCATGCCTA CGGAACGCAG GCTGACCTCC TTCCATACAC CAGGTCTAGT
2151  AATATAACGT CTACAGATAC AGGCTCAGGC TGGGTGCACA TCGGCCTACC
2201  CTCATTTGCT TTCCTCAATC CTCTCGGGTG GCTTAGGGAC CTACTTGCGT
2251  GGGCGGCCTG GTTGGGTGGG GTTCTATACT TAATAAGTCT TTGTGTTTCC
2301  TTACCAGCCT CCTTCGCGAG GAGGAGACGC CTCGGCCGGT GGCAGGAATA
2351  AACCGTACCG ACCAATCTCT TAAAAACCCT CTTCTCGGGA CAGAGGTCTC
2401  TTTCTGCCTT AAATCGAGTT CACTCCCCCA TCACGTACGA GCATTGGGCC
2451  AGATTAAAGC AAAGAACCTG GCATCCTGTG ACTATTACTT GCTATTCCGC
2501  CAAGTTGTAT TGCCCCCTGA AGTATATCCC ATTGGTGTCT TAATAAGAGC
2551  TGCGGAGGCC ATACTAACAG TTATAGTATC AGCTTGGAAG CTGGATCACA
2601  TGACAAAGAC CCTATACTCC TCTGTGAGAT ATGCACTCAC CAATCCCCGG
2651  GTCCGGGC
```

BORNA DISEASE VIRAL SEQUENCES, DIAGNOSTICS AND THERAPEUTICS FOR NERVOUS SYSTEM DISEASES

This invention was made with Government support under Grant No. NS-29425, awarded by the National Institutes of Health. The Government has certain rights in this invention.

FIELD OF THE INVENTION

The present invention relates to the field of virology, immunology, gene therapy, transplantation of viral transfected cells, and in vivo chemical delivery.

BACKGROUND OF THE INVENTION

Borna disease is an immune-mediated neurologic syndrome {Narayan, O., et al., Science 220:1401–1403 (1983)} caused by infection with Borna disease virus (BDV). BDV is a neurotropic, nonsegmented and negative-strand RNA virus that causes a progressive, immune-mediated neurologic disease characterized by disturbances in movement and behavior {Ludwig, H., et al., Prog. Med. Virol, 35:107–151}. It causes fatal disease in expensive domestic animals. Although natural infection was originally considered to be restricted to horses and sheep in Southeastern Germany, recent studies suggest that BDV infects horses in North America {Kao, M., et al., Vet.Rec., 132:241–4 (1993) }, cats in Sweden {Lundgren, A.-L., et al., Zbl. Vet. Med. [B], 40:298–303 (1993)}, ostriches in Israel (Malkinson, M., et al., Vet. Rec., 133:304 (1993)) and some human subjects with neuropsychiatric disorders in Europe and North America {Bode, L., et al., Arch. Virol. [Suppl], 7:159–167 (1993); Bode, L., et al., Lancet, ii:689 (1988); Fu, Z. F., et al., J. Affect. Disorders, 27:61–68 (1993) and Rott, R., et al., Science, 228:755–756 (1985)}.

Experimental infection in rats (Narayan, O., et al., Science, 220:1401–1403 (1983)) results in a multiphasic syndrome characterized by hyperactivity, stereotyped behaviors, dyskinesias and dystonias.

Though natural infection has not been reported in primates, subhuman primates can be infected experimentally {Sprankel, H., et al., Med. Microbiol. Immunol. 165:1–18 (1978) and Stitz, L., et al., J. Med. Virol. 6:333–340 (1980)}. Antibodies to BDV proteins have been found in patients with neuropsychiatric disorders (Rott, R., et al., Science 228:755–756 (1985); Fu, Z. F., et al., J. Affective Disord. 27:61–68 (1993) and Bode, L., et al., Arch. Virol. (Suppl.) 7:159–167 (1993)).

Because BDV grows only to low titer, it was difficult to purify for analysis. However, the identification of BDV cDNA clones by subtractive hybridization (Lipkin, W. I., et al., Proc. Natl. Acad. Sci. USA 87:4184–4188 (1990) and VandeWoude, S., et al., Science 250:1276–1281 (1990)) and, more recently, the advent of a method for isolation of virus particles {Briese, T., et al., Proc. Natl. Acad. Sci. USA 89:11486–11489 (1992)} led to partial characterization of BDV as a negative-strand RNA virus which transcribes its RNA in the cell nucleus {Briese, T., et al., Proc. Natl. Acad. Sci. USA 89:11486–11489 (1992)}.

The diagnosis of BDV infection is based on the appearance of a clinical syndrome consistent with disease, and the presence of serum antibodies that detect viral proteins in infected cells by indirect immnunofluorescent test (IFT) (Pauli, G., et al., Zbl. Vet. Med. [B] 31:552–557 (1984)), Western blot (WB; immunoblotting) or immunoprecipitation (IP) (Ludwig, H., et al., Prog. Med. Virol, 35:107–151 (1988)). These methods are cumbersome and difficult to use for large surveys of human and livestock populations.

SUMMARY OF THE INVENTION

One aspect of the invention presents the nucleotide and amino acid sequences of Borna disease virus (BDV), their derivatives, the vectors for expressing them, and cells transfected by these vectors.

Another aspect of the invention presents novel BDV viral proteins gp18 and p57 and their respective recombinant proteins, recp18 and recp57. Also disclosed are their nucleotide and amino acid sequences, vectors encoding them, cells transfected by these vectors, and antibodies directed to these proteins.

Another aspect of the invention presents assays for detecting ligands which bind BDV proteins or their derivatives. Preferably, these assays are immunoassays for detecting antibodies to BDV protein or its derivatives. The assays are useful for detecting: (1) BDV infection or related pathogenesis; and (2) neurologic and neuropsychiatric disease not due to BDV infection. Preferably, p40, p23 or gp18, and their synthetic versions or fragments are used in these assays. The preferred immunoassays are enzyme-linked immunosorbent assays (ELISAs) based on the use of recombinant viral proteins: recp40, recp23, and/or recp18 to detect ligands, such as antibodies, in the patient's biological sample, that are immunoreactive with these proteins. The assay can also be used to monitor the diseases by monitoring the titer of such ligands. The titer of the ligands can also be prognosticative of the diseases.

Another aspect of the invention presents alternative methods for detecting the above diseases by detecting the hybridization of nucleotide sequences in a patient's biological sample with the nucleotide sequences coding for BDV protein or its derivatives.

Another aspect of the invention presents assay kits for the above diagnostic tests.

Another aspect of the invention presents vaccines against the above diseases.

Another aspect of the invention presents synthetic peptides, based on truncated BDV protein, useful for immunoassays for detecting antibodies to BDV or for raising antibodies for the therapeutic uses described in the next paragraph. The method for obtaining these peptides are also presented.

Another aspect of the invention presents methods, using ligands or chemicals such as antibodies, capable of binding to BDV proteins or their derivatives, for treating: (1) BDV infection or related pathogenesis; and (2) neurologic and neuropsychiatric disease not due to BDV infection. Examples of such antibodies are those specific to gp18 and p57. Also presented are these therapeutic agents, methods for screening for them, especially those that bind to the immunogenic epitopes of BDV protein. The methods for producing the antibodies are also presented.

Another aspect of the invention presents a BDV-based viral vector useful for in vivo delivery of genes and chemicals to the nervous system. Also disclosed are: the cells transfected by the viral vector and cell lines derived therefrom, the in vitro harvesting of the, gene product from such cells and cell lines, and the transplant of such cells into animals.

Other aspects and advantages of the invention will be apparent to those skilled in the art upon consideration of the following detailed description which provides illustrations of the invention in its presently preferred embodiments.

BRIEF DESCRIPTION OF THE DRAWINGS

FIG. 2 shows the complete genomic sequence of BDV (strain V) in 5' to 3' (SEQ ID NO:19) cDNA with the deduced amino acid sequence shown below the cDNA.

FIG. 4 shows alignment of the p180 (also referred to as "pol") open reading frame (ORF) and negative-strand RNA virus L-polymerase amino acid sequences with PILEUP computer program (Sequence Analysis Software Package, Genetics Computer, Inc., Madison, Wis.). BDV sequence (amino acids 377 to 829 of SEQ ID NO:10) is indicated with double arrowheads. Rhabdoviridae: RaV, rabies virus (SEQ ID NO:21); VSV, vesicular stomatitis virus (SEQ ID NO:22); SYN, sonchus yellow net virus (SEQ ID NO:23). Paramyxoviridae: MeV, measles virus (SEQ ID NO:24); SeV, Sendai virus (SEQ ID NO:25); NDV, Newcastle disease virus (SEQ ID NO:26); RSV, respiratory syncytial virus (SEQ ID NO:28). Filoviridae: MaV, Marburg virus (SEQ ID NO:27).

FIG. 5 presents sequence analysis of BDV genomic termini. (a) Similarity of 3'-terminal BDV sequence to leader regions of Rhabdoviridae: RaV (SEQ ID NO:35) and VSV (SEQ ID NO:36); Paramyxoviridae: MeV (SEQ ID NO:34), SeV (SEQ ID NO:32), NDV (SEQ ID NO:33), and RSV (SEQ ID NO:29); and Filoviridae: MaV (SEQ ID NO:31) and Ebola virus (EboV, SEQ ID NO:30). (b) Comparison of complementarity at 3' and 5' termini of BDV genomic RNA with that of four other nonsegmented, negative-strand RNA viruses: RSV (SEQ ID NO:37 and NO:38), MaV (SEQ ID NO:39 and NO:40), SeV (SEQ ID NO:41 and NO:42), and RaV (SEQ ID NO:43 and NO:44).

FIG. 6 presents the map of BDV subgenomic RNAs relative to the viral antigenome. (a) Northern hybridization analysis of rat brain poly(A)+ RNA; (b) position of viral transcripts with respect to antigenome as determined by Northern hybridization and sequence analysis; (c) alignment of the seven potential termination sites of BDV SEQ ID NO:19 positions 1156–1201 (p40/t1/T2); 1856–1901 (p23/T3); 2328–2417 (gp18); 3747–3781 (p57/t4); 4474–4520 (T5); 4738–4783 (t6); and 8819–8874 (p180/T7).

FIG. 7 presents the sequence of ORF gp18 (SEQ ID NOS:5 and 6).

FIG. 18 presents the cDNA of BDV polymerase (SEQ ID NO: 19, positions 2393–2409 and 3704–8821). "V" denotes the site of its intron which is located between nucleotide positions 2410 and 3703 in the figure. "I-2", denotes that this is the second intron in the BDV genome.

FIG. 19 presents the partial cDNA genomic sequence for BDV strain HE/80.

DETAILED DESCRIPTION OF THE INVENTION

BDV Protein, its Amino Acid and Nucleotide Sequences

Table 1 identifies the sequence ID Nos. with their respective nucleotide and amino acid sequences.

TABLE 1

Nucleotide and Amino Acid Sequences of Borna Disease Virus (BDV)

| | Sequence ID No. |
|---|---|
| Nucleotide Sequence | |
| p40 | 1 |
| p23 | 3 |
| gp 18 | 5 |
| p57 | 7 |
| BDV polymerase | 9 |
| BDV genomic cDNA | 19 |
| Amino Acid Sequence | |
| p40 | 2 |
| p23 | 4 |
| gp 18 | 6 |
| p57 | 8 |
| BDV polymerase | 10 |

BDV polymerase is also referred to as "pol" or "p180".

Figure 1:
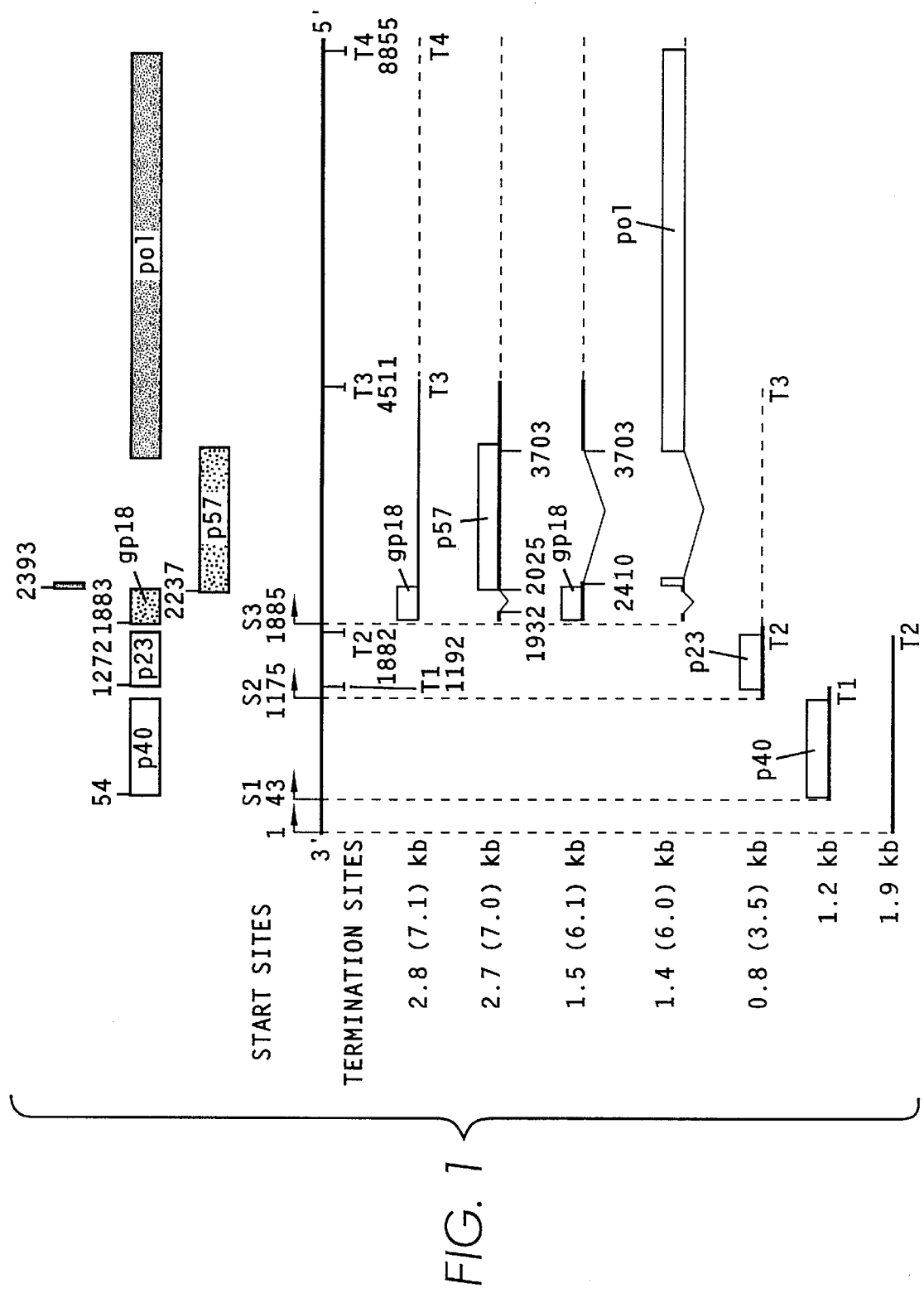
FIG. 1 presents the genomic organization and transcriptional map of BDV.

The present application discloses the complete BDV genomic nucleotide sequence, the locations on the genomic nucleotide sequence which encode the different BDV proteins, the sites of splicing and overlap (see FIGS. 1 and 2). Also disclosed are the novel nucleotide and amino acid sequences of BDV proteins gp18, pol and p57. The following FIGS. 1, 2, 19, and Table 1 summarize this information.

FIG. 1 shows the genomic organization and transcriptional map of BDV. The BDV genome is shown as a solid line in 3' to 5' direction. Coding regions and their respective reading frames are represented as boxes at the top; the number above each upward vertical line indicates the nucleotide position of the first AUG codon in the respective ORF. Transcription initiation sites and their nucleotide positions on the viral genome (BDV strain V) are represented by arrows pointing downstream. Transcription termination sites and splice sites are indicated by downward vertical lines. Dashed lines indicate that readthrough at termination sites T2 and T3 results in synthesis of longer RNAs terminating at T3 and T4, respectively. The 1.2 kb and 0.8 kb RNA have been shown to represent the mRNAs for p40 and p23, respectively. p23 could also be translated from the 3.5 kb RNA. Transcripts that are likely to represent mRNAs for gp18, p57 and pol are indicated. Note that gp18 can only be translated from RNAs containing intron 1. Splicing of intron 1 preserves the gp18 initiation codon but introduces a stop codon such that only the first 13 amino acids could be translated from the 2.7 (7.0) kb transcripts and the RNA or the 1.4 kb RNA serve as messages for the translation of BDV proteins.

FIG. 2 shows the complete genomic sequence of BDV (strain V) in 5' to 3' cDNA. The deduced amino acid sequences are shown for p40, p23, gp18, p57 and pol. Note: the full amino acid sequence for pol after splicing modification is shown in sequence ID No. 10. The stars (*) indicate stop codons. Information on transcription and splicing of the genomic sequence is found in Schneider, P. A. et al., *J. Virol.*, 68:5007–5012 (1994) and Schneemann, A. , et al., *J. Virol.*, 68:6514–6522 (1994), both references are hereby incorporated by reference in their entirety.

FIG. 19 presents the partial cDNA genomic sequence of BDV strain HE/80. Position 1 to 2651 of this sequence corresponds to position 1397 through 4054 of the cDNA genomic sequence of (SEQ ID NO:20) BDV strain V. The cDNA sequence of BDV strain HE/80 disclosed herein encodes part of the p23 and BDV polymerase proteins, and the complete gp18 and p57 proteins.

The term "nucleotide sequence" as used herein, unless otherwise modified, includes both ribonucleic acid (RNA) and deoxyribonucleic acid (DNA).

The sequences in Table 1 include both native and synthetic sequences. Unless otherwise modified, the term "protein" as used herein encompasses both native and synthetic polypeptide and peptide. Synthetic protein includes recombinant and chemically synthesized protein. Unless otherwise indicated, "gp18", "p57", and "pol" proteins include both their native and synthetic versions. "recp18", "recp57" and "recpol" are recombinant proteins of "gp18", "p57", and "pol" proteins, respectively.

Some of the nucleotide sequences disclosed are in the form of DNA. For example, SEQ ID No. 19 presents the BDV viral genomic sequence as cDNA of BDV viral genomic RNA. One skilled in the art would realize that the BDV viral genomic RNA is complementary to its cDNA that is shown in FIG. 2. The term "BDV genomic nucleotide sequence" thus includes both the full cDNA and RNA sequences of the BDV genome. Further, as used in this application and claims, the SEQ ID Nos. and disclosed sequences include: (1) the DNA sequences as disclosed, (2) the complementary nucleotide sequences (which may be RNA or DNA) to the disclosed sequences, (3) the corresponding RNA sequences to the listed DNA sequences wherein the Thymidine ("T") in the disclosed DNA sequences is replaced with Uracil ("U"), (4) nucleotide sequences wherein other nucleotides known in the art such as nucleotide analogs, replace those in the foregoing sequences, for example, 5-methyl-cytosine replacing cytosine, and (5) nucleotide sequences that are within a 10% variance to the respective SEQ ID Nos. or disclosed nucleotide sequences. The above discussion would analogously apply to RNA sequences disclosed in this application.

Since nucleotide codons are redundant, also within the scope of this invention are equivalent nucleotide sequences which include: nucleotide sequences which code for the same proteins or equivalent proteins. Thus, nucleotide sequences which encode substantially the same or functionally equivalent amino acid sequence may be used in the practice of the invention.

The terms "BDV genomic nucleotide sequence", "p18", "recp18", "pol", "recpol", "p57", "recp57", as used in relation to nucleotide sequences are defined above, together with: (1) nucleotide sequences that are within an 10% variance to the respective nucleotide sequences in Table 1; (2) nucleotide sequences that are capable of hybridizing to the coding sequences of the respective nucleotide sequences, under stringent hybridization conditions, (3) nucleotide sequences coding for gp18, recp18, p57, recp57, pol, and recpol proteins, and amino acid sequences of SEQ ID Nos. 6, 8, and 10 respectively; and (4) fragments of SEQ ID Nos. 6; 8; 10; nucleotide number 1 through 53 and nucleotide number 1880 through 8910 of SEQ ID NO 19 and their fragments; or other nucleotide sequences which, for example, encode proteins having substantially the same biological characteristics/activities of gp18, recp18, p57, recp57, pol, recpol proteins, respectively. Preferably, the determinative biological characteristic/activity is the retention of at least one immunoepitope. Preferably, when used in an immunoassay for BDV, these proteins are immunoreactive with antibodies directed to BDV but not detectably immunoreactive with non-BDV specific antibodies found in a biological sample such as a serum sample. Alternatively, the nucleotide sequences can be nucleotide probes of at least 10 nucleotides in length. Preferably, when used in a hybridization assay for BDV, these probes do not detectably hybridize to the nucleotide sequences of non-BDV organisms which are found in a biological sample such as a serum sample. Alternatively, the nucleotide sequences hybridize to at least 10 consecutive nucleotides in the coding sequences of the above listed nucleotide sequences. The nucleotide sequences include a nucleotide sequence which encodes a protein containing at least 8; more preferably, 5 to 6; and most preferably, 4 amino acids. Preferably, the protein is specific to BDV or retain one or more biological functions of BDV. Examples of such biological functions are: BDV's ability to bind a particular cellular receptor, BDV's ability to target its host cells (e.g. cells and tissues of the nervous system, bone marrow, peripheral blood, mononuclear cells or brain), and BDV's effects on the functions of cells infected by it. The discussion herein similarly applies to p23, recp23, p80, recp80 nucleotide sequences, and the cDNA nucleotide sequence of FIG. 19, e.g. in reference to their respective SEQ ID NOs and FIG. 19.

The terms "gp18", "recp18", "p57", "recp57", "pol", and "recpol", as used in relation to proteins are, respectively, as defined above together with: (1) protein variants containing amino acid sequences that have at least 95% of their amino acids matching the sequences of SEQ ID Nos. 6, 8, and 10, respectively; (2) the functional equivalents of these proteins and their variants, respectively; and (3) the derivatives, including fragments, of gp18, recp18, p57, recp57, pol, recpol, proteins and their variants, respectively. Preferably, when used in an immunoassay for BDV, these proteins are immunoreactive with antibodies directed to BDV but not detectably immunoreactive with non-BDV specific antibodies found in a biological sample such as a serum sample. Alternatively, these proteins each contains at least 8; more preferably, 5 to 6; and most preferably, 4 amino acids. Preferably, the latter proteins are specific to BDV or retain one or more biological functions of BDV. Examples of such biological functions are: BDV's ability to bind a particular cellular receptor, BDV's ability to target its host cells (e.g. cells and tissues of the nervous system, bone marrow, peripheral blood, mononuclear cells or brain), and BDV's effects on the functions of cells infected by it. The discussion herein similarly applies to p23, recp23, p80, and recp80 proteins, e.g. in reference to their respective SEQ ID NOs.

Within the definition of "BDV" are BDV isotypes, strains, and BDV related viruses. The term "BDV proteins and their derivatives", includes BDV proteins, fragments of BDV proteins, proteins containing immunoepitopes of BDV, variants and functional equivalents of the foregoing. gp18 and p57 are examples of BDV proteins. Preferably, the immunoepitope is specific to BDV.

The variants can result from, e.g. substitution, insertion, or deletion of the amino acid sequences shown in Table 1. The derivatives of the proteins and their variants, include fragments of these proteins and their immunogenic epitopes. Preferably, each of the fragments contains at least one immunogenic epitope of BDV. More preferably, the fragment is capable of being bound by polyclonal antibodies directed to BDV. In the case of antibodies which recognize linear epitopes, they generally bind to epitopes defined by about 3 to 10 amino acids. Preferably, too, each variant retains at least one immunoepitope of BDV. Preferably the immunoepitope is specific to BDV.

Two amino acid sequences are functionally equivalent if they have substantially the same biological activities. The proteins may be fused to other proteins, for example, signal sequence fusions may be employed in order to more expeditiously direct the secretion of the BDV protein. The heterologous signal replaces the native BDV signal, and when the resulting fusion is recognized, i.e. processed and cleaved by the host cell, the BDV protein is secreted. Signals are selected based on the intended host cell, and may include bacterial, yeast, insect, mammalian, and viral sequences. For example, the native BDV signal or the herpes gD glycoprotein signal is suitable for use in mammalian expression systems.

Substitutional variants of the proteins disclosed herein are those in which at least one residue in the disclosed sequences has been removed and a different residue inserted in its place. Preferably, the amino acid change is conservative. For example, such substitutions generally are made in accordance with the following Table 2.

TABLE 2

| Original Residue | Exemplary Substitutions |
| --- | --- |
| Ala | ser |
| Arg | lys |
| Asn | gln; his |
| Asp | glu |
| Cys | ser; ala |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Novel amino acid sequences, as well as isosteric analogs (amino acid or otherwise), are included within the scope of this invention.

A variant typically is made by site specific mutagenesis of the encoding nucleic acid, expression of the variant nucleic acid in recombinant cell culture and, optionally, purification from the cell culture for example by immunoaffinity adsorption on a column to which are bound polyclonal antibodies directed against the original protein from which the variant is derived.

Another class of variants are deletional variants. Deletions are characterized by the removal of one or more amino acid residues from the original protein sequence. Typically, deletions are used to affect the original protein's biological activities. However, deletions which preserve the biological activity or immune cross-reactivity of the original protein are preferred.

Deletions of cysteine or other labile residues also may be desirable, for example in increasing the oxidative stability of the original protein. Deletion or substitutions of potential proteolysis sites, eg. Arg Arg, is accomplished by deleting one of the basic residues or substituting one by glutaminyl or histidyl residues.

It will be understood that some variants may exhibit reduced or no biological activity. These variants nonetheless are useful as standards in immunoassays for BDV protein so long as they retain at least one immunogenic epitope of BDV protein.

It is presently believed that the three-dimensional structure of the proteins of the present invention is important to their functioning as described herein. Therefore, all related structural analogs which mimic the active structure of those formed by the compositions or proteins claimed herein are specifically included within the scope of the present invention.

Modified proteins are also within the contemplation of this patent application. These modifications may be deliberate, e.g., modifications obtained through site-directed mutagenesis, or may be accidental, e.g., as those obtained through mutation of the hosts.

Further, as is the case for all proteins, the precise chemical structure depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition. Additionally, the primary amino acid sequence may be augmented by derivatization using sugar moieties (glycosylation) or by other supplementary molecules such as lipids, phosphate, acetyl groups and the like, more commonly by conjugation with saccharides. The primary amino acid structure may also aggregate to form complexes, most frequently dimers. Certain aspects of such augmentation are accomplished through post-translational processing systems of the producing host; other such modifications may be introduced in vitro. In any event, such modifications are included in the definition so long as the activity of the protein is not destroyed. It is expected that such modifications may quantitatively or qualitatively affect the activity, either by enhancing or diminishing the activity of the protein in various assays.

Individual amino acid residues in the chain may also be modified by oxidation, reduction, or other derivatization, and the protein may be cleaved to obtain fragments which retain activity. Such alterations which do not destroy activity do not remove the protein sequence from the definition. The following discusses some of the modifications in further detail by way of example.

Thus, glycosylation variants are included within the scope of BDV. They include variants completely lacking in glycosylation (unglycosylated) and variants having at least one less glycosylated site than the native form (deglycosylated) as well as variants in which the glycosylation has been changed. Included are deglycosylated and unglycosylated amino acid sequence variants, deglycosylated and unglycosylated BDV and gp18 having the native, unmodified amino acid sequence of BDV and gp18, and other glycosylation variants, e.g. of p57. For example, substitutional or deletional mutagenesis is employed to eliminate the N- or O-linked glycosylation sites of BDV or gp18, e.g., an asparagine residue is deleted or substituted for by another basic residue such as lysine or histidine. Alternatively, flanking residues making up the glycosylation site are substituted or deleted, even though the asparagine residues remain unchanged, in order to prevent glycosylation by eliminating the glycosylation recognition site.

Unglycosylated protein which has the amino acid sequence of the native protein is preferably produced in recombinant prokaryotic cell culture because prokaryotes are incapable of introducing glycosylation into polypeptides.

Glycosylation variants are produced by selecting appropriate host cells or by in vitro methods. Yeast, for example, introduce glycosylation which varies significantly from that of mammalian systems. Similarly, mammalian cells having a different species (e.g. hamster, murine, insect, porcine, bovine or ovine) or tissue origin (e.g. lung, liver, lymphoid, mesenchymal or epidermal) than the source of the BDV antigen are routinely screened for the ability to introduce variant glycosylation as characterized for example by elevated levels of mannose or variant ratios of mannose, fucose, sialic acid, and other sugars typically found in mammalian glycoproteins. In vitro processing of the proteins of the present invention typically is accomplished by enzymatic hydrolysis, e.g. endoglycosidase digestion.

Derivatization with bifunctional agents is useful for preparing intermolecular aggregates of BDV proteins and their derivatives with polypeptides as well as for cross-linking the protein and derivatives to a water insoluble support matrix or surface for use in the assay or affinity purification of its ligands. In addition, a study of intrachain cross-links will provide direct information on conformational structure. Commonly used cross-linking agents include sulfhydryl reagents, 1,1-bis(diazoacetyl)-2-phenylethane, glutaraldehyde, N-hydroxysuccinimide esters, for example esters with 4-azidosalicylic acid, homobifunctional imidoesters including disuccinimidyl esters such as 3,3'-dithiobis (succinimidyl-propionate), and bifunctional maleimides such as bis-N-maleimido-1,8-octane.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl or threonyl residues, methylation of the α-amino groups of lysine, arginine, and histidine side chains {T. E. Creighton, *Proteins: Structure and Molecular Properties,* W. H. Freeman & Co., San Francisco, pp 79–86 (1983)}, acetylation of the N-terminal amine and, in some instances, amidation of the C-terminal carboxyl.

The claimed proteins are preferably produced using recombinant technologies. The nucleotide, e.g., DNA or RNA, sequences which encode the desired polypeptides are amplified by use of e.g. the polymerase chain reaction in the case of DNA (hereinalso referred to as "PCR"), and reverse transcriptase-polymerase chain reaction (RT-PCR) in the case of RNA. Oligonucleotide sequences to be used as primers which can specifically bind to the ends of the regions of interest are synthesized. After the desired region of the gene has been amplified the desired sequence is incorporated into an expression vector which is transformed into a host cell. The nucleotide sequence is then expressed by the host cell to give the desired polypeptide which is harvested from the host cell. Plant, bacterial, yeast, insect, viral and mammalian expression systems may be used. Vectors which may be used in these expression systems may contain fragments of plant, bacterial, yeast, insect, viral, and/or mammalian origins.

Given the teachings contained herein, one skilled in the art can create the sequences disclosed herein, either by hand or with an automated apparatus. As examples of the current state of the art relating to polynucleotide synthesis, one is directed to Maniatis et al., *Molecular Cloning—A Laboratory Manual,* Cold Spring Harbor Laboratory (1984), and Horvath et al., *An Automated DNA Synthesizer Employing Deoxynucleoside 3'-Phosphoramidites,* Methods in Enzymology 154: 313–326, 1987.

Identification of Nucleotide Sequences, Cloning, and Expression of the Disclosed Protein Alternatively, to obtain RNA encoding the proteins disclosed herein, one needs only to conduct hybridization screening with labelled BDV nucleotide sequence (usually, greater than about 20, and ordinarily about 50 bp) in order to detect clones which contain homologous sequences in the cDNA libraries derived from cells or tissues of a particular animal, followed by analyzing the clones by restriction enzyme analysis and nucleic acid sequencing to identify full-length clones. The cell lines, cells and tissues are preferably from the nervous system, bone marrow, peripheral blood, mononuclear cells or brain of BDV infected animals. Examples of cells from the nervous system are: neurons, oligodendrocytes and astrocytes. The primers shown in Examples 1 to 4 and/or the methods shown therein may also be used.

If full length clones are not present in the library, then appropriate fragments are recovered from the various clones and ligated at restriction sites common to the fragments to assemble a full-length clone.

The techniques shown in this section are also useful for identifying and sequencing various isotypes and strains of BDV and BDV related viruses. The present invention discloses the nucleotide sequences of two strains of BDV; different strains of BDV may exist or arise due to mutation as in the case of human immunodeficiency virus (HIV) which constantly mutates and of which different strains are constantly being discovered. Thus, within the definition of BDV are other BDV isotypes and strains or viruses related to BDV ("BDV related viruses"). For example, the next section of the application describes diagnostic assays for BDV or related pathogenesis. The related pathogenesis include: (1) diseases caused by BDV; (2) opportunistic or attendant diseases arising from BDV infection; and (3) diseases caused by BDV related viruses. The BDV related viruses would be nonsegmented, negative-stranded, neurotropic, post transcriptionally modified (spliced) viruses which share some homology with BDV nucleotide or amino acid sequences. Patients infected by the BDV related viruses would manifest clinical symptoms similar to BDV infected patients, or to that of neurologic or neuropsychiatric diseases.

Thus, DNA or RNA encoding various BDV isotypes and strains, and BDV related viruses, can be similarly obtained by probing libraries from cells and tissues, especially cells of the nervous system, of animals exhibiting clinical symptoms of BDV infection, neurologic or neuropsychiatric disease; or animals that have been purposely infected with BDV strains, isotypes or BDV related viruses, such as shown in Example 2. Once the DNA or RNA sequence of these strains, isotypes, or related viruses are known, primers based on the sequence may be used. The methods shown in Examples 1 and 2, and the primers shown therein may also be used to obtain the genomic nucleotide sequences.

In general, prokaryotes are used for cloning of DNA sequences in constructing the vectors useful in the invention. For example, $E.$ $coli$ K12 strain 294 (ATCC No. 31446) is particularly useful. Other microbial strains which may be used include $E.$ $coli$ B and $E.$ $coli$ X1776 (ATCC No. 31537). These examples are illustrative rather than limiting. Alternatively, in vitro methods of cloning, e.g. polymerase chain reaction, are suitable.

The proteins of this invention may be expressed directly in recombinant cell culture as an N-terminal methionyl analogue, or as a fusion with a polypeptide heterologous to the hybrid/portion, preferably a signal sequence or other polypeptide having a specific cleavage site at the N-terminus of the hybrid/portion. For example, in constructing a prokaryotic secretory expression vector for portion/fragment of BDV protein, the native BDV signal is employed with hosts that recognize that signal. When the secretory leader is "recognized" by the host, the host signal peptidase is capable of cleaving a fusion of the leader polypeptide fused at its C-terminus to the desired mature BDV protein. For host prokaryotes that do not process the BDV signal, the signal is substituted by a prokaryotic signal selected, for example, from the group of the alkaline phosphatase, penicillinase, lpp or heat stable enterotoxin II leaders. For yeast secretion the BDV signal may be substituted by the yeast invertase, alpha factor or acid phosphatase leaders. In mammalian cell expression, the native signal is satisfactory for mammalian BDV, although other mammalian secretory protein signals are suitable, as are viral secretory leaders, for example the herpes simplex gD signal.

The proteins of the present invention may be expressed in any host cell, but preferably are synthesized in mammalian hosts. However, host cells from prokaryotes, fungi, yeast, insects and the like are also are used for expression. Exemplary prokaryotes are the strains suitable for cloning as well as $E.$ $coli$ W3110 (F-$\lambda$-A-prototrophic, ATTC No. 27325), other enterobacteriaceae such as $Serratia$ $marcescans,$ bacilli and various pseudomonads.

Expression hosts typically are transformed with DNA encoding the proteins of the present invention which has been ligated into an expression vector. Such vectors ordinarily carry a replication origin (although this is not necessary where chromosomal integration will occur). Expression vectors also include marker sequences which are capable of providing phenotypic selection in transformed cells, as will be discussed further below. For example, $E.$ $coli$ is typically transformed using pBR322, a plasmid derived from an $E.$ $coli$ species {Bolivar, et al., $Gene$ 2:95 (1977)}. pBR322 contains genes for ampicillin and tetracycline resistance and thus provides easy means for identifying transformed cells, whether for purposes of cloning or expression. Expression vectors also optimally will contain sequences which are useful for the control of transcription and translation, e.g., promoters and Shine-Dalgarno sequences (for prokaryotes) or promoters and enhancers (for mammalian cells). The promoters may be, but need not be, inducible; even powerful constitutive promoters such as the CMV promoter for mammalian hosts may produce BDV proteins without host cell toxicity. While it is conceivable that expression vectors need not contain any expression control, replicative sequences or selection genes, their absence may hamper the identification of transformants and the achievement of high level peptide expression.

Promoters suitable for use with prokaryotic hosts illustratively include the β-lactamase and lactose promoter systems {Chang et al., $Nature$ 275:615 (1978); and Goeddel et al., $Nature$ 281:544 (1979)}, alkaline phosphatase, the tryptophan (trp) promoter system (Goeddel, $Nucleic$ $Acids$ $Res.$ 8:4057 (1980) and EPO Appln. Publ. No. 36,776) and hybrid promoters such as the tac promoter {H. de Boer et al., $Proc.$ $Natl.$ $Acad.$ $Sci.$ $USA$ 80:21–25 (1983)}. However, other functional bacterial promoters are suitable. Their nucleotide sequences are generally known, thereby enabling a skilled worker operably to ligate them to DNA encoding the proteins of the present invention {Siebenlist et al., $Cell$ 20:269 (1980)} using linkers or adaptors to supply any required restriction sites. Promoters for use in bacterial systems also will contain a Shine-Dalgarno (S.D.) sequence operably linked to the DNA encoding the proteins of the present invention In addition to prokaryotes, eukaryotic microbes such as yeast or filamentous fungi are satisfactory. $Saccharomyces$ $cerevisiae$ is the most commonly used eukaryotic microorganism, although a number of other strains are commonly available. The plasmid YRp7 is a satisfactory expression vector in yeast {Stinchcomb, et al., *Nature* 282:39 (1979); Kingsman et al., *Gene* 7:141 (1979); Tschemper et al., *Gene* 10:157 (1980)}. This plasmid already contains the trp1 gene which provides a selection marker for a mutant strain of yeast lacking the ability to grow in tryptophan, for example ATCC no. 44076 or PEP4-1 {Jones, *Genetics* 85:12 (1977)}. The presence of the trp1 lesion as a characteristic of the yeast host cell genome then provides an effective environment for detecting transformation by growth in the absence of tryptophan. Alternatively, viral expression vectors such as retroviral vectors, baculoviral vectors and Semliki Forest viral vectors are used. The expression hosts of these vectors are known in the art.

Suitable promoting sequences for use with yeast hosts include the promoters for 3-phosphoglycerate kinase {Hitzeman et al., *J. Biol. Chem.* 255:2073 (1980)} or other glycolytic enzymes {Hess et al., *J. Adv. Enzyme Reg.* 7:149 (1968); and Holland, *Biochemistry* 17:4900 (1978)}, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucos isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydragenase, and enzymes responsible for maltose and galactose utilization. Suitable vectors and promoters for use in yeast expression are further described in R. Hitzeman et al., European Patent Publication No. 73,657A.

Expression control sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence which may be the signal for addition of the poly A tail to the 3' end of the coding sequence. All of these sequences may be inserted into mammalian expression vectors.

Suitable promoters for controlling transcription from vectors in mammalian host cells are readily obtained from various sources, for example, the genomes of viruses such as polyoma virus, SV40, adenovirus, MMV (steroid inducible), retroviruses (e.g. the LTR of BDV), hepatitis-B virus and most preferably cytomegalovirus, or from heterologous mammalian promoters, e.g. the beta actin promoter. The early and late promoters of SV40 are conveniently obtained as an SV40 restriction fragment which also contains the SV40 viral origin of replication. (Fiers et al., *Nature* 273:113 (1978)). The immediate early promoter of the human cytomegalovirus is conventionally obtained as a HindIII E restriction fragment. {Greenaway, P. J. et al., *Gene* 18:355–360 (1982)}.

Transcription of a DNA encoding the proteins of the present invention by higher eukaryotes is increased by inserting an enhancer sequence into the vector. Enhancers are cis-acting elements of DNA, usually about from 10–300 bp, that act on a promoter to increase its transcription. Enhancers are relatively orientation and position independent having been found 5' {Laimins et al., *Proc. Natl. Acad. Sci*, 78:993 (1981)} and 3' {Lusky, M. L., et al., *Mol. Cell Bio.* 3:1108 (1983)} to the transcription unit, within an intron {Banerji, J. L. et al., *Cell* 33:729 (1983)} as well as within the coding sequence itself {Osborne, T. F., et al., *Mol. Cell Bio.* 4:1293 (1984)}. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA. The 3' untranslated regions also include transcription termination sites.

Expression vectors may contain a selection gene, also termed a selectable marker. Examples of suitable selectable markers for mammalian cells are dihydrofolate reductase (DHFR), thymidine kinase (TK) or neomycin. When such selectable markers are successfully transferred into a mammalian host cell, the transformed mammalian host cell is able to survive if placed under selective pressure. There are two widely used distinct categories of selective regimes. The first category is based on a cell's metabolism and the use of a mutant cell line which lacks the ability to grow independent of a supplemented media. Two examples are CHO DHFR- cells and mouse LTK cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into calls lacking the respective genes, thus altering their growth requirements. Individual cells which were not transformed with the DHFR or TK gene will not be capable of survival in non-supplemented media.

The second category of selective regimes is dominant selection which refers to a selection scheme used in any cell type and does not require the use of a mutant cell line. These schemes typically use a drug to arrest growth of a host cell. Those cells which are successfully transformed with a heterologous gene express a protein conferring drug resistance and thus survive the selection regimen. Examples of such dominant selection use the drugs neomycin {Southern et al., *J. Molec. Appl. Genet.* 1:327 (1982)}, mycophenolic acid {Mulligan et al., *Science* 209:1422 (1980)} or hygromycin {Sugden et al., *Mol. Cell. Biol.* 5:410–413 (1985)}. The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent, e.g. methotrexate (MTX) which inactivates DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene permitting cointegration. One ensures that the cell requires more DHFR, which requirement is met by replication of the selection gene, by selecting only for cells that can grow in the presence of ever-greater MTX concentration. So long as the gene encoding a desired heterologous protein has cointegrated with the selection gene replication of this gene gives rise to replication of the gene encoding the desired protein. The result is that increased copies of the gene, i.e. an amplified gene, encoding the desired heterologous protein express more of the desired protein.

Suitable eukaryotic host cells for expressing the proteins include monkey kidney CV1 line transformed by SV40 (COS-7, ATCC CRL 1651); human embryonic kidney line (293 or 293 cells subcloned for growth in suspension culture, {Graham, F. L. et al., *J. Gen Virol.* 36:59 (1977)}; baby hamster kidney cells (BHK, ATCC CCL 10); chinese hamster ovary-cells-DHFR (CHO, Urlaub and Chasin, *Proc. Natl. Acad. Sci., (USA)* 77:4216, (1980) ); mouse sertoli cells {TM4, Mather, J. P., *Biol. Reprod.* 23:243–251 (1980)); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather, J. P., et al., *Annals N.Y Acad. Sci.* 383:44–68 (1982)}; and $C_6$ glial cell (ATCC CCL 107).

Construction of suitable vectors containing the desired coding and control sequences employ standard ligation techniques. Isolated plasmids or DNA fragments are cleaved, tailored, and religated in the form desired to form the plasmids required.

For analysis to confirm correct sequences in plasmids constructed, the ligation mixtures are used to transform *E. coli* K12 strain 294 (ATCC 31446) and successful transformants selected by ampicillin or tetracycline resistance where appropriate. Plasmids from the transformants are prepared, analyzed by restriction and/or sequenced by the method of Messing et al., *Nucleic Acids Res.* 9:309 (1981) or by the method of Sanger et al., *Proc. Natl. Acad. Sci., (USA)*, 74:5463 (1977).

Host cells are transformed with the expression vectors of this invention and cultured in conventional nutrient media modified as appropriate for inducing promoters, selecting transformants or amplifying the genes encoding the desired sequences. The culture conditions, such as temperature, pH and the like, are those previously used with the host cell selected for expression, and will be apparent to the ordinarily skilled artisan.

The host cells referred to in this disclosure encompass cells in in vitro culture as well as cells which are within a host animal.

Diagnostic, Prognostic, and Monitoring Uses of BDV proteins and their derivatives Another aspect of the present invention presents assays for detecting ligands, e.g., in the biological samples of a test organism, which bind BDV protein(s) or derivatives thereof. These assays are useful as diagnostic tests for: (1) infection by BDV or related pathogenesis; and (2) neurologic and neuropsychiatric disease not due to BDV infection.

The preferred assays are immunoassays which detect antibodies to BDV proteins or its derivatives that are antigenic (herein referred to as "BDV antigen"). The test organism can be human or other animals, such as cats, fowls, ostriches, and horses. The biological samples may be biological fluids such as whole blood, serum, plasma, cerebral spinal fluid, or synovial fluid. Preferably, BDV proteins or its derivatives are used to detect the ligand by binding to it. Preferably, the ligand is an antibody directed to the polypeptides, and BDV antigens are used to detect the antibody. For example, the assay can be used to detect antibodies against BDV in biological fluids.

Alternatively, antibodies to BDV protein(s) or their derivatives can be used to screen for BDV proteins, e.g., in the biological samples of a test organism. Similarly, the alternative detection of antibodies or antigen applies to each of the assay formats described below.

Thus, an example of the assay is an enzyme immunoassay. In an example of a direct assay, these polypeptides serve as antigens and are attached to a solid phase and then incubated with patient sera. Human serum or plasma is preferably diluted in a sample diluent before incubation. If antibodies to BDV are present in the sample they will form an antigen-antibody complex with the polypeptides and become affixed to the solid phase.

After the antigen-antibody complex has formed, unbound materials and reagents are removed by washing the solid phase and the antigen-antibody complex is reacted with a solution containing labelled antibodies directed against the first type of antibody. For example, the labelled antibody can be horseradish peroxidase-labeled goat antibody. This peroxidase labelled antibody then binds to the antigen-antibody complex already affixed to the solid phase. In a final reaction the horseradish peroxidase is contacted with o-phenylenediamine and hydrogen peroxide which results in a yellow-orange color. The intensity of the color is proportional to the amount of antibody which initially binds to the polypeptide affixed to the solid phase.

Another assay format provides for an antibody-capture assay in which anti-immunoglobulin antibody on the solid phase captures the patient's antibody, which is then reacted with the BDV antigen. The application of this format is similar to the serological assay of Lyme disease taught in Berardi et al.,*J. Infect. Dis.* 158:754–760 (1988). If antibody to BDV is present, it captures the BDV antigen, and the bound BDV antigen is detected by means of labelled polyclonal or monoclonal antibodies directed against the BDV antigen. The antibody-capture assay is particularly useful for and can increase the sensitivity of detection of IgM and IgG to BDV antigens. In an example of this assay, the fluid sample is first contacted with a solid support containing a bound antibody capable of binding the mu-chain of IgM or the gamma-chain of IgG antibodies. Specific antibody is detected by reacting this with the BDV antigens followed by non-human antibody to the BDV antigens. The non-human antibody is generally labelled for detection. It is believed that this antibody-capture immunoassay format will have increased sensitivity, especially for IgM. Alternatively, one can forego the non-human antibody and instead label the BDV antigens for direct detection.

Another assay format provides for an immunodot assay for identifying the presence of an antibody that is immunologically reactive with specific BDV antigens by contacting a sample with the BDV antigens bound to a solid support under conditions suitable for complexing the antibody with the BDV antigens and detecting the antibody-antigen complex by reacting the complex.

Suitable methods and reagents for detecting an antibody-antigen complex in an assay of the present invention are commercially available or known in the relevant art. For example, the detector antibodies or polypeptides may be labelled with enzymatic, radioisotopic, fluorescent, luminescent, or chemiluminescent label. These labels may be used in hapten-labelled antihapten detection systems according to known procedures, for example, a biotin-labelled antibiotin system may be used to detect an antibody-antigen complex.

In all of the assays, the sample is preferably diluted before contacting the BDV antigen absorbed on a solid support. Solid support materials may include cellulose materials, such as paper and nitrocellulose; natural and synthetic polymeric materials, such as polyacrylamide, polystyrene, and cotton; porous gels such as silica gel, agarose, dextran and gelatin; and inorganic materials such as deactivated alumina, magnesium sulfate and glass. Suitable solid support materials may be used in assays in a variety of well known physical configurations, including microtiter wells, test tubes, beads, strips, membranes, and microparticles. A preferred solid support for a non-immunodot assay is a polystyrene microwell, polystyrene beads, or polystyrene microparticles. A preferred solid support for an immunodot assay is nitrocellulose or nylon membrane.

In particular, the invention presents an ELISA which is a rapid, sensitive, and inexpensive diagnostic test. The preferred ELISAs are based on recombinant BDV proteins recp40, recp23, and recp18. These assays are more sensitive and rapid than prior art methods employed for serologic diagnosis of infection, such as Western blot, indirect immunofluorescent test or immunoprecipitation.

Examples of the neurologic and neuropsychiatric diseases that can be diagnosed include diseases of the nervous system such as schizophrenia, depressive disorders (e.g., bipolar depression), multiple sclerosis and AIDS-related encephalopathy. The finding is based on applicants' analysis of the art. Although the virus has not been recovered from human subjects, antibodies reactive with BDV proteins have been found in patients with bipolar depression, schizophrenia, or AIDS-related encephalopathy {Bode, L., et al., *Arch. Virol. Suppl.,* 7:159–167 (1993); Bode, L., et al., *Lancet,* ii:689 (1988) and Rott, R., et al., *Science* 228:755–756 (1985)}. BDV has a unique tropism for specific brain regions. Viral nucleic acids and disease-specific proteins have been found in highest concentrations in the hippocampus and limbic circuits, prefrontal and cingulate cortices, and brainstem nuclei (Carbone, K., et al., *J. Neuropathol. Exp. Neurol.,* 50:205–214 (1991); Ludwig, H., et al., *Prog. Med Virol.* 35:107–151 (1988) and Solbrig, M. V., et al., abstr. 10, Abstr. 1992 Am. Acad. Neurol. Annu. Meet., (1992)). Three BDV proteins, p40, p23 and gp18 (disclosed in Example 2 below) have been identified in infected cells and tissues (Ludwig, H., et al., *Prog. Med Virol* 35:107–151 (1988) and Thiedemann, N., et al. , *J. Gen. Virol.,* 73:1057–1064 (1992)). cDNAs for p40 {Lipkin, W. I., et al., *Proc. Natl. Acad. Sci. USA,* 87:4184–4188 (1990); McClure, M. A., et al., *J. Virol.,* 66:6572–6577 (1992) and Pyper, J. M., et al., *Virology,* 195:229–238 (1993)} and p23 {Lipkin, W. I., et al., Proc. Natl. Acad. Sci. USA, 87:4184–4188 (1990); Thierer, J., et al., *J. Gen. Virol.,* 73:413–416 (1992) and VandeWoude, S., et al., *Science,* 250:1276–1281 (1990)) have been isolated, and complementary sequences to open reading frames (ORFs) for these proteins have been mapped to the viral genome {Briese, T., et al., *Proc. Natl. Acad. Sci USA* 91:4362–4366 (1994) which is incorporated into Example 1 of this application; and Cubitt, B., et al., *J. Virol.,* 68:1382–1996 (1994)).

The assay can also be used to monitor the diseases by monitoring the titer of such ligands. The titer of the ligands, and the specific viral proteins that it is immunoreactive with, can also be prognosticative of the diseases.

Thus, an application of this invention may involve contacting the test subject's biological sample, such as serum, with a panel consisting of different immunogenic fragments of BDV protein or its derivatives. These proteins may be synthetic or native proteins, though recombinant proteins are preferred. Such a panel may consist of, for example, recp23, recp40, recp57, recpol and recp18. If the serum is immunoreactive with at least one of the fragments, it indicates that the test subject may either be suffering from (1) BDV or related pathogenesis; or (2) neurologic and neuropsychiatric disease not due to BDV infection. Further, given a fixed amount of sample tested, the amount (i.e. percentage) of ligands immunoreactive with the BDV proteins may also be indicative of the severity of the disease and thus its prognosis. Generally, the higher the percentage of ligands that are immunoreactive, the more severe the disease and the poorer the prognosis. Thus, the assay may also be used to monitor the progress of the disease. In particular, if the test subject is undergoing treatment for the disease, the assay may be used to monitor the efficacy of the drug and treatment regimen. Such monitoring may involve assaying for the ligand titer and/or the specific BDV immunogenic epitopes which the ligand binds to.

Hybridization Diagnostic Assays

Oligonucleotides ("probes") that are unique, or relatively unique to BDV in a test sample, are useful for diagnosing BDV infections. Nucleotide hybridization assay may be used, whereby nucleic acids from a patient's biological sample are contacted to the primers or BDV restriction fragments under hybridization condition, and the hybridization products are detected. This method could be used to detect viral genomic RNA or mRNA. Conventional Western or Northern Blot analysis, RT-PCR or PCR and ligase chain reaction (LCR) may be used as the basis of the assay, these techniques are known to those skilled in the art. PCR and LCR techniques are widely available in the art. For example, the basic PCR techniques are described in U.S. Pat. Nos. 4,683,202; 4,683,195; 4,800,159; and 4,965,188. The basic LCR techniques are described in EPA-320,308; EPA-439, 182; EPA-336,731; WO 89/09835; WO 89/12696, and WO 90/01069.

Since the present invention presents the full nucleotide sequence of the genomic BDV nucleotide sequence, these probes can be identified by comparing this sequence with the sequences of other organisms which may contaminate a test sample. Such comparison can be conducted as described in Example 1 below or using methods known in the art. The probes preferably contain at least 10 contiguous nucleotides or at least 30 contiguous nucleotides with at least 60% homology along the length of the BDV nucleotide sequence being compared. Examples of such probes and methods for conducting the PCR for detection are as described in Examples 1 and 2.

Assay Kits

The present invention also encompasses immunoassay kits containing BDV antigen(s), preferably each antigen per container, in a concentration suitable for use in immunoassay. In the kits, the BDV antigens may be bound to a solid support and where needed, the kits may include sample preparation reagents, wash reagents, detection reagents and signal producing reagents.

Also included are assay kits for nucleotide hybridization assays which include probes which are specific for BDV or its derivatives. The kits may also include sample preparation reagents, wash reagents, detection reagents and signal producing reagents.

Therapeutic Uses of Antibodies Directed to BDV proteins and Their Derivatives

Another aspect of the invention presents methods, using antibodies directed to BDV proteins, for treating: (1) BDV infection or related pathogenesis; and (2) neurologic and neuropsychiatric disease not due to BDV infection. Examples of such antibodies are those specific to gp18 and p57. The antibodies may be administered using methods known in the art. Preferably, this involves passive administration of these antibodies, such as those described in Example 4.

Peptides Useful For Diagnostics and Therapeutics

Another aspect of the invention presents peptides containing at least one BDV immunoepitope. These peptides can be used in diagnostic assays to detect the presence of a patient's antibodies agaisnt BDV. Thus, the peptides are useful for the assays described in the section: "*Diagnostic, Prognostic, and Monitoring Uses of BDV proteins and their derivatives*". For example, as shown in Example 3 below, recp40, recp23, and recp18 have proved useful for detecting BDV infections. Thus, the epitopes of these recombinant proteins can be mapped, and smaller peptides containing these epitopes and routinely tested for their immunoreactivity with antibodies to BDV, e.g. using the ELISA method shown in Example 3.

The above peptides can also be used to raise antibodies that may serve as therapeutics against BDV infections such as shown in Example 4 and as described in the section: "*Therapeutic Uses of Antibodies Directed to BDV proteins and Their Derivatives*". Examples of methods for synthesizing peptide fragments are described in Stuart and Young in "Solid Phase Peptide Synthesis", 2nd ed., Pierce Chemical Co. (1984). It is contemplated that antibodies which precipitate BDV viral particles would be useful for therapeutic uses. In particular, these antibodies are raised against proteins, and their fragments, expressed on the surface of BDV. It is further contemplated that antibodies against gp18, p57 and their fragments, especially antibodies that precipitate BDV viral proteins would be useful for treating or preventing the disease (1) BDV infection or related pathogenesis; and (2) neurologic and neuropsychiatric disease not due to BDV infection.

Thus, fragments of BDV proteins, in particular gp18 and p57 and their fragments, can be made starting from either end of their C-termini and $NH_2$-termini. For example, these fragments can be tested according to the ELISA method shown in Example 3 against, e.g. sera from horses, rats, or human patients infected with BDV. The fragments that react with the sera would be useful for detecting the disease and would be useful for raising therapeutic antibodies to treat the disease. Since different animals may react to different epitopes of BDV proteins, one may even tailor the screening test by using the serum from the same species of animal for which one seeks to develop an assay or therapeutic. For example, if one is seeking a diagnostic test or therapeutic for humans, the sera tested will be preferably that from human patients. Included in this invention are other methods, known in the art, for identifying the immunoreactive epitopes of a protein and raising antibodies thereto. Further, since antibodies which are immunoreactive with BDV protein may also be found in the sera of patients with neurologic and neuropsychiatric disease not necessarily due to BDV infection, the above peptides and antibodies raised thereto may also find usefulness in diagnosing, monitoring and treating these patients. Additionally, these peptides may be identified by their immunoreactivity with sera from patients suffering from neurologic and neuropsychiatric disease not due to BDV infection. Thus, as described in this application, the disease, patient sera to be tested, the diagnostic, monitoring and therapeutic uses are not limited to BDV, and include (1) BDV infection or related pathogenesis; and (2) neurologic and neuropsychiatric disease not due to BDV infection. Further, one can screen for therapeutic ligands or chemicals which bind these peptides. These therapeutic chemicals then may be tested for their therapeutic effect against the above diseases. Other ligands or chemicals which bind the therapeutic ligands or chemicals can be tested for their ability to bind patients' antisera or antibodies and are thus useful as diagnostics for the diseases.

Preferably, the above peptides and antibodies are also respectively tested for their crossreactivity with antibodies raised by and proteins from organisms unrelated to the above diseases but commonly found in the test sample (e.g. patient's biological sample). Peptides and antibodies that are highly non-specific are preferably not used. To obtain peptides of high specificity, one may also compare the amino acid sequence of BDV protein with that of known contaminating proteins in the test sample. The fragments that are unique, or relatively so, to BDV are then chosen for further screening as described above, e.g. for immunoreactivity with patient's test sample. These comparison can also be done on the nucleotide sequence level.

Method for Producing Antibodies to BDV and its Derivatives

Besides whole immunoglobulins, antibodies herein include antigen binding fragments of the immunoglobulins. Examples of these fragments are Fab, F(ab')2 and Fv. Such fragments can be produced by known methods. Unless otherwise indicated, antibodies herein also include: polyclonal and monoclonal antibodies, monospecific antibodies, and antisera which includes monospecific antisera.

Antibodies to BDV proteins and their derivatives can be produced using standard procedures known in the art. For example, antibodies can be produced by inoculating a host animal such as a rabbit, rat, goat, mouse, etc., with BDV proteins and their derivatives. Before inoculation, the polypeptides or fragments may be first conjugated with keyhole limpet hemocyanin (KLH) or bovine serum albumin (BSA). After an appropriate time period for the animal to produce antibodies to the polypeptides or fragments, the anti-serum of the animal is collected and the polyclonal antibodies separated from the anti-serum using techniques known in the art. Monoclonal antibodies can be produced by the method described in Kohler and Milstein (*Nature,* 256:495–497, 1975) by immortalizing spleen cells from an animal inoculated with the polypeptides or fragments thereof. The immortalization of the spleen cell is usually conducted by fusing the cell with an immortal cell line, for example, a myeloma cell line, of the same or different species as the inoculated animal. The immortalized fused cell can then be cloned and the cell screened for production of the desired antibody.

The antibodies may also be recombinant monoclonal antibodies produced according to the methods disclosed in Reading, U.S. Pat. No. 4,474,893, or Cabilly et al., U.S. Pat. No. 4,816,567. The antibodies may also be chemically constructed according to the method disclosed in Segel et al., U.S. Pat. No. 4,676,980.

While the invention is demonstrated using mouse monoclonal antibodies and rat monospecific antisera, the invention is not so limited. In fact, human antibodies may be used and may prove to be preferable. The latter is especially so if the antibodies are used as therapeutics for humans, as there would be less immunorejection from the human patients receiving these antibodies. Such antibodies can be obtained by using human hybridomas (Cote et al., Monoclonal Antibodies and Cancer Therapy, Alan R. Liss, p. 77 (1985)). In fact, according to the invention, techniques developed for the production of chimeric antibodies (Morrison et al., Proc. Natl. Acad. Sci., 81:6851 (1984); Neuberger et al., Nature, 312: 604 (1984); Takeda et al., Nature, 314: 452 (1985)) by splicing the genes from a mouse antibody molecule of appropriate antigen specificity together with genes from a human antibody molecule of appropriate biological activity (such as ability to activate human complement and mediate antibody-dependent cell-mediated cytotoxicity) can be used; such antibodies are within the scope of this invention.

VACCINE

By providing the nucleotide and amino acid sequences of the BDV genome and BDV proteins, respectively, this application enables the production of recombinant BDV (e.g. using the technique shown in Schnell, M. J., EMBO J., 13: 4195–4203 (1994)) which can then be attenuated, e.g. by mutagenesis, heat or formaldehyde treatment, to be used as vaccine against (1) BDV infection or related pathogenesis; and (2) neurologic and neuropsychiatric disease not due to BDV infection. BDV sequences, their mutagenized sequences or fragments thereof, may be directly injected or incorporated into a plasmid and injected into patients. The injections may be by means of a gene gun. gp18, p57, pol, and proteins produced by the mutagenized or fragmented sequences may also serve as vaccines. Proteinaceous vaccines may be delivered orally, intravenously, intraperitoneally, or intramuscularly. The vaccine may also be contained in a physiologically compatible solution.

BDV Viral Vector Based Delivery System

Another aspect of the invention presents: (A) a BDV-mediated gene transfer for the incorporation and expression of eukaryotic or prokaryotic foreign genes into another eukaryotic or prokaryotic host; and (B) an in vitro BDV-mediated delivery of gene(s) or chemical(s) to a target cell.

In Method A, one or more desired genes are inserted into the BDV viral vector. The desired gene transfer can be achieved through in vitro transfection of a cell or cell line by the resulting BDV viral vector. The transfected cell or cell line thus expresses the gene(s) of interest and the expression product(s) are harvested. Alternatively, the transfected cell or cell line is later transplanted into a host, e.g. an animal such as a human, in need of the gene product(s). In this case, the gene(s) is expressed in vivo. The generation of infectious non-segmented, neurotropic, negative-stranded RNA virus entirely from cloned cDNA, has been described in the case of rabies virus {Schnell, M. J., et al., EMBO J., 13(18): 4195–4203 (1994)). The insertion of foreign gene(s) into the BDV viral vector is based on prior art teachings for other viral vectors, which may include insertion of promoters or regulators to control expression of the foreign gene(s). The transfection and gene therapy is similarly based on prior art teaching for viral vectors. Such teachings abound, see e.g., U.S. Pat. No. 5,219,740 to Miller et al., Jun. 15, 1993; U.S. Pat. No. 5,256,553 to Overell, Oct. 26, 1993; and WO 91/12329, assigned to Board of Regents, the University of Texas System, international publication date, Aug. 22, 1991.

Method B utilizes the unique tropism of BDV for specific regions and cells of the nervous systems, e.g. neural cells. Thus, BDV vector can be used for in vivo delivery of chemicals or desired genes to these regions. For example, infectious recombinant BDV containing the gene of interest can be used to infect the specific target cells of BDV in a host animal. The host can be a human suffering from deficiency, lack of, or a malfunctioning of the gene product. The general gene therapy methods can be based on prior art teaching e.g. the references cited for Method A, such as WO 91/12329. In the case of BDV viral vectors, these genes can be those responsible for the survival, proliferation, and proper functioning of the nervous system. For example, in neurodegenerative diseases, the cells in the patients' nervous system suffer premature death, and these cells are not regenerated, eventually causing the patients to die. The inserted gene(s) may supplement or replace the dysfuntional gene(s) in these patients to provide gene product(s) necessary for continued survival and proliferation of these cells. Examples of the inserted genes include genes coding for: neurotransmitters, cytokines, growth factors, receptors for the foregoing, enzymes for activation of therapeutic drugs administered to the patients.

Alternatively, the viral vector may contain a nucleotide sequence coding for a toxin. These vectors would infect the host's cells in vivo, express the toxin and kill the infected cells. The targeted cells are preferably neoplastic cells, or cells infected by or harboring pathogenic organisms. The vector is preferably further designed to selectively target these cells over normal cells. One means to target the desired cells is by localized injection of the recombinant virus, containing the desired gene, near the target of interest. However, for BDV based gene therapy, the vector or recombinant virus may be delivered peripherally, i.e. into subcutaneous tissue, peripheral nerve, or intramuscularly. The neurotropism of the recombinant virus allows it to migrate towards cells of the nervous system to transfect or infect them.

The BDV viral vector is an especially good vehicle for gene therapy and in vivo chemical delivery. It has several advantages over the viral vectors known in the art, the most common of which are retroviral vectors. Retroviral vectors require replication of its host cells for transfection. Therefore, retroviral vectors can only be used with dividing/mitotic cells. In contrast, BDV vectors are autonomous, self-replicating vectors and thus can transfect both dividing and non-dividing cells. Thus, BDV is particularly effective for transfecting nerve cells that normally do not divide and for which BDV is tropic.

Further, BDV does not have a latent stage in its lifecycle, after transfecting a host cell. It thus will continue to express the desired gene once it has transfected a cell. This is unlike some viral vectors currently used in the art, such as the herpes viral vector that may enter a latent stage after transfection and thus not express the desired gene product in the transfected cell. BDV is also unique in that it is a slow growing virus and is not lytic. Thus, chances of the virus lysing and killing the host cells are nonexistent.

As a further safeguard, the BDV viral vectors may be made infective but replication-defective, rendering them useful vectors which are unable to produce infective virus, following introduction into a cell. For initiation of productive infection of BDV, a nucleocapsid containing BDV genomic RNA is required, from which primary transcription of mRNAs and ensuing autonomous and regulated expression of all BDV proteins occurs. Thus, to render the viral vector replication-defective, one may mutate the nucleocapsid protein produced by recombinant virus to prevent encapsidation of newly synthesized genomic RNA. Additionally, the host cell should preferably be devoid of infectious helper virus which may assist in replication of the BDV.

Further, unlike retroviruses and herpes viruses, BDV does not cause disease in and of itself. The deleterious effect of BDV infection is actually caused by the host's immune-mediated rejection of BDV and BDV antigen expressed on infected cells. The rejection involves cellular immune response which activates the host's effector lymphocytes which then kill the transfected cells. Antibodies appear not to be as important in the host's immune response. Thus, one means to avoid Borna disease is to interfere with, avoid, or suppress the host's ability to recognize or mount an immune response to BDV infected cells. For example, immune response in the host is triggered when T lymphocytes recognize a complex of major histocompatibility complex (MHC) and foreign antigen (in this case, BDV proteins) expressed on the host cell's surface. Thus, to reduce the host's immune response, one may choose to interfere with or prevent the expression of MHC on the transfected cells. This may be achieved by inserting, into the BDV viral vector, a nucleotide sequence which codes for a mRNA (i.e. an antisense mRNA) which would bind the mRNA coding for the component of MHC ("mRNA$_{MHC}$") and prevent the translation and expression of MHC in the transfected cell. Absent MHC, the BDV antigens will not be presented on the host cell surface to trigger immune-mediated rejection in the host. Alternatively, other methods known in the art may be used to avoid the immune rejection of BDV transfected cells.

EXAMPLE 1

Cloning and Sequencing of Genomic RNA from Borna Disease Virus (BDV) Particles

The studies in this example and Example 2, except with regard to p57, are also described in Briese, T., et al., *Proc. Natl. Acad. Sci, USA,* 91:4362–4366 (1994) and Kliche, S., et al., *J. Virol.,* 68: 6918–6923 (1994), respectively, both of which are hereby incorporated by reference in their entirety. In this example, the BDV genome was cloned to reveal antisense information for five open reading frames (ORFs). From 5' to 3' on the antigenome, the ORFs are p40, p23, gp18, p57 and pol. Proteins p40, p23 and gp18 have been identified in infected cells and tissues: p40 and p23 are expressed at high levels in vitro and in vivo and are found in the nucleus and cytoplasm of infected cells (Bause-Niedrig, I., M. et al., *Vet. Immunol. Immunopathol.,* 31:361–369 (1992)). gp 18 is a membrane-associated glycoprotein that is expressed at lower levels. gp18 was characterized in Example 2 below.

Messenger RNAs (Kliche, S., et al., *J. Virol.,* 68: 6918–6923 (1994); Lipkin, W. I., et al., *Proc. Natl. Acad. Sci. USA,* 87:4184–4188 (1990); McClure, M. A., et al., *J. Virol.,* 66:6572–6577 (1992); Pyper, J. M., et al., *Virolog,* 195:229–238 (1993); Thibault, K. J., M. S. thesis; University of California, Irvine (1992); Thierer, J., et al., *J. Gen. Virol.,* 73:413–416 (1992) and VandeWoude, S., et al., *Science,* 250:1278–1281 (1990)) and proteins (Bause-Niedrig, I., et al., *Vet. Immunol. Immunopathol.,* 31:361–369 (1992); Haas, B., et al., *J. Gen. Virol.,* 67:235–241 (1986); Ludwig, H., et al., *Progr. Med. Virol,* 35:107–151 (1988); Schädler, R., et al., *J. Gen. Virol.,* 66:2479–2484 (1985) and Thiedemann, N., et al.,*J. Gen. Virol.,* 73:1057–1064 (1992)} corresponding to three of these ORFs, p40, p23 and gp18, have been found in infected cells and tissues in a 5'-3' expression gradient (p40>p23>gp18) {Briese, T., et al., *Proc. Natl. Acad. Sci. USA:* 91:4362–4366 (1994); Cubitt, B., et al.,*J. Virol.,* 68:1382–1396 (1994); and Richt, J. A., et al., *J. Gen. Virol.,* 72:2251–2255 (1991)}.

Though Cubitt, B., et al., *J. Virol.,* 68:1382–1996 (1994) purported to have sequenced the BDV genome, their paper contains numerous errors. The errors included (1) failure to recognize deletions in subgenomic RNAs due to splicing; (2) misplacement of ORFs leading to the prediction of a 40 kD protein instead of a 57 kD protein and failure to detect ORF overlap of p57 with gp18 and pol; and (3) selection of incorrect motifs for initiation of a transcription. These mistakes were implicitly acknowledged in a subsequent paper, de la Torre, J. C.,*J. Virol.,* 68:7669–7675 (1994). FIG. 1 of the latter paper incorporated the correct genomic organization and transcription map described in Example 1 of this application.

In this Example, the 8,910 nucleotide BDV viral genome was cloned and sequenced using RNA from BDV particles. The viral genome has complementary 3' and 5' termini and contains antisense information for five open reading frames. Homology to Filo-, Paramyxo- and Rhabdoviridae is found in both cistronic and extracistronic regions. Northern analysis indicates that the virus transcribes mono- and polycistronic RNAs and uses termination/polyadenylation signals reminiscent of those observed in other negative-strand RNA viruses. BDV is likely to represent a previously unrecognized genus, bornaviruses, or family, Bornaviridae, within the order Mononegavirales.

MATERIALS AND METHODS

BDV cDNA Library Preparation and Screening

Genomic RNA template for library construction was obtained from an oligodendrocyte cell line (Oligo/TL) acutely infected with BDV Strain V (Briese, T., et al., *Proc. Natl. Acad. Sci. USA* 89:11486–11489 (1992)). For the first genomic library, RNA from one viral particle preparation was polyadenylated with poly(A) polymerase (GibcoBRL, Life Technologies, Inc., Grand Island, N.Y.) to facilitate cloning from the 3' terminus by oligo d(T) primed cDNA synthesis. Libraries were prepared in pSPORT using the SuperScript Plasmid system (GibcoBRL, Life Technologies, Inc., Grand Island, N.Y.). The first library was screened using pAB5 and pAF4 radiolabeled restriction fragments (Lipkin, W. I., et al., *Proc. Natl. Acad. Sci. USA* 87:4184–4188 (1990)}. Subsequent libraries were screened using radiolabeled restriction fragments from locations progressively 5' on the genomic RNA. 5'-terminal sequence from each library was used to design an oligonucleotide primer for construction of the next library.DNA sequencing and sequence analysis. Plasmid DNA was sequenced on both strands by the dideoxynucleotide chain termination method {Sanger, F., et al., *Proc. Natl. Acad. Sci. USA* 74:5463–5467 (1977)} using bacteriophage T7 DNA polymerase (Sequenase version 2.0; United States Biochemical, Cleveland, Ohio). Five to ten independent clones from each library were sequenced with overlap so that each region of the genomic RNA was covered by at least two clones. Four libraries were analyzed yielding ≈8.9 kb of continuous sequence. Nucleic acid sequence was analyzed using the Sequence Analysis Software Package (Genetics Computer, Inc., Madison, Wis.). Database searches for related sequences and multiple sequence alignments were performed using FastA and Pileup.

Sequence Determination at the 3' and 5' Termini of BDV Genomic RNA. Genomic RNA from one viral particle preparation (1–2×10$^8$ cells) was treated with tobacco acid pyrophosphatase (Epicentre Technologies, Madison, Wis.) and circularized with T4 RNA ligase (New England Biolabs, Inc., Beverly, Mass.) {Mandl, C. W., et al., *BioTechniques*

10:484–486 (1991)}. The ligated RNA was reverse transcribed with Superscript II (Gibco BRL, Life Technologies, Inc., Grand Island, N.Y.) using primer 5'-GCCTCCCCTTAGCGACACCCTGTA (SEQ ID NO: 11), complementary to a region 465 nucleotides (nt) from the 5' terminus of the BDV genome. A 2 µl aliquot of the reverse transcription reaction was used to amplify the ligated region by the polymerase chain reaction (PCR) using Stoffel fragment (Perkin-Elmer Cetus, Norwalk, Conn.). Primers used in the first round of PCR were 5'-GCCTCCCCTTAGCGACACCCTGTA (SEQ ID NO: 11) and 5'-GAAACATATCGCGCCGTGCA (SEQ ID NO: 12), located 241 nt from the 3' terminus of the BDV genome. Amplified products were subjected to a second round of PCR using a nested set of primers: 5'-TACGTTGGAGTTGTTAGGAAGC (SEQ ID NO: 13), 251 nt from the 5' terminus, and 5'-GAGCTTAGGGAGGCTCGCTG (SEQ ID NO: 14), 120 nt from the 3' terminus. PCR products were cloned (Schneider, P. A., et al., *J. Virol.* 68:63–68 (1994)} and sequence across the 5'/3' junction was determined from five independent isolates.

Northern hybridization. Poly(A)+ enriched RNA extracted from acutely infected rat brain using FastTrack (Invitrogen Corp., San Diego, Calif.) was size-fractionated on 0.22M formaldehyde/1.0% agarose gels {Tsang, S. S., et al., *Bio-Techniques* 14:380–381 (1993)}, transferred to Zeta-Probe GT nylon membranes (Bio-Rad Laboratories, Richmond, Calif.) and hybridized with random-primed 32P-labeled restriction fragments {Feinberg, A. P., et al., *Anal. Biochem.* 132:6–13 (1983)} representing ORFs across the BDV genome (FIG. 6 b). RNA transfer, hybridization and washing were performed following the manufacturer's protocol (Bio-Rad Laboratories, Richmond, Calif.).

RESULTS

Figure 3A:
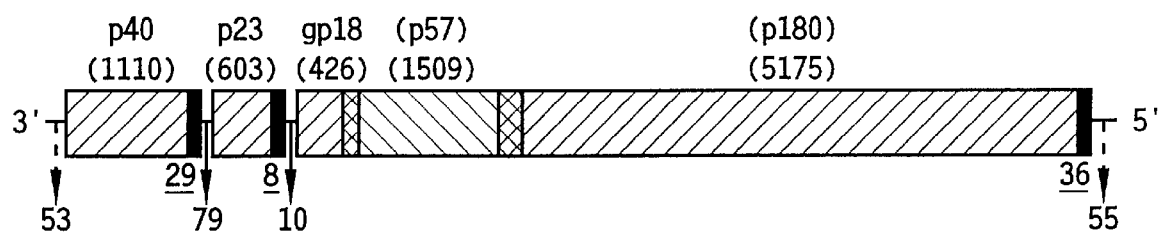
FIG. 3 (a) presents the organization of the BDV genome; (b) presents the coding potential of the genome.
Figure 3B:
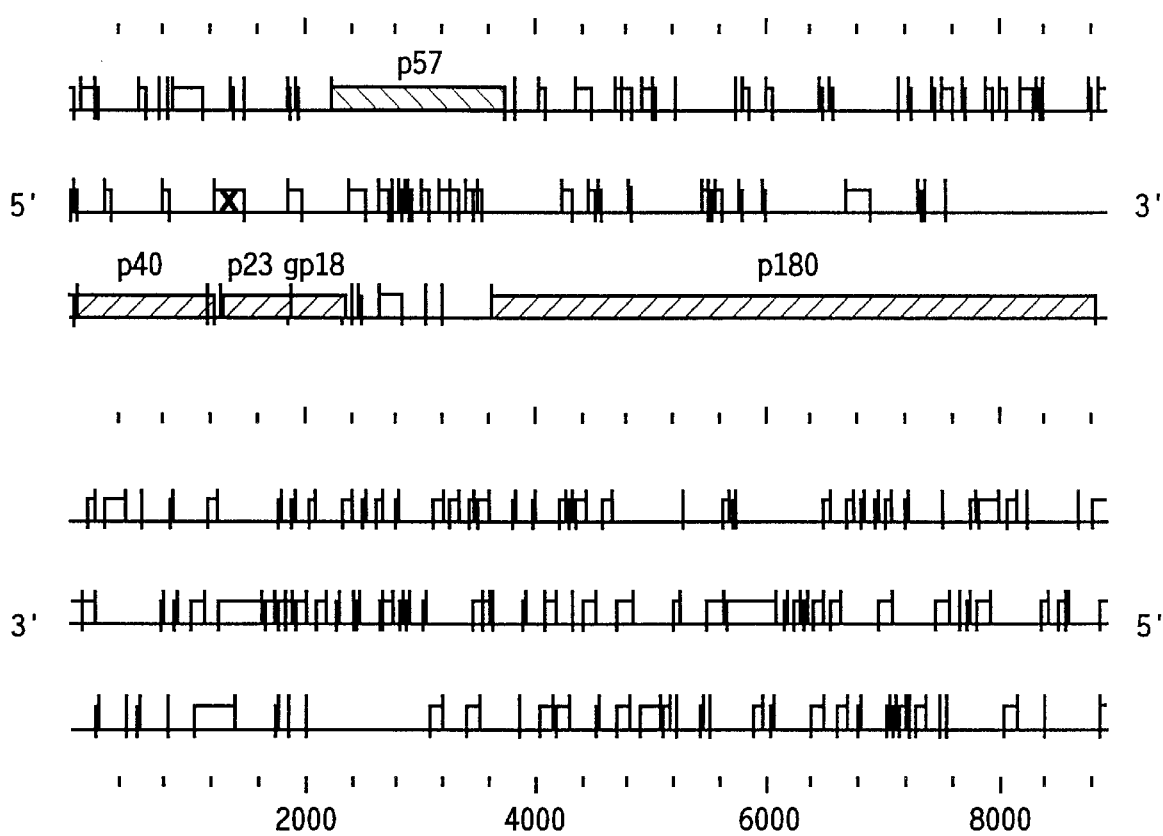

The following figures present some of the results:

FIG. 3. (a) Organization of the BDV genome. Hatched boxes represent coding sequence complementary to ORFs for identified proteins, p40, p23, gp18, or putative proteins, p57, p180. (p180 is also referred to as pol.) Overlap is indicated by cross-hatched areas. Length of coding sequence corresponding to ORFs in nucleotides is indicated in brackets. Underlined italic numbers indicate length of sequence from stop codon complement to last templated uridine of termination/polyadenylylation signal (black boxes). Italics with arrow indicate number of nucleotides in intervening sequence between p40 polyadenylylation signal and p23 coding sequence and between p23 polyadenylylation signal and gp18 coding sequence, respectively. Italics with dashed arrow indicate number of noncoding nucleotides at termini of the genome. (b) Coding potential of genome. Genomic sequence was translated in all six possible reading frames (3'-5' negative sense; 5'-3' positive sense) by using FRAMES (Genetics Computer Group). ORFs are indicated by bars and hatched boxes.

FIG. 4. Alignment of the p180 (pol) ORF and negative-strand RNA virus L-polymerase amino acid sequences with PILEUP. Solid lines indicate conserved L-polymerase motifs (a, A, B, C, D). BDV sequence (amino acide 377 to 829 of SEQ ID NO:10) is indicated with double arrowheads. Rhabdoviridae: RaV, rabies virus (SEQ ID NO:21); VSV, vesicular stomatitis virus (SEQ ID NO:22); SYN, sonchus yellow net virus (SEQ ID NO:23). Paramyxoviridae: MeV, measles virus (SEQ ID NO:24); SeV, Sendai virus (SEQ ID NO:25); NDV, Newcastle disease virus (SEQ ID NO:26); RSV, respiratory syncytial virus (SEQ ID NO:28). Filoviridae: MaV, Marburg virus (SEQ ID NO:27). Numbers indicate amino acid range shown. Uppercase letters in viral sequence lines indicate residues conserved in more than six sequences. Uppercase letters in consensus line (Con) indicate presence of identical or conserved amino acids in BDV. Agreement of BDV sequence with either rhabdo- or paramyxoviruses is indicated by * or x, respectively. +, Nonconserved glycine residue in BDV.

FIG. 5. Sequence analysis of BDV genomic termini. (a) Similarity of 3'-terminal BDV sequence to leader Rhabdoviridae: RaV (SEQ ID NO:35) and VSV (SEQ ID NO:36); Paramyxoviridae: MeV (SEQ ID NO:34), SeV (SEQ ID NO:32), NDV (SEQ ID NO:33), and RSV (SEQ ID NO:29); and Filoviridae: MaV (SEQ ID NO:31) and Ebola virus (EboV, SEQ ID NO:30). Sequences are aligned by using arbitrary gap insertion to optimize nucleotide matching. (b) Comparison of complementarity at 3' and 5' termini of BDV genomic RNA with that of four other nonsegmented, negative-strand RNA viruses. The 3' and 5' terminal sequences for each virus are shown in viral RNA (3'-5', negative sense) orientation. Underlined sequence refers to transcriptional start of first gene or end of the L-polymerase gene (also referred to as "pol gene"), respectively (predicted for BDV). The end of the L-polymerase gene of RaV is located outside the region shown.

FIG. 6. Map of BDV subgenomic RNAs relative to the viral antigenome. (a) Northern hybridization analysis of rat brain poly(A)+ RNA. Each lane was hybridized with a probe representing a major BDV ORF as indicated by the letters A-E (see b). Results of hybridization with probes C* and E* were identical to results of hybridization with probes C and E, respectively (data not shown). Numbers at left indicate size of RNA markers in kilobases. Numbers at right indicate estimated size of major transcripts. (b) Position of viral transcripts with respect to antigenome as determined by Northern hybridization and sequence analysis. Dashed lines indicate regions in the 1.5-kb RNA and the 6.1-kb RNA that contain a deletion. The boundaries of the deletions are not known. Relative positions of probes used for Northern hybridization are shown. On the ORF map, potential start codons are indicated with upward lines; ◇, start codons predicted to be functional; x, potential start codon present in strain V that is absent in strain He/80 (see text). Potential termination sites are indicated with downward lines. Use of T2 and T3 has been confirmed {McClure, M. et al.,*J. Virol.*, 66:6572–6577; Thierer, J. et al.,*J. Gen. Virol.*, 73:413–416}; use of T5 and T7 is consistent with hybridization results. Termination at t1, t4 and t6 has not been observed (see a). (c) Alignment of the seven potential termination sites of BDV. Location of sites is indicated in the ORF map. Stop codons are underlined. Lowercase letters indicate termination/polyadenylylation consensus sequence. No termination/polyadenylylation site was found at or near the end of the gp18 ORF.

Sequencing of Genomic BDV RNA

Beginning from the 3' terminus, a series of four overlapping cDNA libraries was constructed using BDV particle RNA {Briese, T., et al., *Proc. Natl. Acad. Sci. USA* 89:11486–11489 (1992)} as template. Previous studies have shown that the genomic RNA is not polyadenylated {de la Torre, J., et al., *Virology* 179:853–856 (1990)}. Thus, to construct the first library, genomic RNA was polyadenylated in vitro in order to facilitate oligo d(T)-primed cDNA synthesis. For the subsequent three libraries, genome-complementary oligonucleotide primers were designed based on 5' terminal sequence determined in the previous round of cloning. Each region of the genome was sequenced using a minimum of two independent clones. To determine the sequences at the termini, genomic RNA was circularized and sequenced across the junction using five independent clones.

The 8,910 nt BDV genome contained antisense information for five major ORFs flanked by 53 nt of noncoding sequence at the 3' terminus and 91 nt of noncoding sequence at the 5' terminus (FIG. 3). In 3'–5' order, the first two ORFs encoded two previously described viral proteins, p40 {McClure, M. A., et al., *J. Virol.* 66:6572–6577 (1992)} and p23 {Thierer, J., et al., *J. Gen. Virol.* 73:413–416 (1992)}. The third, fourth and fifth ORF had coding capacities of 16 kDa (gp18), 57 kDa (p57) and 190 kDa (p180), respectively (FIG. 3*a*). Note: p180 is now known as "pol". Predicted amino acid sequence for the 16 kDa ORF correlated with microsequence data for an 18 kDa BDV glycoprotein (see the section below for gp18 glycoprotein), originally described as the Borna disease-associated 14.5 kDa protein (Schadler, R., et al., *J. Gen. Virol.* 66:2479–2484 (1985)). The first three ORFs showed no overlap and were in frame with the fifth ORF (FIG. 3*b*). The 57 kDa ORF was in a +1/−2 frame relative to the other four ORFs and overlapped the adjacent ORF for gp18 by 28 amino acids and ORF p180 by 34 amino acids. All ORFs were located on the (+) strand, complementary to the genomic RNA. ORF analysis of the genomic (−) strand showed only three small ORF's, each with a coding capacity of less than 16 kDa (FIG. 3*b*).

Homology analysis of coding sequence

Predicted amino acid sequence for the identified ORFs was used to examine databases for similarity to other proteins. Previous analysis of the ORF encoding p40 had revealed distant sequence similarity to L-proteins of Paramyxoviridae and Rhabdoviridae {McClure, M. A., et al., *J. Virol.* 66:6572–6577 (1992)}. FastA analysis of translated sequence from ORFs p23, gp18 and p57 showed no apparent similarity to other viral sequences; however, ORF p180 sequence consistently retrieved L-polymerases of Paramyxo- and Rhabdoviridae. Alignment of ORF p180 (pol) sequence with sequence of RNA-dependent RNA polymerases of negative-strand RNA viruses showed conservation of both sequence and linear order of regions homologous among these proteins. Extensive conservation was found in the four characteristic motifs for L-polymerases of negative-strand RNA viruses (A–D in FIG. 4) {Poch, O., et al., *EMBO J.* 8:3867–3874 (1989) and Poch, O., et al., *J. Gen. Virol.* 71:1153–1162 (1990)}. With the exception of the glycine residue in motif B (position 322 of the alignment), conservation was found for the individual amino acid residues postulated to participate in polymerase function {Poch, O., et al., *EMBO J.* 8:3867–3874 (1989)}. Conservation was also found for a motif (a in FIG. 4) proposed to participate in template recognition {Poch, O., et al., *J. Gen. Virol.* 71:1153–1162 (1990) and Barik, S., et al., *Virolog* 175:332–337 (1990)}. The GCG/pileup alignment placed ORF p180 sequence between polymerases of Paramyxo- and Rhabdoviridae. This intermediate position is reflected by the presence of conserved amino acids which are in agreement with either the rhabdo- or the paramyxovirus sequences (* or x, respectively; FIG. 4). The distance between conserved motifs a and A was found to be short in BDV as it is in rhabdoviruses, whereas this region is highly variable in length and sequence among paramyxoviruses {Poch, O., et al., *J. Gen. Virol.* 71:1153–1162 (1990)}. The GCG/pileup generated dendrogram, obtained using complete ORF p180 and L-protein sequences, indicated that the putative BDV polymerase was more closely related to L-polymerases of Rhabdoviridae than Paramyxoviridae.

Analysis of Noncoding Sequence at the Genomic Termini

3' terminal genomic sequence had a high A/U content of 60.5% with an A to U ratio of ≈1:2, similar to 3' leader sequences of other negative-strand RNA viruses. At the extreme 3' end, filo-, paramyxo- and rhabdoviruses have a common G/U rich region (FIG. 5*a*). In BDV, as in respiratory syncitial virus, rabies virus and filoviruses, this region was not located at the 3' extremity. Comparison of the 3' and 5' termini of BDV genomic RNA revealed complementarity similar to that found in other negative-strand RNA viruses {Keene, J. D., et al., *J. Virol.* 32:167–174 (1979) and Tordo, N., et al., *Virology* 165:565–576 (1988)} (FIG. 5*b*). Alignment of the genomic termini allowed formation of a terminal panhandle, with the first three nucleotides unpaired. The subsequent complementary area of 6 nucleotides (positions 4–9 and 8907–8902) could be extended by one gap insertion between position 8901/8,902 resulting in an additional 10 nt stretch of complementarity with a single mismatch (positions 18 and 8994; FIG. 5*b*).

Identification of Potential Termination/ Polyadenylation Sites

Sequence preceding the poly(A) tracts of two cloned BDV mRNAs ($UA_5$) {McClure, N. A., et al., *J. Virol.* 66:6572–6577 (1992) and Thierer, J., et al., *J. Gen. Virol.* 73:413–416 (1992)} was used to analyze genomic sequence for homologous sites that could serve as potential termination/polyadenylation signals. Seven sites were found (FIG. 6*c*). Northern hybridization experiments supported use of four of these sites (T2, T3, T5 and T7) and allowed identification of a termination/polyadenylation signal consensus sequence ($CMNMYYMNWA_6$) (SEQ ID NO:45), where M is A or C, Y is C or U, and W is A or U. Only one of the three remaining sites (t6) matched the consensus sequence (FIG. 6*c*).

Northern Hybridization Analysis

Restriction fragments representing the five ORFs were used as probes for hybridization to $poly(A)^+$ enriched RNA isolated from acutely infected rat brain by FastTrack (FIG. 6*a* and *b*). Because this procedure does not entirely eliminate poly(A) RNAs, small levels of BDV genome-size RNA can usually be detected in these preparations. To allow determination of the relative abundance of RNAs detected by each probe, exposure times were normalized to the signal of the 8.9-kb RNA. Consistent with the 3' to 5' transcriptional gradient found for other negative-strand RNA viruses, of the eight subgenomic RNAs identified, those detected by the 3'-most probes (genomic orientation), A and B, were more abundant than those detected by the more 5' probes (FIG. 6*a* and *b*).

Mapping of the eight transcripts to the genome by Northern hybridization indicated use of only three sites for transcriptional initiation and four sites for termination. Probes C* and E* were used to distinguish between termination at T5 or t6 (FIG. 6*b*). The patterns of hybridization with probes C* and E* were identical to those obtained with probes C and E, respectively indicating termination at T5 (data not shown). Probes corresponding to p40 (A) and p23 (B) detected monocistronic RNAs of 1.2 kb and 0.75 kb, respectively (FIG. 6). Probes A and B also detected a 1.9 kb RNA consistent with failure of transcriptional termination at the p40 termination site {Pyper, J. M., et al., *Virolog* 195:229–238 (1993)}. Transcriptional readthrough was also found for polycistronic transcripts of 3.5, 2.8 kb and 7.1 kb. The 3.5 kb RNA detected by probes B, C, D and C*, is likely to initiate at or near the beginning of ORF p23 and terminate at T5. The 2.8 kb RNA detected by probes C, D and C*, is likely to initiate at or near the beginning of ORF gp18 and terminate at T5. The 7.1 kb detected by probes C, D, C*, E* and E, is likely to initiate at or near the beginning of ORF gp18 and to continue through T5 until it terminates at T7. Probes C and C* both hybridized to a 1.5 kb RNA and a 6.1 kb RNA. Interestingly, neither the 1.5 kb RNA nor the 6.1 kb RNAs was detected by probe D, located between C and C* on the viral genome. These findings are consistent with posttranscriptional modification resulting in a 1–1.3 kb deletion (FIG. 6).

DISCUSSION

The order Mononegavirales, which incorporates the families Filoviridae, Paramyxoviridae and Rhabdoviridae, has distinct characteristics that include: (1) a nonsegmented negative sense RNA genome, (2) linear genome organization in the order 3' untranslated region/core protein genes/envelope protein genes/polymerase gene/untranslated 5' region, (3) a virion associated RNA-dependent RNA polymerase, (4) a helical nucleocapsid that serves as template for replication and transcription, (5) transcription of 5–10 discrete, unprocessed mRNAs by sequential interrupted synthesis from a single promoter and (6) replication by synthesis of a positive sense antigenome (Pringle, C. R., et al., *Arch. Virol.* 117:137–140 (1991)). The genomes of rhabdo-, paramyxo- and filoviruses range in size from 11 to 20 kb. The BDV genome has been estimated to be between 8.5 {Lipkin, W. I., et al., *Proc. Natl. Acad. Sci. USA* 87:4184–4188 (1990) and de la Torre, J., et al., *Virology* 179:853–856 (1990)} and 10.5 kb (VandeWoude, S., et al., *Science* 250:1276–1281 (1990) and Richt, J., et al., *J Gen. Virol.* 72:2251–2255 (1991)) in length. Our data confirm that the BDV genome, at only 8910 nt, is smaller than those of other negative-strand RNA viruses. Several features suggest that BDV is a member of the order Mononegavirales: organization of ORFs on the genome, extensive sequence similarities of the largest BDV ORF to L-polymerases of rhabdo-, paramyxo- and filoviruses, homology of 3' non-coding sequence to leader sequences of Mononegavirales and complementarity of BDV genomic termini.

In 5' to 3' antigenomic orientation, the first ORF contains 1110 nt. Due to a more favorable translation initiation context {Kozak, M., *Nucleic Acids Res.* 15:8125–8148 (1987)}, it is likely that the second AUG codon, 39 nt inside the ORF, is used to express a 357 aa protein of 39.5 kDa (p40) {Pyper, J. M., et al., *Virology* 195:229–238 (1993)}. 26 nt downstream of the stop codon is a polyadenylation signal (McClure, M. A., et al., *J. Virol.* 66:6572–6577 (1992)) (T2, FIG. 6b and c). The second ORF starts 79 nt from the p40 polyadenylation site. It has a length of 603 nt coding for a 201 aa protein of 22.5 kDa (p23). The stop codon of ORF p23 is part of the polyadenylation signal {Thierer, J., et al., *J. Gen. Virol.* 73:413–416 (1992)) (T3, FIG. 6b and c). Analysis of the intergenic region between ORFs p40 and p23 has shown that this sequence is less conserved among different BDV isolates than coding sequences for p40 and p23 {Schneider, P. A., et al., *J. Virol.* 68:63–68 (1994)}. Therefore, expression of a small ORF in this region (x, FIG. 3b); {VandeWoude, S., et al., *Science* 250:1276–1281 (1990) and Pyper, J. M., et al., *Virology* 195:229–238 (1993)} that overlaps with ORF p23 seems unlikely (Schneider, P. A., et al., *J. Virol.* 68:63–68 (1994)). Ten nt downstream of the p23 polyadenylation signal is the third ORF, 426 nt in length, that codes for a 142 aa (16.2 kDa) protein. Due to glycosylation, the protein expressed from this ORF has a Mr of ≈18 kDa (gp18).

No polyadenylation signal similar to those identified for p40 and p23 mRNAs (McClure, M. A., et al., *J. Virol.* 66:6572–6577 (1992) and Thierer, J., et al., *J. Gen. Virol.* 73:413–416 (1992)} was found near the end of the gp18 ORF (FIG. 6b and c). Instead, the following ORF overlaps with the end of the gp18 ORF by 28 aa. It has a total size of 1,509 nt that could code for a 503 aa protein of 56.7 kDa (p57). The ORF has two AUG codons in the overlap with gp18. A third AUG located outside the overlap is 451 nt from the beginning of the ORF. Which, if any, of these AUGs is used is unknown as no protein has been identified. A potential polyadenylation site is located 28 nt downstream of the p57 ORF (t4). However, Northern hybridization results suggest that this site is a weak or nonfunctional signal, because no major transcript(s) were found to stop at this position (FIG. 6).

The fifth ORF encompasses more than half the length of the genome. A potential polyadenylation site (T7), similar to that seen at the end of ORFs p40 and p23, is found 33 nt from the stop codon of p180 (pol) ORF (FIG. 6b and c). Deletions identified by Northern hybridization analysis suggested that viral mRNAs might undergo post-transcriptional modification by RNA splicing. This hypothesis was subsequently confirmed by applicants (Schneider, P. A. et al., *J. Virol.*, 68:5007–5012 (1994); Schneemann, A. et al. *J. Virol.*, 68:6514–6522 (1994), hereby incorporated in their entirety.) RNA splicing extends the pol ORF by 459 nucleotides allowing prediction of a protein of 190 kDa. (Schneider, P. et al., *J. Virol.*, 68:5007–5012 (1994)). Although functional studies of BDV proteins have not yet been done, the organization of the viral genome together with the limited biochemical data available suggest possible roles for individual proteins in the virus life cycle. Four lines of evidence suggest that p40 is likely to be a structural protein: (1) like nucleocapsid proteins (N) of rhabdo- and paramyxoviruses (Banerjee, A. K., et al., *Pharmacol, Ther.* 51:47–70 (1991)) (except pneumoviruses {Collins, P. L., *The Paramyxoviruses*, ed. Kingsbury, D. W. (Plenum, New York), pp. 103–162 (1991)}), p40 is found in the most 3' position on the genome; (2) p40 is similar in size to N proteins; (3) both p40 (Pyper, J. M., et al., *Virology* 195:229–238 (1993) and Ludwig, H., et al., *Prog. Med. Virol.* 35:107–151 (1988)) and N proteins {Banerjee, A. K., et al., *Pharmacol, Ther.* 51:47–70 (1991)} are abundant in infected cells and particles; (4) neither N proteins (Banerjee, A. K., et al., *Pharmacol, Ther.* 51:47–70 (1991)) nor p40 {Thiedemann, H., et al., *J. Gen. Virol.* 73:1057–1064 (1992)} are phosphorylated or glycosylated. p23, a phosphorylated protein {Thiedemann, H., et al., *J. Gen. Virol.* 73:1057–1064 (1992)}, is in the next position on the genome. ORF p23 corresponds in position to genes coding for phosphoproteins in Paramyxoviridae (P) and Rhabdoviridae (NS) (Banerjee, A. K., et al., *Pharmacol Ther.* 51:47–70 (1991)). This suggests that p23 might serve a similar role in the BDV system. In support of this hypothesis, GCG analysis showed that the protein has a high Ser/Thr content (16%), is charged (pI 4.8) and contains a N-terminal cluster of acidic amino acids compatible with structural features of P/NS proteins {Banerjee, A. K., et al., *Pharmacol, Ther.* 51:47–70 (1991)}. In previously described Mononegavirales, the next gene codes for matrix protein (M) (Banerjee, A. K., et al., *Pharmacol, Ther.* 51:47–70 (1991)). gp18 occupies this position on the BDV genome. Though small for a matrix protein, gp18 has a predicted pI ,10, that is close to the basic pI of M proteins, ≈9, and its membrane-association would be compatible with a matrix protein function. For p57, computer analysis predicted similarities to glycoproteins of negative-strand RNA viruses: potential glycosylation sites as well as N-terminal and C-terminal hydrophobic "tanchor": domains (data not shown). The largest ORF (pol) is located most 5' on the genome. Its size, 5' position and conservation of motifs considered critical to L-polymerase activity, suggest that this ORF is likely to code for the BDV polymerase (FIG. 6).

Analysis of Northern hybridization experiments in conjunction with genomic sequence data has allowed construction of a tentative transcription map (FIG. 6). While it has not been possible to identify signals for initiation of transcription by using consensus sequences of other negative-strand RNA viruses, we have identified consensus sequence for termination/polyadenylation in BDV using known ends of p40 and p23 mRNAs (McClure, M. A., et al., *J. Virol.* 66:6572–6577 (1992) and Thierer, J., et al., *J. Gen. Virol.* 73:413–416 (1992)) (FIG. 6c). These sequences appear to function as weak termination signals. Unlike other negative-strand RNA viruses, BDV shows a high frequency of readthrough transcripts. Organization and sequence similarities to Filo-, Paramyxo- and Rhabdoviridae suggest that BDV is a member of the order Mononegavirales. Dependent on the parameters and regions selected for homology analysis, BDV can be represented as being more closely related to filo-, paramyxo- or rhabdoviruses. Overlap of coding sequence, high frequency of polycistronic readthrough transcripts and posttranscriptional modification are properties of the BDV system not found in other members of the order Mononegavirales. These features could serve as independent mechanisms for modulation of gene expression to achieve the persistent, non-cytopathic infection that is a cardinal characteristic of this neurotropic virus.

EXAMPLE 2

BDV Glycoprotein gp18

Using methods for isolation of the 14.5-kDa protein {Schädler, R., et al., *J. Gen. Virol.,* 66:2479–2484 (1985)}, we have purified a glycoprotein from BDV-infected rat brain that is encoded by a 429-nucleotide (nt) ORF located 3' to ORF p23 on the viral antigenome. The protein is predicted to be 16.2 kDa; glycosylation results in a 1- to 2-kDa increase in molecular weight. This glycoprotein, gp18, is the first glycoprotein to be identified in the BDV system. Lectin binding and endoglycosidase sensitivity assays suggest that gp18 is an unusual N-linked glycoprotein.

MATERIALS AND METHODS

Infection of animals and cultured cells

Animals and cells were infected with BDV strain He/80 {Herzog, S., et al., *Med. Microbiol. Immunol.,* 168:153–158 (1980) and Schneider, P. et al., *Virol.* 68:63–68 (1994)}. Newborn Lewis rats were infected by intracranial injection with $1.5 \times 10^4$ focus-forming units of BDV. Three weeks after infection, animals were sacrificed and brains were removed for isolation of BDV particles {Carbone, K., et al., *J. Virol.,* 61:3431–3440 (1987)) or gp18. C6 cells and MDCK cells were persistently infected with BDV as described previously {Carbone, K. M., J. Virol., 67:1453–1460 (1993) and Herzog, S., et al., *Med. Microbiol. Immunol.,* 168:153–158 (1980)}. Monolayers of rabbit fetal glial cells were acutely infected by adding BDV at 1.0 focus-forming unit per cell to the culture medium (Dulbecco modified Eagle medium, 5% fetal calf serum; Gibco BRL, Grand Island, N.Y.).

Protein purification and microsequencing

Protein was purified from infected cells and tissues by detergent-salt extraction by the method of Schadler et al. (Schadler, R., et al., *J. Gen. Virol.,* 66:2479–2484 (1985)). For microsequencing, protein was cleaved with 10% cyanogen bromide in 75% formic acid (Sigma Chemical Co., St. Louis, Mo.). Peptide fragments were separated by reverse-phase high-performance liquid chromatography (RP-HPLC) on a Vydac C-18 column, using a trifluoroacetic acidacetonitrile gradient. Sequence determinations were performed by automated Edman degradation on a Hewlett-Packard model G1000A protein sequencer.

Antibodies

Antibodies to purified gp18 were produced in 3-month-old BALB/c mice. Animals were injected subcutaneously with 5 μg of protein in Freund's complete adjuvant and boosted 3 weeks later with a subcutaneous injection of 3 μg of protein in Freund's incomplete adjuvant. For 6 weeks thereafter, at 2-week intervals, animals received intraperitoneal injections of 5 μg of protein in phosphate-buffered saline (PBS) with 5 μg of lipopolysaccharide (*Salmonella typhimurium;* Difco, Detroit, Mich.) (three injections). Blood was drawn every 2 weeks during weeks 7 through 28 for measurement of serum antibody titer to purified protein by Western blotting (immunoblotting). Antisera collected at week 28 were used for virus neutralization studies. Rabbit antisera to recombinant BDV p40 and p23 were used as controls (see Example 3, below).

Cloning and sequencing of CDNA encoding gp18.

gp18-specific oligonucleotides were used to amplify full-length coding sequence for gp18 from two BDV-infected adult rat brain cDNA libraries {Lipkin, W. I., et al., *Proc. Natl. Acad. Sci. USA,* 87:4184–4188 (1990) and McClure, M. A., et al., J. Virol. 66:6572–6577 (1992)} as well as total cellular RNA {Chirgwin, J. J., et al., *Biochemistry,* 18:5294–5299 (1979)} and poly(A)+ RNA (Aviv, H., et al., *Proc. Natl. Acad. Sci. USA,* 69:1408–1412 (1972)} extracted from infected rat brain. Reverse transcription (RT) was performed with an oligo(dT) primer and Superscript II (Gibco BRL, Life Technologies, Inc., Grand Island, N.Y.). PCR was carried out with Ampli-Taq Stoffel fragment according to standard protocols (Perkin-Elmer, Norwalk, Conn.) with the following primer pair: 5'-terminal XhoI-gp18 sense oligonucleotide (XhoI-gp18-S1), TCCTC-GAGATGAATTCAAAACATTCCTATC (nt 1892 to 1914; XhoI restriction site indicated by underlining)(SEQ ID NO: 15); and 3'-terminal gp18 antisense oligonucleotide (gp18-AS1), CTAAGGCCCTGAAGATCGAAT (nt 2301 to 2321) (SEQ ID NO: 16). Products were purified by agarose gel electrophoresis using a USBioclean purification kit (U.S. Biochemical, Cleveland, Ohio) and cloned into Bluescript SKII+ (Stratagene, San Diego, Calif.) prepared with 3' T overhangs {Marchuk, D., et al., *Nucleic Acid Res.,* 19:1154 (1990)}. A minimum of three independent clones from each template source was sequenced on both strands by the dideoxynucleotide chain termination method using bacteriophage T7 DNA polymerase (Sequenase; U.S. Biochemical, Cleveland, Ohio). The plasmid resulting from amplification of neonatally infected rat brain RNA was named pBDV-gp18.

In vitro transcription, translation, and cotranslational processing

Plasmid clones pBDV-gp18 and pBDV-23 {Thibault, K. J., M. S. thesis, University of California, Irvine (1992)} linearized with EcoRI were used as templates for in vitro synthesis of capped RNA transcripts. Transcription products or *Saccharomyces cerevisiae* α-factor mRNA (control for glycosylation) were translated in vitro by using nuclease-treated rabbit reticulocyte lysates (Promega Corp., Madison, Wis.) in the presence of [$^{35}$S]methionine (Amersham Corporation, Arlington Heights, Ill.). Cotranslational processing was assessed by in vitro translation using reticulocyte lysates supplemented with canine microsomal membranes (Promega, Madison, Wis.). Transcription, translation, and cotranslational processing studies were performed according to the manufacturer's protocols. Translation products were immunoprecipitated with mouse anti-gp18 serum and then size fractionated by sodium dodecyl sulfate (SDS)-polyacrylamide gel electrophoresis (PAGE) (13% gel) {Laemmli, U. K., et al., *J. Mol. Biol.,* 80:575–581 (1973)} for autoradiographic analysis. Methods for immunoprecipitation and autoradiography have been described elsewhere {Lipkin, W. I., et al., *Proc. Natl. Acad. Sci. USA,* 87:4184–4188 (1990)}.

Protein gel electrophoresis and immunoblotting

Proteins were size fractionated by SDS-PAGE (12% gel) and then transferred to Immobilon-N membranes (Millipore Corp., Bedford, Mass.). Primary antisera for immunoblotting were from rats chronically infected with BDV (day 100 after intracranial infection) or mice immunized with purified gp18. The secondary antibody was alkaline phosphatase-conjugated goat antimouse immunoglobulin G (Sigma Chemical Co., St. Louis, Mo.); the substrate was Western Blue (Promega Corp., Madison, Wis.).

Carbohydrate analysis

Purified protein was size fractionated by SDS-PAGE (13% gel) and then either silver stained for detection of protein or carbohydrate {Tsai, C. M., et al., *Anal. Biochem.,* 119:115–119 (1982)} or transferred to Immobilon-N membranes (Millipore, Bedford, Mass.) for lectin staining. The carbohydrate composition of immobilized protein was determined by using a DIG Glycan Differentiation Kit (Boehringer Mannheim, Indianapolis, Ind.) and peroxidase-labeled *Bandeiraea simplicifolia* agglutinins I and II (BS-I and BS-II; Sigma Chemical Co., St. Louis, Mo.). The substrate for peroxidase was 4-chloro-1-naphthol (Pierce Chemical Company, Rockford, Ill.). Glycosidase digests of native and denatured protein (incubated for 5 minutes at 100° C. in 0.01% SDS) were performed according to the manufacturer's protocols, using the following endoglycosidases: endoglycosidase F and N-glycosidase F; O-glycosidase; N-glycosidase F; endoglycosidase F, N-glycosidase free; endoglycosidase H; and endo-β-galactosidase (Boehringer Mannheim).

RESULTS

The following figures present some of the results:

FIG. 7. Sequence of ORF gp18. The diagram shows the location of ORF gp18 on the viral antigenome (5'-3') relative to ORFs p40 and p23 (boxes). ORF gp18 sequences were from Oligo/TL cells infected with BDV strain V (SV) and rat brain infected with BDV He/80 (RB). Peptide sequences (P#1, P#2, and P#3) were obtained by microsequencing of purified protein from He/80-infected rat brain. Periods indicate identical nucleotide or amino acid sequences. Variable amino acid residues (large asterisk) and stop codons (small asterisks) are indicated. Underlining indicates potential glycosylation sites.

Figure 8:
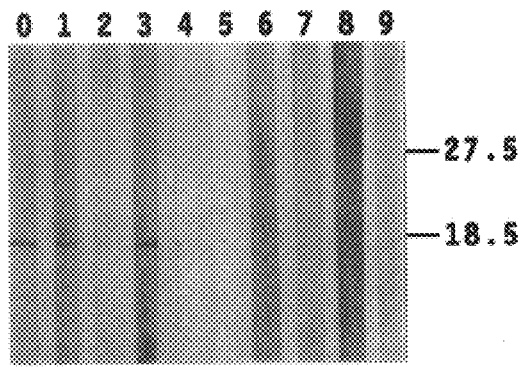
FIG. 8 shows glycan determination of gp18. Lanes: 0, protein detection by mouse anti-gp18 serum; 1, ConA; 2, wheat germ agglutinin; 3, *D. stramonium* agglutinin; 4, BS-I; 5, BS-II; 6, *G. nivalis* agglutinin; 7, *S. nigra* agglutinin; 8, *M. amrensis* agglutinin; 9, peanut agglutinin. Positions of molecular weight markers are shown in kilodaltons at the right.

FIG. 8. Glycan determination of gp18. gp18 isolated from infected rat brain was size fractionated by SDS-PAGE (12% gel) then transferred to an Immobilon-N membrane for lectin staining (see Materials and Methods). Lanes: 0, protein detection by mouse anti-gp18 serum; 1, ConA; 2, wheat germ agglutinin; 3, *D. stramonium* agglutinin; 4, BS-I; 5, BS-II; 6, *G. nivalis agglutinin;* 7, *S. nigra* agglutinin; 8, *M. amrensis* agglutinin; 9, peanut agglutinin. Positions of molecular weight markers are shown in kilodaltons at the right.

Figure 9:
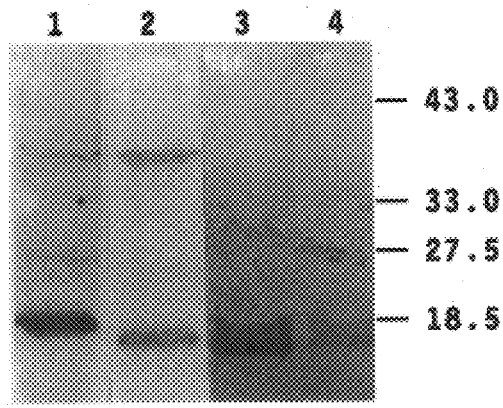
FIG. 9 presents treatment of gp18 with buffer alone or endoglycosidase. Lanes: 1, buffer; 2, endoglycosidase F plus N-glycosidase F; 3, endoglycosidase F (N-glycosidase free); 4, endo-β-galactosidase. Positions of molecular weight markers are shown in kilodaltons at the right.

FIG. 9. gp18 is sensitive to endoglycosidases. gp18 isolated from infected rat brain was treated with either buffer alone or endoglycosidase. Protein was size fractionated by SDS-PAGE (13% gel) and detected by silver staining. Lanes: 1, buffer; 2, endoglycosidase F plus N-glycosidase F; 3, endoglycosidase F (N-glycosidase free); 4, endo-β-galactosidase. Positions of molecular weight markers are shown in kilodaltons at the right.

Figure 10A:
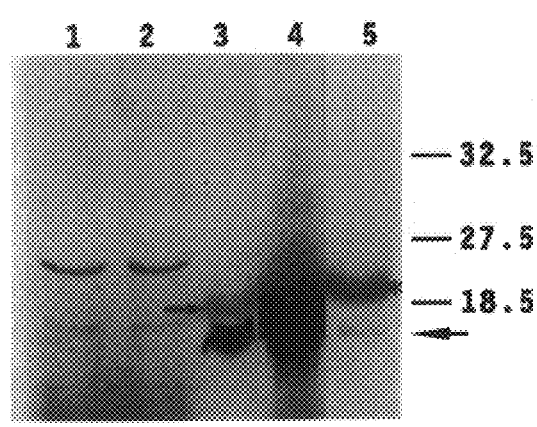
FIG. 10 presents in vitro transcription, translation, and cotranslational processing of gp18. (A) Lanes: 1, pBDV-23 RNA; 2, pBDV-23 RNA plus microsomal membranes; 3, pBDV-gp18 RNA; 4, pBDV-gp18 RNA plus microsomal membranes; 5, pBDV-gp18 RNA plus microsomal membranes, incubated with endoglycosidases. (B) Lanes: 1, pBDV-gp18 RNA; 2, pBDV-gp18 RNA plus microsomal membranes; 3, pBDV-gp18 RNA plus microsomal membranes, incubated with endoglycosidases.
Figure 10B:
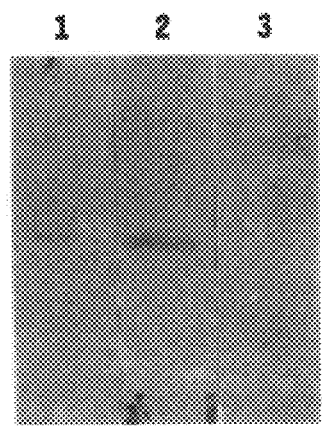

FIG. 10. In vitro transcription, translation, and cotranslational processing of gp18. RNA transcripts were synthesized from pBDV-23 (a nonglycosylated BDV protein control) or pBDV-gp18 and translated in vitro by using rabbit reticulocyte lysates in either the absence or presence of canine microsomal membranes. [$^{35}$S]methionine-labeled translation products were immunoprecipitated with antisera to p23 or gp18 and protein A-Sepharose and then size fractionated by SDS-PAGE (13% gel) for autoradiography (A) or transferred to Immobilon-N membranes for ConA lectin staining (B). Translated gp18 in lane 5 of panel A and lane 3 of panel B was incubated with endoglycosidase F plus N-glycosidase F prior to SDS-PAGE. (A) Lanes: 1, pBDV-23 RNA; 2, pBDV-23 RNA plus microsomal membranes; 3, PBDV-gp18 RNA; 4, pBDV-gp18 RNA plus microsomal membranes; 5, pBDV-gp18 RNA plus microsomal membranes, incubated with endoglycosidases. The long arrow indicates the position of glycosylated protein (lanes 3 and 4); the short arrow indicates the position of protein after treatment with endoglycosidase F plus N-glycosidase F (lane 5). The asterisk indicates nonspecific background signal (lane 5). Positions of molecular weight markers are shown in kilodaltons at the right. (B) Lanes: 1, pBDV-gp18 RNA; 2, pBDV-gp18 RNA plus microsomal membranes; 3, pBDV-gp18 RNA plus microsomal membranes, incubated with endoglycosidases.

Isolation of gp18

Protein was isolated from neonatally infected rat brain, acutely infected rabbit fetal glial cells (two passages), persistently infected C6 cells, and persistently infected MDCK cells, using the method of Schadler et al. {Schädler, R., et al., *J. Gen. Virol.,* 66:2479–2484 (1985)}. The purity of the protein was confirmed by silver staining of the protein after SDS-PAGE (data not shown). The quantity of protein was estimated in silver-stained gels by using lysozyme standards. Typical yields were 5 μg of protein from one neonatally infected rat brain and 2 μg of protein from $10^8$ infected cultured cells. Protein from neonatally infected rat brain was used for microsequencing, carbohydrate analysis, and immunization of mice.

Protein and nucleic acid sequence analysis

Direct microsequencing of gp18 was not possible because of a blocked amino terminus; thus, to allow analysis, the protein was cleaved with cyanogen bromide. Sequencing of the cleavage mixture indicated the presence of three N termini. From the mixture, two peptides (peptides 1 and 3; FIG. 7) were isolated by RP-HPLC and sequenced individually, allowing inference of a third sequence (peptide 2; FIG. 7) by subtraction. Peptide sequences were used as probes to search ORFs located on the BDV antigenome. The peptide sequences obtained from the purified gp18 mapped to a 429-nt ORF (ORF gp18) on the viral antigenome that predicts a 142-amino-acid protein with a molecular weight of 16,244 (FIG. 7).

Genomic sequence corresponding to the gp18 ORF was used to design probes and primers for identifying mRNA encoding gp18. In each of two cDNA libraries prepared from BDV-infected adult rat brain poly(A)$^+$ RNA {Lipkin, W. I., et al., *Proc Natl. Acad. Sci. USA,* 87:4184–4188 (1990) and McClure, M. A., et al., *J. Virol.,* 66:6572–6577 (1992)}, 100,000 recombinants were screened by hybridization with a 271-bp HincII-HinfI restriction fragment from pTB-BDV 5.82 (nt 2062 to 2333 in the viral genome) {Briese, T., et al., *Proc. Natl. Acad. Sci. USA* 91:4362–4366 (1994)}. These libraries were also screened by PCR using the 5'-terminal XhoI-gp18 sense primer (nt 1892 to 1914) and oligo(dT). Total cellular and poly(A)$^+$ RNAs extracted from persistently infected C6 cells, BDV-infected adult rat brain, or 3-week-old neonatally infected rat brain (the peak time point for in vivo expression of gp18) were subjected to RT-PCR using oligo(dT) in combination with the 5'-terminal XhoI-gp18 sense primer. No gp18-specific transcript corresponding to the size of ORF gp18 was obtained in these experiments. In contrast, use of the 5'-terminal XhoI-gp18 sense primer in combination with a 3'-terminal gp18 antisense primer (nt 2301 to 2321) allowed amplification of gp18 sequences from any of these sources by RT-PCR. In spite of variability at the nucleic acid level, the predicted amino acid sequence obtained from the different sources was the same as for strain V genomic sequence, with the exception of a single exchange in position 108 (E→D) (FIG. 7).

Characterization of gp18 as a glycoprotein

Purified gp18 was size fractionated by SDS-PAGE. Modified silver staining revealed the presence of carbohydrate; thus, fractionated protein was blotted onto Immobilon-N membranes to determine the presence of individual saccharides through lectin binding studies. Binding was observed with *Cancanavalia ensifonnis* agglutinin (ConA), wheat germ agglutinin, *Datura stramonium* agglutinin, BS-I, and BS-II but not with *Galanthus nivalis* agglutinin, *Sambucus nigra* agglutinin, *Maackia amurensis* agglutinin, and peanut agglutinin (FIG. 8). This staining pattern was consistent with the presence of N-acetylglucosamine, N-acetylgalactosamine, mannose, and galactose. In addition, native and denatured proteins were digested with specific endoglycosidases, size fractionated by SDS-PAGE, and then stained to assess molecular weight shift and presence or absence of carbohydrate. Treatment with O-glycosidase or endoglycosidase H had no effect (data not shown). In contrast, treatment with endoglycosidase F and N-glycosidase F resulted in a loss of 1 to 2 kDa (FIG. 9) and abrogation of lectin staining with ConA (data not shown). Treatment with endoglycosidase F (N-glycosidase free) or endo-β-galactosidase also resulted in a loss of 1 to 2 kDa (FIG. 9).

In vitro transcription, translation, and processing of gp18.

With linearized pBDV-gp18 used as a template, gp18 RNA was transcribed and translated invitro in either the presence or absence of canine microsomal membranes. The gp18 RNA directed translation of two proteins of 16 and 18 kDa that were recognized by monospecific murine antiserum to purified gp18. Translation in the presence of microsomal membranes led to an increase in the relative proportion of the 18-kDa protein. Treatment with endoglycosidase F resulted in loss of the 18-kDa protein species (FIG. 10A). Glycosylation of the 18-kDa species was also shown by lectin binding studies performed after translation products were size fractionated by SDS-PAGE and transferred to membranes. The 18-kDa protein was recognized by ConA, whereas the 16-kDa protein did not bind ConA (FIG. 10B). Modification of translated protein by the microsomal membranes was specific for gp18. Translation of RNA encoding BDV p23, which encodes a potential N-glycosylation site (amino acids 53 to 55), included as a negative control for in vitro glycosylation, was not influenced by the presence of microsomal membranes (FIG. 10A).

DISCUSSION

We have isolated and partially characterized a BDV glycoprotein with unusual properties. This protein, previously reported as 14.5 kDa {Schädler, R., et al., *J. Gen. Virol.,* 66:2479–2484 (1985)}, is 16.2 kDa prior to carbohydrate modification and ∞18 kDa after glycosylation. Though no classical sites for N linkage (N-x-S/T {Marshall, R. D., *Annu. Rev. Biochem,* 41:673–702 (1972)}) are found in the gp18 sequence, the protein is readily modified in vitro in the presence of a microsomal membrane system capable of N glycosylation {Gahmberg, C. G., et al., p. 281–297, In S. Fleischer and B. Fleischer (ed.), *Biomembranes, Academic Press, New York (*1983) and Lau, J. T. Y., et al., *J. Biol. Chem.,* 258:15255–15260 (1983)}. In addition, gp18 is sensitive to N-glycosidase F, an enzyme which cleaves between asparagine and N-acetylglucosamine {Plummer, T. H., et al., *J. Biol. Chem.,* 259:10700–10704 (1984) and Tarentino, A. L., et al., *Biochem.,* 24:4665–4671 (1985)}. These findings indicate that gp18 is N glycosylated at a nonclassical site. One potential site is N-I-Y (amino acids 74 to 76). The presence of a hydroxyl amino acid (T or S) or cysteine in position +2 (N-x-T/S or C) has been proposed as essential for hydrogen bond donor function in N glycosylation (Bause, E., et al., *Biochem. J.,* 195:639–644 (1981)). It is possible that tyrosine (Y), another hydroxyl amino acid in position +2, could serve as a hydrogen bond donor in gp18. A second potential site for N glycosylation is L-N-S-L-S (amino acids 87 to 91 of SEQ ID NO:6), which is similar to S-N-S-G-phosphorylated S (SEQ ID NO:45), the site for N glycosylation in a glycopeptide from hen yolk phosvitin {Shainkin, R., et al., *J. Biol. Chem.,* 246:2278–2284 (1971)}.

gp18 is sensitive to endoglycosidase F, an enzyme that cleaves after the N-linked N-acetylglucosamine in high mannose-, biantennary hybrid-, and biantennary complex-type oligosaccharides {Tarentino, A. L., et al., *Biochem.,* 24:4665–4671 (1985) and Tarentino, A. L., et al., *Methods Enzymol.,* 230:44–57 (1994)}. The protein is not sensitive to endoglycosidase H, an enzyme which cleaves after the N-linked N-acetylglucosamine in high-mannose- and most hybrid-type oligosaccharides but does not cleave complex-type oligosaccharides {Trimbel, R. B., et al., *Anal. Biochem.,* 141:515–522 (1984)}. Lectin staining using *G. nivalis* agglutinin shows no evidence of terminal mannose characteristic for hybrid- and high-mannose-type glycosylation. In contrast, staining with ConA (mannose, N-acetylglucosamine, branched trimannosyl core) {Ogata, S., et al., *J. Biochem.,* 78:687–696 (1975)}, wheat germ agglutinin (N-acetylglucosamine), and BS-II (terminal N-acetylglucosamine) {Ebisu, S., et al., *Methods Enzymol.,* 50:350–354 (1978)} indicates the presence of terminal N-acetylglucosamine and internal mannose. Thus, there is evidence from the pattern of endoglycosidase sensitivity and lectin staining that gp18 is likely to be a biantennary complex-type glycoprotein.

gp18 is sensitive to endo-β-galactosidase. This enzyme cleaves between galactose and either N-acetylglucosamine or galactose when these saccharides occur in unbranched sequence {Scudder, P., et al., *J. Biol. Chem.,* 259:6586–6592 (1984)}. The presence of galactose was confirmed by BS-I lectin binding (FIG. 8). The presence of both N-acetylglucosamine and galactose was confirmed by high-performance anion-exchange chromatography with pulsed amperometric detection. The combination of N-acetylgalactosamine and galactose is usually found in O-linked carbohydrates {Hayes, B. K., et al., *J. Biol. Chem.* 268:16170–16178 (1993)}. Though it is possible that gp18 is both N and O glycosylated, N-acetylgalactosamine has also been reported to occur in complex-type N-linked glycosylation {Hayes, B. K., et al., *J Biol. Chem.* 268:16170–16178 (1993)}.

We did not detect a monocistronic ∞429-nt mRNA for gp18 by PCR using oligo(dT), a 5' sense primer, and template from a variety of sources, including infected cell lines and rat brain. In contrast, a 429-nt gp18 cDNA was readily amplified by using gene-specific primers and total RNA or poly(A)$^+$ RNA as a template. Northern (RNA) hybridization experiments with gp18-specific probes using total RNA or poly(A)$^+$ RNA from infected cells or rat brain detected only 1.5-, 2.8-, 3.5-, 6.1-, and 7.1-kb transcripts. Recent experiments confirmed that the 1.5- and 2.8-kb RNAs can serve as templates for in vitro translation of the gp18 (data not shown). These data suggest that gp18 is likely to be translated from one or more of the larger RNA transcripts.

The role of gp18 in the BDV life cycle remains to be determined. Though the virus has not been characterized morphologically, genetic analysis has characterized BDV as a member of the order Mononegavirales {Briese, T., et al., *Proc. Natl. Acad. Sci. USA* 91:4362–4366 (1994) and Cubitt, B., et al., *J. Virol.*, 68:1382–1996 (1994)}. In nonsegmented, negative-strand RNA viruses, the third gene usually directs expression of a matrix protein. Matrix proteins in members of the order Mononegavirales are not known to be glycosylated; however, glycosylated matrix proteins that resemble gp18 in size and pI ($\approx$10) have been found in other viral systems (e.g., E1 in coronaviruses (Armstrong, J., et al., *Nature* (London), 308:751–752 (1984))). Preliminary observations suggest that gp18 is present on the surface of the viral envelope. Monospecific antisera and monoclonal antibodies to gp18 precipitated viral particles and had neutralizing activity. In contrast, antibodies to p40 and p23 did not precipitate viral particles or neutralize infectivity (see Example 4 below). Preincubation of primary rabbit fetal glia (cells highly susceptible to BDV) with gp18 prevented infection. No such effect was observed with either p40 or p23. Last, gp18 and BDV particles compete for binding to a $\approx$100-kDa membrane protein present in cells susceptible to infection.

Expression of Recombinant P57 cDNAs representing the p57 ORF were amplified by RT-PCR using BDV (strain He/80)-rat brain RNA as template. The amplified p57 cDNA was subcloned into two plasmid vectors, pET21b (Novagen) and pSFV-1 (GIBCO BRL).

pET21b, a prokaryotic expression vector, was selected because it allows for tight control of protein expression, an important feature for expression of proteins toxic to host cells. The N-terminus of p57 contains a hydrophobic sequence that confers extreme toxicity to prokaryotic cells. Therefore, to facilitate the expression of p57, the first 152 N-terminal amino acids were excluded during the cloning. PCR amplified cDNA representing nucleotides 2697 to 3743 of p57 ORF (amino acids 153 to 503) was generated by using oligonucleotide primers designed with a 5' restriction site (BamHI for sense primer; XhoI for antisense primer). The PCR product was cloned into pET21b at the BamHI and XhoI restriction sites, thus generating pET21b-BDV57$_{153-503}$. The pET21b-BDV57$_{153-503}$ plasmid was transformed into BL21 host cells and recombinant protein was expressed and purified by using protocols provided by the manufacturer.

An eukaryotic expression system, which allows for post-translational modification, was selected for the expression of a recombinant protein more similar to native p57. pSFV-1 is a eukaryotic expression vector that can be used to generate a replication defective Semliki Forest virus (SFV) genomic RNA. The entire p57 ORF was PCR amplified and cloned into pSFV-1 prepared with 3' T-overhangs at the SmaI site, thus generating pSFV-BDV57. Transfection of pSFV-BDV57 transcripts into mammalian cells, results in overexpression of the posttranslationally processed p57 gene product.

EXAMPLE 3

ELISA for the Detection of Antibodies to Borna Disease Virus Proteins

We have expressed p40, p23 and gp18 as recombinant proteins and established a sensitive, specific ELISA for analyzing immunoreactivity to BDV. This assay system is more sensitive and rapid than methods currently employed for serologic diagnosis of infection such as Western blot, indirect immunofluorescent test (IFT) or immunoprecipitation.

This system provides a convenient tool for diagnosing disease, determining the prevalence of infection in animal and human populations and mapping the antigenic determinants for the immune response in infected hosts.

MATERIALS AND METHODS

Infection of Animals and Cultured Cells

Six week old Lewis rats (Charles River) were infected intranasally with 6×10$^4$ focus forming units (ffu) of BDV strain He/80-1 {Carbone, K., et al., *J. Virol.*, 61:3431–3440 (1987) and Schneider, P. A., et al., *J. Virol.*, 68:63–68 (1994)}. C6 cells were persistently infected with BDV He/80-1 (C6BDV) {Carbone, K. M., et al., *J. Virol.*, 67:1453–1460 (1993)}. Rabbit fetal glial cells were infected with BDV He/80-1 at a multiplicity of one ffu per cell then passaged once before use in IFT assays. BDV strain He/80 was originally isolated from infected horse brain, passaged twice in rabbits, three times in rabbit fetal glial cells, and twice in Lewis rats {Herzog, S., et al., *Med. Microbiol Immunol*, 168:153–158 (1980)}. He/80-1 was passaged four additional times in Lewis rats and used for infection of animals and cell lines.

Generation of Recombinant Proteins (recp40, recp23, and recp18)

Full length cDNAs encoding p40, p23 or gp18 were cloned into the prokaryotic expression vector pET15b (Novagen) for production of recombinant proteins. pBDV-40 in pcDNA II {McClure, M. A., et al., *J. Virol.*, 66:6572–6577 (1992)} was amplified using the primers p40Xho I (5'- CCCTCGAGGACCAAGATTT-3')(SEQ ID NO: 17) and Sp6 (20 mer, Promega Corp., Madison, Wis.). pBDV-23 in pBluescript SKII+(Thibault, K. J., M. S. thesis, University of California, Irvine (1992)) was amplified with the primers p24Nde I (5'-AGAATCATATGGCAACGCGACCATC-3')(SEQ ID NO: 18) and T7 (20 mer Promega). Polymerase chain reaction was performed using Taq polymerase (Perkin-Elmer Cetus Corp., Norfolk, Conn.) according to the manufacturer's protocol. Products amplified from PBDV-40 and pBDV-23 were phenol/chloroform extracted, precipitated and digested with BamH I and either Xho I (pBDV-40) or Nde I (pBDV-23) (Promega Corp., Madison, Wis.). pBDV-cp18 in pBluescript SKII+ (see Example 2 above) was digested with Xho I and BamH I. Digested fragments were purified by agarose gel electrophoresis (USB, USBioclean, Cleveland, Ohio) and cloned into pET15b (Novagen Corporation, Madison, Wis.). Protein expression in plasmid containing *Escherischia coli* cells was induced by addition of isopropyl-P- thiogalactopyranoside (1 mM) for 3 hours at 37° C. Proteins (recp40, recp23, and recp18) were purified by nickel-chelate affinity chromatography according to manufacturer's instructions (Novagen Corp.). Purification was assessed by SDS-PAGE and antigenicity was confirmed by Western blot using sera from infected rats. Proteins were dialyzed against 150 mM NaCl and 2.5 mM $CaCl_2$ and digested with biotinylated thrombin (1 unit/mg recombinant protein, Novagen Corp.) overnight at room temperature. Thrombin was removed using streptavidin-agarose (Novagen Corp.) according to manufacturer's protocol. Protein concentrations were estimated by BioRad protein assay according to manufacturer's instructions.

Antibodies to BDV and recombinant BDVproteins

Sera were collected from infected rats at time of sacrifice or by tail bleeding at 2-week intervals after inoculation with BDV. Antibodies to recp40 and recp23 were each produced in two rabbits. Animals were injected subcutaneously (s.c.) with 25 pg of protein in Freund's complete adjuvant and then boosted 3 weeks later s.c. with 25 µg of protein in Freund's incomplete adjuvant. After 6 weeks some animals received an additional s.c. injection of 25 µg protein in Freund's incomplete adjuvant. Blood was collected at 2-week intervals during weeks 7 through 14 for detection of antibodies by Western blot and ELISA.

Indirect Immunofluorescent Test (IFT)

Rabbit fetal glial cells were processed for titration of serum antibodies against BDV using the immunohistochemical methods of Pauli et al. (Pauli, G., et al., Zbl. Vet. Med. [B] 31:552–557 (1984)). Briefly, infected and noninfected cells were fixed with 4% formaldehyde in PBS, permeabilized with 1% Triton X-100 in PBS and blocked with 1% fetal bovine serum (FBS) in PBS. After incubation with sera diluted in 1% FBS in PBS, cells were incubated with fluorescein-conjugated goat anti-rat IgG and IgM or goat anti-rabbit IgG (Sigma Chemical Co., St. Louis, Mo.) diluted 1:200 in 1% FBS in PBS and then examined by fluorescent microscopy. The IFT titer for each serum was determined to be the endpoint dilution at which specific inununoflourescence was detected.

Sodium dodecyl sulfate polyacrylamide gel electrophoresis (SDS-PAGE), Western blot (WB) and Immunoprecipitation (IP)

For WB, lysates from infected and noninfected C6 cells were prepared according to Bause-Niedrig, et al. (Bause-Niedrig, I., M. et al., Vet. Immunol Immunopathol., 31:361–369 (1992)). Proteins from these lysates (30 µg) and recombinant BDV proteins (250 ng) were subjected to 12% SDS-PAGE (Laemmli, U. K., et al., J. Mol. Biol., 80:575–581 (1973)) and then transferred to nitrocellulose membranes (Schleicher & Schuell, Keene, New Hampshire) {Towbin, H., et al., Proc. Natl. Acad. Sci. USA, 76:4350–4354 (1979)}. Membranes were incubated at room temperature first with WB-diluent (0.5% nonfat dry milk (Carnation Company, Los Angeles, Calif.) and 0.05% Tween-20 (Fisher Scientific, Raleigh, N.C.) in TBS (tris balanced saline, 50 mM Tris-HCl pH 7.5 and 150 mM NaCl)) for one hour, then overnight with various dilutions (1:10 to 1:2,000) of rat sera or monospecific rabbit sera in WB-diluent. Membranes were washed 3 times in TBS, incubated for 2 hours with the appropriate secondary antibody (horseradish peroxidase-conjugated goat anti-rat IgG and IgM or goat anti-rabbit IgG, Sigma Chemical Co., St. Louis, Mo.) diluted 1:500 in WB-diluent, washed 5 times in TBS and then incubated with hydrogen peroxide and 4-chloro-1-naphthol (Pierce Chemical Company, Rockford, Ill.) according to manufacturer's instructions. Methods for synthesis and analysis of radiolabeled BDV proteins and iminunoprecipitation have been described {Lipkin, W. I., et al., Proc. Natl Acad. Sci., USA, 87:4184–4188 (1990)}. Briefly, plasmid clones pBDV-gp18, pBDV-23 and pBDV-40 were linearized and used as template for in vitro transcription and translation of [$^{35}$S] methionine-labeled proteins. After precipitation with rat or rabbit sera and protein A-sepharose (Sigma Chemical Co., St. Louis, Mo.), proteins were analyzed by SDS-PAGE and autoradiography.

ELISA

Ninety-six well, Immulon I microtiter plates with lids (Dynatech Laboratories, Chantilly, Va.) were coated overnight at 37° C. with 10 ng of recombinant protein per well in 100 µl of borate buffer (100 mM boric acid, 50 mM sodium borate and 75 mM sodium chloride, pH 8.4). Plates were washed three times with washing buffer (0.05% Tween-20 in PBS) and incubated for 1 hour at 37° C. with ELISA-diluent (0.5% bovine serum albumin (BSA) fraction V (USB) in washing buffer). Two-fold serial dilutions of sera were prepared in ELISA-diluent; 100 µl of sera diluted from 1:250 to 1:500,000 was then added to each well and incubated for 2 hours at 37° C. Plates were washed three times with washing buffer. Next, 100 µl of horseradish peroxidase-conjugated goat anti-rat IgG and IgM (Sigma Chemical Co., St. Louis, Mo.) diluted 1:5,000 in ELISA-diluent were added to each well and incubated for 1 hour at 37° C. After washing the plates five times, 100 µl of substrate solution was added to each well. Substrate solution consisted of 9.9 ml of 100 mM sodium acetate adjusted to pH 6.0 with 100 mM citric acid, 100 µl of 10 mg of 3,3',5,5'-tetramethylbenzidine (Sigma Chemical Co., St. Louis, Mo.) per ml in dimethyl sulfoxide and 1.5 µl of 30% hydrogen peroxide (Fisher Scientific, Raleigh, N.C.). After incubation in the dark at room temperature for 30 minutes, the reaction was stopped by the addition of 50 µl of 25% sulphuric acid (Sigma Chemical Co., St. Louis, Mo.) to each well. The absorbance at 450 nm was determined for each well using a microplate reader (Molecular Devices, Thermo max, Menlo Park, Calif.). Negative control wells, without primary antisera, were used for calibration. The ELISA titer for each serum was defined as the endpoint dilution that yielded an optical density of 0.3.

RESULTS

The figures below present some of the results:

FIG. 11. Western blot analysis of native and recombinant proteins with monospecific antisera to recombinant proteins and sera from infected rats. Recombinant viral proteins and lysates from infected C6BDV or noninfected C6BDV cells were size-fractionated and screened by Western blot. A) Sera from infected and noninfected rats were used to detect native or recombinant proteins. Lane 1, C6BDV lysate; lane 2, recp40; lane 3, recp23; lane 4, recp18; lane 5, C6 lysate; lane 6, recp40, recp23 and recp18. Lanes 1–4 were treated with serum from infected rat; lanes 5 and 6 were treated with serum from noninfected rat. B) Monospecific antisera were used to detect BDV-specific proteins. C6BDV lysates (lanes 1–3) and C6 lysates (lanes 4 and 5) were incubated with: lanes 1 and 4, serum from infected rat; lane 2, anti-p40 rabbit serum; lane 3, anti-p23 rabbit serum; and lane 5, pooled anti-p40 and anti-p23 sera.

Figure 12:
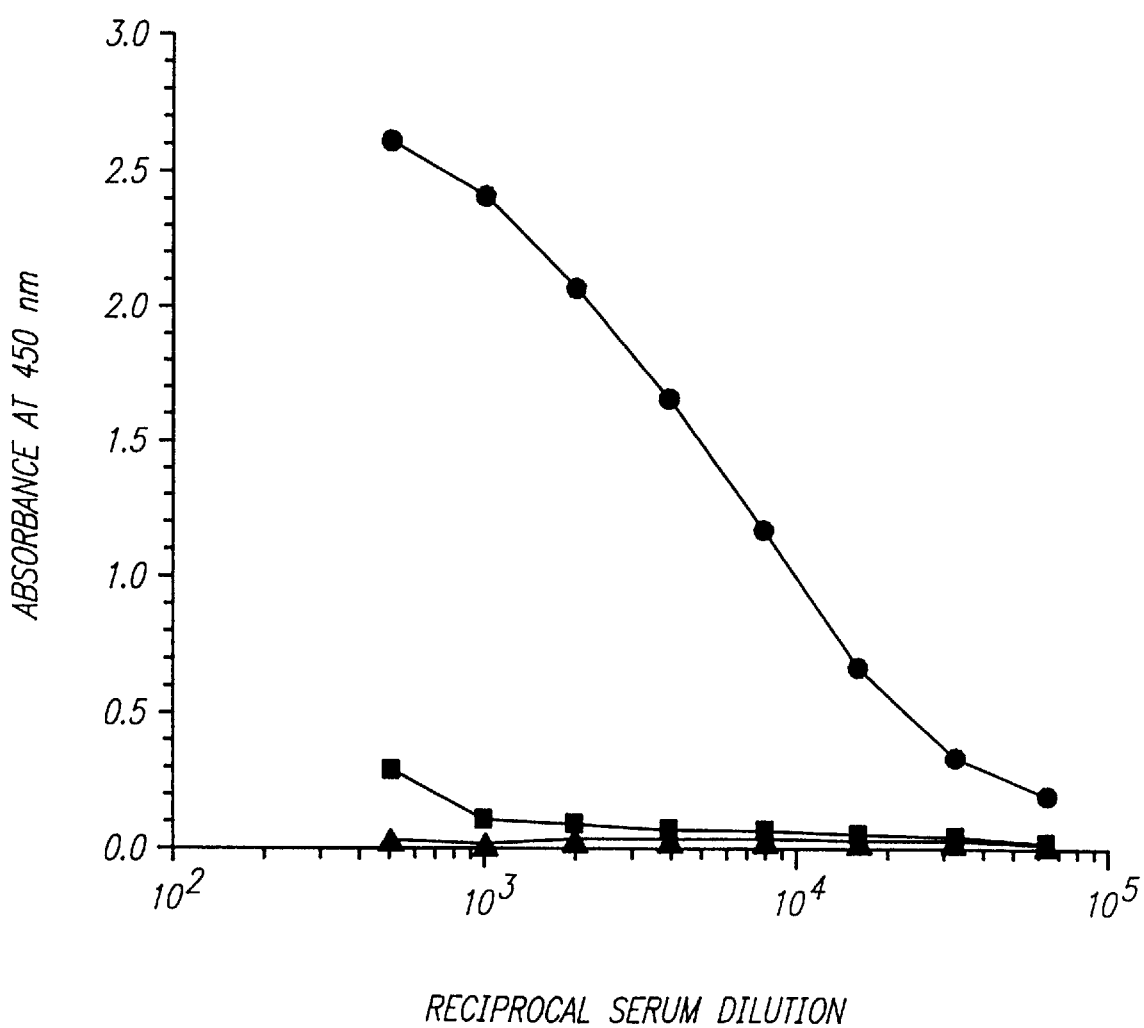
FIG. 12 presents ELISA of infected rat serum reacted with recp40. Circles, recp40 and serum from chronically infected rat; squares, recp40 and serum from noninfected rat; triangles, BSA and serum from chronically infected rat.

FIG. 12. ELISA of infected rat serum reacted with recp40. ELISA was performed with 10 ng/well recp40 or BSA as described in Materials and Methods. Circles, recp40 and serum from chronically infected rat; squares, recp40 and serum from noninfected rat; triangles, BSA and serum from chronically infected rat.

Figure 13A:
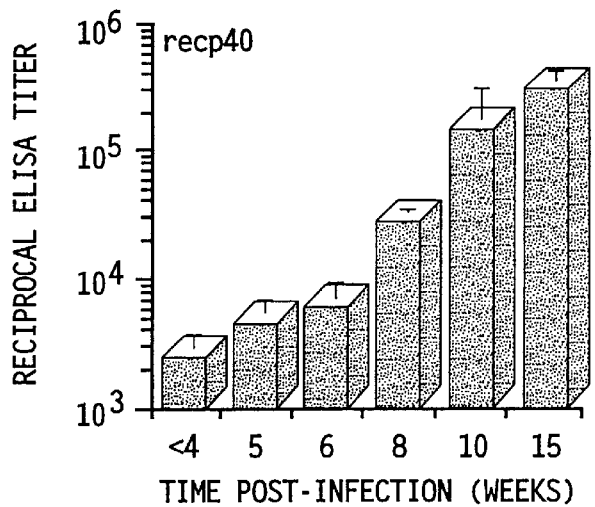
FIG. 13 presents timecourse for the appearance of antibodies to BDV-proteins. (A) recp40; (B) recp23; and (C) recp18.
Figure 13B:
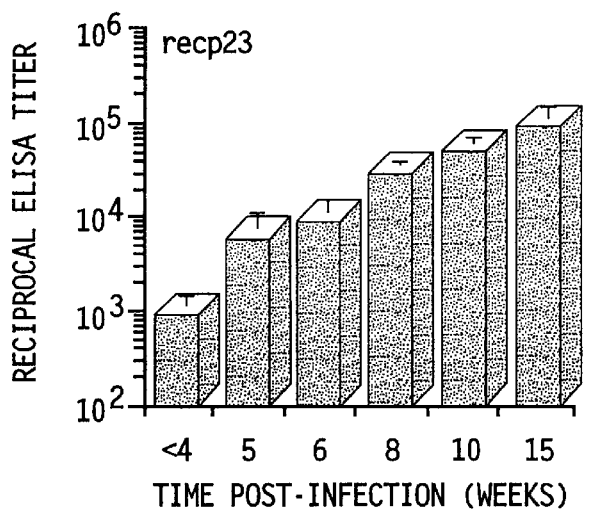
Figure 13C:
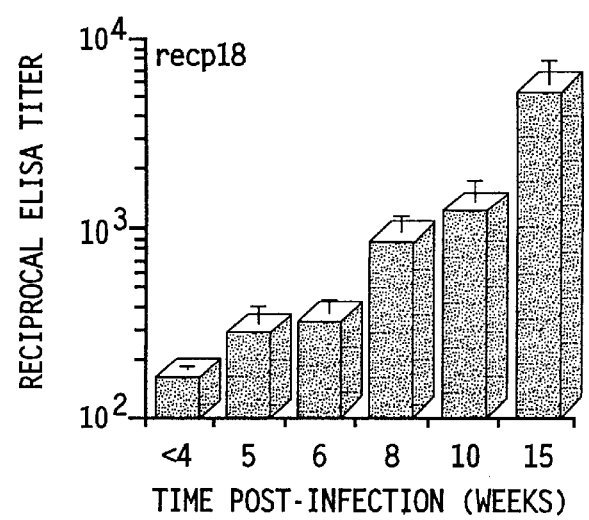

FIG. 13. Timecourse for appearance of antibodies to BDV-proteins. Sera were collected at different times post-infection and assayed by ELISA for antibodies to (A) recp40; (B) recp23; and (C) recp18. Error bars represent standard error of the mean. Number of animals analyzed at each time point: <4 wks, 15; 5 wks, 6; 6 wks, 12; 8 wks, 4; 10 wks, 5; and 15 wks, 9.

Figure 11A:
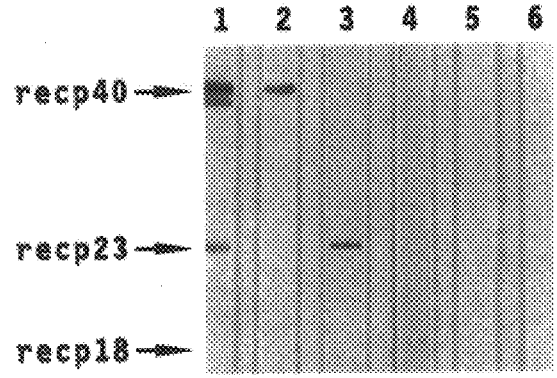
FIG. 11 presents Western blot analysis of native and recombinant proteins with monospecific antisera to recombinant proteins and sera from infected rats. (A) Lane 1, C6BDV lysate; lane 2, recp40; lane 3, recp23; lane 4, recp18; lane 5, C6 lysate; lane 6, recp40, recp23 and recp18. Lanes 1–4 were treated with serum from infected rat; lanes 5 and 6 were treated with serum from noninfected rat. (B) C6BDV lysates (lanes 1–3) and C6 lysates (lanes 4 and 5) were incubated with: lanes 1 and 4, serum from infected rat; lane 2, anti-p40 rabbit serum; lane 3, anti-p23 rabbit serum; and lane 5, pooled anti-p40 and anti-p23 sera.
Figure 11B:
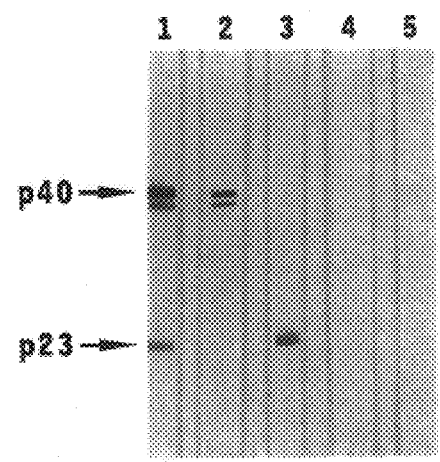

Production of recombinant viral proteins and monospecific antisera to recombinant viral proteins Full length coding sequences for p40, p23 and gp18 were expressed in *Escherichia coli* and recombinant proteins were purified. The yield of protein in 100 ml of bacterial culture was: recp40, 1 mg; recp23, 500 µg; and recp18, 50 µg. Recombinant proteins were analyzed by SDS-PAGE. A predominant band of the expected molecular weight was observed for each protein and tested for antigenicity by WB using sera from BDV-infected and noninfected rats (FIG. 11A). Recombinant proteins were detected by sera from BDV-infected rats but not by sera from noninfected rats. Recombinant proteins, recp40 and recp23 were used to produce antibodies in rabbits. The production of antibodies was monitored by ELISA. Rabbits were sacrificed when the ELISA titer reached 1:500,000 (week 16 of immunization). The specificity of the antisera was then tested by WB using lysates from infected cells and recombinant proteins (FIG. 11B). Antisera were monospecific: rabbits immunized with recp40 produced antibodies that reacted only with p40 and recp40; rabbits immunized with recp23 produced antibodies that reacted only with p23 and recp23. At week 16 of immunization, the antisera were also titered by IFT. Antisera to recp40 and recp23 had IFT titers of 1:50,000 and 1:100,000, respectively.

Specificity and sensitivity demonstrated in the BDV-ELISA systems

In order to establish a sensitive and specific ELISA for all three recombinant BDV proteins, the optimal antigen concentration was determined by checkerboard titration of positive and negative sera versus various antigen concentrations. For each protein, the concentration that resulted in the most linear response was 10 ng/well. The sensitivity of the ELISA system for each recombinant protein was established using sera from infected rats known to be reactive by IFT, IP and WB. For each of the proteins, 100% of sera that had been found to be positive by other methods were also positive by ELISA. Specificity was tested using sera from 15 noninfected rats. ELISA for each protein proved to be highly specific for detection of antibodies to BDV proteins: recp40-ELISA with noninfected rat sera showed 80% specificity at 1:500 dilution or 100% specificity at 1:2,000, recp23-ELISA showed 93% specificity at 1:250 and 100% specificity at 1:1,000, recp18-ELISA showed 100% specificity at 1:250. FIG. 12 shows a representative ELISA using recp40 as target antigen. Various dilutions of sera from chronically infected and noninfected rats were tested with 10 ng of recombinant protein or BSA per well in comparison with BSA. No nonspecific background reactivity was observed at serum dilutions of 1:500 or higher (FIG. 12). Results were similar when recp23 and recp18 were used as target antigen.

Analysis of immunoreactivity to viral proteins by IFT WB, IP and ELISA in sera from infected rats Adult rats infected intranasally with BDV did not display abnormal behaviors prior to the fourth week post-infection (predisease, PD). Four to six weeks post-infection, in the acute phase of disease (AD), animals had hyperactivity, weight loss, disheveled fur, dystonic posture and hindlimb paresis. Eight to fifteen weeks post-infection, signs of disease stabilized: there was no additional weight loss, hyperactivity diminished and paresis did not progress. This chronic phase of the disease (CD) persisted for the life of the animals. Sera was collected from adult-infected rats between 3 and 15 weeks after infection with BDV, and analyzed for the presence of antibodies to viral proteins using four different methods: IFT, WB, IP and ELISA (Table 3).

TABLE 3

Detection of BDV-specific antibodies in sera from infected rats by different methods

| Serum | WB | | | IP[a] | | | Reciprocal ELISA titer[b] | | | Reciprocal IFT titer |
|---|---|---|---|---|---|---|---|---|---|---|
| | recp40 | recp23 | recp18 | p40 | p23 | p18 | recp40 | recp23 | recp18 | |
| PD (3–4 wk pi[c]; n = 15) | − | − | − | − | − | − | 2,388 ± 256 | 904 ± 181 | 163 ± 5[d] | <10 |
| AD (4–6 wk pi; n = 18) | + | + | − | + | + | − | 3,217 ± 829 | 2,644 ± 20 | 279 ± 19 | 20–200 |
| CD (10–15 wk pi; n = 14) | + | + | + | + | + | + | 291,889 ± 56,590 | 76,527 ± 13,309 | 4,680 ± 1,467 | 10,000–20,000 |

[a]In vitro-translated proteins.
[b]Values are mean ± standard error of the mean titer.
[c]pi, postinfection.
[d]Nonspecific. Value below the level of specificity of the recp18 ELISA (1:250).

IFT allowed detection of antibodies to BDV in both AD rats and CD rats. In AD rats, the titer was between 1:20 and 1:200, whereas in CD rats, the titer was between 1:10,000 and 1:20,000. Sera from PD rats were not reactive by IFT. WB using lysates from infected cells or recombinant proteins, and IP using proteins translated in vitro yielded identical results: sera from CD animals were reactive with p40, p23 and gp18; sera from AD rats detected only p40 and p23; sera from PD rats did not react with p40, p23 or gp18. ELISA detected antibodies reactive with p40, p23 and gp18 in sera from all CD and AD rats (Table 3). In PD rats, ELISA only detected antibodies reactive with p40 and p23; immunoreactivity with gp18 was below specificity (Table 3).

The timecourse for the appearance of antibodies to BDV-proteins in sera was determined by ELISA. Sera collected at regular intervals from adult-infected rats were tested in the recp40, recp23 and recp18 ELISA systems. Titers of antibodies to all three proteins increased throughout the period of observation from weeks 4 to 15 post infection (FIG. 13).

DISCUSSION

Three recombinant BDV proteins, recp40, recp23 and recp18, were expressed and used as immunogens for production of monospecific sera in rabbits. Two of these antisera, directed against recp40 and recp23, are reported here; antisera to recp18 are described in Example 4 below. These three recombinant proteins were detected by sera from infected rats (FIG. 11A) and by monoclonal antibodies to purified native proteins. Monospecific antisera to the recombinant proteins were immunogen-specific as determined by WB (FIG. 11B) and detected proteins in infected cells by IFT.

ELISA systems were established, based on recombinant proteins, that have several advantages over methods currently used for detection of BDV-specific antibodies including IFT, WB and IP. Although IFT is widely accepted as a method for diagnosing BDV infection and titering antibodies to the virus, it has two disadvantages. First, IFT does not define the viral protein(s) responsible for immunoreactivity. Second, as shown here, IFT titers are 10–100 fold less sensitive than ELISA for detection of antibodies to p40 or p23. This relative insensitivity resulted in failure of IFT to show evidence of infection in PD rats (Table 3). WB and IP allowed detection of antibodies to individual viral proteins but were also less sensitive than ELISA. Sera from PD rats were not reactive by either WB or IP.

For diagnostic purposes, the recp40-ELISA is the most sensitive method for detection of antibodies in infected animals. Antibodies to recp40 were present prior to disease onset and had higher titers than antibodies to recp23 or recp18. Although the recp23-ELISA was also positive in PD and AD rats, the recp18-ELISA was not. Because high titer antibodies to gp18 only appear in chronic disease, the recp18-ELISA may be used to estimate the duration of infection. Low antibody titers to recp18 are not due to the lack of glycosylation on this recombinant protein because similar ELISA titers were found with native gp18 antigen. Failure to produce high titer antibody response to recp18 may be due to lower levels of expression of this protein than p40 or p23.

Growing recognition that BDV has a broader species and geographic range than previously appreciated suggests the importance of designing sensitive, reliable assays for infection. The ELISA systems described here, provide inexpensive, rapid methods for BDV-serology. In contrast to IFT, WB and IP, which require at least 2 days for completion and are not well suited to screening multiple samples, ELISA allows analysis of hundreds of sera in several hours with only minimal equipment. Plates coated with these proteins have been stable in ELISA for up to one month at room temperature and thus are practical for use in remote laboratories. In addition to serving as a tool for clinical diagnosis and epidemiology of Borna disease infection, the BDV ELISA is a useful tool for studies in immunopathogenesis and virus biology. For example, applicants have mapped antigen binding sites on p40 and p23 by ELISA using sera from infected animals and monoclonal antibodies to BDV proteins.

Dependent on the population studied and the methods used for analysis (WB, IP or IFT), the prevalence of antibodies reactive with BDV proteins in patients with neuropsychiatric disorders has been estimated to be between 4% and 23% {Bode, L., In W. I. Lipkin and H. Koprowski (ed.), Borna Disease. Springer-Verlag, Heidelberg, in press (1995) }. Variability between laboratories could be due to differences in populations analyzed, antigen preparations or experimental technique. The BDV ELISA based on recombinant proteins provides a standardized method for investigating human immunoreactivity to this neurotropic infectious agent.

EXAMPLE 4

Neutralizing Antibodies in BDV Infected Animals

We examined the timecourse for the development of neutralization activity and the expression of antibodies to individual BDV viral proteins in sera of infected rats. The appearance of neutralizing activity correlated with the development of immunoreactivity to gp18, but not p40 or p23. Monospecific and monoclonal antibodies to native gp18 and recombinant non-glycosylated gp18 were also found to have neutralizing activity and to immunoprecipitate viral particles or subparticles. These findings suggest that gp18 is likely to be present on the surface of the viral particles and to contain epitopes important for virus neutralization.

Antibodies to p40 and p23 (soluble antigens) are readily detected in both sera and cerebrospinal fluid (CSF) of naturally and experimentally infected animals {Ludwig, H., et al., *Progr. Med. Virol*, 35:107–151 (1988); Ludwig, H., et al., *Arch. Virol.*, 55:209–223 (1977) and Ludwig, H., et al., *Med. Microbiol. Immunol.*, 163:215–226 (1977)}. Antibodies to gp18, a membrane-associated glycoprotein (previously described as 14.5 kDa), have been reported less frequently {Ludwig, H., et al., *Progr. Med. Virol.*, 35:107–151 (1988) and Rubin, S. A., et al., *J. Virol*, 67:548–52 (1993)}. Although neutralization activity has been found in sera of animals infected with BDV {Danner, K., et al., *Zbl Vet.-Med*. [B], 25:345–355 (1978); Hirano, N., et al., *J. Gen Virol.*, 64:1521–1530 (1983); Ludwig, H., et al., *Progr. Med. Virol.*, 35:107–151 (1988) and Ludwig, H., et al., *Arch. Virol.* [*Suppl*] 7:111–133 (1993)}, the antibodies responsible for neutralization activity have not been investigated. An enzyme-linked immunosorbent assay (ELISA) based on recombinant BDV proteins has been established in Example 3 above, that provides a sensitive method for detection of antibodies to gp18. We find that the appearance of neutralizing antibodies in infected rats correlates with immunological reactivity to gp18. Furthermore, monospecific and monoclonal antibodies (MAbs) directed against gp18 neutralize BDV infectivity and immunoprecipitate viral particles or subparticles.

MATERIALS AND METHODS

BDV infected animals: Sixty-thousand focus forming units (ffu) of BDV strain He/80-1 {Carbone, K. M., et al., *J. Virol.*, 61:3431–3440 (1987); Herzog, S., et al., *Med. Microbiol. Immunol.*, 168:158-8 (1980) and Schneider, P. A., et al., *J. Virol.*, 68:63–68 (1994)} were used to intranasally (i.n.) infect each of seventy 6-week old Lewis rats. Rats were observed at three days intervals for weight loss, ruffled fur or postural abnormalities consistent with acute disease. Sera were collected at time of sacrifice. Under metofane anesthesia, rats were perfused with buffered 4% paraformaldehyde; brains were fixed overnight in perfusate at 4° C. Twenty-micron sagittal sections were collected onto gelatin coated slides and stained with hematoxylin and eosin. Inflammation was scored using the scale of Stitz, Sobbe and Bilzer {Stitz, L., et al., *J. Virol.*, 66:3316–23 (1992)}.

Virus titration and neutralization assay

Viral infectivity in 20% brain homogenates was determined using the method of Pauli et al. {Pauli, G., et al., *Zbl. Vet.-Med.* [B] 31:552–557 (1984)}. Virus neutralization was performed using a modification of Danner et al. {Danner, K., et al., *Zbl. Vet.-Med.* [B], 25:345–355 (1978)}. Briefly, 50 ffu of BDV were incubated with serial dilutions of antibodies or sera for one hour at 37° C., added to rabbit fetal glial cells and incubated for 5 days. Sera was heat inactivated at 56° C. for 30 minutes. In selected assays, mouse complement (1:50) (Sigma Chemical Co., St. Louis, Mo.) was added to the virus concurrent with the addition of MAbs to determine the effects of complement on neutralization activity. The dilution of serum or antibody required to reduce the number of ffu by 50% was defined as the neutralization titer ($NT_{50}$).

As controls for each neutralization assay, rabbit fetal cells were exposed to medium without virus, treated with virus in medium alone (no antibodies), or treated with virus incubated with sera from normal rats. Pilot studies showed that approximately 8% of normal rat sera interfered with BDV infectivity at dilutions up to 1:16. Therefore, sera were considered to be neutralizing only if the $NT_{50}$ exceeded 1:32. Supernatant from nonproducing myeloma cell lines as well as monoclonal antibodies directed against BDV-p23 (24/36F1) and BDV-p40 (38/17C1) {Thiedemann, N., et al., J. Gen. Virol., 73:1057–1064 (1992)} were found to neutralize infectivity at dilutions of 1:2. Thus, monoclonal antibodies were considered to be neutralizing only if the NT50 exceeded 1:4.

Preparation of proteins (recp40, recp23, recp18 and gp18):

Plasmids encoding p40 (pBDV-40 disclosed in McClure, M. A., et al., J. Virol, 66:6572–6577 (1992)), p23 {pBDV-23 disclosed in Thibault, K. J., M. S. thesis; University of California, Irvine (1992)} and gp18 (PBDV-gp18 disclosed in Kliche, S. et al., J. Virol., 68:6918–6923 and Example 2 above) were subcloned (see Example 3 above) into the prokaryotic expression vector pet15b (Novagen, Madison, Wis.). Recombinant proteins (recp40, recp23 and recp18) were expressed in *Escherichia coli* and purified according to manufacturer's protocol (Novagen, Madison, Wis.). Purity and antigenicity were assessed by SDS-PAGE and Western blot analysis using sera from infected rats. Native, glycosylated gp18 was prepared from infected rat brain as described previously {Schadler, R., et al., J. Gen. Virol., 66:2479–2484 (1985)}.

Enzyme-linked immunosorbent assay (ELISA):

ELISA was performed as described in Example 3 above. Briefly, plates coated with recombinant protein were incubated with serially diluted sera or MAbs. Bound horseradish peroxidase (HRPO)-coupled secondary antibody (goat antimouse F'ab-HRPO, goat anti-rat IgG and IgM HRPO; Sigma Chemical Co.) was quantified on a microplate reader (Thermo max, Molecular Devices, Menlo Park, Calif.) using the chromagen 3,3'-5,5' Tetramethylbenzidine (Sigma Chemical Co.). The ELISA endpoint titer was defined as the serum or antibody dilution that generated an optical density of 0.3.

Sodium dodecyl sulfate polyacrylamide gel electrophoresis (SDS-PAGE), Western blot and Immunoprecipitation (IP):

Recombinant or native BDV proteins were subjected to SDS-PAGE {Laemmli, U. K., et al., J. Mol. Biol., 80:575–581 (1973)} and transferred to nitrocellulose (Schleicher & Schuell, Inc., Keene, N.H.) or Immobilon-N membranes (Millipore Corp., Bedford, Md.) (Towbin, H., et al., Proc. Natl. Acad. Sci. USA, 76:4350–4354 (1979)). Membranes were blocked and incubated with primary antibody as described in Example 3 above. After incubation with secondary antibody (goat antimouse IgG-alkaline phosphatase [AP], goat anti-rat IgG-AP or goat anti-rat IgG and IgM-HRPO, Sigma Chemical Co., St. Louis, Mo.), immune complexes were visualized using Western Blue (Promega, Madison, Wic.) for AP or chemiluminescence (ECL kit, Amersham, Arlington Heights, Ill.) for HRPO according to manufacturer's instructions. gp18 or recp18 were precipitated using sera from infected rats, monospecific antibodies or MAbs and Protein A-Sepharose (Pharmacia Biotech Inc., Piscataway, N.J.) as described by Persson, H., et al. {Persson, H., et al. Science, 225:687–693 (1984)} then assayed by Western blot.

Monoclonal antibodies

MAbs to gp18 were generated according to Thiedemann et al. {Thiedemann, N., et al., J. Gen. Virol., 73:1057–1064 (1992)}. Briefly, Balb/c mice were immunized intraperitoneally (i.p.) with 5 µg of gp18 in complete Freund's adjuvant. Three and 6 weeks after the initial immunization, mice were boosted i.p. with 5 µg of gp18 in incomplete Freund's adjuvant. Four days before fusion of spleen cells with the mouse myeloma cells X63-Ag8.653 {Kearney, J. F., et al., J. Immunol., 123:1548–1550 (1979)}, mice were boosted intravenously with 15 µg of gp18. All hybridomas were initially screened for reactivity to gp18 by ELISA. Tissue culture supernatants from positive hybridomas were concentrated by ammonium sulfate precipitation (Jonak, Z. L., p. 405–406, In R. H. Kennett, T. J. McKean, and K. B. Becktol (ed.), "Monoclonal antibodies, Hybridomas: A new dimension in biological analyses", Plenum Press, New York (1982)) and tested by Western blot and IP for reactivity with gp18 and recp18. The immunoglobulin isotype was determined using an agglutination isotyping kit (Serotec, Oxford, England) according to manufacturer's instructions. Monoclonal antibody, 24/36F1 directed against BDV-p23 {Thiedemann, N., et al., J. Gen. Virol., 73:1057–1064 (1992) }, was used as a negative control in Western blot and IP experiments.

Generation of polyclonal sera against recp18 protein

To produce antibodies against recp18, two 2-month old Lewis rats were injected subcutaneously (s.c.) with 25 µg of protein in Freund's complete adjuvant and boosted 3 weeks later with 25 µg of protein s.c. in Freund's incomplete adjuvant. After 6 weeks, animals received i.p. injections of 25 µg protein in phosphate buffered saline (PBS) with 20 µg lipopolysaccharide (S. typhimurium, Difco, Detroit, Mich.) at two-week intervals for a total of three injections. Serum was collected every two weeks during weeks 7 through 14 for analysis by ELISA and Western blot and for determination of neutralization titer. Mouse antibodies to native gp18 have been described in Example 2 above.

Affinity adsorption of BDV-specific serum-antibodies

Antibodies that bound to recp23 and recp40 were sequentially removed from serum of an infected rat according to Crabb et. al. (Crabb, B. S., et al., Virolog, 190:143–154 (1992)). Serum (D2) from an adult-infected Lewis rat (15 weeks post intranasal infection), was diluted 1:10 in TBS (tris balanced saline, 50 mM Tris pH 7.4 and 100 mM NaCl) and incubated overnight at 4° C. with membrane-bound recp23. The anti-recp23 antibody-depleted serum (D2 Δ recp23) was removed, the membrane was washed with TBS and adsorbed anti-recp23 antibodies were eluted (recp23 eluant) by incubation with 1 ml of 0.1M glycine, 0.15M NaCl pH 2.7 for 3 minutes. The pH of the eluant was adjusted by addition of 300 µl of 10 mM Tris HCl pH 7.5. The anti-recp23 antibody-depleted serum was then incubated with membrane-bound recp40 (D2 Δ recp23, Δ recp40) and purified as before (recp40 eluant). Antibody depletion from serum and antibody elution from membrane-bound proteins was monitored by Western blot and ELISA. At each step during the purification, antibody-depleted sera and eluted antibodies were analyzed for neutralizing activity. Antibodies to gp18 or recp18 were also adsorbed (D2 Δ gp18, D2 Δ recp18) and eluted (gp18 eluant, recp18 eluant) by this method. These adsorption and elution experiments were repeated using serum (B3) from an additional adult-infected rat (15 week post intranasal infection).

IP of BDV particles or sub particles and analysis by reverse transcription polymerase chain reaction (PCR)

Forty-thousand ffu of BDV in a volume of 200 µl were treated with 50 µg/ml of DNase I and RNase A (Boehringer Mannheim Corp., Indianapolis, Ind.) for 30 minutes at 37° C. then incubated for 2 hours at room temperature with 100

μl of one of the following: (1) serum from acutely or chronically infected rats at 1:10 dilution in PBS; (2) purified serum-antibodies at 1:10 dilution; (3) mouse anti-gp18 sera or rat anti-recp18 sera at 1:20 dilution; or (4) monoclonal antibodies against gp18 at 1:5 dilution. Next, 100 μl of 1 mg/ml Protein A-Sepharose (Pharmacia, Puscataway, N.J.) in PBS was added, and the mixture was incubated overnight at 4° C. The Protein A-Sepharose-antibody-virus complex was washed three times in PBS then resuspended in 100 μl water. Total RNA was extracted {Chomczynski, P., et al., *Anal. Biochem.*, 162: 156–159 (1987)} and used for RT-PCR amplification of a 693 nucleotide region of the viral genome (nucleotide 753 to 1446) according to Schneider et al. (primer 7 and primer 9) {Schneider, P. A., et al., *J. Virol.*, 68:63–68 (1994)}. PCR products were analyzed by agarose gel electrophoresis. PCR products were cloned and sequenced to confirm that they represented the predicted region of the genomic RNA (Schneider, P. A., et al., *J. Virol.*, 68:63–68 (1994)). Negative controls for RT-PCR included the omission of virus from immunoprecipitation reactions and the use of genomic sense primers during first strand cDNA synthesis.

RESULTS

Figure 14A:
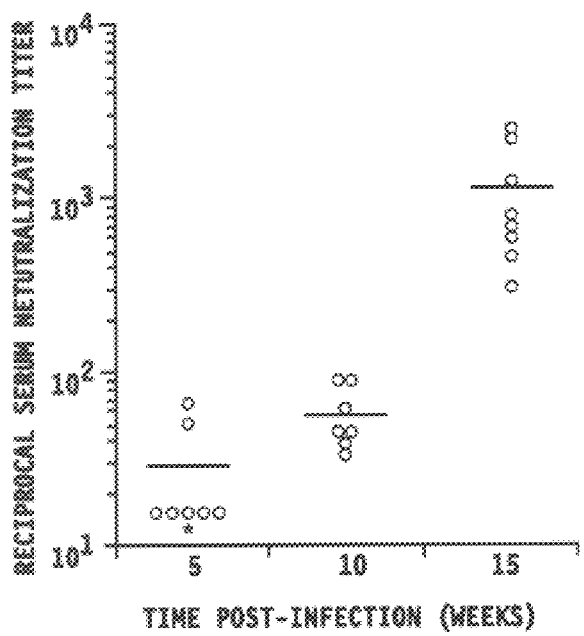
FIG. 14 presents timecourse for the appearance of antibodies to BDV proteins in sera from individual rats after intranasal infection. (A) Neutralization activity in sera from BDV-infected rats at three timepoints (5, 10 and 15 weeks post-infection). (B) Plot of mean recp18 ELISA titers (open columns) with neutralization titers (hatched columns) at three time points (5, 10 and 15 weeks post-infection). Sera analyzed were the same as those in panel A. (C) Timecourse for the appearance of antibodies to recp40, recp23, and gp18 by Western blot analysis.

The following figures present part of the results:

FIG. 14. Timecourse for the appearance of antibodies to BDV proteins in sera from individual rats after i.n. infection. (A) Neutralization activity in sera from BDV-infected rats at three timepoints (5, 10 and 15 weeks post-infection). Each serum is represented by a circle. Bars indicate mean neutralization titer for each group (5, 10 or 15 weeks post-infection). Asterisk represents sera with neutralization titer less than or equal to 1:16. (B) Plot of mean recp18 ELISA titers (open columns) with neutralization titers (hatched columns) at three time points (5, 10 and 15 weeks post-infection). Sera analyzed were the same as those in panel A. Mean values for neutralization activity were determined as described in FIG. 14A. Arrows indicate threshold for significance in neutralization assay (1:32) and recp18 ELISA (1:250). These values were selected because normal rat sera reacted in the neutralization assay and reccp18 ELISA at titers of 1:16 and 1:125, respectively. (C) Timecourse for the appearance of antibodies to recp40, recp23, and gp18 by Western blot analysis. Proteins were size-fractionated by SDS-PAGE and transferred to nitrocellulose membranes. Membranes were incubated first with sera and then with horseradish peroxidase-coupled goat anti-rat IgG. Bound secondary antibody was detected by chemiluminescence. Results shown are from serum of one representative animal at several different timepoints post BDV infection (p.i.).

Figure 15A:
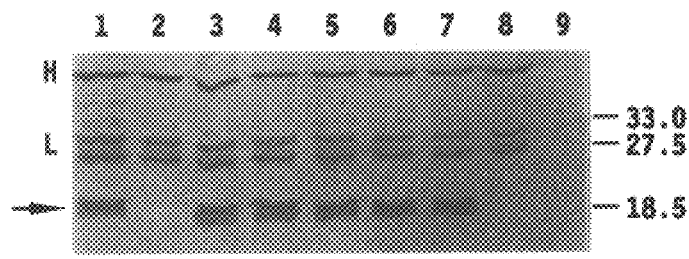
FIG. 15 presents (A) Immunoprecipitation of gp18 with monoclonal antibodies (Mabs). Lanes: 1, serum from infected rat (15 week pi); 2, serum from noninfected rat; 3, MAb 14/29A5; 4, MAb 14/26B9; 5, MAb 14/8E1; 6, MAb 14/13E10; 7, MAb 14/18H7; 8, MAb 24/36F1 (MAb directed against the BDV 23 kDa protein, negative control); 9, no antibody. (B) MAbs were analyzed for binding to native gp18 in Western blot. Lanes: 1, serum from infected rat (15 week p.i., D2); 2, serum from noninfected rat; 3, MAb 14/29A5; 4, MAb 14/26B9; 5, MAb 14/8E1; 6, MAb 14/13E10; 7, MAb 14/18H7; and 8, MAb 24/36F1 (MAb directed against the BDV 23 kDa protein, negative control).
Figure 15B:
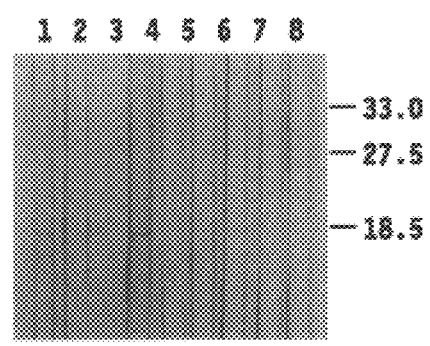

FIG. 15. Monoclonal antibody (MAb) detection of gp18. A) Immunoprecipitation of gp18 with MAbs. gp18 was first incubated with MAbs or sera from infected or noninfected rats, then precipitated with Protein-A Sepharose, size-fractionated by 12% SDS-PAGE and transferred to Immobilon-N membranes. Precipitated gp18 was visualized with rat anti-recp18 sera, goat anti-rat IgG-AP, and Western Blue. Lanes 1, serum from infected rat (15 week p.i.); 2, serum from noninfected rat; 3, MAb 14/29A5; 4, MAb 14/26B9; 5, MAb 14/8E1; 6, MAb 14/13E10; 7, MAb 14/18H7; 8, MAb 24/36F1 (MAb directed against the BDV 23 kDa protein, negative control); 9, no antibody. Arrow indicates gp18; H and L represent heavy and light chains of immunoglobulin, respectively. B) MAbs were analyzed for binding to native gp18 in Western blot. gp18 was separated on 12% SDS-PAGE and transferred to an Immobilon-N membrane. Strips were incubated with MAbs or sera from infected or noninfected rats. Bound antibodies were detected with alkaline phosphatase conjugated goat anti-rat IgG or goat anti-mouse Fab-specific and Western Blue substrate. Lanes: 1, serum from infected rat (15 week p.i., D2); 2, serum from noninfected rat; 3, MAb 14/29A5; 4, MAb 14/26B9; 5, MAb 14/8E1; 6, MAb 14/13E10; 7, MAb 14/18H7; and 8, MAb 24/36F1 (MAb directed against the BDV 23 kDa protein, negative control). Molecular weight markers (103 Da) are shown at the right.

FIG. 16. Neutralization profile of sera and MAbs. BDV (50 ffu) was preincubated with serial dilutions of serum or MAb and then added to ten thousand rabbit fetal glial cells. After four days of incubation, the infected cells were visualized as described in Pauli et al. {Pauli, G., et al., *Zbl. Vet-Med.* [B] 31:552–557 (1984)). The number of infected cell-foci per well was counted. (A) Serum from noninfected rat. (B) serum from infected rat (15 week p.i., D2). (C) MAb 14/13E10. (D) MAb 14/29A5.

Figure 17A:
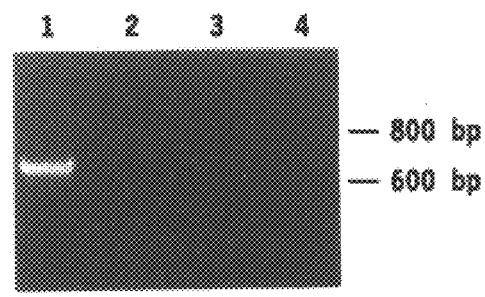
FIG. 17 presents precipitation of BDV with sera from infected rats. (A) Lanes: 1, serum from infected rat, 15 week p.i.; 2, serum from infected rat, 5 week p.i.; 3, serum from infected rat, 15 week p.i., no BDV; 4, serum from infected rat,15 week p.i., genome sense primer used for first strand cDNA synthesis. (B) Precipitation of BDV by monospecific antisera to recp18 and MAbs to gp18. Lanes: 1, monospecific rat antisera to recp18; 2, MAb 14/13E10; 3, MAb 14/29A5. DNA markers (basepairs) are shown at the right.
Figure 17B:
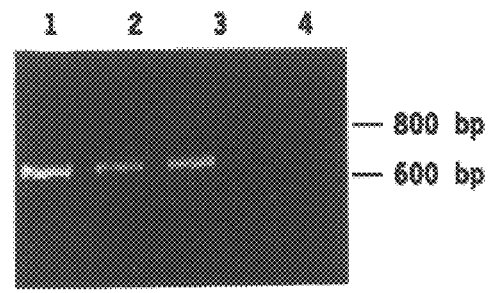
Figure 16A:
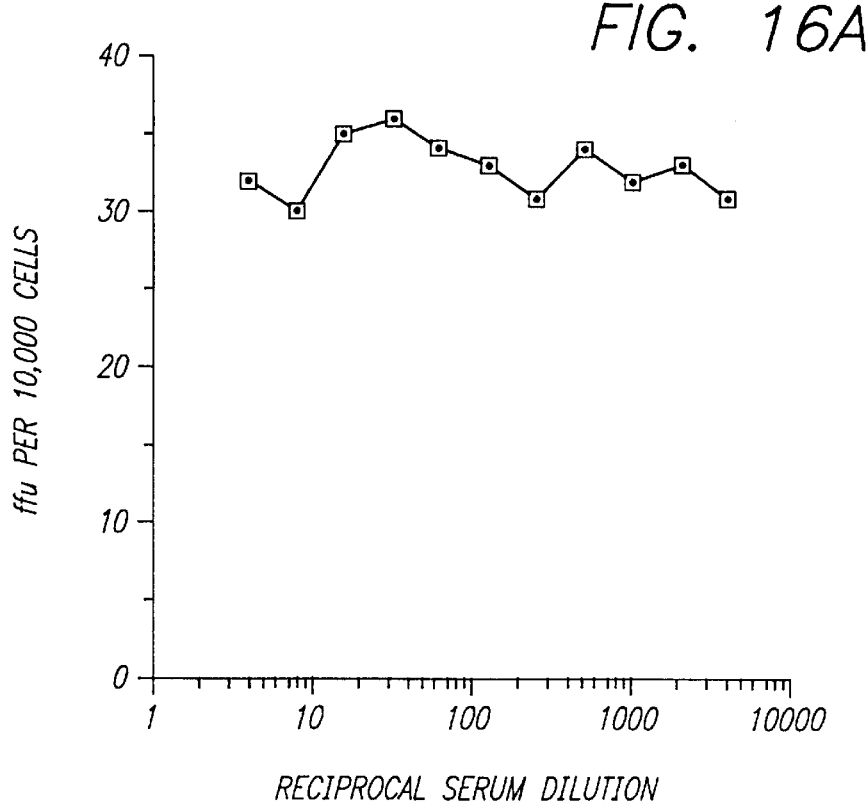
FIG. 16 presents neutralization profile of sera and MAbs. (A) Serum from noninfected rat. (B) serum from infected rat (15 week p.i., D2). (C) MAb 14/13E10. (D) MAb 14/29A5.
Figure 16B:
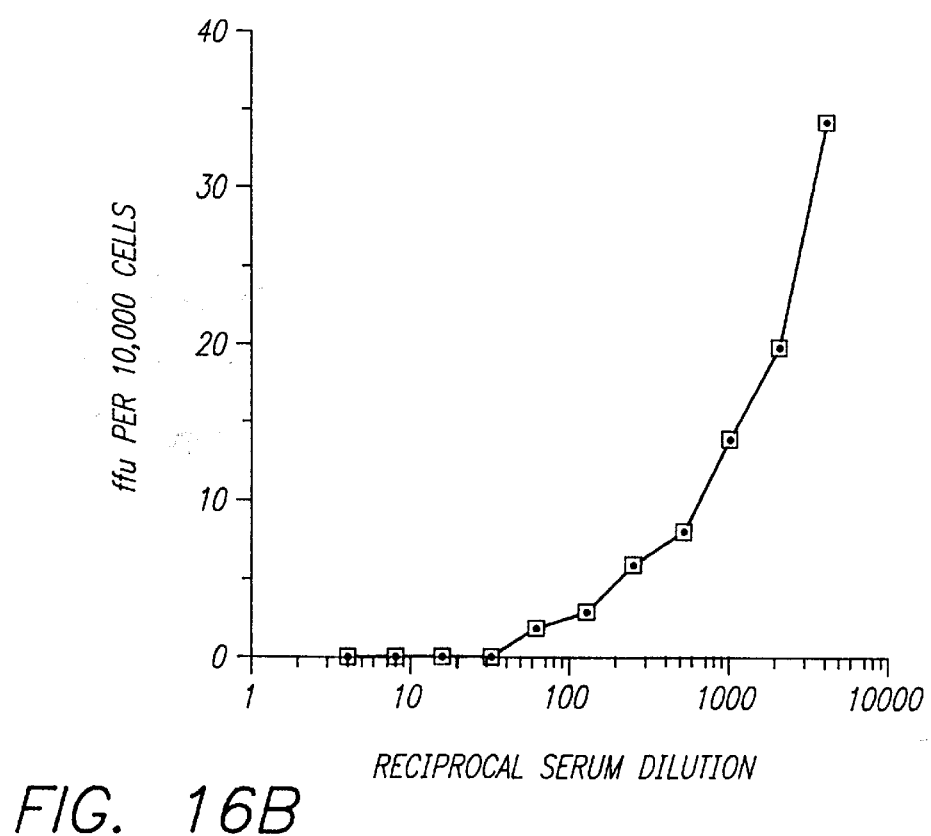
Figure 16C:
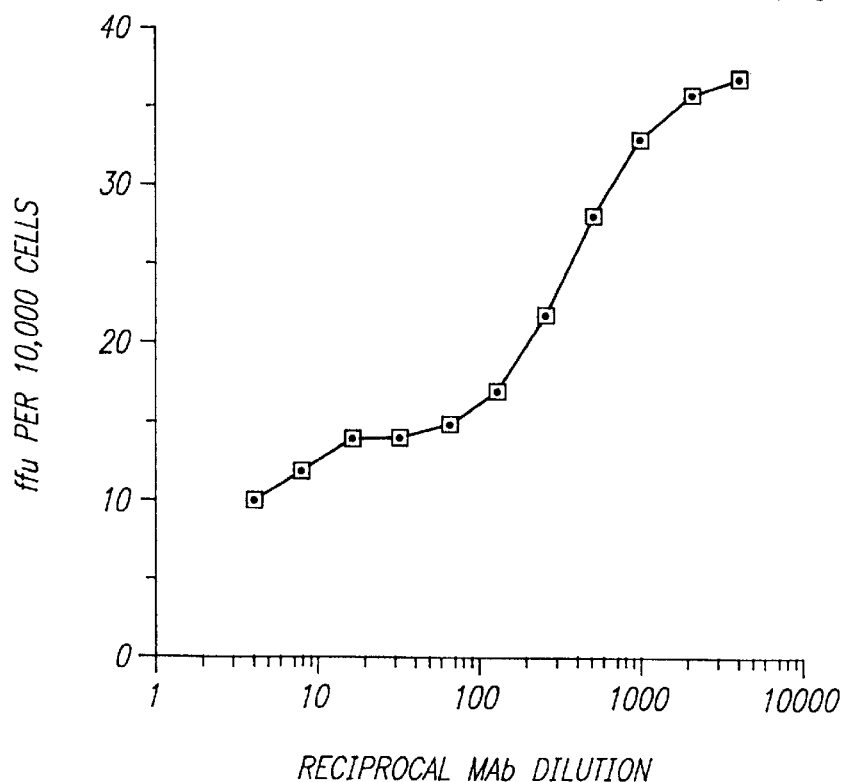
Figure 16D:
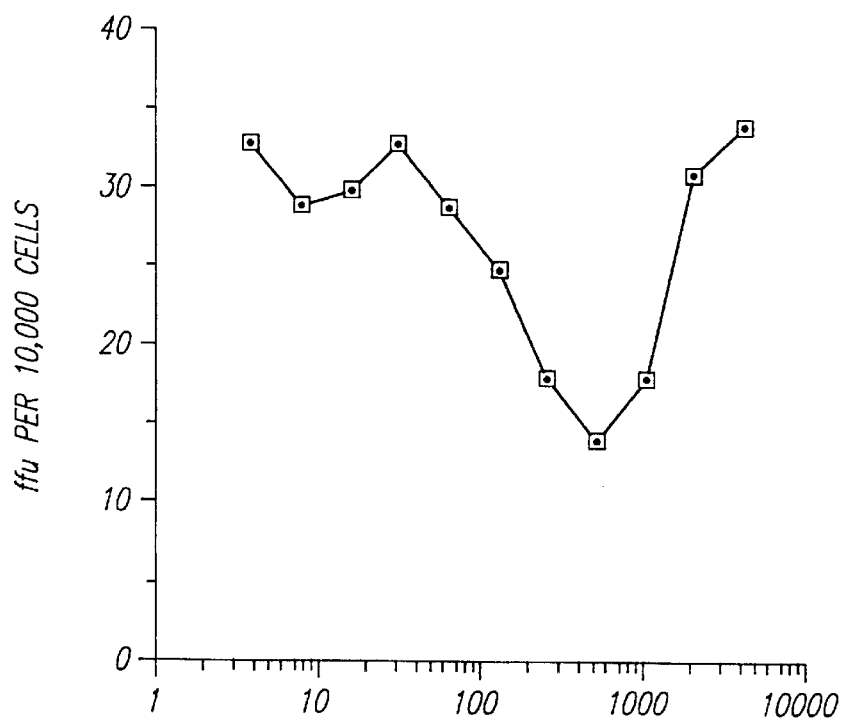

FIG. 17. Precipitation of BDV using sera from infected rats, monospecific rat antisera to recp18 and monoclonal antibodies (MAbs) to gp18. Virus was treated with nucleases to eliminate nucleic acid not contained within virions then immunoprecipitated with sera or MAbs and Protein A-Sepharose. RNA was extracted and subjected to RT-PCR to amplify a 693 nucleotide viral genomic sequence. PCR-products were visualized in an ethidium bromide-stained 1% agarose gel. (A) Precipitation of BDV with sera from infected rats. Lanes: 1, serum from infected rat, 15 week p.i.; 2, serum from infected rat, 5 week p.i.; 3, serum from infected rat, 15 week p.i., no BDV; 4, serum from infected rat,15 week p.i., genome sense primer used for first strand cDNA synthesis. (B) Precipitation of BDV by monospecific antisera to recp18 and MAbs to gp18. Lanes: 1, monospecific rat antisera to recp18; 2, MAb 14/13E10; 3, MAb 14/29A5. DNA markers (basepairs) are shown at the right. Timecourse of disease and appearance of antibodies to BDV in infected rates:

Rats developed Borna disease (BD) within 5 weeks post infection. The acute phase of the disease, 4–8 weeks post infection, was associated with marked weight loss, disheveled fur, dystonic posture, hind limb paresis and paralysis, mortality of 35%, and prominent inflammatory cell infiltrates in the brain. In the chronic phase of disease, 10–15 weeks post-infection, signs of disease stabilized and inflammation receded. Virus titers in the brains of animals acutely (5 weeks p.i.) and chronically infected (15 weeks p.i.) were $2.4 \pm 0.4 \times 10^5$ ffu/ml and $4.4 \pm 0.2 \times 10^4$ ffu/ml, respectively.

Figure 14C:
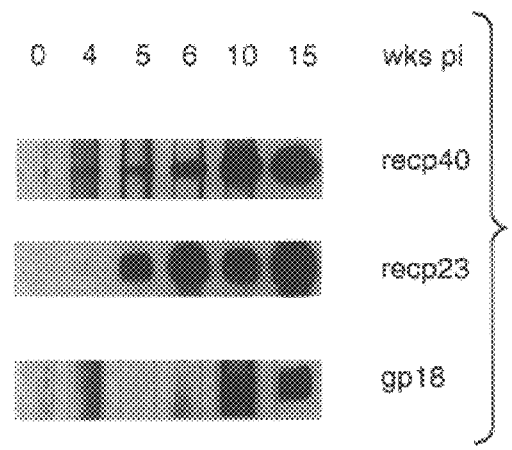
Figure 14B:
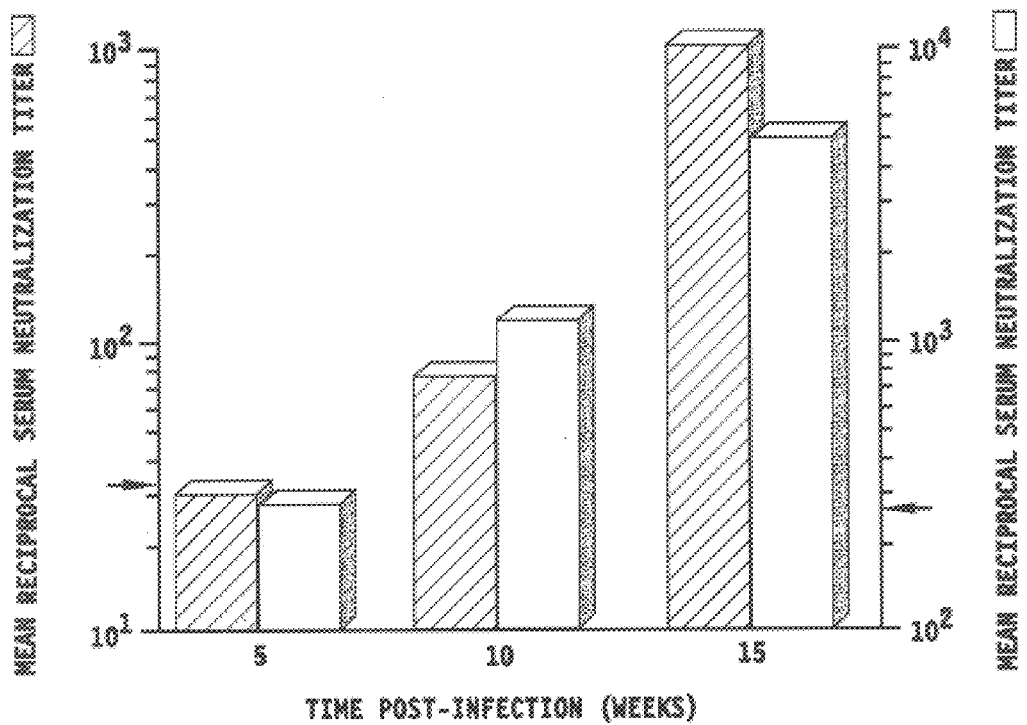

Sera were monitored for virus neutralization activity (FIGS. 14A, B and C) and the presence of antibodies reactive with recp40, recp23, recp18 or native gp18 in Western blot (FIG. 14C) and ELISA. Neutralization activity was first detected in sera (28% of the animals) at 5 weeks p.i. By week 15 p.i., all sera had neutralization activity with a mean titer of $1:977 \pm 246$. Antibodies to recp18 were first detected by ELISA at week 5 p.i. and showed a marked increase in titer by 15 weeks p.i. ($1:4,610 \pm 1,463$) (FIG. 14B). In contrast, antibodies reactive with recp40 and recp23 were detected by ELISA within 4 weeks of infection, reached a titer greater than 1:20,000 by 8 weeks p.i. and remained elevated through 15 weeks p.i. (see Example 3 above). Antibodies reactive with recp40 and recp23 were detected by Western blot between weeks four and five p.i., whereas antibodies to gp18 were detectable only after week 10 p.i. (FIG. 14C).

Affinity adsorption of neutralizing sera

To determine whether the presence of antibodies to gp18 correlate with neutralization activity, two rat sera (D2 and B3, 15 weeks p.i.), were tested in the neutralization assay after successive depletions of antibodies to individual BDV-proteins. Antibodies to BDV-specific proteins were removed from D2 rat serum by adsorption with membrane-bound protein. The efficiency of antibody depletion from serum was monitored by Western blot and ELISA. Prior to adsorption, the titers to recp40 and recp23 were each greater than 1:20,000. Following adsorption with recp23, the titer to recp23 decreased to 1:200. After adsorption with recp40, the titer to recp40 decreased to 1:150. Eluted antibodies were reactive by ELISA with the proteins used for adsorption: recp23 eluant titer, 1:5,000; recp40 eluant titer, 1:15,000. Serum antibodies remaining after adsorption, and eluted antibodies, were then tested for neutralizing activity. The neutralization titer of the D2 serum ($NT_{50}$ 1:1,000–1,500) did not change after adsorption with recp23 and recp40 antigens (D2 Δ recp23, Δ recp40) (Table 4). Antibodies eluted from proteins recp40 (recp40 eluant) and recp23 (recp23 eluant) had no neutralization activity (Table 4). In contrast, the $NT_{50}$ of the D2 serum decreased from 1:1, 000–1,500 to 1:600–700 after adsorption with recp18 (D2 Δ recp18) and to 1:160–200 after adsorption with gp18 (D2 Δ gp18) (Table 5). The neutralization titers of antibodies eluted from recp18 (recp18 eluant) and gp18 (gp18 eluant) were 1:60–100 and 1:240–400, respectively (Table 4). Similar results were obtained with serum from rat B3.

TABLE 4

Characterization of serum antibodies

| Serum | Reciprocal NT | IP-RT-PCR[a] | Reciprocal rp18 ELISA titer |
|---|---|---|---|
| Chronic (15 wk p.i. [D2]) | 1,000–1,500 | + | 4,300–5,000 |
| D2 Δαrecp23, Δαrecp40[b] | 1,000–1,500 | + | 4,000–5,000 |
| D2 Δαrecp18[b] | 600–700 | + | NS[c] |
| D2 Δαgp18[b] | 160–200 | + | 800–840 |
| recp18 eluant[d] | 60–100 | + | 2,400–3,000 |
| gp18 eluant[d] | 240–400 | + | 1,200–2,000 |
| recp23 eluant[d] | NS | – | NS |
| recp40 eluant[d] | NS | – | NS |
| Ratαrecp18 | 320–480 | + | >5,000 |
| Mouseαgp18 | 160–320 | + | >5,000 |

[a]IP of BDV and detection of genomic RNA by RT-PCR.
[b]Chronic rat sera (D2) adsorbed with recombinant (recp23, recp40, recp18) or native (gp18) protein.
[c]NS, not significant. The NT was considered to be not significant below 1:32; the recp18 ELISA titer was considered to be not significant below 1:250.
[d]Antibodies in chronic rat sera (D2) eluted from recombinant or native protein.

Monospecific antibodies to recp18 and gp18

Sera from rats and mice immunized with recp18 and gp18, respectively, were tested for neutralization activity. Neutralizing antibodies in both rats and mice were detected at 12 weeks post-immunization. Sixteen-weeks after immunization with recp18, 2 rats had neutralization titers between 1:320 and 1:480 (Table 4); sera from 2 mice immunized with gp18 had neutralization titers between 1:160 and 1:320 (Table 4).

Monoclonal antibodies to gp18

MAbs were generated against gp18. Five positive clones were identified by ELISA using gp18 as antigen. The MAbs represented three different immunoglobulin isotypes, yet all contained the kappa light chain (Table 5). Although each of the monoclonal antibodies immunoprecipitated gp18 (Table 5, FIG. 5A) and recp18 (Table 5), only MAb, 14/29A5 reacted by Western blot (Table 5, FIG. 15B).

Concentrated supernatants from all five MAbs neutralized BDV infectivity (Table 5). Similar to sera from chronically-infected rats (FIG. 16B), the neutralization titer of four MAbs was greatest at highest antibody concentration (FIG. 16C). In contrast, one MAb, 14/29A5, neutralized BDV only when used at a dilution of 1:400–1:1,000 (FIG. 16D). Neutralizing sera from chronically-infected rats, mice immunized with gp18 or rats immunized with recp18 (Table 4) had the capacity to inhibit 100% of BDV infectivity (FIG. 16B). In contrast, MAbs to gp18, used individually or in concert, inhibited a maximum of 68% of BDV infectivity (FIG. 16C and D). Supernatants of two MABS, 14/18H7, $NT_{50}$ 1:16 and 14/13E10, $NT_{50}$ 1:32, showed cooperativity in neutralization assays; pooling of these MAbs resulted in a higher neutralization titer ($NT_{50}$ 1:100–150). To determine the extent to which neutralization was complement-dependent, neutralization activity of MAbs was tested with addition of either active or heat-inactivated mouse complement. No increase in neutralization titer was detected with addition of mouse complement. Serum from noninfected (normal) rats was not neutralizing at dilutions greater than 1:16 (FIG. 16A).

Immunoprecipitation of BDV with neutralizing antibodies

BDV stock was treated with nucleases to eliminate free nucleic acids then incubated with sera or MAbs and Protein A-Sepharose. RNA was extracted from immunoprecipitated viral particles or subparticles and subjected to RT-PCR for amplification of viral genomic RNA. Neutralizing rat sera (FIG. 17A), monospecific sera to recp18 (FIG. 17B) or gp18, and D2 serum antibodies eluted from recp18 or gp18 precipitated BDV particles. Removal of antibodies to recp23, recp40, recp18 or gp18 did not affect the capacity of neutralizing sera to precipitate viral particles. Four MAbs also precipitated BDV (FIG. 17B and Table 5). One MAb,

TABLE 5

Characterization of anti-gp18 MAbs

| MAb | Ig class | Reciprocal NT | Characterization by: Western blot gp18 | Western blot rp18 | IP gp18 | IP rp18 | Reciprocal rp18 ELISA titer | IP-RT-PCR* |
|---|---|---|---|---|---|---|---|---|
| 14/29A5 | IgG2b | >400–1,000 | + | + | + | + | 500–1,000 | – |
| 14/26B9 | IgM | 8–16 | – | – | + | + | 4–8 | + |
| 14/8E1 | IgM | 50 | – | – | + | + | 200–300 | + |
| 14/13E10 | IgM | 50–100 | – | – | + | + | 16–64 | + |
| 14/18H7 | IgG3 | 100–200 | – | – | + | + | 128–256 | + |

*IP of BDV and detection of genomic RNA by RT-PCR.

14/29A5, did not precipitate viral particles at any dilution (1:5, 1:100, 1:200 or 1:500). Sera from noninfected or two acutely infected rats (5 weeks p.i.) (FIG. 17A) did not precipitate BDV. Experiments with sera and monoclonal antibodies are summarized in Tables 4 and 5. Negative controls for RT-PCR included the omission of virus from immunoprecipitation (FIG. 17A) and the use of genomic sense primers for first strand cDNA synthesis (FIG. 17A).

DISCUSSION

The presence (or absence) of neutralizing antibodies in BDV-infected animals has been controversial. Some reports have not shown evidence for neutralizing antibodies (Carbone, K. M., et al., *J. Virol.*, 61:3431–3440 (1987); Herzog, S., et al., *J. Gen. Virol.*, 66:503–8 (1985) and Narayan, O., et al., *J. Inf Dis.*, 148:305–315 (1983)}, however, this may reflect different timepoints for collection of sera or variation in the assay system for neutralization. Although there are reports of neutralizing antibodies in serum and CSF of both naturally and experimentally infected animals {Danner, K., et al., *Zbl. Vet-Med.* [B], 25:345–355 (1978); Hirano, N., et al., *J. Gen. Virol.*, 64:1521–1530 (1983); Ludwig, H., et al., *Progr. Med. Virol.*, 35:107–151 (1988) and Ludwig, H., et al., *Arch. Virol.* [Suppl] 7:111–133 (1993)}, neither the timecourse for development of neutralizing antibodies nor their target antigens have been characterized. Here, we show that the neutralizing activity of BDV-rat sera increases dramatically from the acute (5 weeks p.i.) to the chronic (15 weeks p.i.) phase of disease and provide evidence to indicate that neutralization activity is due, at least in part, to antibodies that react with a BDV glycoprotein, gp18. The timecourse for the appearance of neutralizing antibodies seems to correlate with immunoreactivity to gp18. Furthermore, removal of antibodies to gp18 or recp18 dramatically decreased the neutralization titer of BDV-rat sera. In contrast, subtraction of antibodies to two other viral proteins, p40 and p23, had no effect.

Neutralization activity was detected with monospecific antiserum against both gp18 and recp18 as well as with monoclonal antibodies against gp18. These MAbs represent three different isotypes, IgM, IgG2b and IgG3, indicating that multiple isotypes are capable of virus neutralization. Addition of complement did not enhance neutralization activity of the MAbs, suggesting that the mechanism for neutralization was neither complement-mediated inactivation of virus nor steric hindrance by a complement-MAb-virus complex.

It is likely that at least three different antibody binding sites on gp18 were involved in neutralization. Four MAbs, which immunoprecipitated both gp18 and recp18 but did not detect protein in Western blots, presumably bound to discontinuous epitopes. The observation that use of MAbs 14/13E10 and 14/18H7 in combination, resulted in greater neutralization activity than use of either MAb alone, suggests that these MAbs recognized either different discontinuous epitopes or different binding sites on a single discontinuous epitope. One MAb, 14/29A5, detected protein in Western blots as well as immunoprecipitation assays indicating that it bound to a continuous epitope. Unlike the other MAbs, 14/29A5 neutralized infectivity only after dilution (FIG. 16D), a profile consistent with neutralization by virus aggregation as reported in other viral systems {Dimmock, N.J., A. Capron, et al. (ed.), "Current Topics in Microbiology and Immunology", Springer-Verlag, Berlin (1993) and Outlaw, M. C., et al., *J. Gen. Virol.*, 71:69–76 (1990)}. Although all of the gp18 MAbs detected recp18 (nonglycosylated protein), it is possible that there are additional epitopes for neutralization which include the carbohydrate portion of gp18.

Sera from chronically-infected rats had greater neutralization activity than monospecific sera or monoclonal antibodies directed against gp18. Higher neutralization activity in sera from infected animals could reflect factors that influence epitope presentation such as interactions between gp18 and other proteins or the virion envelope. Alternatively, gp18 may not be the only BDV protein that elicits neutralizing antibodies. Sera from chronically-infected animals retained partial neutralizing activity and the capacity to precipitate virus after adsorption with gp18. Although this may be due to incomplete subtraction of antibodies to gp18 (Table 4) neutralizing antibodies may be directed against other viral proteins as well. For example, an additional candidate for a virion surface protein that may elicit neutralizing antibodies is p57. This putative protein contains multiple potential N-glycosylation sites and, as the product of the fourth ORF on the BDV genome, is in the gene position generally occupied by glycoproteins in *Mononegavirales* {Briese, T., et al., *Proc. Natl. Acad. Sci. USA:* 91:4362–4366 (1994)}. It is contemplated that passive administration of neutralizing antibodies or immunization with gp18 and other virion surface proteins can alter BDV pathogenesis.

Deposit

The cDNA of BDV genomic RNA sequence has been deposited in the GenBank data base (accession no. U04608). This GenBank sequence is hereby incorporated by reference in its entirety.

The recombinant transfer vector, suitable for transformation into *Escherichia coli* DH10, containing four overlapping cDNA libraries (as described in Example 1, above) representing the entire BDV viral genome has been deposited under the Budapest Treaty, at the American Type Culture Collection, Rockville, Md. 20852 (U.S.A.) on Dec. 30, 1994 under the deposit name BDVU04608, and ATCC Accession No. 97008.

Availability of the deposited recombinant tranfer vector is not to be construed as a license to practice the invention in contravention of the rights granted under the authority of any government in accordance with its patent laws.

Also, the present invention is not to be considered limited in scope by the deposited recombinant transfer vector, since the deposited vector is intended only to be illustrative of particular aspects of the invention. Any recombinant transfer vector which can be used to prepare recombinant microorganism which can function to produce a recombinant protein product described herein is considered to be within the scope of this invention. Further, various modifications of the invention in addition to those shown and described herein which are apparent to those skilled in the art from the preceding description are considered to fall within the scope of the appended claims.

---

We claim:

1. A method of detecting, in a sample, a ligand capable of binding a BDV protein, said method comprising the steps of:
    a) contacting the sample with at least one isolated protein selected from the group consisting of: p23, recp23, and a protein comprising an amino acid sequence as set forth in SEQ ID NO:4, wherein said isolated protein is prebound to a solid support without gel size fractionation; and
    b) determining whether a ligand binds to the protein.

2. The method of claim 1, wherein the sample is a biological sample.

3. The method of claim 2, wherein the biological sample is selected from the group consisting of: whole blood, serum, plasma, cerebral spinal fluid, and synovial fluid.

4. The method of claim 2, wherein the ligand is an antibody.

5. The method of claim 1, wherein the ligand is selected from the group consisting of polyclonal, monospecific or monoclonal antibodies; and Fab, F(ab')$_2$, or Fv fragments of antibodies.

6. An immunoassay method of testing a sample for antibody ligands immunoreactive with Borna disease virus, comprising the steps of;
    a) contacting a test sample with an isolated protein, said protein being prebound to a solid support without gel size fractionation, wherein said prebound isolated protein is selected from the group consisting of: p23, recp23, and a protein comprising an amino acid sequence as set forth in SEQ ID NO:4;
    b) contacting the test sample with at least one other prebound isolated protein, wherein the other prebound isolated protein is selected from the group consisting of: gp18, recp18, p57, recp57, pol, recpol, p40, recp40, and a protein comprising an amino acid sequence as set forth in SEQ ID NO: 2, 6, 8, or 10; and
    c) detecting whether any antibody ligands in the sample bind to any of the prebound isolated proteins.

7. The immunoassay method of claim 6, wherein the immunoassay method is an ELISA or an immunodot assay.

8. The method of claim 1 or 6, wherein the sample is from a test subject suspected of having (1) BDV infection or related pathogenesis; or (2) neurologic and neuropsychiatric disease not due to BDV infection.

9. The method of claim 8, further comprising the steps of determining the amount of ligand binding to the proteins and correlating the amount with onset or progression of the infection or disease.

10. The method of claim 8, wherein the test subject is selected from the group consisting of: humans and domestic animals.

11. A method for selecting for a ligand capable of binding p23, said method comprising the steps of:
    a) contacting the ligand with an isolated protein prebound to a solid support, wherein the prebound isolated protein is selected from the group consisting of: p23, recp23, and a protein comprising an amino acid sequence as set forth in SEQ ID NO:4; and
    b) selecting for the ligand which binds to the protein.

12. The method of claim 11, wherein said ligand is a monospecific antiserum and said selection step comprises eluting the ligand bound to the protein.

13. The method of claim 12, wherein said ligand is a monoclonal antibody.

14. A panel for use in the method of claim 1 or 11, said panel comprising one or more isolated proteins prebound to a solid support without gel size fractionation, wherein at least one of said proteins is selected from the group consisting of: p23, recp23, and a protein comprising an amino acid sequence as set forth in SEQ ID NO:4.

15. A panel for use in the immunoassay method of claim 6, said panel comprising:
    a) at least one isolated protein prebound to a solid support without gel size fractionation, wherein the isolated prebound protein is selected from the group consisting of: p23, recp23, and a protein comprising an amino acid sequence as set forth in SEQ ID NO:4; and
    b) at least one other isolated protein prebound to the solid support without gel size fractionation, wherein the other isolated prebound polypeptide is selected from the group consisting of: gp18, recp18, p57, recp57, pol, recpol, p40, recp40, and a protein comprising an amino acid sequence as set forth in SEQ ID NO: 2, 6, 8, or 10.

16. The panel of claim 15, wherein the solid support is selected from the group consisting of: microtiter wells, test tubes, beads, strips, membranes, and microparticles.

17. A kit for use in the method of claim 1, said kit comprising:
 a) a first container comprising a purified protein selected from the group consisting of: p23, recp23, and a protein comprising an amino acid sequence as set forth in SEQ ID NO:4; and
 b) a second container comprising a positive control, wherein said positive control contains an antibody ligand capable of binding to the purified protein.

18. A kit for use in the immunoassay method of claim 6, said kit comprising:
 a) a first container comprising a purified polypeptide selected from the group consisting of: p23, recp23, and a protein comprising an amino acid sequence as set forth in SEQ ID NO:4; and
 b) a second container comprising another purified polypeptide selected from the group consisting of: gp18, recp18, p57, recp57, pol, recpol, p40, recp40, and a protein comprising an amino acid sequence as set forth in SEQ ID NO: 2, 6, 8, or 10.

* * * * *

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
       (A) LENGTH: 1112 base pairs
       (B) TYPE: nucleic acid
       (C) STRANDEDNESS: single
       (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:1:

```
ATGCCACCCA AGAGACGCCT GGTTGATGAC GCCGATGCCA TGGAGGATCA AGATCTATAT       60
GAACCCCCAG CGAGCCTCCC TAAGCTCCCT GGGAAATTCC TACAATACAC CGTTGGGGGG      120
TCTGACCCGC ATCCGGGTAT AGGGCATGAG AAAGACATCA GGCAGAACGC AGTGGCATTG      180
TTAGACCAGT CACGGCGCGA TATGTTTCAC ACAGTAACGC CTAGCCTTGT GTTTCTATGT      240
TTGCTAATCC CAGGACTGCA CGCTGCGTTT GTTCACGGAG GGGTGCCTCG TGAATCCTAC      300
CTGTCGACGC CTGTCACGCG TGGAGAACAG ACTGTTGTTA AGACTGCGAA GTTTTACGGG      360
GAAAAGACGA CGCAGCGTGA TCTCACCGAG CTGGAGATCT CCTCTATCTT CAGCCATTGT      420
TGCTCATTAC TAATAGGGGT TGTGATAGGA TCGTCGTCTA AGATCAAAGC AGGAGCCGAG      480
CAGATCAAGA AAAGGTTTAA AACTATGATG GCAGCCTTAA ACCGGCCATC CCATGGTGAG      540
ACTGCTACAC TACTCCAGAT GTTTAATCCA CATGAGGCTA TAGATTGGAT TAACGGCCAA      600
CCCTGGGTAG GCTCCTTTGT GTTGTCTCTA CTAACTACAG ACTTTGAGTC CCCAGGTAAA      660
GAATTTATGG ACCAGATTAA GCTTGTCGCA AGTTATGCAC AGATGACTAC GTACACTACT      720
ATAAAGGAGT ACCTCGCAGA ATGCATGGAT GCTACCCTTA CAATCCCCGT AGTTGCATAT      780
GAGATCCGTG ACTTTTTAGA AGTTTCAGCA AAGCTTAAGG AGGATCATGC TGACCTGTTC      840
CCGTTTCTGG GGGCCATTAG ACACCCCGAC GCTATCAAGC TGGCGCCACG AAGCTTTCCC      900
AATCTGGCCT CCGCAGCGTT TTACTGGAGT AAGAAGGAAA ACCCCACAAT GGCAGGCTAC      960
CGGGCCTCCA CCATCCAGCC GGGCGCAAGT GTCAAGGAAA CCCAGCTTGC CCGGTATAGG     1020
CGCCGCGAGA TATCTCGTGG AGAGGACGGG GCAGAGCTCT CAGGTGAGAT CTCTGCCATA     1080
ATGAAGATGA TAGGTGTGAC TGGTCTAAAC TA                                   1112
```

(2) INFORMATION FOR SEQ ID NO:2:

(i) SEQUENCE CHARACTERISTICS:
       (A) LENGTH: 370 amino acids
       (B) TYPE: amino acid
       (C) STRANDEDNESS: single
       (D) TOPOLOGY: unknown (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:2:

Met Pro Pro Lys Arg Arg Leu Val Asp Asp Ala Asp Ala Met Glu Asp

-continued

```
            1               5                   10                  15
        Gln Asp Leu Tyr Glu Pro Pro Ala Ser Leu Pro Lys Leu Pro Gly Lys
                        20                  25                  30

Phe Leu Gln Tyr Thr Val Gly Gly Ser Asp Pro His Pro Gly Ile Gly
                        35                  40                  45

His Glu Lys Asp Ile Arg Gln Asn Ala Val Ala Leu Leu Asp Gln Ser
                        50                  55                  60

Arg Arg Asp Met Phe His Thr Val Thr Pro Ser Leu Val Phe Leu Cys
         65                  70                  75                  80

Leu Leu Ile Pro Gly Leu His Ala Ala Phe Val His Gly Gly Val Pro
                        85                  90                  95

Arg Glu Ser Tyr Leu Ser Thr Pro Val Thr Arg Gly Glu Gln Thr Val
                        100                 105                 110

Val Lys Thr Ala Lys Phe Tyr Gly Glu Lys Thr Thr Gln Arg Asp Leu
                        115                 120                 125

Thr Glu Leu Glu Ile Ser Ser Ile Phe Ser His Cys Cys Ser Leu Leu
                        130                 135                 140

Ile Gly Val Val Ile Gly Ser Ser Lys Ile Lys Ala Gly Ala Glu
        145                 150                 155                 160

Gln Ile Lys Lys Arg Phe Lys Thr Met Met Ala Ala Leu Asn Arg Pro
                        165                 170                 175

Ser His Gly Glu Thr Ala Thr Leu Leu Gln Met Phe Asn Pro His Glu
                        180                 185                 190

Ala Ile Asp Trp Ile Asn Gly Gln Pro Trp Val Gly Ser Phe Val Leu
                        195                 200                 205

Ser Leu Leu Thr Thr Asp Phe Glu Ser Pro Gly Lys Glu Phe Met Asp
        210                 215                 220

Gln Ile Lys Leu Val Ala Ser Tyr Ala Gln Met Thr Thr Tyr Thr Thr
        225                 230                 235                 240

Ile Lys Glu Tyr Leu Ala Glu Cys Met Asp Ala Thr Leu Thr Ile Pro
                        245                 250                 255

Val Val Ala Tyr Glu Ile Arg Asp Phe Leu Glu Val Ser Ala Lys Leu
                        260                 265                 270

Lys Glu Asp His Ala Asp Leu Phe Pro Phe Leu Gly Ala Ile Arg His
                        275                 280                 285

Pro Asp Ala Ile Lys Leu Ala Pro Arg Ser Phe Pro Asn Leu Ala Ser
        290                 295                 300

Ala Ala Phe Tyr Trp Ser Lys Lys Glu Asn Pro Thr Met Ala Gly Tyr
        305                 310                 315                 320

Arg Ala Ser Thr Ile Gln Pro Gly Ala Ser Val Lys Glu Thr Gln Leu
                        325                 330                 335

Ala Arg Tyr Arg Arg Arg Glu Ile Ser Arg Gly Glu Asp Gly Ala Glu
                        340                 345                 350

Leu Ser Gly Glu Ile Ser Ala Ile Met Lys Met Ile Gly Val Thr Gly
                        355                 360                 365

Leu Asn
        370
```

(2) INFORMATION FOR SEQ ID NO:3:

(i) SEQUENCE CHARACTERISTICS:
        (A) LENGTH: 609 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:3:

ATGGCAACGC GACCATCGAG TCTGGTCGAC TCCCTGGAGG ACGAAGAAGA TCCCCAGACA      60

CTACGACGGG AACGACCGGG GTCACCAAGA CCACGGAAGG TCCCAAGGAA TGCATTGACC     120

CAACCAGTAG ACCAGCTCCT GAAGGACCTC AGGAAGAACC CCTCCATGAT CTCAGACCCA     180

GACCAGCGAA CCGGAAGGGA GCAGCTGTCG AATGATGAGC TAATCAAGAA GTTAGTGACG     240

GAGCTGGCCG AGAATAGCAT GATCGAGGCT GAGGAGGTGC GGGGCACTCT TGGAGACATC     300

TCGGCTCGTA TCGAGGCAGG GTTTGAGTCC CTGTCCGCCC TCCAAGTGGA AACCATCCAG     360

ACAGCTCAGC GGTGCGATCA CTCCGACAGC ATCAGGATCC TCGGCGAGAA CATCAAGATA     420

CTAGATCGCT CCATGAAGAC AATGATGGAG ACAATGAAGC TCATGATGGA GAAGGTGGAT     480

CTCCTCTACG CATCAACCGC CGTTGGGACC TCTGCACCCA TGTTGCCCTC CCATCCTGCA     540

CCTCCGCGCA TTTATCCCCA GCTCCCAAGT GCCCCGACAA CGGATGAATG GGACATCATA     600

CCATAAAAA                                                             609

(2) INFORMATION FOR SEQ ID NO:4:

(i) SEQUENCE CHARACTERISTICS:
            (A) LENGTH: 201 amino acids
            (B) TYPE: amino acid
            (C) STRANDEDNESS: single
            (D) TOPOLOGY: unknown (ii) MOLECULE TYPE: protein (iii) HYPOTHETICAL: NO (iv) ANTI-SENSE: NO (xi) SEQUENCE DESCRIPTION: SEQ ID NO:4:

Met Ala Thr Arg Pro Ser Ser Leu Val Asp Ser Leu Glu Asp Glu Glu
1               5                   10                  15

Asp Pro Gln Thr Leu Arg Arg Glu Arg Pro Gly Ser Pro Arg Pro Arg
            20                  25                  30

Lys Val Pro Arg Asn Ala Leu Thr Gln Pro Val Asp Gln Leu Leu Lys
        35                  40                  45

Asp Leu Arg Lys Asn Pro Ser Met Ile Ser Asp Pro Asp Gln Arg Thr
    50                  55                  60

Gly Arg Glu Gln Leu Ser Asn Asp Glu Leu Ile Lys Lys Leu Val Thr
65                  70                  75                  80

Glu Leu Ala Glu Asn Ser Met Ile Glu Ala Glu Val Arg Gly Thr
                85                  90                  95

Leu Gly Asp Ile Ser Ala Arg Ile Glu Ala Gly Phe Glu Ser Leu Ser
                100                 105                 110

Ala Leu Gln Val Glu Thr Ile Gln Thr Ala Gln Arg Cys Asp His Ser
            115                 120                 125

Asp Ser Ile Arg Ile Leu Gly Glu Asn Ile Lys Ile Leu Asp Arg Ser
    130                 135                 140

Met Lys Thr Met Met Glu Thr Met Lys Leu Met Met Glu Lys Val Asp
145                 150                 155                 160

Leu Leu Tyr Ala Ser Thr Ala Val Gly Thr Ser Ala Pro Met Leu Pro
                165                 170                 175

```
Ser His Pro Ala Pro Pro Arg Ile Tyr Pro Gln Leu Pro Ser Ala Pro
            180                 185                 190

Thr Thr Asp Glu Trp Asp Ile Ile Pro
        195                 200
```

(2) INFORMATION FOR SEQ ID NO:5:

(i) SEQUENCE CHARACTERISTICS:
        (A) LENGTH: 428 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:5:

```
ATGAATTCAA AACATTCCTA TGTGGAGCTC AAGGACAAGG TAATCGTCCC TGGATGGCCC      60

ACACTGATGC TTGAGATAGA CTTTGTAGGG GGGACTTCAC GGAACCAGTT CCTTAACATC     120

CCATTTCTTT CAGTGAAAGA GCCTCTGCAG CTTCCACGCG AGAAGAAGTT GACCGACTAC     180

TTTACTATTG ACGTAGAACC AGCAGGTCAT TCCCTGGTCA ATATATACTT CCAGATTGAC     240

GACTTCTTGC TCCTAACACT CAACTCACTA TCTGTGTACA AGGACCCGAT TAGAAAATAC     300

ATGTTCCTAC GCCTCAACAA GGACCAGAGC AAGCACGCAA TCAATGCAGC CTTCAATGTC     360

TTTTCTTATC GGCTTCGGAA CATTGGTGTT GGTCCTCTCG GCCCGGACAT TCGATCTTCA     420

GGGCCTTA                                                              428
```

(2) INFORMATION FOR SEQ ID NO:6:

(i) SEQUENCE CHARACTERISTICS:
        (A) LENGTH: 142 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:6:

```
Met Asn Ser Lys His Ser Tyr Val Glu Leu Lys Asp Lys Val Ile Val
1               5                   10                  15

Pro Gly Trp Pro Thr Leu Met Leu Glu Ile Asp Phe Val Gly Gly Thr
            20                  25                  30

Ser Arg Asn Gln Phe Leu Asn Ile Pro Phe Leu Ser Val Lys Glu Pro
            35                  40                  45

Leu Gln Leu Pro Arg Glu Lys Lys Leu Thr Asp Tyr Phe Thr Ile Asp
        50                  55                  60

Val Glu Pro Ala Gly His Ser Leu Val Asn Ile Tyr Phe Gln Ile Asp
65                  70                  75                  80

Asp Phe Leu Leu Leu Thr Leu Asn Ser Leu Ser Val Tyr Lys Asp Pro
                85                  90                  95

Ile Arg Lys Tyr Met Phe Leu Arg Leu Asn Lys Asp Gln Ser Lys His
            100                 105                 110

Ala Ile Asn Ala Ala Phe Asn Val Phe Ser Tyr Arg Leu Arg Asn Ile
        115                 120                 125

Gly Val Gly Pro Leu Gly Pro Asp Ile Arg Ser Ser Gly Pro
        130                 135                 140
```

(2) INFORMATION FOR SEQ ID NO:7:

(i) SEQUENCE CHARACTERISTICS:
        (A) LENGTH: 1515 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:7:

```
ATGCAGCCTT CAATGTCTTT TCTTATCGGC TTCGGAACAT TGGTGTTGGT CCTCTCGGCC      60
CGGACATTCG ATCTTCAGGG CCTTAGCTGC AATACTGACT CCACTCCTGG ACTGATTGAC     120
CTGGAGATAA GGCGACTTTG CCACACCCCA ACGGAAAATG TCATTTCATG CGAGGTTAGT     180
TATCTCAACC ACACGACTAT TAGCCTCCCG GCAGTCCACA CATCATGCCT CAAGTACCAC     240
TGCAAAACCT ATTGGGGATT CTTTGGTAGC TACAGCGCTG ACCGAATCAT AAATCGGTAC     300
ACTGGTACTG TTAAGGGTTG TCTAAACAAC TCAGCACCAG AGGACCCCTT CGAGTGCAAC     360
TGGTTCTACT GCTGCTCGGC GATTACAACA GAGATCTGCC GATGCTCTAT TACAAATGTC     420
ACGGTGGCTG TGCAAACATT CCCACCGTTC ATGTACTGCA GTTTTGCAGA CTGCAGTACC     480
GTGAGCCAAC AGGAGCTAGA GAGTGGAAAG GCAATGCTGA GCGATGGCAG TACATTAACT     540
TATACCCCGT ATATCCTACA GTCAGAAGTC GTGAACAAAA CCCTCAATGG GACCATACTC     600
TGCAACTCAT CCTCTAAGAT AGTTTCCTTC GATGAATTTA GGCGTTCATA CTCCCTAACG     660
AATGGTAGTT ACCAGAGCTC ATCAATCAAT GTGACGTGTG CAAACTACAC GTCGTCCTGC     720
CGGCCCAGGT TGAAAAGGCG GCGTAGGGAC ACCCAGCAGA TTGAGTATCT AGTTCACAAG     780
CTTAGGCCCA CACTGAAAGA TGCATGGGAG GACTGTGAGA TCCTCCAGTC TCTGCTCCTA     840
GGGGTGTTTG GTACTGGGAT CGCAAGTGCT TCTCAATTTT TGAGGAGCTG GCTCAACCAC     900
CCTGACATCA TCGGGTATAT AGTTAATGGA GTTGGGGTTG TCTGGCAATG CCATCGTGTT     960
AATGTCACGT TCATGGCGTG GAATGAGTCC ACCTATTACC CTCCAGTAGA TTACAATGGG    1020
CGGAAGTACT TCCTGAATGA TGAGGGAAGG TTACAAACAA ACACCCCCGA GGCAAGGCCA    1080
GGGCTTAAGC GGGTCATGTG GTTCGGCAGG TACTTCCTAG GACAGTAGG GTCTGGGGTG     1140
AAACCGAGGA GGATTCGGTA CAATAAGACC TCACATGACT ACCACCTGGA GGAGTTTGAG    1200
GCAAGTCTCA ACATGACCCC TCAGACCAGT ATCGCCTCGG GTCATGAGAC AGACCCCATA    1260
AATCATGCCT ACGAACGCA GGCTGATCTC CTTCCATACA CCAGGTCTAG TAATATAACA     1320
TCTACGGATA CAGGCTCAGG CTGGGTGCAC ATCGGCCTAC CCTCATTTGC TTTCCTCAAT    1380
CCCCTCGGGT GGCTCAGGGA CCTACTTGCA TGGGCAGCCT GGTTGGGTGG GGTTCTATAC    1440
TTAATAAGTC TTTGTGTTTC CTTACCAGCC TCCTTCGCGA GGAGGAGACG CCTCGGCCGG    1500
TGGCAGGAAT AAACC                                                     1515
```

(2) INFORMATION FOR SEQ ID NO:8:

(i) SEQUENCE CHARACTERISTICS:
        (A) LENGTH: 503 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:8:

```
Met Gln Pro Ser Met Ser Phe Leu Ile Gly Phe Gly Thr Leu Val Leu
1               5                   10                  15

Val Leu Ser Ala Arg Thr Phe Asp Leu Gln Gly Leu Ser Cys Asn Thr
            20                  25                  30

Asp Ser Thr Pro Gly Leu Ile Asp Leu Glu Ile Arg Arg Leu Cys His
            35                  40                  45

Thr Pro Thr Glu Asn Val Ile Ser Cys Glu Val Ser Tyr Leu Asn His
        50                  55                  60

Thr Thr Ile Ser Leu Pro Ala Val His Thr Ser Cys Leu Lys Tyr His
65                  70                  75                  80

Cys Lys Thr Tyr Trp Gly Phe Phe Gly Ser Tyr Ser Ala Asp Arg Ile
                85                  90                  95

Ile Asn Arg Tyr Thr Gly Thr Val Lys Gly Cys Leu Asn Asn Ser Ala
                100                 105                 110

Pro Glu Asp Pro Phe Glu Cys Asn Trp Phe Tyr Cys Ser Ala Ile
            115                 120                 125

Thr Thr Glu Ile Cys Arg Cys Ser Ile Thr Asn Val Thr Val Ala Val
130                 135                 140

Gln Thr Phe Pro Pro Phe Met Tyr Cys Ser Phe Ala Asp Cys Ser Thr
145                 150                 155                 160

Val Ser Gln Gln Glu Leu Glu Ser Gly Lys Ala Met Leu Ser Asp Gly
                165                 170                 175

Ser Thr Leu Thr Tyr Thr Pro Tyr Ile Leu Gln Ser Glu Val Val Asn
                180                 185                 190

Lys Thr Leu Asn Gly Thr Ile Leu Cys Asn Ser Ser Lys Ile Val
                195                 200                 205

Ser Phe Asp Glu Phe Arg Arg Ser Tyr Ser Leu Thr Asn Gly Ser Tyr
210                 215                 220

Gln Ser Ser Ser Ile Asn Val Thr Cys Ala Asn Tyr Thr Ser Ser Cys
225                 230                 235                 240

Arg Pro Arg Leu Lys Arg Arg Arg Asp Thr Gln Gln Ile Glu Tyr
                245                 250                 255

Leu Val His Lys Leu Arg Pro Thr Leu Lys Asp Ala Trp Glu Asp Cys
                260                 265                 270

Glu Ile Leu Gln Ser Leu Leu Leu Gly Val Phe Gly Thr Gly Ile Ala
275                 280                 285

Ser Ala Ser Gln Phe Leu Arg Ser Trp Leu Asn His Pro Asp Ile Ile
            290                 295                 300

Gly Tyr Ile Val Asn Gly Val Gly Val Val Trp Gln Cys His Arg Val
305                 310                 315                 320

Asn Val Thr Phe Met Ala Trp Asn Glu Ser Thr Tyr Tyr Pro Pro Val
                325                 330                 335

Asp Tyr Asn Gly Arg Lys Tyr Phe Leu Asn Asp Glu Gly Arg Leu Gln
                340                 345                 350

Thr Asn Thr Pro Glu Ala Arg Pro Gly Leu Lys Arg Val Met Trp Phe
            355                 360                 365

Gly Arg Tyr Phe Leu Gly Thr Val Gly Ser Val Lys Pro Arg Arg
370                 375                 380

Ile Arg Tyr Asn Lys Thr Ser His Asp Tyr His Leu Glu Glu Phe Glu
385                 390                 395                 400

Ala Ser Leu Asn Met Thr Pro Gln Thr Ser Ile Ala Ser Gly His Glu
                405                 410                 415
```

-continued

```
Thr Asp Pro Ile Asn His Ala Tyr Gly Thr Gln Ala Asp Leu Leu Pro
            420                 425                 430

Tyr Thr Arg Ser Ser Asn Ile Thr Ser Thr Asp Thr Gly Ser Gly Trp
            435                 440                 445

Val His Ile Gly Leu Pro Ser Phe Ala Phe Leu Asn Pro Leu Gly Trp
450                 455                 460

Leu Arg Asp Leu Leu Ala Trp Ala Ala Trp Leu Gly Gly Val Leu Tyr
465                 470                 475                 480

Leu Ile Ser Leu Cys Val Ser Leu Pro Ala Ser Phe Ala Arg Arg Arg
            485                 490                 495

Arg Leu Gly Arg Trp Gln Glu
            500
```

(2) INFORMATION FOR SEQ ID NO:9:

(i) SEQUENCE CHARACTERISTICS:
        (A) LENGTH: 5135 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:9:

```
ATGTCATTTC ATGCGAGCCT CCTTCGCGAG GAGGAGACGC CTCGGCCGGT GGCAGGAATA      60

AACCGTACCG ACCAGTCTCT TAAAAACCCT CTCCTCGGAA CAGAGGTCTC TTTCTGCCTT     120

AAGTCGAGCT CACTCCCCCA TCATGTACGA GCACTAGGCC AGATTAAAGC AAGGAACCTG     180

GCATCCTGTG ACTATTACTT GCTATTCCGC CAAGTTGTAT TGCCCCCTGA AGTATATCCC     240

ATTGGTGTTC TAATAAGAGC TGCGGAGGCT ATACTAACAG TTATAGTATC AGCTTGGAAG     300

CTGGATCATA TGACGAAGAC CCTATACTCC TCTGTGAGAT ATGCACTCAC CAATCCCCGG     360

GTCCGAGCCC AACTTGAGCT TCACATTGCC TACCAGCGCA TAGTGGGTCA GGTCTCGTAC     420

AGCCGGGAGG CAGACATAGG GCCAAAAAGG CTTGGGAATA TGTCATTGCA ATTCATCCAA     480

TCTCTCGTTA TTGCCACCAT AGACACGACA AGCTGCCTAA TGACCTACAA CCACTTTCTT     540

GCTGCAGCAG ACACAGCCAA GAGCAGATGC CATCTCCTAA TCGCCTCAGT GGTCCAGGGG     600

GCCCTTTGGG AACAAGGGTC ATTTCTTGAT CATATAATCA ACATGATCGA CATAATTGAC     660

TCAATCAACC TCCCCCATGA TGATTACTTC ACAATTATTA AGTCTATCTT TCCCTACTCC     720

CAAGGGCTTG TTATGGGGAG GCATAATGTA TCAGTCTCCT CTGATTTCGC GTCCGTATTT     780

GCCATTCCTG AATTATGCCC GCAACTAGAC AGCTTACTAA AAAAACTGCT CCAACTTGAC     840

CCCGTTCTCC TCCTCATGGT CTCTTCGGTG CAGAAGTCAT GGTACTTCCC TGAGATCCGA     900

ATGGTCGACG GGTCACGGGA GCAGCTCCAC AAGATGCGTG TCGAGCTGGA AACGCCCCAA     960

GCCCTGCTGT CGTACGGCCA TACCCTCCTG TCAATATTTC GGGCAGAGTT TATCAAAGGC    1020

TATGTCTCAA AGAATGCGAA GTGGCCGCCC GTACACCTGC TCCCAGGCTG TGACAAATCC    1080

ATAAAAAATG CGAGAGAGCT GGGCCGCTGG AGCCCGGCAT TGACCGACG ATGGCAGCTC    1140

TTCGAGAAGG TTGTCATTCT AAGAATTGCT GACCTAGATA TGGATCCCGA CTTCAACGAT    1200

ATTGTTAGCG ATAAGGCGAT AATCAGCTCA AGAAGGGACT GGGTATTCGA GTACAATGCA    1260

GCGGCCTTTT GGAAGAAATA CGGTGAACGG TTGGAGAGGC CTCCTGCCAG GTCGGGACCG    1320

TCACGACTTG TGAATGCTCT AATCGATGGA CGCTTAGACA ATATCCCAGC CCTGCTAGAG    1380
```

```
CCATTTTACA GGGGAGCGGT TGAGTTCGAG GATCGGTTGA CTGTGCTCGT GCCTAAGGAG    1440

AAAGAGTTAA AGGTAAAGGG AAGGTTCTTC TCGAAGCAAA CATTGGCAAT CAGGATATAT    1500

CAGGTTGTTG CTGAAGCTGC ACTTAAGAAT GAGGTTATGC CATACCTAAA GACACACTCA    1560

ATGACCATGA GCTCAACGGC TCTAACTCAC CTTCTTAACC GGCTATCACA TACTATCACT    1620

AAGGGTGACT CCTTTGTTAT TAACCTTGAC TATAGTTCCT GGTGCAACGG TTTCCGACCA    1680

GAACTGCAGG CCCCAATCTG TCGTCAGTTG GATCAGATGT TCAATTGCGG GTACTTCTTC    1740

AGGACTGGGT GCACACTGCC ATGCTTTACC ACGTTTATTA TTCAAGACAG GTTCAACCCG    1800

CCCTATTCCC TCAGTGGTGA GCCCGTTGAA GACGGAGTTA CATGCGCGGT TGGGACTAAA    1860

ACAATGGGGG AGGGCATGAG GCAGAAACTA TGGACAATCC TTACGAGCTG CTGGGAGATA    1920

ATTGCTCTTC GGGAAATTAA CGTGACGTTT AACATACTAG GCCAAGGTGA TAATCAGACA    1980

ATCATCATAC ATAAATCTGC AAGCCAAAAT AACCAGCTAT TAGCGGAGCG AGCACTAGGG    2040

GCCCTGTACA AGCATGCTAG ATTAGCTGGC CATAACCTCA AGGTAGAGGA ATGCTGGGTG    2100

TCAGATTGTC TGTATGAGTA TGGAAAGAAG CTTTTCTTCC GTGGTGTACC TGTCCCGGGC    2160

TGTTTGAAGC AGCTCTCACG GGTGACGGAT TCTACTGGAG AGCTATTCCC AAACCTATAC    2220

TCAAAGTTAG CCTGCTTAAC ATCATCGTGT TTAAGCGCAG CGATGGCAGA CACATCTCCA    2280

TGGGTGGCAC TCGCGACAGG TGTCTGTCTG TATCTTATCG AGTTATATGT TGAGCTGCCT    2340

CCAGCAATCA TGCAGGATGA GTCGCTATTG ACGACCCTCT GCCTCGTAGG CCCATCCATT    2400

GGTGGGCTTC CGACCCCTGC AACCCTACCC AGTGTCTTTT TCAGAGGAAT GTCCGACCCA    2460

CTGCCCTTTC AGCTAGCACT CTTGCAGACC CTCATTAAGA CGACAGGGGT GACCTGTAGC    2520

TTGGTGAATC GTGTGGTCAA GTTACGGATA GCACCCTATC CAGACTGGCT CTCTCTAGTG    2580

ACTGACCCGA CCTCACTCAA CATTGCCCAA GTGTACCGGC CAGAACGTCA GATCAGGAGG    2640

TGGATTGAGG AAGCGATAGC GACAAGCTCA CACTCGTCAC GCATAGCAAC TTTCTTCCAG    2700

CAGCCCCTCA CGGAGATGGC TCAGTTGCTT GCGAGGGACC TTTCAACAAT GATGCCTCTT    2760

CGACCCCGGG ATATGTCGGC CTTATTCGCA TTATCAAATG TCGCATACGG TTTAAGCATT    2820

ATAGATCTAT TTCAAAAATC CTCTACCGTT GTTTCTGCAA GTCAAGCTGT CCATATCGAG    2880

GATGTTGCCC TAGAGAGTGT AAGGTATAAG GAATCTATCA TCCAGGGTCT GTTAGACACC    2940

ACTGAGGGGT ATAACATGCA ACCTTATTTG GAAGGTTGCA CTTACCTTGC AGCCAAACAG    3000

TTACGTAGGT TGACATGGGG TCGAGACCTA GTTGGAGTCA CAATGCCGTT TGTTGCCGAG    3060

CAATTCCATC CTCACAGTTC TGTGGGTGCA AAGGCGGAAC TCTACCTCGA CGCTATTATA    3120

TACTGCCCAC AGGAGACATT GCGGTCACAC CATCTGACTA CCAGGGGGA CCAGCCGCTT    3180

TACCTCGGAT CCAATACGGC TGTCAAGGTC CAGCGAGGTG AGATCACGGG CCTAACAAAG    3240

TCAAGGGCTG CAAATCTAGT CAGGGACACT CTCGTTCTCC ATCAGTGGTA TAAAGTCCGT    3300

AAAGTTACCG ATCCACACTT GAACACCCTC ATGGCACGCT TCTTACTTGA GAAGGGGTAC    3360

ACATCTGACG CTCGACCTAG CATCCAGGGT GGGACCCTCA CGCATCGTCT CCCATCCCGC    3420

GGAGACTCAC GGCAGGGGCT TACTGGGTAT GTAAATATAC TAAGTACGTG GCTTCGATTC    3480

TCAAGTGATT ATCTTCACTC TTTCTCGAAA TCATCAGACG ACTATACAAT CCACTTTCAG    3540

CATGTATTCA CATACGGTTG CCTCTATGCT GATTCGGTGA TTAGATCGGG CGGTGTTATT    3600

TCCACTCCTT ACCTTTTGAG TGCAAGTTGT AAAACATGCT TGAGAAGAT AGACTCAGAG    3660

GAGTTCGTCC TGGCATGTGA ACCCCAATAC AGGGGTGCTG AGTGGCTGAT ATCAAAGCCA    3720

GTCACTGTCC CTGAGCAGAT AACTGATGCT GAAGTCGAGT TTGACCCCTG TGTGAGTGCG    3780
```

-continued

```
GGTTATTGTC TCGGGATTCT CATTGGCAAG TCATTCTTAG TTGACATAAG GGCAAGTGGG    3840

CATGATATCA TGGAGCAGCG GACATGGGCT AACCTGGAGA GGTTTTCTGT ATCGGACATG    3900

CAGAAACTTC CGTGGAGTAT TGTAATTCGG TCTCTCTGGA GATTCCTTAT TGGCGCACGG    3960

CTCCTTCAGT TTGAGAAGGC TGGCCTCATT AGAATGCTGT ATGCTGCGAC AGGTCCAACC    4020

CCTAGCTTCC TAATGAAAGT TTTTCAAGAC TCAGCCCTCC TCATGGACTG CGCACCCCTC    4080

GATCGGCTGT CCCCTAGGAT CAACTTTCAT AGTCGGGGAG ACCTCGTTGC TAAGCTTGTT    4140

TTATTGCCCT TCATCAACCC GGGTATAGTG GAGATTGAAG TGTCTGGAAT TAATAGCAAG    4200

TACCATGCAG TATCGGAGGC CAATATGGAT CTGTACATCG CTGCTGCCAA GTCTGTGGGC    4260

GTGAAGCCCA CACAGTTTGT TGAGGAAACA AACGACTTTA CGGCCCGCGG CCACCACCAT    4320

GGTTGTTATT CCCTTTCTTG GTCTAAGTCA CGCAATCAAT CACAGGTCCT AAAGATGGTA    4380

GTACGGAAGC TGAAGCTCTG TGTCCTGTAT ATATACCCCA CAGTCGATCC CGCCGTTGCT    4440

CTCGACCTGT GCCATCTACC AGCATTAACT ATAATCCTAG TGCTCGGCGG TGACCCAGCG    4500

TACTATGAGC GATTACTTGA GATGGACCTG TGCGGGGCTG TGTCAAGTCG AGTCGATATC    4560

CCCCATTCTC TGGCTGGCAG AACGCACAGG GGGTTCGCAG TGGGCCCAGA CGCTGGTCCA    4620

GGTGTAATTA GACTCGACAG GTTAGAGTCA GTTTGTTATG CTCACCCCTG TTTAGAGGAA    4680

CTAGAGTTTA ATGCATATCT AGACTCTGAG TTGGTTGACA TTAGTGATAT GTGCTGCCTC    4740

CCCTTAGCGA CACCCTGTAA GGCCCTTTTC AGGCCAATAT ATCGGAGCTT ACAGTCGTTC    4800

AGGTTAGCCT TAATGGACAA CTATAGTTTT GTCATGGACC TCATTATGAT CCGAGGACTG    4860

GACATTAGGC CTCACCTTGA GGAATTTGAC GAGCTGCTTG TGGTAGGACA GCACATCCTC    4920

GGCCAGCCCG TCCTAGTAGA GGTTGTTTAC TACGTTGGAG TTGTTAGGAA GCGCCCTGTG    4980

TTAGCGAGGC ATCCGTGGTC AGCAGATCTT AAGCGAATTA CTGTGGGGGG GCGGGCTCCC    5040

TGCCCCTCTG CTGCCAGATT GCGTGATGAG GATTGTCAGG GGTCTCTGTT GGTTGGGCTT    5100

CCTGCTGGGT TGACGCAGTT ATTGATAATT GATTA                               5135
```

(2) INFORMATION FOR SEQ ID NO:10:

(i) SEQUENCE CHARACTERISTICS:
        (A) LENGTH: 1711 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:10:

```
Met Ser Phe His Ala Ser Leu Leu Arg Glu Glu Thr Pro Arg Pro
1               5                   10                  15

Val Ala Gly Ile Asn Arg Thr Asp Gln Ser Leu Lys Asn Pro Leu Leu
            20                  25                  30

Gly Thr Glu Val Ser Phe Cys Leu Lys Ser Ser Leu Pro His His
        35                  40                  45

Val Arg Ala Leu Gly Gln Ile Lys Ala Arg Asn Leu Ala Ser Cys Asp
    50                  55                  60

Tyr Tyr Leu Leu Phe Arg Gln Val Val Leu Pro Pro Glu Val Tyr Pro
65                  70                  75                  80

Ile Gly Val Leu Ile Arg Ala Ala Glu Ala Ile Leu Thr Val Ile Val
                85                  90                  95

Ser Ala Trp Lys Leu Asp His Met Thr Lys Thr Leu Tyr Ser Ser Val
            100                 105                 110
```

```
Arg Tyr Ala Leu Thr Asn Pro Arg Val Arg Ala Gln Leu Glu Leu His
            115                 120                 125

Ile Ala Tyr Gln Arg Ile Val Gly Gln Val Ser Tyr Ser Arg Glu Ala
            130                 135                 140

Asp Ile Gly Pro Lys Arg Leu Gly Asn Met Ser Leu Gln Phe Ile Gln
145                 150                 155                 160

Ser Leu Val Ile Ala Thr Ile Asp Thr Thr Ser Cys Leu Met Thr Tyr
                165                 170                 175

Asn His Phe Leu Ala Ala Ala Asp Thr Ala Lys Ser Arg Cys His Leu
            180                 185                 190

Leu Ile Ala Ser Val Val Gln Gly Ala Leu Trp Glu Gln Gly Ser Phe
            195                 200                 205

Leu Asp His Ile Ile Asn Met Ile Asp Ile Ile Asp Ser Ile Asn Leu
            210                 215                 220

Pro His Asp Asp Tyr Phe Thr Ile Ile Lys Ser Ile Phe Pro Tyr Ser
225                 230                 235                 240

Gln Gly Leu Val Met Gly Arg His Asn Val Ser Val Ser Ser Asp Phe
                245                 250                 255

Ala Ser Val Phe Ala Ile Pro Glu Leu Cys Pro Gln Leu Asp Ser Leu
            260                 265                 270

Leu Lys Lys Leu Leu Gln Leu Asp Pro Val Leu Leu Leu Met Val Ser
            275                 280                 285

Ser Val Gln Lys Ser Trp Tyr Phe Pro Glu Ile Arg Met Val Asp Gly
            290                 295                 300

Ser Arg Glu Gln Leu His Lys Met Arg Val Glu Leu Glu Thr Pro Gln
305                 310                 315                 320

Ala Leu Leu Ser Tyr Gly His Thr Leu Leu Ser Ile Phe Arg Ala Glu
                325                 330                 335

Phe Ile Lys Gly Tyr Val Ser Lys Asn Ala Lys Trp Pro Pro Val His
            340                 345                 350

Leu Leu Pro Gly Cys Asp Lys Ser Ile Lys Asn Ala Arg Glu Leu Gly
            355                 360                 365

Arg Trp Ser Pro Ala Phe Asp Arg Arg Trp Gln Leu Phe Glu Lys Val
            370                 375                 380

Val Ile Leu Arg Ile Ala Asp Leu Asp Met Asp Pro Asp Phe Asn Asp
385                 390                 395                 400

Ile Val Ser Asp Lys Ala Ile Ile Ser Ser Arg Arg Asp Trp Val Phe
                405                 410                 415

Glu Tyr Asn Ala Ala Ala Phe Trp Lys Lys Tyr Gly Glu Arg Leu Glu
            420                 425                 430

Arg Pro Pro Ala Arg Ser Gly Pro Ser Arg Leu Val Asn Ala Leu Ile
            435                 440                 445

Asp Gly Arg Leu Asp Asn Ile Pro Ala Leu Leu Glu Pro Phe Tyr Arg
            450                 455                 460

Gly Ala Val Glu Phe Glu Asp Arg Leu Thr Val Leu Val Pro Lys Glu
465                 470                 475                 480

Lys Glu Leu Lys Val Lys Gly Arg Phe Phe Ser Lys Gln Thr Leu Ala
                485                 490                 495

Ile Arg Ile Tyr Gln Val Val Ala Glu Ala Leu Lys Asn Glu Val
            500                 505                 510

Met Pro Tyr Leu Lys Thr His Ser Met Thr Met Ser Ser Thr Ala Leu
            515                 520                 525

Thr His Leu Leu Asn Arg Leu Ser His Thr Ile Thr Lys Gly Asp Ser
```

-continued

```
            530                 535                 540
Phe Val Ile Asn Leu Asp Tyr Ser Ser Trp Cys Asn Gly Phe Arg Pro
545                 550                 555                 560
Glu Leu Gln Ala Pro Ile Cys Arg Gln Leu Asp Gln Met Phe Asn Cys
                    565                 570                 575
Gly Tyr Phe Phe Arg Thr Gly Cys Thr Leu Pro Cys Phe Thr Thr Phe
                580                 585                 590
Ile Ile Gln Asp Arg Phe Asn Pro Pro Tyr Ser Leu Ser Gly Glu Pro
            595                 600                 605
Val Glu Asp Gly Val Thr Cys Ala Val Gly Thr Lys Thr Met Gly Glu
610                 615                 620
Gly Met Arg Gln Lys Leu Trp Thr Ile Leu Thr Ser Cys Trp Glu Ile
625                 630                 635                 640
Ile Ala Leu Arg Glu Ile Asn Val Thr Phe Asn Ile Leu Gly Gln Gly
                645                 650                 655
Asp Asn Gln Thr Ile Ile Ile His Lys Ser Ala Ser Gln Asn Asn Gln
                660                 665                 670
Leu Leu Ala Glu Arg Ala Leu Gly Ala Leu Tyr Lys His Ala Arg Leu
            675                 680                 685
Ala Gly His Asn Leu Lys Val Glu Glu Cys Trp Val Ser Asp Cys Leu
        690                 695                 700
Tyr Glu Tyr Gly Lys Lys Leu Phe Phe Arg Gly Val Pro Val Pro Gly
705                 710                 715                 720
Cys Leu Lys Gln Leu Ser Arg Val Thr Asp Ser Thr Gly Glu Leu Phe
                    725                 730                 735
Pro Asn Leu Tyr Ser Lys Leu Ala Cys Leu Thr Ser Ser Cys Leu Ser
                740                 745                 750
Ala Ala Met Ala Asp Thr Ser Pro Trp Val Ala Leu Ala Thr Gly Val
            755                 760                 765
Cys Leu Tyr Leu Ile Glu Leu Tyr Val Glu Leu Pro Pro Ala Ile Met
        770                 775                 780
Gln Asp Glu Ser Leu Leu Thr Thr Leu Cys Leu Val Gly Pro Ser Ile
785                 790                 795                 800
Gly Gly Leu Pro Thr Pro Ala Thr Leu Pro Ser Val Phe Phe Arg Gly
                    805                 810                 815
Met Ser Asp Pro Leu Pro Phe Gln Leu Ala Leu Leu Gln Thr Leu Ile
                820                 825                 830
Lys Thr Thr Gly Val Thr Cys Ser Leu Val Asn Arg Val Lys Leu
            835                 840                 845
Arg Ile Ala Pro Tyr Pro Asp Trp Leu Ser Leu Val Thr Asp Pro Thr
        850                 855                 860
Ser Leu Asn Ile Ala Gln Val Tyr Arg Pro Glu Arg Gln Ile Arg Arg
865                 870                 875                 880
Trp Ile Glu Glu Ala Ile Ala Thr Ser Ser His Ser Ser Arg Ile Ala
                    885                 890                 895
Thr Phe Phe Gln Gln Pro Leu Thr Glu Met Ala Gln Leu Leu Ala Arg
                900                 905                 910
Asp Leu Ser Thr Met Met Pro Leu Arg Pro Arg Asp Met Ser Ala Leu
            915                 920                 925
Phe Ala Leu Ser Asn Val Ala Tyr Gly Leu Ser Ile Ile Asp Leu Phe
        930                 935                 940
Gln Lys Ser Ser Thr Val Val Ser Ala Ser Gln Ala Val His Ile Glu
945                 950                 955                 960
```

-continued

Asp Val Ala Leu Glu Ser Val Arg Tyr Lys Glu Ser Ile Ile Gln Gly
             965                 970                 975

Leu Leu Asp Thr Thr Glu Gly Tyr Asn Met Gln Pro Tyr Leu Glu Gly
             980                 985                 990

Cys Thr Tyr Leu Ala Ala Lys Gln Leu Arg Arg Leu Thr Trp Gly Arg
    995                1000                1005

Asp Leu Val Gly Val Thr Met Pro Phe Val Ala Glu Gln Phe His Pro
    1010                1015                1020

His Ser Ser Val Gly Ala Lys Ala Glu Leu Tyr Leu Asp Ala Ile Ile
1025                1030                1035                1040

Tyr Cys Pro Gln Glu Thr Leu Arg Ser His His Leu Thr Thr Arg Gly
             1045                1050                1055

Asp Gln Pro Leu Tyr Leu Gly Ser Asn Thr Ala Val Lys Val Gln Arg
             1060                1065                1070

Gly Glu Ile Thr Gly Leu Thr Lys Ser Arg Ala Ala Asn Leu Val Arg
    1075                1080                1085

Asp Thr Leu Val Leu His Gln Trp Tyr Lys Val Arg Lys Val Thr Asp
    1090                1095                1100

Pro His Leu Asn Thr Leu Met Ala Arg Phe Leu Leu Glu Lys Gly Tyr
1105                1110                1115                1120

Thr Ser Asp Ala Arg Pro Ser Ile Gln Gly Gly Thr Leu Thr His Arg
             1125                1130                1135

Leu Pro Ser Arg Gly Asp Ser Arg Gln Gly Leu Thr Gly Tyr Val Asn
             1140                1145                1150

Ile Leu Ser Thr Trp Leu Arg Phe Ser Ser Asp Tyr Leu His Ser Phe
    1155                1160                1165

Ser Lys Ser Ser Asp Asp Tyr Thr Ile His Phe Gln His Val Phe Thr
    1170                1175                1180

Tyr Gly Cys Leu Tyr Ala Asp Ser Val Ile Arg Ser Gly Gly Val Ile
1185                1190                1195                1200

Ser Thr Pro Tyr Leu Leu Ser Ala Ser Cys Lys Thr Cys Phe Glu Lys
             1205                1210                1215

Ile Asp Ser Glu Glu Phe Val Leu Ala Cys Glu Pro Gln Tyr Arg Gly
             1220                1225                1230

Ala Glu Trp Leu Ile Ser Lys Pro Val Thr Val Pro Glu Gln Ile Thr
    1235                1240                1245

Asp Ala Glu Val Glu Phe Asp Pro Cys Val Ser Ala Gly Tyr Cys Leu
    1250                1255                1260

Gly Ile Leu Ile Gly Lys Ser Phe Leu Val Asp Ile Arg Ala Ser Gly
1265                1270                1275                1280

His Asp Ile Met Glu Gln Arg Thr Trp Ala Asn Leu Glu Arg Phe Ser
             1285                1290                1295

Val Ser Asp Met Gln Lys Leu Pro Trp Ser Ile Val Ile Arg Ser Leu
             1300                1305                1310

Trp Arg Phe Leu Ile Gly Ala Arg Leu Leu Gln Phe Glu Lys Ala Gly
    1315                1320                1325

Leu Ile Arg Met Leu Tyr Ala Ala Thr Gly Pro Thr Pro Ser Phe Leu
    1330                1335                1340

Met Lys Val Phe Gln Asp Ser Ala Leu Leu Met Asp Cys Ala Pro Leu
1345                1350                1355                1360

Asp Arg Leu Ser Pro Arg Ile Asn Phe His Ser Arg Gly Asp Leu Val
             1365                1370                1375

Ala Lys Leu Val Leu Leu Pro Phe Ile Asn Pro Gly Ile Val Glu Ile
             1380                1385                1390

```
Glu Val Ser Gly Ile Asn Ser Lys Tyr His Ala Val Ser Glu Ala Asn
        1395                1400                1405

Met Asp Leu Tyr Ile Ala Ala Lys Ser Val Gly Val Lys Pro Thr
    1410                1415                1420

Gln Phe Val Glu Glu Thr Asn Asp Phe Thr Ala Arg Gly His His His
1425                1430                1435                1440

Gly Cys Tyr Ser Leu Ser Trp Ser Lys Ser Arg Asn Gln Ser Gln Val
            1445                1450                1455

Leu Lys Met Val Val Arg Lys Leu Lys Leu Cys Val Leu Tyr Ile Tyr
            1460                1465                1470

Pro Thr Val Asp Pro Ala Val Ala Leu Asp Leu Cys His Leu Pro Ala
            1475                1480                1485

Leu Thr Ile Ile Leu Val Leu Gly Gly Asp Pro Ala Tyr Tyr Glu Arg
            1490                1495                1500

Leu Leu Glu Met Asp Leu Cys Gly Ala Val Ser Ser Arg Val Asp Ile
1505                1510                1515                1520

Pro His Ser Leu Ala Gly Arg Thr His Arg Gly Phe Ala Val Gly Pro
            1525                1530                1535

Asp Ala Gly Pro Gly Val Ile Arg Leu Asp Arg Leu Glu Ser Val Cys
            1540                1545                1550

Tyr Ala His Pro Cys Leu Glu Glu Leu Glu Phe Asn Ala Tyr Leu Asp
            1555                1560                1565

Ser Glu Leu Val Asp Ile Ser Asp Met Cys Cys Leu Pro Leu Ala Thr
            1570                1575                1580

Pro Cys Lys Ala Leu Phe Arg Pro Ile Tyr Arg Ser Leu Gln Ser Phe
1585                1590                1595                1600

Arg Leu Ala Leu Met Asp Asn Tyr Ser Phe Val Met Asp Leu Ile Met
                1605                1610                1615

Ile Arg Gly Leu Asp Ile Arg Pro His Leu Glu Glu Phe Asp Glu Leu
            1620                1625                1630

Leu Val Val Gly Gln His Ile Leu Gly Gln Pro Val Leu Val Glu Val
1635                1640                1645

Val Tyr Tyr Val Gly Val Val Arg Lys Arg Pro Val Leu Ala Arg His
1650                1655                1660

Pro Trp Ser Ala Asp Leu Lys Arg Ile Thr Val Gly Arg Ala Pro
1665                1670                1675                1680

Cys Pro Ser Ala Ala Arg Leu Arg Asp Glu Asp Cys Gln Gly Ser Leu
            1685                1690                1695

Leu Val Gly Leu Pro Ala Gly Leu Thr Gln Leu Leu Ile Ile Asp
            1700                1705                1710

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA to genomic RNA (iii) HYPOTHETICAL: NO (iv) ANTI-SENSE: YES (xi) SEQUENCE DESCRIPTION: SEQ ID NO:11:

GCCTCCCCTT AGCGACACCC TGTA                                          24
```

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to genomic RNA (iii) HYPOTHETICAL: NO (iv) ANTI-SENSE: NO (xi) SEQUENCE DESCRIPTION: SEQ ID NO:12:

GAAACATATC GCGCCGTGCA                                  20

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA to genomic RNA (iii) HYPOTHETICAL: NO (iv) ANTI-SENSE: YES (xi) SEQUENCE DESCRIPTION: SEQ ID NO:13:

TACGTTGGAG TTGTTAGGAA GC                               22

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to genomic RNA (iii) HYPOTHETICAL: NO (iv) ANTI-SENSE: YES (xi) SEQUENCE DESCRIPTION: SEQ ID NO:14:

GAGCTTAGGG AGGCTCGCTG                                  20

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:15:

TCCTCGAGAT GAATTCAAAA CATTCCTATC                       30

(2) INFORMATION FOR SEQ ID NO:16:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA to mRNA (iii) HYPOTHETICAL: NO (iv) ANTI-SENSE: YES (xi) SEQUENCE DESCRIPTION: SEQ ID NO:16:

CTAAGGCCCT GAAGATCGAA T                                         21

(2) INFORMATION FOR SEQ ID NO:17:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:17:

CCCTCGAGGA CCAAGATTT                                            19

(2) INFORMATION FOR SEQ ID NO:18:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:18:

AGAATCATAT GGCAACGCGA CCATC                                     25

(2) INFORMATION FOR SEQ ID NO:19:

(i) SEQUENCE CHARACTERISTICS:
    (A) LENGTH: 8910 base pairs
    (B) TYPE: nucleic acid
    (C) STRANDEDNESS: single
    (D) TOPOLOGY: linear (ii) MOLECULE TYPE: cDNA to genomic RNA (iii) HYPOTHETICAL: NO (iv) ANTI-SENSE: NO (xi) SEQUENCE DESCRIPTION: SEQ ID NO:19:

GTTGCGTTAA CAACAAACCA CTCATCATTC TTCTAACAAA ATGAACACAC GCAATGCCAC    60

CCAAGAGACG CCTGGTTGAT GACGCCGATG CCATGGAGGA TCAAGATCTA TATGAACCCC   120

CAGCGAGCCT CCCTAAGCTC CCTGGGAAAT TCCTACAATA CACCGTTGGG GGGTCTGACC   180

CGCATCCGGG TATAGGGCAT GAGAAAGACA TCAGGCAGAA CGCAGTGGCA TTGTTAGACC   240

AGTCACGGCG CGATATGTTT CACACAGTAA CGCCTAGCCT TGTGTTTCTA TGTTTGCTAA   300

```
TCCCAGGACT GCACGCTGCG TTTGTTCACG GAGGGGTGCC TCGTGAATCC TACCTGTCGA      360

CGCCTGTCAC GCGTGGAGAA CAGACTGTTG TTAAGACTGC GAAGTTTTAC GGGGAAAAGA      420

CGACGCAGCG TGATCTCACC GAGCTGGAGA TCTCCTCTAT CTTCAGCCAT TGTTGCTCAT      480

TACTAATAGG GGTTGTGATA GGATCGTCGT CTAAGATCAA AGCAGGAGCC GAGCAGATCA      540

AGAAAAGGTT TAAAACTATG ATGGCAGCCT TAAACCGGCC ATCCCATGGT GAGACTGCTA      600

CACTACTCCA GATGTTTAAT CCACATGAGG CTATAGATTG GATTAACGGC CAACCCTGGG      660

TAGGCTCCTT TGTGTTGTCT CTACTAACTA CAGACTTTGA GTCCCAGGT AAAGAATTTA       720

TGGACCAGAT TAAGCTTGTC GCAAGTTATG CACAGATGAC TACGTACACT ACTATAAAGG      780

AGTACCTCGC AGAATGCATG GATGCTACCC TTACAATCCC CGTAGTTGCA TATGAGATCC      840

GTGACTTTTT AGAAGTTTCA GCAAAGCTTA AGGAGGATCA TGCTGACCTG TTCCCGTTTC      900

TGGGGGCCAT TAGACACCCC GACGCTATCA AGCTGGCGCC ACGAAGCTTT CCCAATCTGG      960

CCTCCGCAGC GTTTTACTGG AGTAAGAAGG AAAACCCCAC AATGGCAGGC TACCGGGCCT     1020

CCACCATCCA GCCGGGCGCA AGTGTCAAGG AAACCCAGCT TGCCCGGTAT AGGCGCCGCG     1080

AGATATCTCG TGGAGAGGAC GGGGCAGAGC TCTCAGGTGA GATCTCTGCC ATAATGAAGA     1140

TGATAGGTGT GACTGGTCTA AACTAAAAAA CAATGAACAA ACCAATAAAA AACCAAATGC     1200

GGCAAACCCT CCGCGACCTG CGATGAGCTC CGACCTCCGG CTGACATTGC TTGAACTAGT     1260

CAGGAGGCTC AATGGCAACG CGACCATCGA GTCTGGTCGA CTCCCTGGAG GACGAAGAAG     1320

ATCCCCAGAC ACTACGACGG GAACGACCGG GGTCACCAAG ACCACGGAAG GTCCCAAGGA     1380

ATGCATTGAC CCAACCAGTA GACCAGCTCC TGAAGGACCT CAGGAAGAAC CCCTCCATGA     1440

TCTCAGACCC AGACCAGCGA ACCGGAAGGG AGCAGCTGTC GAATGATGAG CTAATCAAGA     1500

AGTTAGTGAC GGAGCTGGCC GAGAATAGCA TGATCGAGGC TGAGGAGGTG CGGGGCACTC     1560

TTGGAGACAT CTCGGCTCGT ATCGAGGCAG GGTTTGAGTC CCTGTCCGCC CTCCAAGTGG     1620

AAACCATCCA GACAGCTCAG CGGTGCGATC ACTCCGACAG CATCAGGATC CTCGGCGAGA     1680

ACATCAAGAT ACTAGATCGC TCCATGAAGA CAATGATGGA GACAATGAAG CTCATGATGG     1740

AGAAGGTGGA TCTCCTCTAC GCATCAACCG CCGTTGGGAC CTCTGCACCC ATGTTGCCCT     1800

CCCATCCTGC ACCTCCGCGC ATTTATCCCC AGCTCCCAAG TGCCCCGACA ACGGATGAAT     1860

GGGACATCAT ACCATAAAAA AATCGAATCA CCATGAATTC AAAACATTCC TATGTGGAGC     1920

TCAAGGACAA GGTAATCGTC CCTGGATGGC CCACACTGAT GCTTGAGATA GACTTTGTAG     1980

GGGGGACTTC ACGGAACCAG TTCCTTAACA TCCCATTTCT TTCAGTGAAA GAGCCTCTGC     2040

AGCTTCCACG CGAGAAGAAG TTGACCGACT ACTTTACTAT TGACGTAGAA CCAGCAGGTC     2100

ATTCCCTGGT CAATATATAC TTCCAGATTG ACGACTTCTT GCTCCTAACA CTCAACTCAC     2160

TATCTGTGTA CAAGGACCCG ATTAGAAAAT ACATGTTCCT ACGCCTCAAC AAGGACCAGA     2220

GCAAGCACGC AATCAATGCA GCCTTCAATG TCTTTTCTTA TCGGCTTCGG AACATTGGTG     2280

TTGGTCCTCT CGGCCCGGAC ATTCGATCTT CAGGGCCTTA GCTGCAATAC TGACTCCACT     2340

CCTGGACTGA TTGACCTGGA GATAAGGCGA CTTTGCCACA CCCCAACGGA AAATGTCATT     2400

TCATGCGAGG TTAGTTATCT CAACCACACG ACTATTAGCC TCCCGGCAGT CCACACATCA     2460

TGCCTCAAGT ACCACTGCAA AACCTATTGG GGATTCTTTG GTAGCTACAG CGCTGACCGA     2520

ATCATAAATC GGTACACTGG TACTGTTAAG GGTTGTCTAA ACAACTCAGC ACCAGAGGAC     2580

CCCTTCGAGT GCAACTGGTT CTACTGCTGC TCGGCGATTA CAACAGAGAT CTGCCGATGC     2640

TCTATTACAA ATGTCACGGT GGCTGTGCAA ACATTCCCAC CGTTCATGTA CTGCAGTTTT     2700
```

```
GCAGACTGCA GTACCGTGAG CCAACAGGAG CTAGAGAGTG GAAAGGCAAT GCTGAGCGAT    2760

GGCAGTACAT TAACTTATAC CCCGTATATC CTACAGTCAG AAGTCGTGAA CAAAACCCTC    2820

AATGGGACCA TACTCTGCAA CTCATCCTCT AAGATAGTTT CCTTCGATGA ATTTAGGCGT    2880

TCATACTCCC TAACGAATGG TAGTTACCAG AGCTCATCAA TCAATGTGAC GTGTGCAAAC    2940

TACACGTCGT CCTGCCGGCC CAGGTTGAAA AGGCGGCGTA GGGACACCCA GCAGATTGAG    3000

TATCTAGTTC ACAAGCTTAG GCCCACACTG AAAGATGCAT GGGAGGACTG TGAGATCCTC    3060

CAGTCTCTGC TCCTAGGGGT GTTTGGTACT GGGATCGCAA GTGCTTCTCA ATTTTTGAGG    3120

AGCTGGCTCA ACCACCCTGA CATCATCGGG TATATAGTTA ATGGAGTTGG GGTTGTCTGG    3180

CAATGCCATC GTGTTAATGT CACGTTCATG GCGTGGAATG AGTCCACCTA TTACCCTCCA    3240

GTAGATTACA ATGGGCGGAA GTACTTCCTG AATGATGAGG GAAGGTTACA AACAAACACC    3300

CCCGAGGCAA GGCCAGGGCT TAAGCGGGTC ATGTGGTTCG GCAGGTACTT CCTAGGGACA    3360

GTAGGGTCTG GGGTGAAACC GAGGAGGATT CGGTACAATA AGACCTCACA TGACTACCAC    3420

CTGGAGGAGT TTGAGGCAAG TCTCAACATG ACCCCTCAGA CCAGTATCGC CTCGGGTCAT    3480

GAGACAGACC CCATAAATCA TGCCTACGGA ACGCAGGCTG ATCTCCTTCC ATACACCAGG    3540

TCTAGTAATA TAACATCTAC GGATACAGGC TCAGGCTGGG TGCACATCGG CCTACCCTCA    3600

TTTGCTTTCC TCAATCCCCT CGGGTGGCTC AGGGACCTAC TTGCATGGGC AGCCTGGTTG    3660

GGTGGGGTTC TATACTTAAT AAGTCTTTGT GTTTCCTTAC CAGCCTCCTT CGCGAGGAGG    3720

AGACGCCTCG GCCGGTGGCA GGAATAAACC GTACCGACCA GTCTCTTAAA AACCCTCTCC    3780

TCGGAACAGA GGTCTCTTTC TGCCTTAAGT CGAGCTCACT CCCCCATCAT GTACGAGCAC    3840

TAGGCCAGAT TAAAGCAAGG AACCTGGCAT CCTGTGACTA TTACTTGCTA TTCCGCCAAG    3900

TTGTATTGCC CCCTGAAGTA TATCCCATTG GTGTTCTAAT AAGAGCTGCG GAGGCTATAC    3960

TAACAGTTAT AGTATCAGCT TGGAAGCTGG ATCATATGAC GAAGACCCTA TACTCCTCTG    4020

TGAGATATGC ACTCACCAAT CCCCGGGTCC GAGCCCAACT TGAGCTTCAC ATTGCCTACC    4080

AGCGCATAGT GGGTCAGGTC TCGTACAGCC GGGAGGCAGA CATAGGGCCA AAAAGGCTTG    4140

GGAATATGTC ATTGCAATTC ATCCAATCTC TCGTTATTGC CACCATAGAC ACGACAAGCT    4200

GCCTAATGAC CTACAACCAC TTTCTTGCTG CAGCAGACAC AGCCAAGAGC AGATGCCATC    4260

TCCTAATCGC CTCAGTGGTC CAGGGGGCCC TTTGGGAACA AGGGTCATTT CTTGATCATA    4320

TAATCAACAT GATCGACATA ATTGACTCAA TCAACCTCCC CCATGATGAT TACTTCACAA    4380

TTATTAAGTC TATCTTTCCC TACTCCCAAG GGCTTGTTAT GGGGAGGCAT AATGTATCAG    4440

TCTCCTCTGA TTTCGCGTCC GTATTTGCCA TTCCTGAATT ATGCCCGCAA CTAGACAGCT    4500

TACTAAAAAA ACTGCTCCAA CTTGACCCCG TTCTCCTCCT CATGGTCTCT TCGGTGCAGA    4560

AGTCATGGTA CTTCCCTGAG ATCCGAATGG TCGACGGGTC ACGGGAGCAG CTCCACAAGA    4620

TGCGTGTCGA GCTGGAAACG CCCCAAGCCC TGCTGTCGTA CGGCCATACC CTCCTGTCAA    4680

TATTTCGGGC AGAGTTTATC AAAGGCTATG TCTCAAAGAA TGCGAAGTGG CCGCCCGTAC    4740

ACCTGCTCCC AGGCTGTGAC AAATCCATAA AAAATGCGAG AGAGCTGGGC CGCTGGAGCC    4800

CGGCATTTGA CCGACGATGG CAGCTCTTCG AGAAGGTTGT CATTCTAAGA ATTGCTGACC    4860

TAGATATGGA TCCCGACTTC AACGATATTG TTAGCGATAA GGCGATAATC AGCTCAAGAA    4920

GGGACTGGGT ATTCGAGTAC AATGCAGCGG CCTTTTGGAA GAAATACGGT GAACGGTTGG    4980

AGAGGCCTCC TGCCAGGTCG GGACCGTCAC GACTTGTGAA TGCTCTAATC GATGGACGCT    5040

TAGACAATAT CCCAGCCCTG CTAGAGCCAT TTTACAGGGG AGCGGTTGAG TTCGAGGATC    5100
```

```
GGTTGACTGT GCTCGTGCCT AAGGAGAAAG AGTTAAAGGT AAAGGGAAGG TTCTTCTCGA    5160

AGCAAACATT GGCAATCAGG ATATATCAGG TTGTTGCTGA AGCTGCACTT AAGAATGAGG    5220

TTATGCCATA CCTAAAGACA CACTCAATGA CCATGAGCTC AACGGCTCTA ACTCACCTTC    5280

TTAACCGGCT ATCACATACT ATCACTAAGG GTGACTCCTT TGTTATTAAC CTTGACTATA    5340

GTTCCTGGTG CAACGGTTTC CGACCAGAAC TGCAGGCCCC AATCTGTCGT CAGTTGGATC    5400

AGATGTTCAA TTGCGGGTAC TTCTTCAGGA CTGGGTGCAC ACTGCCATGC TTTACCACGT    5460

TTATTATTCA AGACAGGTTC AACCCGCCCT ATTCCCTCAG TGGTGAGCCC GTTGAAGACG    5520

GAGTTACATG CGCGGTTGGG ACTAAAACAA TGGGGGAGGG CATGAGGCAG AAACTATGGA    5580

CAATCCTTAC GAGCTGCTGG GAGATAATTG CTCTTCGGGA AATTAACGTG ACGTTTAACA    5640

TACTAGGCCA AGGTGATAAT CAGACAATCA TCATACATAA ATCTGCAAGC CAAAATAACC    5700

AGCTATTAGC GGAGCGAGCA CTAGGGGCCC TGTACAAGCA TGCTAGATTA GCTGGCCATA    5760

ACCTCAAGGT AGAGGAATGC TGGGTGTCAG ATTGTCTGTA TGAGTATGGA AAGAAGCTTT    5820

TCTTCCGTGG TGTACCTGTC CCGGGCTGTT TGAAGCAGCT CTCACGGGTG ACGGATTCTA    5880

CTGGAGAGCT ATTCCCAAAC CTATACTCAA AGTTAGCCTG CTTAACATCA TCGTGTTTAA    5940

GCGCAGCGAT GGCAGACACA TCTCCATGGG TGGCACTCGC GACAGGTGTC TGTCTGTATC    6000

TTATCGAGTT ATATGTTGAG CTGCCTCCAG CAATCATGCA GGATGAGTCG CTATTGACGA    6060

CCCTCTGCCT CGTAGGCCCA TCCATTGGTG GGCTTCCGAC CCCTGCAACC CTACCCAGTG    6120

TCTTTTTCAG AGGAATGTCC GACCCACTGC CCTTTCAGCT AGCACTCTTG CAGACCCTCA    6180

TTAAGACGAC AGGGGTGACC TGTAGCTTGG TGAATCGTGT GGTCAAGTTA CGGATAGCAC    6240

CCTATCCAGA CTGGCTCTCT CTAGTGACTG ACCCGACCTC ACTCAACATT GCCCAAGTGT    6300

ACCGGCCAGA ACGTCAGATC AGGAGGTGGA TTGAGGAAGC GATAGCGACA AGCTCACACT    6360

CGTCACGCAT AGCAACTTTC TTCCAGCAGC CCCTCACGGA GATGGCTCAG TTGCTTGCGA    6420

GGGACCTTTC AACAATGATG CCTCTTCGAC CCCGGGATAT GTCGGCCTTA TTCGCATTAT    6480

CAAATGTCGC ATACGGTTTA AGCATTATAG ATCTATTTCA AAAATCCTCT ACCGTTGTTT    6540

CTGCAAGTCA AGCTGTCCAT ATCGAGGATG TTGCCCTAGA GAGTGTAAGG TATAAGGAAT    6600

CTATCATCCA GGGTCTGTTA GACACCACTG AGGGGTATAA CATGCAACCT TATTTGGAAG    6660

GTTGCACTTA CCTTGCAGCC AAACAGTTAC GTAGGTTGAC ATGGGGTCGA GACCTAGTTG    6720

GAGTCACAAT GCCGTTTGTT GCCGAGCAAT TCCATCCTCA CAGTTCTGTG GGTGCAAAGG    6780

CGGAACTCTA CCTCGACGCT ATTATATACT GCCCACAGGA GACATTGCGG TCACACCATC    6840

TGACTACCAG GGGGGACCAG CCGCTTTACC TCGGATCCAA TACGGCTGTC AAGGTCCAGC    6900

GAGGTGAGAT CACGGGCCTA ACAAAGTCAA GGGCTGCAAA TCTAGTCAGG GACACTCTCG    6960

TTCTCCATCA GTGGTATAAA GTCCGTAAAG TTACCGATCC ACACTTGAAC ACCCTCATGG    7020

CACGCTTCTT ACTTGAGAAG GGGTACACAT CTGACGCTCG ACCTAGCATC CAGGGTGGGA    7080

CCCTCACGCA TCGTCTCCCA TCCCGCGGAG ACTCACGGCA GGGGCTTACT GGGTATGTAA    7140

ATATACTAAG TACGTGGCTT CGATTCTCAA GTGATTATCT TCACTCTTTC TCGAAATCAT    7200

CAGACGACTA TACAATCCAC TTTCAGCATG TATTCACATA CGGTTGCCTC TATGCTGATT    7260

CGGTGATTAG ATCGGGCGGT GTTATTTCCA CTCCTTACCT TTTGAGTGCA AGTTGTAAAA    7320

CATGCTTTGA GAAGATAGAC TCAGAGGAGT TCGTCCTGGC ATGTGAACCC CAATACAGGG    7380

GTGCTGAGTG GCTGATATCA AAGCCAGTCA CTGTCCCTGA GCAGATAACT GATGCTGAAG    7440

TCGAGTTTGA CCCCTGTGTG AGTGCGGGTT ATTGTCTCGG GATTCTCATT GGCAAGTCAT    7500
```

```
TCTTAGTTGA CATAAGGGCA AGTGGGCATG ATATCATGGA GCAGCGGACA TGGGCTAACC      7560

TGGAGAGGTT TTCTGTATCG GACATGCAGA AACTTCCGTG GAGTATTGTA ATTCGGTCTC      7620

TCTGGAGATT CCTTATTGGC GCACGGCTCC TTCAGTTTGA GAAGGCTGGC CTCATTAGAA      7680

TGCTGTATGC TGCGACAGGT CCAACCCCTA GCTTCCTAAT GAAAGTTTTT CAAGACTCAG      7740

CCCTCCTCAT GGACTGCGCA CCCCTCGATC GGCTGTCCCC TAGGATCAAC TTTCATAGTC      7800

GGGGAGACCT CGTTGCTAAG CTTGTTTTAT TGCCCTTCAT CAACCCGGGT ATAGTGGAGA      7860

TTGAAGTGTC TGGAATTAAT AGCAAGTACC ATGCAGTATC GGAGGCCAAT ATGGATCTGT      7920

ACATCGCTGC TGCCAAGTCT GTGGGCGTGA AGCCCACACA GTTTGTTGAG GAAACAAACG      7980

ACTTTACGGC CCGCGGCCAC CACCATGGTT GTTATTCCCT TTCTTGGTCT AAGTCACGCA      8040

ATCAATCACA GGTCCTAAAG ATGGTAGTAC GGAAGCTGAA GCTCTGTGTC CTGTATATAT      8100

ACCCCACAGT CGATCCCGCC GTTGCTCTCG ACCTGTGCCA TCTACCAGCA TTAACTATAA      8160

TCCTAGTGCT CGGCGGTGAC CCAGCGTACT ATGAGCGATT ACTTGAGATG GACCTGTGCG      8220

GGGCTGTGTC AAGTCGAGTC GATATCCCCC ATTCTCTGGC TGGCAGAACG CACAGGGGGT      8280

TCGCAGTGGG CCCAGACGCT GGTCCAGGTG TAATTAGACT CGACAGGTTA GAGTCAGTTT      8340

GTTATGCTCA CCCCTGTTTA GAGGAACTAG AGTTTAATGC ATATCTAGAC TCTGAGTTGG      8400

TTGACATTAG TGATATGTGC TGCCTCCCCT TAGCGACACC CTGTAAGGCC CTTTTCAGGC      8460

CAATATATCG GAGCTTACAG TCGTTCAGGT TAGCCTTAAT GGACAACTAT AGTTTTGTCA      8520

TGGACCTCAT TATGATCCGA GGACTGGACA TTAGGCCTCA CCTTGAGGAA TTTGACGAGC      8580

TGCTTGTGGT AGGACAGCAC ATCCTCGGCC AGCCCGTCCT AGTAGAGGTT GTTTACTACG      8640

TTGGAGTTGT TAGGAAGCGC CCTGTGTTAG CGAGGCATCC GTGGTCAGCA GATCTTAAGC      8700

GAATTACTGT GGGGGGGCGG GCTCCCTGCC CCTCTGCTGC CAGATTGCGT GATGAGGATT      8760

GTCAGGGGTC TCTGTTGGTT GGGCTTCCTG CTGGGTTGAC GCAGTTATTG ATAATTGATT      8820

AAGATCAAGC CACCTACTAC CCTATTCTTA AAAAACCATA TGTCAGTGGT GCAGTGCTTG      8880

GGCTTGGTTG TTGCTTTGTT GTAGCGCGTT                                      8910

(2) INFORMATION FOR SEQ ID NO:20:

(i) SEQUENCE CHARACTERISTICS:
        (A) LENGTH: 2658 base pairs
        (B) TYPE: nucleic acid
        (C) STRANDEDNESS: single
        (D) TOPOLOGY: linear (ii) MOLECULE TYPE: cDNA to genomic RNA (iii) HYPOTHETICAL: NO (iv) ANTI-SENSE: NO (xi) SEQUENCE DESCRIPTION: SEQ ID NO:20:

GGTAGACCAG CTCCTGAAGG ACCTCAGGAA GAACCCCTCC ATGATCTCAG                   50

ACCCAGACCA GCGAACCGGA AGGGAGCAGC TATCGAATGA TGAGCTTATC                  100

AAGAAGCTAG TGACGGAGCT GGCCGAGAAT AGCATGATCG AGGCTGAGGA                  150

GGTGCGGGGC ACTCTTGGGG ACATCTCGGC TCGCATCGAG GCAGGGTTTG                  200

AGTCCCTGTC CGCCCTCCAA GTGGAAACCA TCCAGACAGC TCAGCGGTGC                  250

GACCACTCCG ATAGCATCAG AATCCTTGGC GAGAACATCA AGATACTGGA                  300

TCGCTCCATG AAGACAATGA TGGAGACAAT GAAGCTCATG ATGGAGAAGG                  350
```

| | |
|---|---|
| TGGACCTCCT CTACGCATCA ACCGCCGTTG GGACCTCTGC ACCCATGTTG | 400 |
| CCCTCCCATC CTGCACCTCC GCGCATTTAT CCCCAGCTCC CAAGTGCCCC | 450 |
| GACAGCGGAT GAGTGGGACA TCATACCATA AAAAAATCGA ATCACCATGA | 500 |
| ATTCAAAGCA TTCCTATGTG GAGCTCAAGG ACAAGGTAAT CGTCCCTGGA | 550 |
| TGGCCCACAC TGATGCTTGA GATAGACTTT GTAGGAGGGA CTTCACGGAA | 600 |
| CCAGTTCCTT AACATCCCAT TTCTTTCAGT GAAAGAGCCT CTGCAGCTTC | 650 |
| CACGCGAGAA GAAGTTGACC GACTACTTCA CCATTGACGT AGAGCCAGCA | 700 |
| GGTCATTCCC TGGTCAACAT ATACTTCCAG ATTGACGACT TCTTGCTCCT | 750 |
| AACACTCAAC TCACTGTCCG TATACAAGGA CCCGATTAGG AAATACATGT | 800 |
| TCCTACGCCT CAACAAGGAA CAGAGCAAGC ACGCAATTAA TGCAGCTTTC | 850 |
| AATGTCTTCT CTTATCGGCT TCGGAACATT GGTGTTGGCC CTCTCGGCCC | 900 |
| AGACATTCGA TCTTCAGGGC CTTAGTTGCA ATACTGACTC CACTCCTGGA | 950 |
| TTAATCGATC TGGAGATAAG GCGACTTTGC CACACCCCAA CGGAAAATGT | 1000 |
| CATTTCATGC GAGGTTAGTT ATCTTAACCA CACGACTATT AGCCTCCCGG | 1050 |
| CAGTCCACAC GTCATGCCTC AAGTACCACT GCAAAACCTA TTGGGGATTC | 1100 |
| TTTGGTAGCT ACAGCGCTGA CCGAATCATC AATCGGTACA CTGGTACTGT | 1150 |
| TAAGGGTTGT TTAAACAACT CAGCGCCAGA GGATCCCTTC GAGTGCAACT | 1200 |
| GGTTCTACTG CTGCTCGGCG ATTACAACAG AGATCTGCCG ATGCTCTATT | 1250 |
| ACAAATGTCA CGGTGGCTGT ACAGACATTC CCACCGTTCA TGTACTGCAG | 1300 |
| TTTCGCGGAC TGTAGTACTG TGAGTCAGCA GGAGCTAGAG AGTGGAAAGG | 1350 |
| CAATGCTGAG CGATGGCAGT ACCTTAACTT ATACCCCGTA TATCTTACAA | 1400 |
| TCAGAAGTCG TGAACAAAAC CCTTAATGGG ACTATACTCT GCAACTCATC | 1450 |
| CTCCAAGATA GTTTCCTTCG ATGAATTTAG GCGTTCATAC TCCCTAGCGA | 1500 |
| ATGGTAGTTA CCAGAGCTCA TCAATCAATG TGACGTGTGT AAACTACACG | 1550 |
| TCGTCCTGCC GGTCCAAGTT GAGAAGGCGG CGTAGGGATA CTCAACAGAT | 1600 |
| TGAGTACCTA GTTCACAAGC TTAGGCCTAC ACTGAAAGAT GCGTGGGAGG | 1650 |
| ACTGTGAGAT CCTCCAGTCT CTGCTCCTAG GGGTGTTTGG TACTGGGATT | 1700 |
| GCAAGTGCTT CGCAATTCTT GAGGGGCTGG CTCAACCACC CTGATATCAT | 1750 |
| CGGGTATATA GTTAATGGAG TTGGGGTAGT CTGGCAATGC CATCGTGTTG | 1800 |
| ATGTCACGTT CATGGCGTGG AATGAGTCCA CATATTACCC TCCAGTAGAT | 1850 |
| TACAATGGAC GGAAGTACTT TCTGAATGAT GAGGGGAGGC TACAAACAAA | 1900 |
| CACCCCCGAG GCAAGGCCAG GGCTTAAGCG GGTCATGTGG TTCGGCAGGT | 1950 |
| ACTTCCTAGG GACAGTAGGG TCTGGGGTGA AACCGAGGAG GATTCGGTAC | 2000 |
| AATAAGACCT CACATGATTA CCATCTAGAG GAGTTTGAGG CAAGTCTCAA | 2050 |
| CATGACCCCC CAGACCAGTA TCGCCTCGGG TCATGAGACA GACCCCATAA | 2100 |
| ATCATGCCTA CGGAACGCAG GCTGACCTCC TTCCATACAC CAGGTCTAGT | 2150 |
| AATATAACGT CTACAGATAC AGGCTCAGGC TGGGTGCACA TCGGCCTACC | 2200 |
| CTCATTTGCT TTCCTCAATC CTCTCGGGTG GCTTAGGGAC CTACTTGCGT | 2250 |
| GGGCGGCCTG GTTGGGTGGG GTTCTATACT TAATAAGTCT TTGTGTTTCC | 2300 |
| TTACCAGCCT CCTTCGCGAG GAGGAGACGC CTCGGCCGGT GGCAGGAATA | 2350 |

```
AACCGTACCG ACCAATCTCT TAAAAACCCT CTTCTCGGGA CAGAGGTCTC         2400

TTTCTGCCTT AAATCGAGTT CACTCCCCCA TCACGTACGA GCATTGGGCC         2450

AGATTAAAGC AAAGAACCTG GCATCCTGTG ACTATTACTT GCTATTCCGC         2500

CAAGTTGTAT TGCCCCCTGA AGTATATCCC ATTGGTGTCT TAATAAGAGC         2550

TGCGGAGGCC ATACTAACAG TTATAGTATC AGCTTGGAAG CTGGATCACA         2600

TGACAAAGAC CCTATACTCC TCTGTGAGAT ATGCACTCAC CAATCCCCGG         2650

GTCCGGGC                                                      2658
```

(2) INFORMATION FOR SEQ ID NO:21:

(i) SEQUENCE CHARACTERISTICS:
        (A) LENGTH: 484 amino acids
        (B) TYPE: amino acid
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:21:

```
Thr Trp Pro Pro Lys His Ile Val Asp Leu Val Gly Asp Thr Trp
              5                  10                  15

His Lys Leu Pro Ile Thr Gln Ile Phe Glu Ile Pro Glu Ser Met
             20                  25                  30

Asp Pro Ser Glu Ile Leu Asp Asp Lys Ser His Ser Phe Thr Arg
             35                  40                  45

Thr Arg Leu Ala Ser Trp Leu Ser Glu Asn Arg Gly Gly Pro Val
             50                  55                  60

Pro Ser Glu Lys Val Ile Ile Thr Ala Leu Ser Lys Pro Pro Val
             65                  70                  75

Asn Pro Arg Glu Phe Leu Arg Ser Ile Asp Leu Gly Gly Leu Pro
             80                  85                  90

Asp Glu Asp Leu Ile Ile Gly Leu Lys Pro Lys Glu Arg Glu Leu
             95                 100                 105

Lys Ile Glu Gly Arg Phe Phe Ala Leu Met Ser Trp Asn Leu Arg
            110                 115                 120

Leu Tyr Phe Val Ile Thr Glu Lys Leu Leu Ala Asn Tyr Ile Leu
            125                 130                 135

Pro Leu Phe Asp Ala Leu Thr Met Thr Asp Asn Leu Asn Lys Val
            140                 145                 150

Phe Lys Lys Leu Ile Asp Arg Val Thr Gly Gln Gly Leu Leu Asp
            155                 160                 165

Tyr Ser Arg Val Thr Tyr Ala Phe His Leu Asp Tyr Glu Lys Trp
            170                 175                 180

Asn Asn His Gln Arg Leu Glu Ser Thr Glu Asp Val Phe Ser Val
            185                 190                 195

Leu Asp Gln Val Phe Gly Leu Lys Arg Val Phe Ser Arg Thr His
            200                 205                 210

Glu Phe Phe Gln Lys Ala Trp Ile Tyr Tyr Ser Asp Arg Ser Asp
            215                 220                 225

Leu Ile Gly Leu Arg Glu Asp Gln Ile Tyr Cys Leu Asp Ala Ser
            230                 235                 240

Asn Gly Pro Thr Cys Trp Asn Gly Gln Asp Gly Gly Leu Glu Gly
            245                 250                 255
```

```
Leu Arg Gln Lys Gly Trp Ser Leu Val Ser Leu Leu Met Ile Asp
            260                 265                 270

Arg Glu Ser Gln Ile Arg Asn Thr Arg Thr Lys Ile Leu Ala Gln
        275                 280                 285

Gly Asp Asn Gln Val Leu Cys Pro Thr Tyr Met Leu Ser Pro Gly
        290                 295                 300

Leu Ser Gln Glu Gly Leu Leu Tyr Glu Leu Glu Arg Ile Ser Arg
        305                 310                 315

Asn Ala Leu Ser Ile Tyr Arg Ala Val Glu Glu Gly Ala Ser Lys
        320                 325                 330

Leu Gly Leu Ile Ile Lys Lys Glu Glu Thr Met Cys Ser Tyr Asp
        335                 340                 345

Phe Leu Ile Tyr Gly Lys Thr Pro Leu Phe Arg Gly Asn Ile Leu
        350                 355                 360

Val Pro Glu Ser Lys Arg Trp Ala Arg Val Ser Cys Val Ser Asn
        365                 370                 375

Asp Gln Ile Val Asn Leu Ala Asn Ile Met Ser Thr Val Ser Thr
        380                 385                 390

Asn Ala Leu Thr Val Ala Gln His Ser Gln Ser Leu Ile Lys Pro
        395                 400                 405

Met Arg Asp Phe Leu Leu Met Ser Val Gln Ala Val Phe His Tyr
        410                 415                 420

Leu Leu Phe Ser Pro Ile Leu Lys Gly Arg Val Tyr Lys Ile Leu
        425                 430                 435

Ser Ala Glu Gly Glu Ser Phe Leu Leu Ala Met Ser Arg Ile Ile
        440                 445                 450

Tyr Leu Asp Pro Ser Leu Gly Gly Ile Ser Gly Met Ser Leu Gly
        455                 460                 465

Arg Phe His Ile Arg Gln Phe Ser Asp Pro Val Ser Glu Gly Leu
        470                 475                 480

Ser Phe Trp Arg (2) INFORMATION FOR SEQ ID NO:22:

(i) SEQUENCE CHARACTERISTICS:
        (A) LENGTH: 483 amino acids
        (B) TYPE: amino acid
        (D) TOPOLOGY: linear (ii) MOLECULE TYPE: peptide (iii) HYPOTHETICAL:   NO (iv) ANTI-SENSE:  NO (xi) SEQUENCE DESCRIPTION: SEQ ID NO:22:

Thr Trp Pro Thr Ala Ala Lys Ile Gln Asp Phe Gly Asp Asn Trp
            5                   10                  15

His Lys Leu Pro Leu Ile Gln Cys Phe Glu Ile Pro Asp Leu Ile
            20                  25                  30

Asp Pro Ser Val Ile Tyr Ser Asp Lys Ser His Ser Met Asn Lys
            35                  40                  45

Lys Glu Val Ile Gln His Val Arg Ser Lys Pro Asn Ile Pro Ile
            50                  55                  60

Pro Ser Asn Lys Val Leu Gln Thr Met Leu Thr Asn Arg Ala Thr
            65                  70                  75
```

-continued

```
Asn Trp Lys Ala Phe Leu Lys Asp Ile Asp Glu Asn Gly Leu Asp
             80                  85                  90

Asp Asp Asp Leu Ile Ile Gly Leu Lys Gly Lys Glu Arg Glu Leu
             95                 100                 105

Lys Ile Ala Gly Arg Phe Phe Ser Leu Met Ser Trp Arg Leu Arg
            110                 115                 120

Glu Tyr Phe Val Ile Thr Glu Tyr Leu Ile Lys Thr Tyr Tyr Val
            125                 130                 135

Pro Leu Phe Lys Gly Leu Thr Met Ala Asp Asp Leu Thr Ser Val
            140                 145                 150

Ile Lys Lys Met Met Asp Ser Ser Ser Gly Gln Gly Leu Asp Asp
            155                 160                 165

Tyr Ser Ser Val Cys Leu Ala Asn His Ile Asp Tyr Glu Lys Trp
            170                 175                 180

Asn Asn His Gln Arg Lys Glu Ser Asn Gly Pro Ile Phe Arg Val
            185                 190                 195

Met Gly Gln Phe Leu Gly Tyr Pro Ser Leu Ile Glu Arg Thr His
            200                 205                 210

Glu Phe Phe Glu Lys Ser Leu Ile Tyr Tyr Asn Gly Arg Pro Asp
            215                 220                 225

Leu Met Thr Ile Arg Asn Gly Thr Leu Cys Asn Ser Thr Lys His
            230                 235                 240

Arg Val Cys Trp Asn Gly Gln Lys Gly Gly Leu Glu Gly Leu Arg
            245                 250                 255

Gln Lys Gly Trp Ser Ile Val Asn Leu Leu Val Ile Gln Arg Glu
            260                 265                 270

Ala Lys Ile Arg Asn Thr Ala Val Lys Val Leu Ala Gln Gly Asp
            275                 280                 285

Asn Gln Val Ile Cys Thr Gln Tyr Lys Thr Lys Thr Arg Ser
            290                 295                 300

Glu Leu Glu Leu Arg Ala Val Leu His Gln Met Ala Gly Asn Asn
            305                 310                 315

Asn Lys Ile Met Glu Glu Ile Lys Arg Gly Thr Glu Lys Leu Gly
            320                 325                 330

Leu Ile Ile Asn Asp Asp Glu Thr Met Gln Ser Ala Asp Tyr Leu
            335                 340                 345

Asn Tyr Gly Lys Ile Pro Ile Phe Arg Gly Val Ile Arg Gly Leu
            350                 355                 360

Glu Thr Lys Arg Trp Ser Arg Val Thr Cys Val Thr Asn Asp Gln
            365                 370                 375

Ile Pro Thr Cys Ala Asn Leu Met Ser Ser Val Ser Thr Asn Ala
            380                 385                 390

Leu Thr Val Ala His Phe Ala Glu Asn Pro Ile Asn Ala Met Ile
            395                 400                 405

Gln Tyr Asn Tyr Phe Gly Thr Phe Ala Arg Leu Leu Leu Phe Met
            410                 415                 420

His Asp Pro Ala Ile Arg Gln Ser Leu Tyr Lys Val Gln Glu Lys
            425                 430                 435

Ile Pro Gly Leu His Thr Arg Thr Phe Lys Tyr Ala Met Leu Tyr
            440                 445                 450

Leu Asp Pro Ser Ile Gly Gly Val Cys Gly Met Ala Leu Ser Arg
            455                 460                 465

Phe Leu Ile Arg Ala Phe Pro Asp Pro Val Thr Glu Ser Leu Ser
            470                 475                 480
```

Phe Trp Lys (2) INFORMATION FOR SEQ ID NO:23:

(i) SEQUENCE CHARACTERISTICS:
        (A) LENGTH: 515 amino acids
        (B) TYPE: amino acid
        (D) TOPOLOGY: linear (ii) MOLECULE TYPE: peptide (iii) HYPOTHETICAL:   NO (iv) ANTI-SENSE:  NO (xi) SEQUENCE DESCRIPTION: SEQ ID NO:23:

Asn Lys Lys Ile Phe Gln Arg Ser Ser Leu Tyr Asn His Lys Asp
          5                   10                 15

Trp Asp Gln Val Val Ile Leu Gln Ser Phe Gln Ile Pro Lys Ser
          20                 25              30

Val Asn Leu Ala Thr Met Ile Lys Asp Lys Ala Ile Ser Met Thr
          35                 40              45

Arg Ser Glu Leu Ile Glu Ser Val Asn Thr Lys Asn Ser Val Phe
          50                 55              60

Asp Ser Thr Lys Arg Arg Gly Ile Leu Lys Trp Leu Asn Glu Gln
          65                 70              75

Ser Asp Lys Ile Tyr Asn Phe Leu Met Arg Ile Asp Asp Lys Gly
          80                 85              90

Leu Asp Glu Asp Asp Cys Ile Ile Gly Leu Tyr Pro Lys Glu Arg
          95                100             105

Glu Met Lys Thr Lys Ala Arg Phe Phe Ser Leu Met Ser Tyr Lys
          110              115             120

Leu Arg Met Tyr Val Thr Ser Thr Glu Glu Leu Leu Gly Lys Tyr
          125              130             135

Val Leu Lys Tyr Phe Pro Met Ile Thr Met Ser Asp Asn Leu Leu
          140              145             150

Ser Met Val Ile Arg Leu Phe Asp Met Thr Thr Leu Ile Gly Asp
          155              160             165

Lys Gly Val Ala Val Thr Tyr Ser Met Asn Ile Asp Phe Ser Lys
          170              175             180

Trp Asn Gln Asn Met Arg Glu Arg Thr Asn Ala Gly Ile Phe Asp
          185              190             195

Asn Leu Asp Arg Ile Leu Gly Phe Arg Ser Leu Ile Ser Arg Thr
          200              205             210

His Ser Ile Phe Lys Ala Cys Tyr Leu Tyr Leu Cys Ser Gly Glu
          215              220             225

Tyr Val Pro Val Ile Ser Asn Asn Gln Leu Thr Ala Gln Ser Pro
          230              235             240

Trp Ser Arg Thr Gly Asp Glu Ser Gly Lys Glu Gly Leu Arg Gln
          245              250             255

Lys Gly Trp Thr Ile Thr Thr Val Cys Asp Ile Leu Ser Leu Ala
          260              265             270

Phe Lys Tyr Asn Ala Arg Ile Gln Leu Ile Gly Gly Asp Asn
          275              280             285

Gln Val Leu Thr Val Thr Met Leu Pro Ser Glu Ser Met Gln Ser
          290              295             300

Gln Gly Arg Asp Ser Gln Leu Leu Lys Val Arg Glu Arg Met Thr

```
                    305                 310                 315
Ser Phe Arg Asn Ala Leu Ala Lys Lys Met Val Lys Arg Gly Leu
                320                 325                 330

Pro Leu Lys Leu Glu Glu Thr Trp Ile Ser His Asn Leu Leu Met
                335                 340                 345

Tyr Asn Lys Ile Met Tyr Tyr Ser Gly Val Pro Leu Arg Gly Arg
                350                 355                 360

Leu Lys Val Ile Ser Arg Leu Phe Ser Asn Ser Asn Val Gly Val
                365                 370                 375

Thr Ser Leu Gly Gly Ile Thr Ser Thr Leu Gly Thr Gly Phe Gln
                380                 385                 390

Ser Ile Ser Thr Lys Asp Tyr Thr Pro Thr Leu Ala Trp Leu Ile
                395                 400                 405

Ser Arg Val Phe Thr Asp Ile Tyr Ile Ser Thr Tyr His Leu Leu
                410                 415                 420

Asn Pro Ile Ser Gly Thr Gln Arg Leu Asp Lys Gln Val Leu Met
                425                 430                 435

Ser Arg Gly Asn Ile Arg Gln Gly Arg Asn Glu Leu Gly Gly Glu
                440                 445                 450

Thr Ser Val Pro Ile Ile Asn Lys Ile Arg Asn His Ala Ala Leu
                455                 460                 465

Ala Thr Asp His Thr Leu Asp Leu Asp Ser Leu Leu Ile Cys Val
                470                 475                 480

Leu Tyr Tyr His Lys Ile Leu Gly Gly Pro Gly Ile Gly Pro Pro
                485                 490                 495

Thr Ala Tyr Val Met Lys Gly Phe Pro Asp Pro Leu Ser Glu Gly
                500                 505                 510

Leu Thr Phe Asn Tyr (2) INFORMATION FOR SEQ ID NO:24:

(i) SEQUENCE CHARACTERISTICS:
        (A) LENGTH: 535 amino acids
        (B) TYPE: amino acid
        (D) TOPOLOGY: linear (ii) MOLECULE TYPE: peptide (iii) HYPOTHETICAL:   NO (iv) ANTI-SENSE:  NO (xi) SEQUENCE DESCRIPTION: SEQ ID NO:24:

Glu Gly Leu Thr His Glu Gln Cys Val Asp Asn Trp Lys Ser Phe
                  5                  10                  15

Ala Gly Val Lys Phe Gly Cys Phe Met Pro Leu Ser Leu Asp Ser
                 20                  25                  30

Asp Leu Thr Met Tyr Leu Lys Asp Lys Ala Leu Ala Ala Leu Gln
                 35                  40                  45

Arg Glu Trp Asp Ser Val Tyr Pro Lys Glu Phe Leu Arg Tyr Asp
                 50                  55                  60

Pro Pro Lys Gly Thr Gly Ser Arg Arg Leu Val Asp Val Phe Leu
                 65                  70                  75

Asn Asp Ser Ser Phe Asp Pro Tyr Asp Val Ile Met Tyr Val Val
                 80                  85                  90

Ser Gly Ala Tyr Leu His Asp Pro Glu Phe Asn Leu Ser Tyr Ser
                 95                 100                 105
```

-continued

Leu Gln Glu Lys Glu Ile Lys Glu Thr Gly Arg Leu Phe Ala Lys
            110                 115                 120

Met Thr Tyr Lys Met Arg Ala Cys Gln Val Ile Ala Glu Asn Leu
            125                 130                 135

Ile Ser Asn Gly Ile Gly Lys Tyr Phe Lys Asp Asn Gly Met Ala
            140                 145                 150

Lys Asp Glu Gln Asp Leu Thr Lys Ala Leu His Thr Leu Ala Val
            155                 160                 165

Ser Gly Val Pro Lys Asp Leu Lys Glu Ser His Arg Gly Gly Pro
            170                 175                 180

Val Leu Lys Thr Tyr Ser Arg Ser Pro Val His Thr Ser Thr Arg
            185                 190                 195

Asn Val Arg Ala Ala Lys Gly Phe Ile Gly Phe Pro Gln Val Ile
            200                 205                 210

Arg Gln Asp Gln Asp Thr Asp His Pro Glu Asn Met Glu Ala Tyr
            215                 220                 225

Glu Thr Val Ser Ala Phe Ile Thr Thr Asp Leu Lys Lys Tyr Cys
            230                 235                 240

Leu Asn Trp Arg Tyr Glu Thr Ile Ser Leu Phe Ala Gln Arg Leu
            245                 250                 255

Asn Glu Ile Tyr Gly Leu Pro Ser Phe Phe Gln Trp Leu His Lys
            260                 265                 270

Arg Leu Glu Thr Ser Val Leu Tyr Val Ser Asp Pro His Cys Pro
            275                 280                 285

Pro Asp Leu Asp Ala His Ile Pro Leu Tyr Lys Val Pro Asn Asp
            290                 295                 300

Gln Ile Phe Ile Lys Tyr Pro Met Gly Gly Ile Glu Gly Tyr Cys
            305                 310                 315

Gln Lys Leu Trp Thr Ile Ser Thr Ile Pro Tyr Leu Tyr Leu Ala
            320                 325                 330

Ala Tyr Glu Ser Gly Val Arg Ile Ala Ser Leu Val Gln Gly Asp
            335                 340                 345

Asn Gln Thr Ile Ala Val Thr Lys Arg Val Pro Ser Thr Trp Pro
            350                 355                 360

Tyr Asn Leu Lys Lys Arg Glu Ala Ala Arg Val Thr Arg Asp Tyr
            365                 370                 375

Phe Val Ile Leu Arg Gln Arg Leu His Asp Ile Gly His His Leu
            380                 385                 390

Lys Ala Asn Glu Thr Ile Val Ser Ser His Phe Phe Val Tyr Ser
            395                 400                 405

Lys Gly Ile Tyr Tyr Asp Gly Leu Leu Val Ser Gln Ser Leu Lys
            410                 415                 420

Ser Ile Ala Arg Cys Val Phe Trp Ser Glu Thr Ile Val Asp Glu
            425                 430                 435

Thr Arg Ala Ala Cys Ser Asn Ile Ala Thr Thr Met Ala Lys Ser
            440                 445                 450

Ile Glu Arg Gly Tyr Asp Arg Tyr Leu Ala Tyr Ser Leu Asn Phe
            455                 460                 465

Leu Lys Val Ile Gln Gln Ile Leu Ile Ser Leu Gly Phe Thr Ile
            470                 475                 480

Asn Ser Thr Met Thr Arg Asp Val Val Ile Pro Leu Leu Thr Asn
            485                 490                 495

Asn Asp Leu Leu Ile Arg Met Ala Leu Leu Pro Ala Pro Ile Gly
            500                 505                 510

```
Gly Met Asn Tyr Leu Asn Met Ser Arg Leu Phe Val Arg Asn Ile
                515                 520                 525
Gly Asp Pro Val Thr Ser Ser Ile Ala Asp
                530                 535
```

(2) INFORMATION FOR SEQ ID NO:25:

(i) SEQUENCE CHARACTERISTICS:
        (A) LENGTH: 527 amino acids
        (B) TYPE: amino acid
        (D) TOPOLOGY: linear (ii) MOLECULE TYPE: peptide (iii) HYPOTHETICAL:  NO (iv) ANTI-SENSE:  NO (xi) SEQUENCE DESCRIPTION: SEQ ID NO:25:

```
Thr Ala Ile Ser Tyr Glu Cys Ala Val Asp Asn Tyr Thr Ser Phe
                 5                  10                  15
Ile Gly Phe Lys Phe Arg Lys Phe Ile Glu Pro Gln Leu Asp Glu
                20                  25                  30
Asp Leu Thr Ile Tyr Met Lys Asp Lys Ala Leu Ser Pro Arg Lys
                35                  40                  45
Glu Ala Trp Asp Ser Val Tyr Pro Asp Ser Asn Leu Tyr Tyr Lys
                50                  55                  60
Ala Pro Glu Ser Glu Thr Arg Arg Leu Ile Glu Val Phe Ile
                65                  70                  75
Asn Asp Glu Asn Phe Asn Pro Glu Glu Ile Ile Asn Tyr Val Glu
                80                  85                  90
Ser Gly Asp Trp Leu Lys Asp Glu Glu Phe Asn Ile Ser Tyr Ser
                95                  100                 105
Leu Lys Glu Lys Glu Ile Lys Gln Glu Gly Arg Leu Phe Ala Lys
                110                 115                 120
Met Thr Tyr Lys Met Arg Ala Val Gln Val Leu Ala Glu Thr Leu
                125                 130                 135
Leu Ala Lys Gly Ile Gly Glu Leu Phe Ser Glu Asn Gly Met Val
                140                 145                 150
Lys Gly Glu Ile Asp Leu Leu Lys Arg Leu Thr Thr Leu Ser Val
                155                 160                 165
Ser Gly Val Pro Arg Thr Asp Ser Val Tyr Asn Asn Ser Lys Ser
                170                 175                 180
Ser Glu Lys Arg Asn Glu Gly Met Gly Asn Lys Asn Ser Gly Gly
                185                 190                 195
Tyr Trp Asp Glu Lys Lys Arg Ser Arg His Glu Phe Lys Ala Thr
                200                 205                 210
Asp Ser Ser Thr Asp Gly Tyr Glu Thr Leu Ser Cys Phe Leu Thr
                215                 220                 225
Thr Asp Leu Lys Lys Tyr Cys Leu Asn Trp Arg Phe Glu Ser Thr
                230                 235                 240
Ala Leu Phe Gly Gln Arg Cys Asn Glu Ile Phe Gly Phe Lys Thr
                245                 250                 255
Phe Phe Asn Trp Met His Pro Val Leu Glu Arg Cys Thr Ile Tyr
                260                 265                 270
Val Gly Asp Pro Tyr Cys Pro Val Ala Asp Arg Met His Arg Gln
                275                 280                 285
```

```
Leu Gln Asp His Ala Asp Ser Gly Ile Phe Ile His Asn Pro Arg
            290                 295                 300

Gly Gly Ile Glu Gly Tyr Cys Gln Lys Leu Trp Thr Leu Ile Ser
            305                 310                 315

Met Ser Ala Ile His Leu Ala Ala Val Arg Gly Val Arg Val
            320                 325                 330

Ser Ala Met Val Gln Gly Asp Asn Gln Ala Ile Ala Val Thr Ser
            335                 340                 345

Arg Val Pro Val Ala Gln Thr Tyr Lys Gln Lys Asn His Val
            350                 355                 360

Tyr Glu Glu Ile Thr Lys Tyr Phe Gly Ala Leu Arg His Val Met
            365                 370                 375

Phe Asp Val Gly His Glu Leu Lys Leu Asn Glu Thr Ile Ile Ser
            380                 385                 390

Ser Lys Met Phe Val Tyr Ser Lys Arg Ile Tyr Tyr Asp Gly Lys
            395                 400                 405

Ile Leu Pro Gln Cys Leu Lys Ala Leu Thr Lys Cys Val Phe Trp
            410                 415                 420

Ser Glu Thr Leu Val Asp Glu Asn Arg Ser Ala Cys Ser Asn Ile
            425                 430                 435

Ser Thr Ser Ile Ala Lys Ala Ile Glu Asn Gly Tyr Ser Pro Ile
            440                 445                 450

Leu Gly Tyr Cys Ile Ala Leu Tyr Lys Thr Cys Gln Gln Val Cys
            455                 460                 465

Ile Ser Leu Gly Met Thr Ile Asn Pro Thr Ile Ser Pro Thr Val
            470                 475                 480

Arg Asp Gln Tyr Phe Lys Gly Lys Asn Trp Leu Arg Cys Ala Val
            485                 490                 495

Leu Ile Pro Ala Asn Val Gly Gly Phe Asn Tyr Met Ser Thr Ser
            500                 505                 510

Arg Cys Phe Val Arg Asn Ile Gly Asp Pro Ala Val Ala Ala Leu
            515                 520                 525

Ala Asp (2) INFORMATION FOR SEQ ID NO:26:

(i) SEQUENCE CHARACTERISTICS:
        (A) LENGTH: 509 amino acids
        (B) TYPE: amino acid
        (D) TOPOLOGY: linear (ii) MOLECULE TYPE: peptide (iii) HYPOTHETICAL:  NO (iv) ANTI-SENSE:  NO (xi) SEQUENCE DESCRIPTION: SEQ ID NO:26:

Ala Glu Ile Ser His Asp Ile Met Leu Arg Glu Tyr Lys Ser Leu
                5                  10                  15

Ser Ala Leu Glu Phe Glu Pro Cys Ile Glu Tyr Asp Pro Val Thr
            20                  25                  30

Asn Leu Ser Met Phe Leu Lys Asp Lys Ala Ile Ala His Pro Asn
            35                  40                  45

Asp Asn Trp Leu Ala Ser Phe Arg Arg Asn Leu Leu Ser Glu Asp
            50                  55                  60

Gln Lys Lys His Val Lys Glu Ala Thr Ser Thr Asn Arg Leu Leu
            65                  70                  75
```

```
Ile Glu Phe Leu Glu Ser Asn Asp Phe Asp Pro Tyr Lys Glu Met
                 80                  85                  90

Glu Tyr Leu Thr Thr Leu Glu Tyr Leu Arg Asp Asp Asp Val Ala
                 95                 100                 105

Val Ser Tyr Ser Leu Lys Glu Lys Glu Val Lys Val Asn Gly Arg
                110                 115                 120

Ile Phe Ala Lys Leu Thr Lys Lys Leu Arg Asn Cys Gln Val Met
                125                 130                 135

Ala Glu Gly Ile Leu Ala Asp Gln Ile Ala Pro Phe Phe Gln Gly
                140                 145                 150

Asn Gly Val Ile Gln Asp Ser Ile Ser Leu Thr Lys Ser Thr Leu
                155                 160                 165

Ala Met Ser Gln Leu Ser Phe Asn Ser Asn Lys Lys Arg Ile Thr
                170                 175                 180

Asp Cys Lys Glu Arg Val Ser Ser Asn Arg Asn His Asp Pro Lys
                185                 190                 195

Ser Lys Asn Arg Arg Val Ala Thr Phe Ile Thr Thr Asp Leu
                200                 205                 210

Gln Lys Tyr Cys Leu Asn Trp Arg Tyr Gln Thr Ile Lys Leu Phe
                215                 220                 225

Ala His Ala Ile Asn Gln Leu Met Gly Leu Pro His Phe Phe Glu
                230                 235                 240

Trp Ile His Leu Arg Leu Met Asp Thr Thr Met Phe Val Gly Asp
                245                 250                 255

Pro Phe Asn Pro Pro Ser Asp Pro Thr Asp Cys Asp Leu Ser Arg
                260                 265                 270

Val Pro Asn Asp Asp Ile Tyr Ile Val Ser Ala Arg Gly Gly Ile
                275                 280                 285

Glu Gly Leu Cys Gln Lys Leu Trp Thr Met Ile Ser Ile Ala Ala
                290                 295                 300

Ile Gln Leu Ala Ala Ala Arg Ser His Cys Arg Val Ala Cys Met
                305                 310                 315

Val Gln Gly Asp Asn Gln Val Ile Ala Val Thr Arg Glu Val Arg
                320                 325                 330

Ser Asp Asp Ser Pro Glu Met Val Leu Thr Gln Leu His Gln Ala
                335                 340                 345

Ser Asp Asn Phe Phe Lys Glu Leu Ile His Val Asn His Leu Ile
                350                 355                 360

Gly His Asn Leu Lys Asp Arg Glu Thr Ile Arg Ser Asp Thr Phe
                365                 370                 375

Phe Ile Tyr Ser Lys Arg Ile Phe Lys Asp Gly Ala Ile Leu Ser
                380                 385                 390

Gln Val Leu Lys Asn Ser Ser Lys Leu Val Met Val Ser Gly Asp
                395                 400                 405

Leu Ser Glu Asn Thr Val Met Ser Cys Ala Asn Ile Ala Ser Thr
                410                 415                 420

Val Ala Arg Leu Cys Glu Asn Gly Leu Pro Lys Asp Phe Cys Tyr
                425                 430                 435

Tyr Leu Asn Tyr Ile Met Ser Cys Val Gln Thr Tyr Phe Asp Ser
                440                 445                 450

Glu Phe Ser Tyr Asn Asn Asn Ser His Pro Asp Leu Asn Gln Ser
                455                 460                 465

Trp Ile Glu Asp Ile Ser Phe Val His Ser Tyr Val Leu Thr Pro
```

470                 475                 480
Ala Gln Leu Gly Gly Leu Ser Asn Leu Gln Tyr Ser Arg Leu Tyr
                485                 490                 495

Thr Arg Asn Ile Gly Asp Pro Gly Thr Thr Ala Phe Ala Glu
                500                 505

(2) INFORMATION FOR SEQ ID NO:27:

(i) SEQUENCE CHARACTERISTICS:
        (A) LENGTH: 489 amino acids
        (B) TYPE: amino acid
        (D) TOPOLOGY: linear (ii) MOLECULE TYPE: peptide (iii) HYPOTHETICAL:   NO (iv) ANTI-SENSE:  NO (xi) SEQUENCE DESCRIPTION: SEQ ID NO:27:

Ser Phe Pro Ser Gln Ala Glu Ile Tyr Gln His Leu Trp Glu Trp
                5                   10                  15

Tyr Phe Val Glu His Glu Pro Leu Phe Ser Thr Lys Ile Ile Ser
                20                  25                  30

Asp Leu Ser Ile Phe Ile Lys Asp Arg Leu Thr Ala Val Asn Gln
                35                  40                  45

Glu Cys Trp Asp Ser Val Phe Asp Arg Ser Val Leu Gly Tyr Asn
                50                  55                  60

Pro Pro Val Arg Phe Gln Ser Lys Arg Val Pro Glu Gln Phe Leu
                65                  70                  75

Gly Gln Ala Asp Phe Ser Leu Asn Gln Ile Leu Glu Phe Ala Glu
                80                  85                  90

Lys Leu Glu Tyr Leu Ala Pro Ser Tyr Arg Asn Phe Ser Phe Ser
                95                  100                 105

Leu Lys Glu Lys Glu Leu Asn Ile Gly Arg Thr Phe Gly Lys Leu
                110                 115                 120

Pro Tyr Arg Val Arg Asn Val Gln Thr Leu Ala Glu Ala Leu Leu
                125                 130                 135

Ala Asp Gly Leu Ala Lys Ala Phe Pro Ser Asn Met Met Val Val
                140                 145                 150

Thr Glu Arg Glu Gln Lys Glu Ala Leu Leu His Gln Ala Ser Trp
                155                 160                 165

His His Asn Ser Ala Ser Ile Gly Glu Asn Ala Ile Val Arg Gly
                170                 175                 180

Ala Ser Phe Val Thr Asp Leu Glu Lys Tyr Asn Leu Ala Phe Arg
                185                 190                 195

Tyr Glu Phe Thr Arg His Phe Ile Asp Tyr Cys Asn Arg Cys Tyr
                200                 205                 210

Gly Val Lys Asn Leu Phe Asp Trp Met His Phe Leu Ile Pro Leu
                215                 220                 225

Cys Tyr Met His Val Ser Asp Phe Tyr Ser Pro Pro His Cys Val
                230                 235                 240

Thr Glu Asp Asn Arg Asn Asn Pro Pro Asp Cys Ala Asn Ala Tyr
                245                 250                 255

His Tyr His Leu Gly Gly Ile Glu Gly Leu Gln Gln Lys Leu Trp
                260                 265                 270

Thr Cys Ile Ser Cys Ala Gln Ile Thr Leu Val Glu Leu Lys Thr
                275                 280                 285

```
Lys Leu Lys Leu Lys Ser Ser Val Met Gly Asp Asn Gln Cys Ile
            290                 295                 300

Thr Thr Leu Ser Leu Phe Pro Ile Asp Ala Pro Asn Asp Tyr Gln
            305                 310                 315

Glu Asn Glu Ala Glu Leu Asn Ala Ala Arg Val Ala Val Glu Leu
            320                 325                 330

Ala Ile Thr Thr Gly Tyr Ser Gly Ile Phe Leu Lys Pro Glu Glu
            335                 340                 345

Thr Phe Val His Ser Gly Phe Ile Tyr Phe Gly Lys Lys Gln Tyr
            350                 355                 360

Leu Asn Gly Val Gln Leu Pro Gln Ser Leu Lys Thr Met Ala Arg
            365                 370                 375

Cys Gly Pro Leu Ser Asp Ser Ile Phe Asp Asp Leu Gln Gly Ser
            380                 385                 390

Leu Ala Ser Ile Gly Thr Ser Phe Glu Arg Gly Thr Ser Glu Thr
            395                 400                 405

Arg His Ile Phe Pro Ser Arg Trp Ile Ala Ser Phe His Ser Met
            410                 415                 420

Leu Ala Ile Asn Leu Leu Asn Gln Asn His Leu Gly Phe Pro Leu
            425                 430                 435

Gly Phe Asn Ile Asp Ile Ser Cys Phe Lys Lys Pro Leu Thr Phe
            440                 445                 450

Ser Glu Lys Leu Ile Ala Leu Ile Thr Pro Gln Val Leu Gly Gly
            455                 460                 465

Leu Ser Phe Leu Asn Pro Glu Lys Leu Phe Tyr Arg Asn Ile Ser
            470                 475                 480

Asp Pro Leu Thr Ser Gly Leu Phe Gln
            485

(2) INFORMATION FOR SEQ ID NO:28:

(i) SEQUENCE CHARACTERISTICS:
        (A) LENGTH: 513 amino acids
        (B) TYPE: amino acid
        (D) TOPOLOGY: linear (ii) MOLECULE TYPE: peptide (iii) HYPOTHETICAL:   NO (iv) ANTI-SENSE:  NO (xi) SEQUENCE DESCRIPTION: SEQ ID NO:28:

Thr Tyr Pro Ser Leu Leu Glu Leu Thr Glu Arg Asp Leu Ile Val
              5                  10                  15

Leu Ser Gly Leu Arg Phe Tyr Arg Glu Phe Arg Leu Pro Lys Lys
             20                  25                  30

Val Asp Leu Glu Met Ile Ile Asn Asp Lys Ala Ile Ser Pro Pro
             35                  40                  45

Lys Asn Leu Ile Trp Thr Ser Phe Pro Arg Asn Tyr Met Pro Ser
             50                  55                  60

His Ile Gln Asn Tyr Ile Glu His Glu Lys Leu Lys Phe Ser Glu
             65                  70                  75

Ser Asp Lys Ser Arg Arg Val Leu Glu Tyr Tyr Leu Arg Asp Asn
             80                  85                  90

Lys Phe Asn Glu Cys Asp Leu Tyr Asn Cys Val Val Asn Gln Ser
             95                 100                 105
```

```
Tyr Leu Asn Asn Pro Asn His Val Val Ser Leu Thr Gly Lys Glu
                110                 115                 120

Arg Glu Leu Ser Val Gly Arg Met Phe Ala Met Gln Pro Gly Met
                125                 130                 135

Phe Arg Gln Val Gln Ile Leu Ala Glu Lys Met Ile Ala Glu Asn
                140                 145                 150

Ile Leu Gln Phe Phe Pro Glu Ser Leu Thr Arg Tyr Gly Asp Leu
                155                 160                 165

Glu Leu Gln Lys Ile Leu Glu Leu Lys Ala Gly Ile Ser Asn Lys
                170                 175                 180

Ser Asn Arg Tyr Asn Asp Asn Tyr Asn Tyr Ile Ser Lys Cys
                185                 190                 195

Ser Ile Ile Thr Asp Leu Ser Lys Phe Asn Gln Ala Phe Arg Tyr
                200                 205                 210

Glu Thr Ser Cys Ile Cys Ser Asp Val Leu Asp Glu Leu His Gly
                215                 220                 225

Val Gln Ser Leu Phe Ser Trp Leu His Leu Thr Ile Pro His Val
                230                 235                 240

Thr Ile Ile Cys Thr Tyr Arg His Ala Pro Pro Tyr Ile Gly Asp
                245                 250                 255

His Ile Val Asp Leu Asn Asn Val Asp Glu Gln Ser Gly Leu Tyr
                260                 265                 270

Arg Tyr His Met Gly Gly Ile Glu Gly Trp Cys Gln Lys Leu Trp
                275                 280                 285

Thr Ile Glu Ala Ile Ser Leu Leu Asp Leu Ile Ser Leu Lys Gly
                290                 295                 300

Lys Phe Ser Ile Thr Ala Leu Ile Asn Gly Asp Asn Gln Ser Ile
                305                 310                 315

Asp Ile Ser Lys Pro Ile Arg Leu Met Glu Gly Gln Thr His Ala
                320                 325                 330

Gln Ala Asp Tyr Leu Leu Ala Leu Asn Ser Leu Lys Leu Leu Tyr
                335                 340                 345

Lys Glu Tyr Ala Gly Ile Gly His Lys Leu Lys Gly Thr Glu Thr
                350                 355                 360

Tyr Ile Ser Arg Asp Met Gln Phe Met Ser Lys Thr Ile Gln His
                365                 370                 375

Asn Gly Val Tyr Tyr Pro Ala Ser Ile Lys Lys Val Leu Arg Val
                380                 385                 390

Gly Pro Trp Ile Asn Thr Ile Leu Asp Asp Phe Lys Val Ser Leu
                395                 400                 405

Glu Ser Ile Gly Ser Leu Thr Gln Glu Leu Glu Tyr Arg Gly Glu
                410                 415                 420

Ser Leu Leu Cys Ser Leu Ile Phe Arg Asn Val Trp Leu Tyr Asn
                425                 430                 435

Gln Ile Ala Leu Gln Leu Lys Asn His Ala Leu Cys Asn Asn Lys
                440                 445                 450

Leu Tyr Leu Asp Ile Leu Lys Val Leu Lys His Leu Lys Thr Phe
                455                 460                 465

Phe Asn Leu Asp Asn Ile Asp Thr Ala Leu Thr Leu Tyr Met Asn
                470                 475                 480

Leu Pro Met Leu Phe Gly Gly Asp Pro Asn Leu Leu Tyr Arg
                485                 490                 495

Ser Phe Tyr Arg Arg Thr Pro Asp Phe Leu Thr Glu Ala Ile Val
                500                 505                 510
```

His Ser Val (2) INFORMATION FOR SEQ ID NO:29:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:29:

UUUUUUUGGU UUAUGCAAGU UUGUUGUACG CAUUUUUUCG CGU               43

(2) INFORMATION FOR SEQ ID NO:30:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:30:

UAGUUAUUCG CACACAAAAG AUCCUAAAAA UUCUUCUUUC UUUUUGUGUG CCCA      54

(2) INFORMATION FOR SEQ ID NO:31:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:31:

UAUUUAUAUG AUACACAAAA UCAUCAUCUC UUGUUUUUGU GUGUCU           46

(2) INFORMATION FOR SEQ ID NO:32:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:32:

UAUAACUUCA UUACAUAUCC CAUACAUGUU UUUUCUCUUG UUUGGU           46

(2) INFORMATION FOR SEQ ID NO:33:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:33:

UGCUCCUUCG CCUUUUAUCG UAACUUACGG AUUCUCUGUU UGGU          44

(2) INFORMATION FOR SEQ ID NO:34:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:34:

UGAUCAUUGA UUUGAACUAU CCUUACCCAA CUUUGUUUGG U             41

(2) INFORMATION FOR SEQ ID NO:35:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:35:

UUUGCUUUGC AAUUGACAAU GUCUGUUUUU UCUUUGAUCU GGUUGUUAAG CGU      53

(2) INFORMATION FOR SEQ ID NO:36:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:36:

UUCCCUCUAG GCCAAAUAAU UGUAAGAAUG GUUUUUUUGU CUUCGU        46

(2) INFORMATION FOR SEQ ID NO:37:

(i) SEQUENCE CHARACTERISTICS:
        (A) LENGTH: 48 base pairs (B) TYPE: nucleic acid
            (C) STRANDEDNESS: single
            (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:37:

CCCCAUUUUU UUGGUUUAUG CAAGUUUGUU GUACGCAUUU UUUCGCGU                48

(2) INFORMATION FOR SEQ ID NO:38:

(i) SEQUENCE CHARACTERISTICS:
            (A) LENGTH: 58 base pairs
            (B) TYPE: nucleic acid
            (C) STRANDEDNESS: single
            (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:38:

ACGAGAAAAA AAGUGUCAAA AACUAAUAUC UCGUAAUUUA GUUAAUUUUU UAAUAACU         58

(2) INFORMATION FOR SEQ ID NO:39:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:39:

UCUUUAUUUA UAUGAUACAC AAAAUCAUCA UCUCUUGUUU UUGUGUGUCU                  50

(2) INFORMATION FOR SEQ ID NO:40:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:40:

ACACACACAA AAAAGAUGAA GAAUGUUUUG UUUUACUUAU AUCAAAGCUU UUUUCUUAAU       60

(2) INFORMATION FOR SEQ ID NO:41:

(i) SEQUENCE CHARACTERISTICS:
            (A) LENGTH: 59 base pairs
            (B) TYPE: nucleic acid
            (C) STRANDEDNESS: single
            (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:41:

CCCUAAAAUC CUGUAUAACU UCAUUACAUA UCCCAUACAU GUUUUUCUC UUGUUUGGU        59

(2) INFORMATION FOR SEQ ID NO:42:

(i) SEQUENCE CHARACTERISTICS:
            (A) LENGTH: 65 base pairs
            (B) TYPE: nucleic acid
            (C) STRANDEDNESS: single
            (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:42:

ACCAGACAAG AGUUUAAGAG AUAUGUAUCC

UUUUAAAUUU UCUUGUCUUC UUGUAAGUUU UUCUU        65

(2) INFORMATION FOR SEQ ID NO:43:

(i) SEQUENCE CHARACTERISTICS:
            (A) LENGTH: 62 base pairs
            (B) TYPE: nucleic acid
            (C) STRANDEDNESS: single
            (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:43:

UGUUACAUUU UUGCUUUGCA AUUGACAAUG UCUGUUUUUU CUUUGAUCUG GUUGUUAAGC GU        62

(2) INFORMATION FOR SEQ ID NO:44:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: genomic RNA (iii) HYPOTHETICAL: NO (iv) ANTI-SENSE: NO (xi) SEQUENCE DESCRIPTION: SEQ ID NO:44:

ACGCUUAACA AAUAAACAAC AAAAAUGAGA AAAACAAUCA
AACAACCAAA GGUUCAGAUU UAG        63

(2) INFORMATION FOR SEQ ID NO:45:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: genomic RNA -continued (iii) HYPOTHETICAL: NO (iv) ANTI-SENSE: NO (xi) SEQUENCE DESCRIPTION: SEQ ID NO:45:

CMNMYYMNWA AAAAA                                                                15

(2) INFORMATION FOR SEQ ID NO:46:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL:    NO (iv) ANTI-SENSE:  NO (xi) SEQUENCE DESCRIPTION: SEQ ID NO:46:

Ser Asn Ser Gly Ser
1               5